(12) United States Patent
McGuan et al.

(10) Patent No.: US 11,596,479 B2
(45) Date of Patent: Mar. 7, 2023

(54) COMPUTER-ASSISTED ARTHROPLASTY SYSTEM

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Shawn P. McGuan, San Clemente, CA (US); Elizabeth Duxbury, San Clemente, CA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

(*) Notice: Subject to any disclaimer, the term of this patent is extended or adjusted under 35 U.S.C. 154(b) by 64 days.

(21) Appl. No.: 17/358,614

(22) Filed: Jun. 25, 2021

(65) Prior Publication Data
US 2021/0315642 A1    Oct. 14, 2021

Related U.S. Application Data

(63) Continuation of application No. 16/975,192, filed as application No. PCT/US2020/016605 on Feb. 4, 2020, now Pat. No. 11,071,592.
(Continued)

(51) Int. Cl.
*A61B 34/10* (2016.01)
*A61B 34/00* (2016.01)
(Continued)

(52) U.S. Cl.
CPC .......... *A61B 34/10* (2016.02); *A61B 17/1764* (2013.01); *A61B 34/25* (2016.02);
(Continued)

(58) Field of Classification Search
CPC .............. A61B 34/10; A61B 2034/104; A61B 2034/105; A61B 2034/108; A61B 34/20;
(Continued)

(56) References Cited

U.S. PATENT DOCUMENTS 5,995,738 A * 11/1999 DiGioia, III .......... A61F 2/4657
   703/11
8,412,669 B2 * 4/2013 Bergeon ................. G16H 50/50
   706/62

(Continued)

*Primary Examiner* — Brenda C Bernardi
(74) *Attorney, Agent, or Firm* — DLA Piper LLP

(57) ABSTRACT

A computer-implemented method for creating an activity-optimized cutting guides for surgical procedures includes receiving one or more pre-operative images depicting one or more anatomical joints of a patient, and creating a three-dimensional anatomical model of the one or more anatomical joints based on the one or more pre-operative images. One or more patient-specific anatomical measurements are determined based on the three-dimensional anatomical model. A statistical model of joint performance is applied to the patient-specific anatomical measurements to identify one or more cut angles for performing a surgical procedure. A patient-specific cutting guide is created that comprises one or more apertures positioned based on the one or more cut angles.

20 Claims, 62 Drawing Sheets

Related U.S. Application Data

(60) Provisional application No. 62/939,946, filed on Nov. 25, 2019, provisional application No. 62/885,673, filed on Aug. 12, 2019, provisional application No. 62/864,663, filed on Jun. 21, 2019, provisional application No. 62/801,257, filed on Feb. 5, 2019, provisional application No. 62/801,245, filed on Feb. 5, 2019.

(51) Int. Cl.

| | | |
|---|---|---|
| *G16H 20/40* | (2018.01) | |
| *G16H 50/50* | (2018.01) | |
| *G16H 10/60* | (2018.01) | |
| *G16H 50/70* | (2018.01) | |
| *A61B 17/17* | (2006.01) | |
| *G06N 20/00* | (2019.01) | |
| *A61B 90/00* | (2016.01) | |
| *G16H 40/63* | (2018.01) | |
| *G06N 20/10* | (2019.01) | |
| *G06N 5/04* | (2006.01) | |
| *A61F 2/46* | (2006.01) | |
| *G02B 27/01* | (2006.01) | |
| *G06N 3/08* | (2006.01) | |
| *G16H 30/40* | (2018.01) | |
| *G09B 19/00* | (2006.01) | |
| *G09B 19/24* | (2006.01) | |
| *A61B 17/00* | (2006.01) | |
| *A61B 34/20* | (2016.01) | |
| *G06N 5/046* | (2023.01) | |
| *A61B 34/30* | (2016.01) | |
| *A61B 90/96* | (2016.01) | |
| *A61B 17/15* | (2006.01) | |
| *A61B 90/50* | (2016.01) | |
| *A61F 2/30* | (2006.01) | |

(52) U.S. Cl.
CPC ............ *A61B 90/361* (2016.02); *A61B 90/37* (2016.02); *A61B 90/39* (2016.02); *A61F 2/461* (2013.01); *G02B 27/0172* (2013.01); *G06N 3/08* (2013.01); *G06N 5/046* (2013.01); *G06N 20/00* (2019.01); *G06N 20/10* (2019.01); *G09B 19/003* (2013.01); *G09B 19/24* (2013.01); *G16H 10/60* (2018.01); *G16H 20/40* (2018.01); *G16H 30/40* (2018.01); *G16H 40/63* (2018.01); *G16H 50/50* (2018.01); *G16H 50/70* (2018.01); *A61B 17/15* (2013.01); *A61B 17/17* (2013.01); *A61B 34/20* (2016.02); *A61B 34/30* (2016.02); *A61B 90/96* (2016.02); *A61B 2017/00199* (2013.01); *A61B 2017/00526* (2013.01); *A61B 2034/102* (2016.02); *A61B 2034/104* (2016.02); *A61B 2034/105* (2016.02); *A61B 2034/107* (2016.02); *A61B 2034/108* (2016.02); *A61B 2034/2048* (2016.02); *A61B 2034/2057* (2016.02); *A61B 2034/2063* (2016.02); *A61B 2034/2065* (2016.02); *A61B 2034/2068* (2016.02); *A61B 2034/2072* (2016.02); *A61B 2034/2074* (2016.02); *A61B 2034/252* (2016.02); *A61B 2034/254* (2016.02); *A61B 2034/256* (2016.02); *A61B 2034/258* (2016.02); *A61B 2090/363* (2016.02); *A61B 2090/365* (2016.02); *A61B 2090/371* (2016.02); *A61B 2090/376* (2016.02); *A61B 2090/3916* (2016.02); *A61B 2090/502* (2016.02); *A61F 2002/30952* (2013.01); *A61F 2002/4633* (2013.01); *G02B 2027/0138* (2013.01)

(58) Field of Classification Search
CPC ......... A61B 34/25; A61B 34/30; A61B 90/96; A61B 17/15; A61B 17/17; A61B 2017/00526; G16H 20/40; G06N 20/00
See application file for complete search history.

(56) References Cited

U.S. PATENT DOCUMENTS

| | | | |
|---|---|---|---|
| 8,794,977 B2 * | 8/2014 | McGuan | A61B 34/10 623/20.14 |
| 9,737,367 B2 * | 8/2017 | Steines | A61B 34/10 |
| 9,827,106 B2 * | 11/2017 | Hensley | A61F 2/389 |
| 10,342,636 B2 * | 7/2019 | Nowatschin | B25J 9/06 |
| 10,426,571 B2 * | 10/2019 | Krinninger | A61B 1/00149 |
| 10,595,943 B2 * | 3/2020 | Barsoum | A61F 2/32 |
| 2004/0034283 A1 * | 2/2004 | Quaid | A61B 34/32 600/300 |
| 2010/0076563 A1 * | 3/2010 | Otto | A61B 5/103 623/20.14 |
| 2010/0106475 A1 * | 4/2010 | Smith | G16H 50/50 703/11 |
| 2011/0087465 A1 * | 4/2011 | Mahfouz | G06K 9/6267 703/2 |
| 2011/0282473 A1 * | 11/2011 | Pavlovskaia | G06V 10/46 700/98 |
| 2012/0116562 A1 * | 5/2012 | Agnihotri | A61B 34/10 700/98 |
| 2012/0189996 A1 * | 7/2012 | Hager | G09B 5/00 434/262 |
| 2013/0203031 A1 * | 8/2013 | Mckinnon | G09B 23/28 434/262 |
| 2013/0211531 A1 * | 8/2013 | Steines | A61F 2/3859 623/20.14 |
| 2014/0018813 A1 * | 1/2014 | Mckinnon | A61B 17/155 606/88 |
| 2014/0081659 A1 * | 3/2014 | Nawana | A61B 5/4833 705/3 |
| 2014/0135985 A1 * | 5/2014 | Coste-Maniere | A61B 34/30 700/255 |
| 2014/0244220 A1 * | 8/2014 | McKinnon | A61F 2/02 703/1 |
| 2016/0225192 A1 * | 8/2016 | Jones | G06F 3/012 |
| 2016/0228204 A1 * | 8/2016 | Quaid | A61B 34/10 |
| 2016/0278754 A1 * | 9/2016 | Todorov | A61B 17/025 |
| 2016/0377595 A1 * | 12/2016 | Demirjian | G01N 33/84 506/7 |
| 2017/0061375 A1 * | 3/2017 | Laster | G16H 50/30 |
| 2017/0245940 A1 * | 8/2017 | Piron | G06T 7/0014 |
| 2017/0258526 A1 * | 9/2017 | Lang | A61B 34/74 |
| 2017/0367766 A1 * | 12/2017 | Mahfouz | A61B 17/155 |
| 2018/0055577 A1 * | 3/2018 | Barral | A61B 34/20 |
| 2018/0055644 A1 * | 3/2018 | Mahfouz | A61F 2/34 |
| 2018/0071049 A1 * | 3/2018 | Nowatschin | A61B 1/00149 |
| 2018/0071050 A1 * | 3/2018 | Nowatschin | A61B 90/03 |
| 2018/0168740 A1 * | 6/2018 | Ryan | A61B 90/36 |
| 2018/0233222 A1 * | 8/2018 | Daley | G16H 50/50 |
| 2019/0000372 A1 * | 1/2019 | Gullotti | A61B 17/7086 |
| 2020/0205900 A1 * | 7/2020 | Buckland | G06K 9/627 |

* cited by examiner

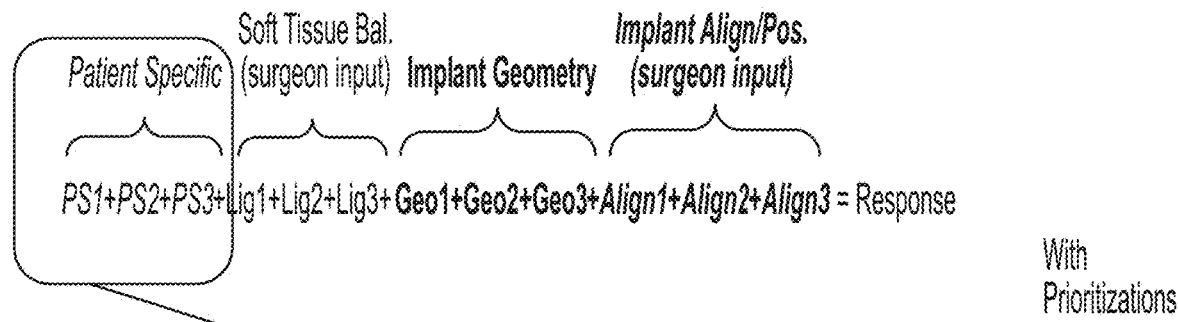
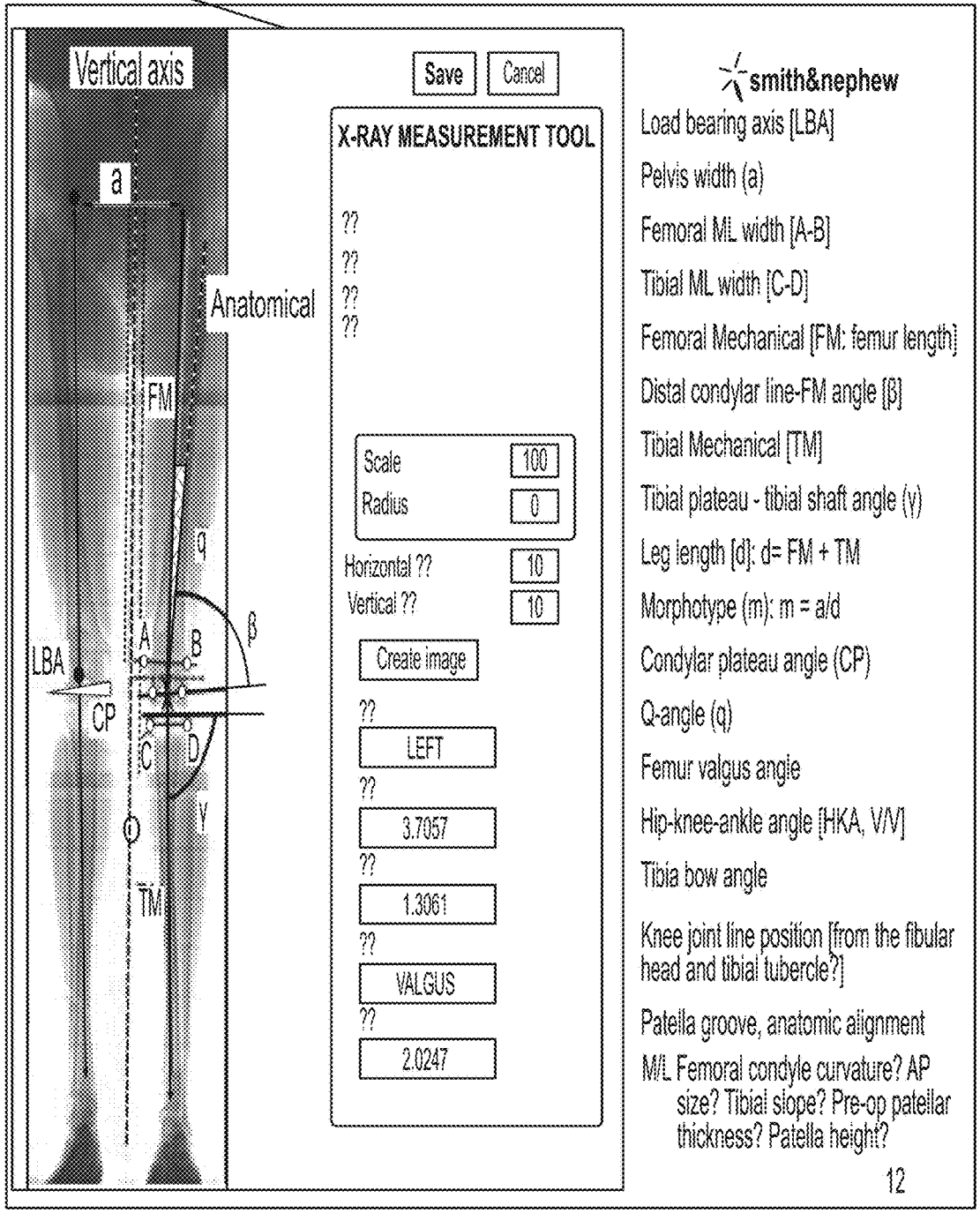
FIG. 5B

| | Factors | Ranking 1 | Ranking 2 | Ranking 3 | Ranking 4 | Ranking 5 | Ranking 6 | Total |
|---|---|---|---|---|---|---|---|---|
| 26 | Tibial tubercle location | 11 | 96 | 11 | 11 | 9 | 12 | 150 |
| 31 | Ligaments insertion points location/translation | 11 | 98 | 11 | 5 | 11 | 9 | 145 |
| 20 | Q-angle | 11 | 92.5 | 10 | 9 | 9 | 11 | 142.5 |
| 22 | Trochelor groove ML position | 10 | 94.5 | 10 | 6 | 11 | 11 | 142.5 |
| 33 | Patellar tendon attachment | 11 | 92.5 | 11 | 5 | 9 | 9 | 137.5 |
| 11 | Femoral posterior radius | 5 | 98 | 8 | 6 | 7 | 11 | 135 |
| 29 | Patellar alta baja | 10 | 88.5 | 10 | 5 | 11 | 10 | 134.5 |
| 10 | ML width Femoral | 9 | 88.5 | 10 | 7 | 9 | 10 | 133.5 |
| 28 | Patellar thickness | 11 | 98 | 8 | 4 | 7 | 4 | 132 |
| 7 | Full leg deformity | 6 | 90.5 | 10 | 7 | 11 | 7 | 131.5 |
| 8 | Tibial deformity | 5 | 90.5 | 10 | 6 | 11 | 7 | 129.5 |
| 30 | Patellar button S-I position | 6 | 94.5 | 9 | 4 | 9 | 6 | 128.5 |
| 24 | Height of the joint space | 10 | 77 | 10 | 7 | 12 | 12 | 128 |
| 34 | Patellar tendon orientation | 11 | 61.5 | 11 | 5 | 9 | 9 | 126.5 |
| 25 | Posterior tibial slope (3°) | 8 | 85 | 9 | 7 | 9 | 8 | 126 |
| 15 | Tibial ML width | 7 | 83.5 | 10 | 7 | 8 | 8 | 123.5 |
| 13 | Intercondylar notch | 10 | 76 | 8 | 7 | 12 | 7 | 120 |
| 14 | Tibial component size | 7 | 87 | 9 | 2 | 8 | 7 | 120 |
| 9 | Femoral component size | 6 | 86 | 8 | 1 | 6 | 11 | 118 |
| 23 | Trochlear groove orientation | 10 | 70 | 10 | 6 | 11 | 11 | 118 |
| 27 | Patella ML width | 9 | 83.5 | 7 | 5 | 7 | 5 | 116.5 |
| 32 | Ligaments insertion points orientation | 11 | 70 | 11 | 5 | 11 | 7 | 115 |
| 37 | Mechanical axis | 11 | 68 | 12 | 2 | 9 | 7 | 109 |
| 16 | Pelvis width | 5 | 61.5 | 9 | 1 | 6 | 5 | 107.5 |
| 12 | Femoral distal radius | 5 | 70 | 8 | 6 | 7 | 11 | 107 |
| 17 | Femur length | 3 | 79 | 48 | 5 | 8 | 4 | 107 |
| 18 | Tibia length | 3 | 79 | 8 | 5 | 7 | 4 | 106 |
| 6 | BMI (vertical hip load) | 3 | 75 | 6 | 5 | 10 | 5 | 104 |
| 4 | Weight | 4 | 72.5 | 4 | 6 | 11 | 5 | 102.5 |
| 19 | Leg Length | 3 | 79 | 7 | 1 | 7 | 4 | 101 |
| 38 | Anatomic axis | 5 | 72.5 | 8 | 1 | 8 | 6 | 100.5 |
| 35 | Muscles length | 3 | 66.5 | 7 | 5 | 6 | 6 | 93.5 |
| 2 | Gender | 4 | 64.5 | 7 | 5 | 7 | 3 | 90.5 |
| 5 | Height | 2 | 74 | 4 | 0 | 7 | 3 | 90 |
| 1 | Age | 4 | 64.5 | 4 | 5 | 6 | 4 | 87.5 |
| 36 | Muscles cross-sectional areas | 3 | 66.5 | 7 | 1 | 3 | 1 | 81.5 |
| 3 | Ethnicity | 3 | 62 | 3 | 4 | 4 | 3 | 79 |
| 21 | BMO | 2 | 63 | 0 | 4 | 0 | 0 | 69 |

FIG. 5B continued

1. Default
   1. Rely on atlas of landmarks based on bone geometry
2. Clinical (broad characterizations:
   1. Anterior Drawer,
   2. V/V stability
3. Intro-Op (if available)
   1. Anterior Drawer,
   2. V/V stability
   3. Tissue attachment estimates
   4. Tissue condition 1. Femoral S-I position (4mm superior to 2mm inferior)
2. Femoral A-P position (± 2mm)
3. Femoral V-V position (±4° from mechanical axis)
4. Femoral I-E position (±6° from A-P axis)
5. Tibial posterior slope (9° posterior slope to 3° anterior slope)
6. Tibial V-V position (±6° from mechanical axis)
7. Tibial I-E position (±6° from A-P axis)
8. Tibial depth determined by extension gap (4mm gap/2mm interference)

Soft Tissue Bal.    Implant Align/Pos.
Patient Specific (surgeon input) Implant Geometry (surgeon input)

PS1+PS2+PS3+ Lig1+Lig2+Lig3+ Geo1+Geo2+Geo3 +Align1+Align2+Align3 = Response

- 30 Deg Flexion
  - aMCL 30
  - pMCL 30
  - LCL 30
  - pLC 30
  - (ITB30)^2
  - ITB-P30
  - med Ret 30
  - rollback Med 30
  - rollback Lat 30
  - IE 30
  - VV 30
  - (pat shear ML 30 + 189.00)^2
  - (Quad Force 30)^2

- 60 Deg Flexion
  - aMCL 60
  - pMCL 60
  - LCL 60
  - pLC 60
  - (ITB30)^2
  - ITB-P30
  - med Ret 60
  - rollback Med 60
  - rollback Lat 60
  - IE 60
  - VV 60
  - (pat shear ML 60 + 189.00)^2
  - (Quad Force 60)^2

- 90 Deg Flexion
  - aMCL 90
  - pMCL 90
  - LCL 90
  - pLC 90
  - (ITB30)^2
  - ITB-P30
  - med Ret 90
  - rollback Med 90
  - rollback Lat 90
  - IE 90
  - VV 90
  - (pat shear ML 90 + 189.00)^2
  - (Quad Force 90)^2

- 120 Deg Flexion
  - aMCL 120
  - pMCL 120
  - LCL 120
  - pLC 120
  - (ITB30)^2
  - ITB-P30
  - med Ret 120
  - rollback Med 120
  - rollback Lat 120
  - IE 120
  - VV 120
  - (pat shear ML 120 + 189.00)^2
  - (Quad Force 120)^2

FIG. 5F

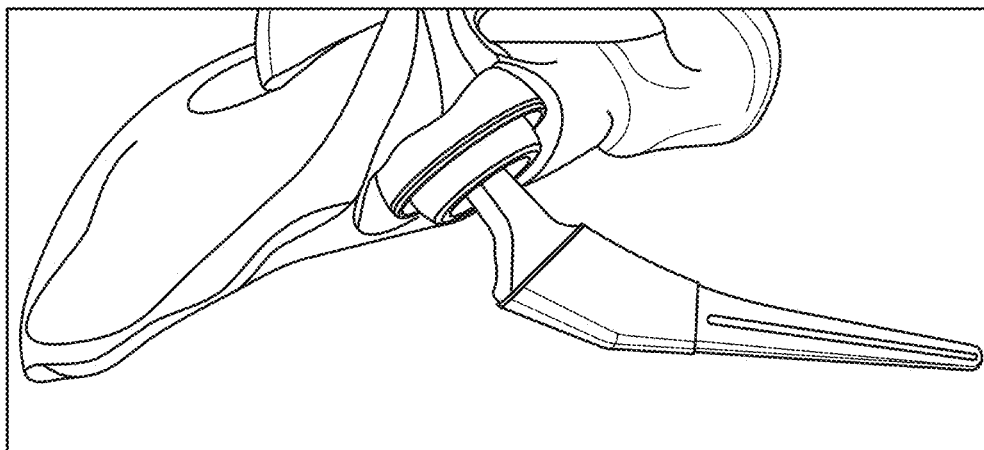
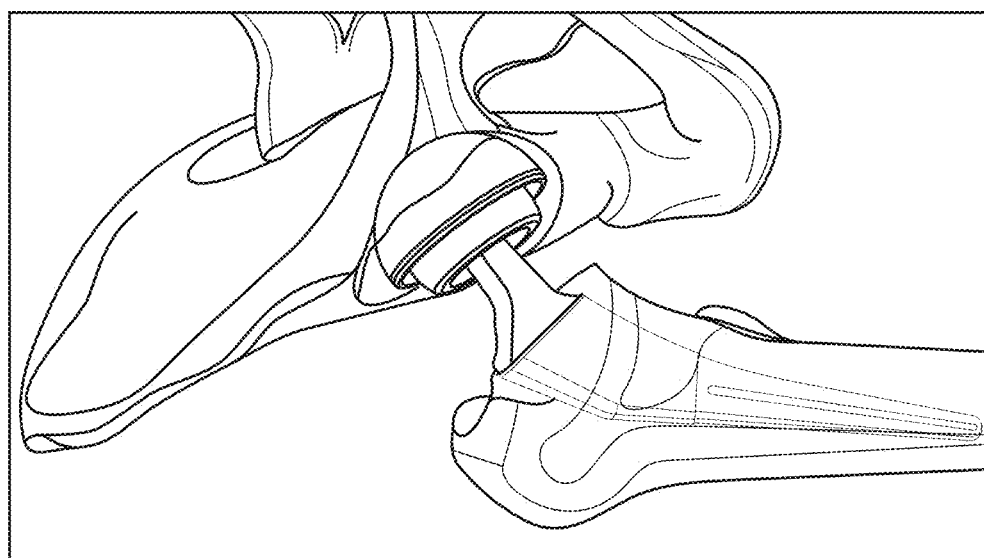
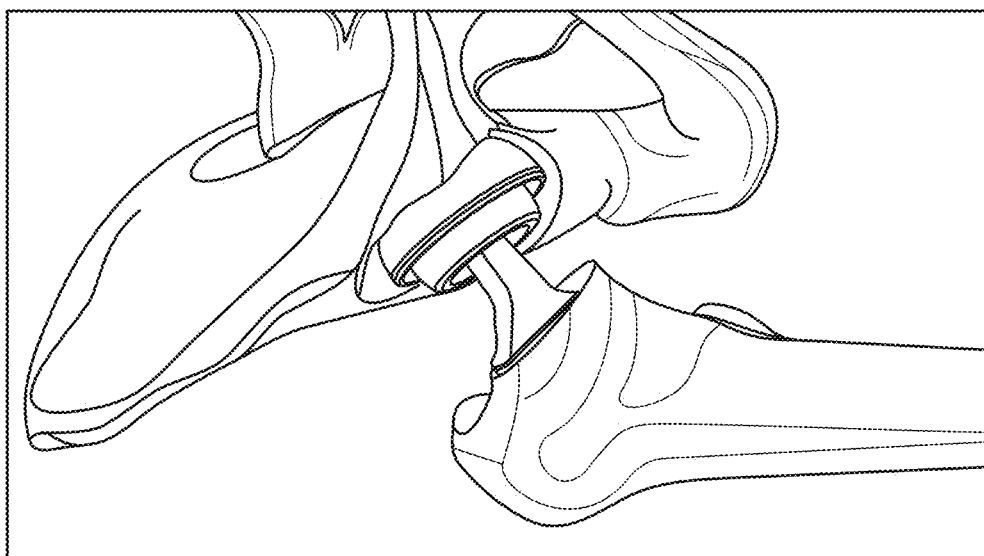
FIG. 12D

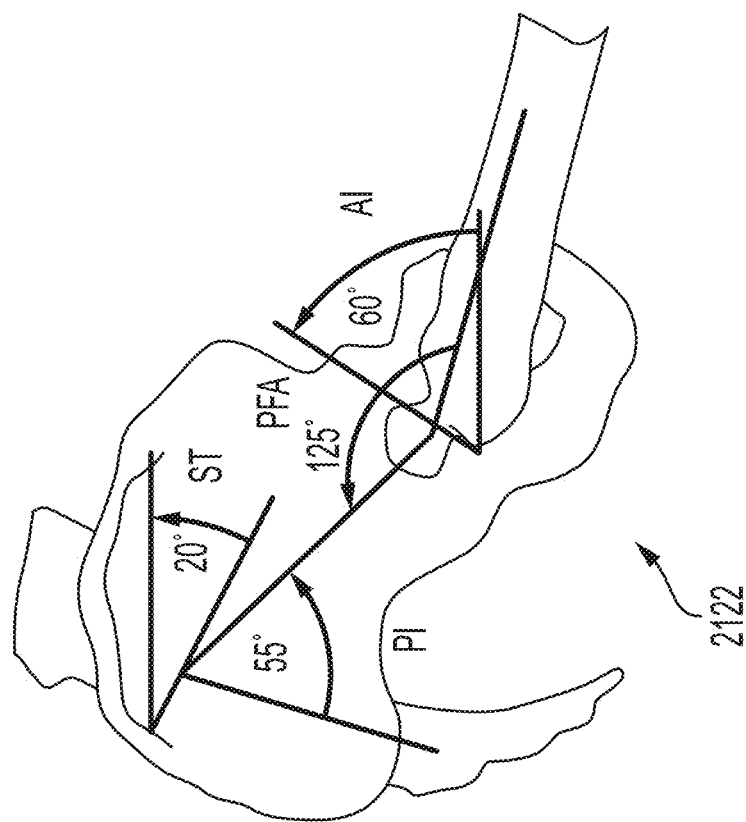
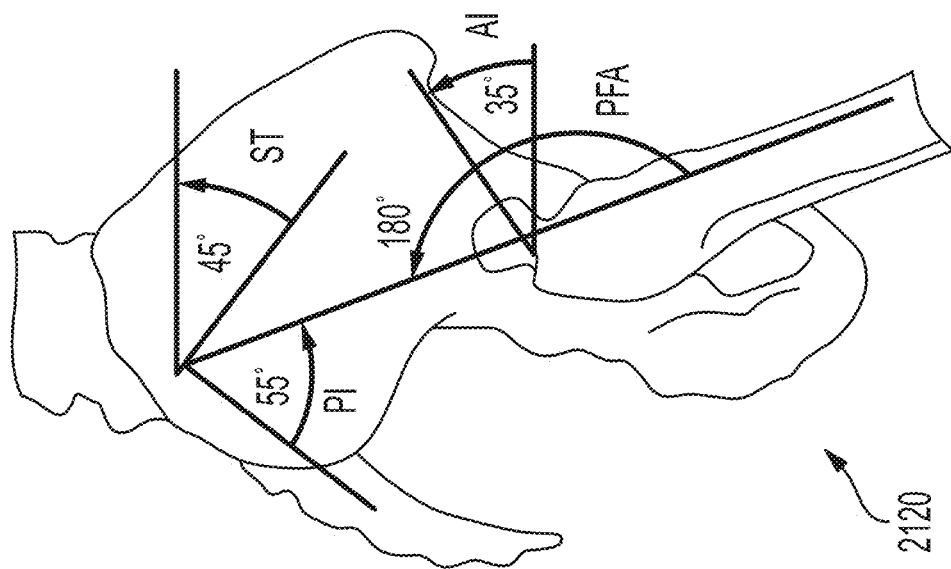
FIG. 22

| Angle | Standing | Category | Seated | Category |
|---|---|---|---|---|
| Sacral Tilt (ST) | 44 | Normal (20-50) | 39 | Abnormal (11-29) |
| Pelvic Incidence (PI) | 73 | Abnormal (42-64) | 73 | Abnormal (42-64) |
| Pelvic Femoral Angle (PFA) | 201 | Abnormal (170-190) | 122 | Normal (120-144) |
| Anti-Inclination (AI) | 52 | Abnormal (25-45) | 57 | Normal (41-63) |
| Delta ST | Delta AI | SpinoPelvic Mobility | SpinoPelvic Balance | |
| 5 | 5 | Normal | Stuck Standing | |

FIG. 25

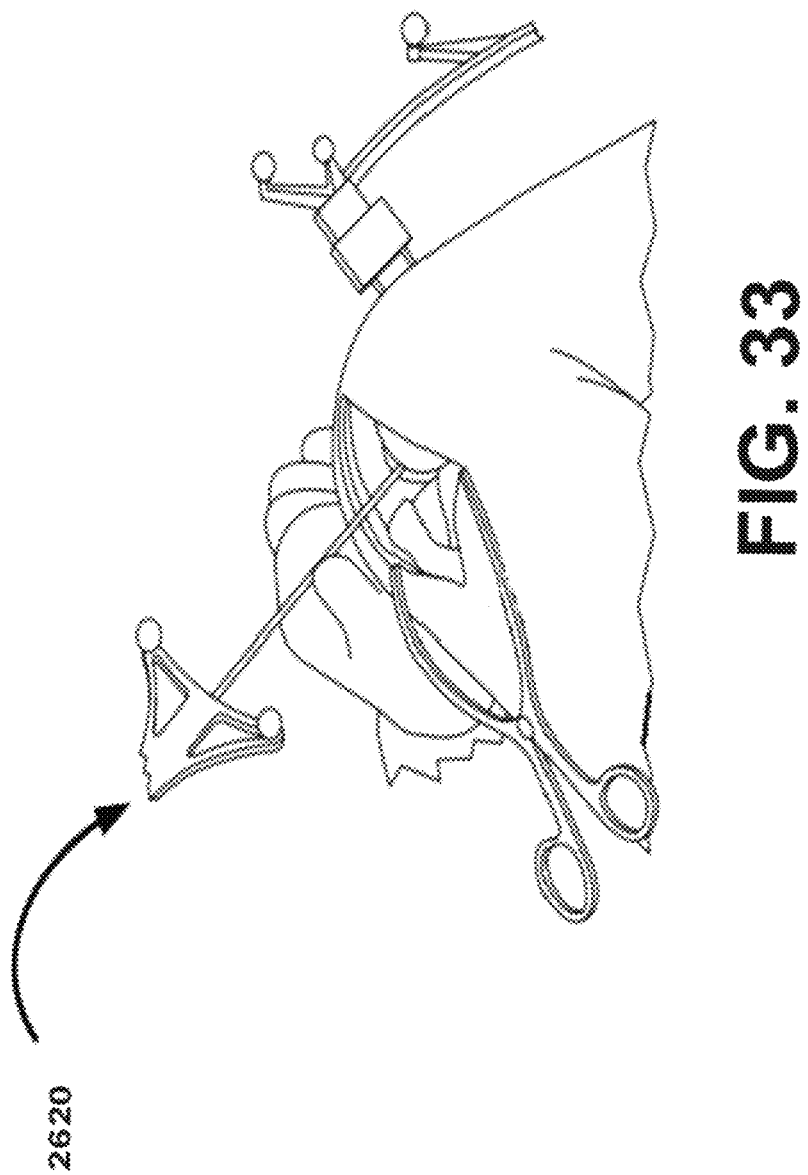

COMPUTER-ASSISTED ARTHROPLASTY SYSTEM

RELATED APPLICATIONS

This application is a continuation of U.S. patent application Ser. No. 16/975,192, filed Aug. 24, 2020, which is a U.S. national stage filing under 35 U.S.C. § 371 of International PCT Application No. PCT/US2020/016605, filed Feb. 4, 2020, which claims the benefit of priority to U.S. Provisional Patent Application No. 62/801,245, filed Feb. 5, 2019, U.S. Provisional Patent Application Nos. 62/801,257, 62/801,257 (filed Feb. 5, 2019, U.S. Provisional Patent Application No. 62/864,663, filed Jun. 21, 2019, U.S. Provisional Patent Application Nos. 62/885,673, filed Aug. 12, 2019, and U.S. Provisional Patent Application No. 62/939,946, filed Nov. 25, 2019, which are incorporated herein by reference in their entireties.

TECHNOLOGY FIELD

The present disclosure relates generally to methods, systems, and apparatuses related to a computer-assisted surgical system that includes various hardware and software components that work together to enhance surgical workflows. The disclosed techniques may be applied to, for example, shoulder, hip, and knee arthroplasties.

BACKGROUND

Common types of arthroplasty, such as partial knee arthroplasty (PKA), total knee arthroplasty (TKA), or total hip arthroplasty (THA) utilize a surgical plan to define one or more predefined cutting planes to resect bone to accommodate the implantation orientation and position (pose) of a knee or hip implant/replacement joint. By resecting bone in accordance with the surgical plan, patient bone can be shaped to a normalized, planned manner to accept a joint replacement implant with a given pose. The exact orientation and position of the joint replacement implant is typically planned according to a surgical plan developed before commencing surgery. However, a surgeon will often modify the plan in the surgical theater based on information gathered about the patient's joint. Various systems exist to improve the surgical plan and workflow, yet there remains room for improvement.

SUMMARY

Embodiments of the present invention address and overcome one or more of the above shortcomings and drawbacks, by providing methods, systems, and apparatuses related to activity-optimized cutting guides for knee arthroplasty.

According to some embodiments, a computer-implemented method for creating an activity-optimized cutting guides for surgical procedures includes receiving one or more pre-operative images depicting one or more anatomical joints of a patient, and creating a three-dimensional anatomical model of the one or more anatomical joints based on the one or more pre-operative images. One or more patient-specific anatomical measurements are determined based on the three-dimensional anatomical model. A statistical model of joint performance is applied to the patient-specific anatomical measurements to identify one or more cut angles for performing a surgical procedure. A patient-specific cutting guide is created that comprises one or more apertures positioned based on the one or more cut angles. For example, in some embodiments, creating the patient-specific cutting guide includes modifying a computer model of a cutting guide blank to include the one or more apertures. The computer model of the modified cutting guide blank is provided to a device configured to manufacture the patient-specific cutting guide based on the computer model.

Various enhancements, refinements, and other modifications may be made to the aforementioned method in different embodiments. For example, in some embodiments, the one or more patient-specific anatomical measurements comprise distal and anterior condyle radii measurements. In other embodiments, identifying one or more cut angles comprises identifying one or more cut angles that provide balanced condylar gaps throughout a range of motion associated with one or more physical activities. In some embodiments, the statistical model of joint performance comprises a plurality of transfer functions. In some embodiments, the statistical model of joint performance is applied to the one or more patient-specific anatomical measurements by applying a Monte Carlo method to iteratively evaluate a plurality of possible cut angles. Each iteration of the Monte Carlo method applies the one or more transfer functions with a distinct set of parameters. In some embodiments, the statistical model of joint performance is a machine learning model.

In some embodiments, the aforementioned method (with or without the modifications discussed above) further includes generating the statistical model by first selecting a plurality of implants. Each implant is defined by a distinct set of implantation features. The implantation features may include, for example, one or more of an implant position, an implant orientation, and an implant type. A database of simulation results is populated by simulating a motion of a plurality of joint geometries while performing one or more physical activities and an expected stress on the plurality of implants resulting from the motion. The statistical model of joint performance is then generated based on the simulation results.

According to another aspect of the present invention, an article of manufacture for creating an activity-optimized cutting guide for a surgical procedure comprises a non-transitory computer-readable storage medium storing computer-executable instructions for performing the method discussed above (with or without the modifications discussed above).

According to other embodiments, a system for creating an activity-optimized cutting guide for a surgical procedure comprises a database and a computing system comprising one or more processors. The database includes one or more pre-operative images of one or more anatomical joints of a patient. The computing system creates a three-dimensional anatomical model of the one or more anatomical joints based on the one or more pre-operative images, and determines one or more patient-specific anatomical measurements based on the three-dimensional anatomical model. These patient-specific anatomical measurements may include, for example, distal and anterior condyle radii measurements. The computing system further applies a statistical model of joint performance to the one or more patient-specific anatomical measurements, and identifies one or more cut angles for performing a surgical procedure based on the application of the statistical model. For example, the cut angles could be identified such they provide balanced condylar gaps throughout a range of motion associated with one or more physical activities. The computing system can then create a patient-specific cutting guide comprising one or more apertures positioned based on the one or more cut angles. In some embodiments, the system further includes a manufacturing device configured to manufacture the patient-specific cutting guide design. This manufacturing device may be, for example, a 3D printer.

Additional features and advantages of the invention will be made apparent from the following detailed description of illustrative embodiments that proceeds with reference to the accompanying drawings.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 5A-F provide an overview of a knee predictor equation, in accordance with some embodiments;

FIGS. 7A-1, 7A-2, 7A-3, and 7B provide an overview of an exemplary user interface, for use with some embodiments;

FIGS. 11C-1, 11C-2, and 11C-3 provide an overview of an exemplary user interface for implant placement, for use with some embodiments;

FIG. 12D provides an exemplary visualization of a hip implant, for use with some embodiments;

FIG. 22 is an anatomical diagram of hip geometry that may be used in some embodiments;

FIG. 25 is a table depicting exemplary values for hip geometry, for use with some embodiments;

FIG. 33 is a view of a surgical scene using some of the techniques disclosed herein.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The disclosed devices are particularly well adapted for surgical procedures that utilize surgical navigation systems, such as the NAVIO® surgical navigation system. Such procedures can include knee replacement and/or revision surgery, as well as shoulder and hip surgeries. NAVIO is a registered trademark of BLUE BELT TECHNOLOGIES, INC. of Pittsburgh, Pa., which is a subsidiary of SMITH & NEPHEW, INC. of Memphis, Tenn.

Definitions

For the purposes of this disclosure, the term "implant" is used to refer to a prosthetic device or structure manufactured to replace or enhance a biological structure. For example, in a total hip replacement procedure a prosthetic acetabular cup (implant) is used to replace or enhance a patient's worn or damaged acetabulum. While the term "implant" is generally considered to denote a man-made structure (as contrasted with a transplant), for the purposes of this specification an implant can include a biological tissue or material transplanted to replace or enhance a biological structure.

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Although much of this disclosure refers to surgeons or other medical professionals by specific job title or role, nothing in this disclosure is intended to be limited to a specific job title or function. Surgeons or medical professionals can include any doctor, nurse, medical professional, or technician. Any of these terms or job titles can be used interchangeably with the user of the systems disclosed herein unless otherwise explicitly demarcated. For example, a reference to a surgeon could also apply, in some embodiments to a technician or nurse.

CASS Ecosystem Overview

Figure 1:
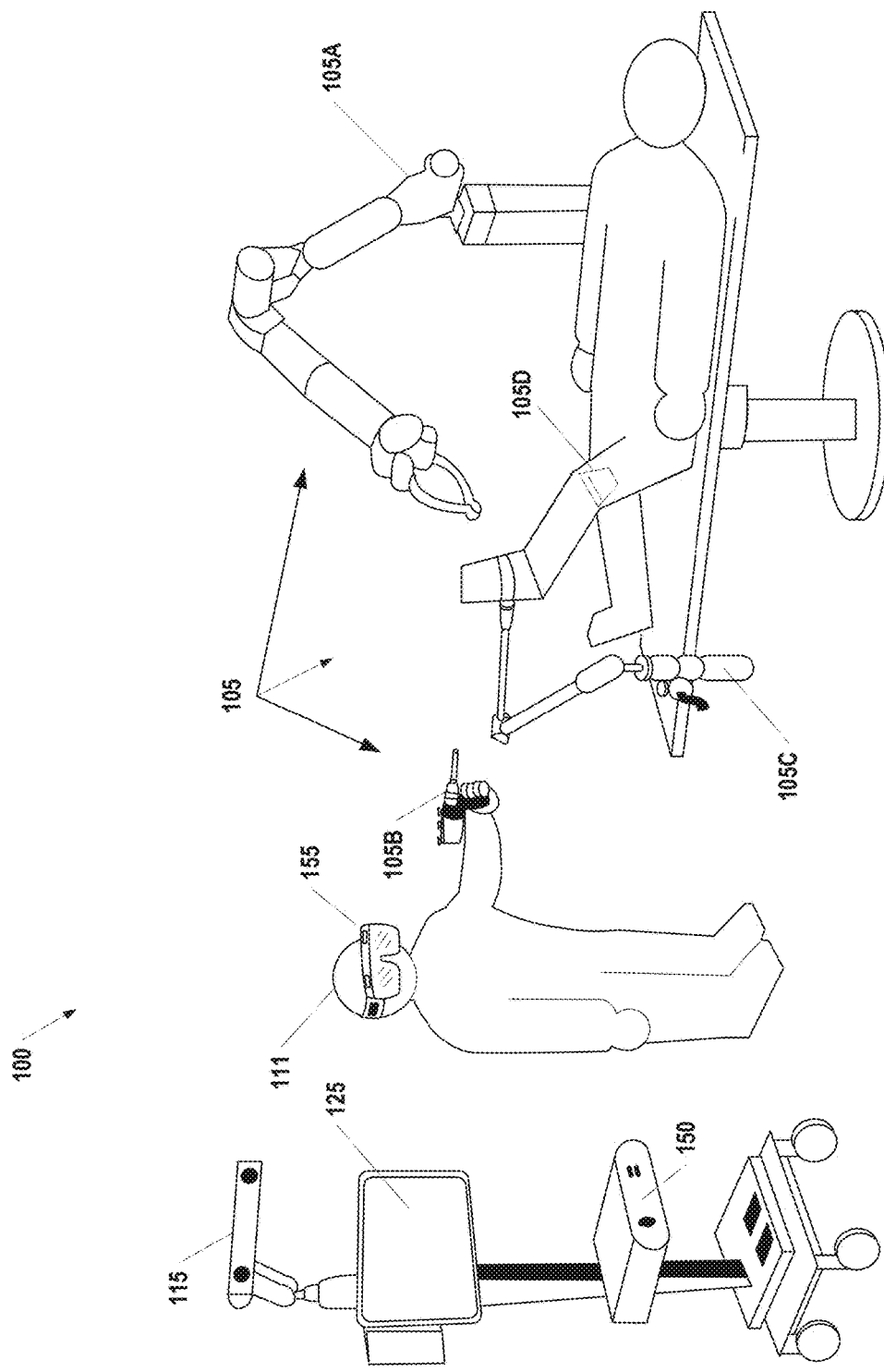
FIG. 1 illustrates an exemplary computer assisted surgical system for use with some embodiments.

FIG. 1 provides an illustration of an example computer-assisted surgical system (CASS) 100, according to some embodiments. As described in further detail in the sections that follow, the CASS uses computers, robotics, and imaging technology to aid surgeons in performing orthopedic surgery procedures such as total knee arthroplasty (TKA) or total hip arthroplasty (THA). For example, surgical navigation systems can aid surgeons in locating patient anatomical structures, guiding surgical instruments, and implanting medical devices with a high degree of accuracy. Surgical navigation systems such as the CASS 100 often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

An Effector Platform 105 positions surgical tools relative to a patient during surgery. The exact components of the Effector Platform 105 will vary, depending on the embodiment employed. For example, for a knee surgery, the Effector Platform 105 may include an End Effector 105B that holds surgical tools or instruments during their use. The End Effector 105B may be a handheld device or instrument used by the surgeon (e.g., a NAVIO® hand piece or a cutting guide or jig) or, alternatively, the End Effector 105B can include a device or instrument held or positioned by a Robotic Arm 105A. While one Robotic Arm 105A is illustrated in FIG. 1, in some embodiments there may be multiple devices. As examples, there may be one Robotic Arm 105A on each side of an operating table or two devices on one side of the table. The Robotic Arm 105A may be mounted directly to the table, be located next to the table on a floor platform (not shown), mounted on a floor-to-ceiling pole, or mounted on a wall or ceiling of an operating room. The floor platform may be fixed or moveable. In one particular embodiment, the robotic arm 105A is mounted on a floor-to-ceiling pole located between the patient's legs or feet. In some embodiments, the End Effector 105B may include a suture holder or a stapler to assist in closing wounds. Further, in the case of two robotic arms 105A, the surgical computer 150 can drive the robotic arms 105A to work together to suture the wound at closure. Alternatively, the surgical computer 150 can drive one or more robotic arms 105A to staple the wound at closure.

The Effector Platform 105 can include a Limb Positioner 105C for positioning the patient's limbs during surgery. One example of a Limb Positioner 105C is the SMITH AND NEPHEW SPIDER2™ system. The Limb Positioner 105C may be operated manually by the surgeon or alternatively change limb positions based on instructions received from the Surgical Computer 150 (described below). While one Limb Positioner 105C is illustrated in FIG. 1, in some embodiments there may be multiple devices. As examples, there may be one Limb Positioner 105C on each side of the operating table or two devices on one side of the table. The Limb Positioner 105C may be mounted directly to the table, be located next to the table on a floor platform (not shown), mounted on a pole, or mounted on a wall or ceiling of an operating room. In some embodiments, the Limb Positioner 105C can be used in non-conventional ways, such as a retractor or specific bone holder. The Limb Positioner 105C may include, as examples, an ankle boot, a soft tissue clamp, a bone clamp, or a soft-tissue retractor spoon, such as a hooked, curved, or angled blade. In some embodiments, the Limb Positioner 105C may include a suture holder to assist in closing wounds.

The Effector Platform 105 may include tools, such as a screwdriver, light or laser, to indicate an axis or plane, bubble level, pin driver, pin puller, plane checker, pointer, finger, or some combination thereof.

Resection Equipment 110 (not shown in FIG. 1) performs bone or tissue resection using, for example, mechanical, ultrasonic, or laser techniques. Examples of Resection Equipment 110 include drilling devices, burring devices, oscillatory sawing devices, vibratory impaction devices, reamers, ultrasonic bone cutting devices, radio frequency ablation devices, reciprocating devices (such as a rasp or broach), and laser ablation systems. In some embodiments, the Resection Equipment 110 is held and operated by the surgeon during surgery. In other embodiments, the Effector Platform 105 may be used to hold the Resection Equipment 110 during use.

The Effector Platform 105 can also include a cutting guide or jig 105D that is used to guide saws or drills used to resect tissue during surgery. Such cutting guides 105D can be formed integrally as part of the Effector Platform 105 or Robotic Arm 105A, or cutting guides can be separate structures that can be matingly and/or removably attached to the Effector Platform 105 or Robotic Arm 105A. The Effector Platform 105 or Robotic Arm 105A can be controlled by the CASS 100 to position a cutting guide or jig 105D adjacent to the patient's anatomy in accordance with a pre-operatively or intraoperatively developed surgical plan such that the cutting guide or jig will produce a precise bone cut in accordance with the surgical plan.

The Tracking System 115 uses one or more sensors to collect real-time position data that locates the patient's anatomy and surgical instruments. For example, for TKA procedures, the Tracking System 115 may provide a location and orientation of the End Effector 105B during the procedure. In addition to positional data, data from the Tracking System 115 can also be used to infer velocity/acceleration of anatomy/instrumentation, which can be used for tool control. In some embodiments, the Tracking System 115 may use a tracker array attached to the End Effector 105B to determine the location and orientation of the End Effector 105B. The position of the End Effector 105B may be inferred based on the position and orientation of the Tracking System 115 and a known relationship in three-dimensional space between the Tracking System 115 and the End Effector 105B. Various types of tracking systems may be used in various embodiments of the present invention including, without limitation, Infrared (IR) tracking systems, electromagnetic (EM) tracking systems, video or image based tracking systems, and ultrasound registration and tracking systems. Using the data provided by the tracking system 115, the surgical computer 150 can detect objects and prevent collision. For example, the surgical computer 150 can prevent the Robotic Arm 105A from colliding with soft tissue.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, tri-scopic, quad-scopic, etc., imaging. In addition to the camera array, which in some embodiments is affixed to a cart, additional cameras can be placed throughout the surgical theatre. For example, handheld tools or headsets worn by operators/surgeons can include imaging capability that communicates images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in quick response (QR) codes or barcodes. This can be helpful in identifying specific objects not manually registered with the system. In some embodiments, the camera may be mounted on the Robotic Arm 105A.

In some embodiments, specific objects can be manually registered by a surgeon with the system preoperatively or intraoperatively. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one or two dimensional optical codes (barcode, QR code, etc.) can be affixed to objects in the theater to provide passive identification that can occur based on image analysis. If these codes are placed asymmetrically on an object, they can also be used to determine an orientation of an object by comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality headsets can be worn by surgeons and other staff to provide additional camera angles and tracking capabilities.

In addition to optical tracking, certain features of objects can be tracked by registering physical properties of the object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

The registration process that registers the CASS 100 to the relevant anatomy of the patient can also involve the use of anatomical landmarks, such as landmarks on a bone or cartilage. For example, the CASS 100 can include a 3D model of the relevant bone or joint and the surgeon can intraoperatively collect data regarding the location of bony landmarks on the patient's bone using a probe that is connected to the CASS. Bony landmarks can include, for example, the medial malleolus and lateral malleolus, the ends of the proximal femur and distal tibia, and the center of the hip joint. The CASS 100 can compare and register the location data of bony landmarks collected by the surgeon with the probe with the location data of the same landmarks in the 3D model. Alternatively, the CASS 100 can construct a 3D model of the bone or joint without pre-operative image data by using location data of bony landmarks and the bone surface that are collected by the surgeon using a CASS probe or other means. The registration process can also include determining various axes of a joint. For example, for a TKA the surgeon can use the CASS 100 to determine the anatomical and mechanical axes of the femur and tibia. The surgeon and the CASS 100 can identify the center of the hip joint by moving the patient's leg in a spiral direction (i.e., circumduction) so the CASS can determine where the center of the hip joint is located.

A Tissue Navigation System 120 (not shown in FIG. 1) provides the surgeon with intraoperative, real-time visualization for the patient's bone, cartilage, muscle, nervous, and/or vascular tissues surrounding the surgical area. Examples of systems that may be employed for tissue navigation include fluorescent imaging systems and ultrasound systems.

The Display 125 provides graphical user interfaces (GUIs) that display images collected by the Tissue Navigation System 120 as well other information relevant to the surgery. For example, in one embodiment, the Display 125 overlays image information collected from various modalities (e.g., CT, MRI, X-ray, fluorescent, ultrasound, etc.) collected pre-operatively or intra-operatively to give the surgeon various views of the patient's anatomy as well as real-time conditions. The Display 125 may include, for example, one or more computer monitors. As an alternative or supplement to the Display 125, one or more members of the surgical staff may wear an Augmented Reality (AR) Head Mounted Device (HMD). For example, in FIG. 1 the Surgeon 111 is wearing an AR HMD 155 that may, for example, overlay pre-operative image data on the patient or provide surgical planning suggestions. Various example uses of the AR HMD 155 in surgical procedures are detailed in the sections that follow.

Surgical Computer 150 provides control instructions to various components of the CASS 100, collects data from those components, and provides general processing for various data needed during surgery. In some embodiments, the Surgical Computer 150 is a general purpose computer. In other embodiments, the Surgical Computer 150 may be a parallel computing platform that uses multiple central processing units (CPUs) or graphics processing units (GPU) to perform processing. In some embodiments, the Surgical Computer 150 is connected to a remote server over one or more computer networks (e.g., the Internet). The remote server can be used, for example, for storage of data or execution of computationally intensive processing tasks.

Various techniques generally known in the art can be used for connecting the Surgical Computer 150 to the other components of the CASS 100. Moreover, the computers can connect to the Surgical Computer 150 using a mix of technologies. For example, the End Effector 105B may connect to the Surgical Computer 150 over a wired (i.e., serial) connection. The Tracking System 115, Tissue Navigation System 120, and Display 125 can similarly be connected to the Surgical Computer 150 using wired connections. Alternatively, the Tracking System 115, Tissue Navigation System 120, and Display 125 may connect to the Surgical Computer 150 using wireless technologies such as, without limitation, Wi-Fi, Bluetooth, Near Field Communication (NFC), or ZigBee.

Powered Impaction and Acetabular Reamer Devices

Part of the flexibility of the CASS design described above with respect to FIG. 1 is that additional or alternative devices can be added to the CASS 100 as necessary to support particular surgical procedures. For example, in the context of hip surgeries, the CASS 100 may include a powered impaction device. Impaction devices are designed to repeatedly apply an impaction force that the surgeon can use to perform activities such as implant alignment. For example, within a total hip arthroplasty (THA), a surgeon will often insert a prosthetic acetabular cup into the implant host's acetabulum using an impaction device. Although impaction devices can be manual in nature (e.g., operated by the surgeon striking an impactor with a mallet), powered impaction devices are generally easier and quicker to use in the surgical setting. Powered impaction devices may be powered, for example, using a battery attached to the device. Various attachment pieces may be connected to the powered impaction device to allow the impaction force to be directed in various ways as needed during surgery. Also in the context of hip surgeries, the CASS 100 may include a powered, robotically controlled end effector to ream the acetabulum to accommodate an acetabular cup implant.

In a robotically-assisted THA, the patient's anatomy can be registered to the CASS 100 using CT or other image data, the identification of anatomical landmarks, tracker arrays attached to the patient's bones, and one or more cameras. Tracker arrays can be mounted on the iliac crest using clamps and/or bone pins and such trackers can be mounted externally through the skin or internally (either posterolaterally or anterolaterally) through the incision made to perform the THA. For a THA, the CASS 100 can utilize one or more femoral cortical screws inserted into the proximal femur as checkpoints to aid in the registration process. The CASS 100 can also utilize one or more checkpoint screws inserted into the pelvis as additional checkpoints to aid in the registration process. Femoral tracker arrays can be secured to or mounted in the femoral cortical screws. The CASS 100 can employ steps where the registration is verified using a probe that the surgeon precisely places on key areas of the proximal femur and pelvis identified for the surgeon on the display 125. Trackers can be located on the robotic arm 105A or end effector 105B to register the arm and/or end effector to the CASS 100. The verification step can also utilize proximal and distal femoral checkpoints. The CASS 100 can utilize color prompts or other prompts to inform the surgeon that the registration process for the relevant bones and the robotic arm 105A or end effector 105B has been verified to a certain degree of accuracy (e.g., within 1 mm).

For a THA, the CASS 100 can include a broach tracking option using femoral arrays to allow the surgeon to intraoperatively capture the broach position and orientation and calculate hip length and offset values for the patient. Based on information provided about the patient's hip joint and the planned implant position and orientation after broach tracking is completed, the surgeon can make modifications or adjustments to the surgical plan.

For a robotically-assisted THA, the CASS 100 can include one or more powered reamers connected or attached to a robotic arm 105A or end effector 105B that prepares the pelvic bone to receive an acetabular implant according to a surgical plan. The robotic arm 105A and/or end effector 105B can inform the surgeon and/or control the power of the reamer to ensure that the acetabulum is being resected (reamed) in accordance with the surgical plan. For example, if the surgeon attempts to resect bone outside of the boundary of the bone to be resected in accordance with the surgical plan, the CASS 100 can power off the reamer or instruct the surgeon to power off the reamer. The CASS 100 can provide the surgeon with an option to turn off or disengage the robotic control of the reamer. The display 125 can depict the progress of the bone being resected (reamed) as compared to the surgical plan using different colors. The surgeon can view the display of the bone being resected (reamed) to guide the reamer to complete the reaming in accordance with the surgical plan. The CASS 100 can provide visual or audible prompts to the surgeon to warn the surgeon that resections are being made that are not in accordance with the surgical plan.

Following reaming, the CASS 100 can employ a manual or powered impactor that is attached or connected to the robotic arm 105A or end effector 105B to impact trial implants and final implants into the acetabulum. The robotic arm 105A and/or end effector 105B can be used to guide the impactor to impact the trial and final implants into the acetabulum in accordance with the surgical plan. The CASS 100 can cause the position and orientation of the trial and final implants vis-à-vis the bone to be displayed to inform the surgeon as to how the trial and final implant's orientation and position compare to the surgical plan, and the display 125 can show the implant's position and orientation as the surgeon manipulates the leg and hip. The CASS 100 can provide the surgeon with the option of re-planning and re-doing the reaming and implant impaction by preparing a new surgical plan if the surgeon is not satisfied with the original implant position and orientation.

Preoperatively, the CASS 100 can develop a proposed surgical plan based on a three dimensional model of the hip joint and other information specific to the patient, such as the mechanical and anatomical axes of the leg bones, the epicondylar axis, the femoral neck axis, the dimensions (e.g., length) of the femur and hip, the midline axis of the hip joint, the ASIS axis of the hip joint, and the location of anatomical landmarks such as the lesser trochanter landmarks, the distal landmark, and the center of rotation of the hip joint. The CASS-developed surgical plan can provide a recommended optimal implant size and implant position and orientation based on the three dimensional model of the hip joint and other information specific to the patient. The CASS-developed surgical plan can include proposed details on offset values, inclination and anteversion values, center of rotation, cup size, medialization values, superior-inferior fit values, femoral stem sizing and length.

For a THA, the CASS-developed surgical plan can be viewed preoperatively and intraoperatively, and the surgeon can modify CASS-developed surgical plan preoperatively or intraoperatively. The CASS-developed surgical plan can display the planned resection to the hip joint and superimpose the planned implants onto the hip joint based on the planned resections. The CASS 100 can provide the surgeon with options for different surgical workflows that will be displayed to the surgeon based on a surgeon's preference. For example, the surgeon can choose from different workflows based on the number and types of anatomical landmarks that are checked and captured and/or the location and number of tracker arrays used in the registration process.

According to some embodiments, a powered impaction device used with the CASS 100 may operate with a variety of different settings. In some embodiments, the surgeon adjusts settings through a manual switch or other physical mechanism on the powered impaction device. In other embodiments, a digital interface may be used that allows setting entry, for example, via a touchscreen on the powered impaction device. Such a digital interface may allow the available settings to vary based, for example, on the type of attachment piece connected to the power attachment device. In some embodiments, rather than adjusting the settings on the powered impaction device itself, the settings can be changed through communication with a robot or other computer system within the CASS 100. Such connections may be established using, for example, a Bluetooth or Wi-Fi networking module on the powered impaction device. In another embodiment, the impaction device and end pieces may contain features that allow the impaction device to be aware of what end piece (cup impactor, broach handle, etc.) is attached with no action required by the surgeon, and adjust the settings accordingly. This may be achieved, for example, through a QR code, barcode, RFID tag, or other method.

Examples of the settings that may be used include cup impaction settings (e.g., single direction, specified frequency range, specified force and/or energy range); broach impaction settings (e.g., dual direction/oscillating at a specified frequency range, specified force and/or energy range); femoral head impaction settings (e.g., single direction/single blow at a specified force or energy); and stem impaction settings (e.g., single direction at specified frequency with a specified force or energy). Additionally, in some embodiments, the powered impaction device includes settings related to acetabular liner impaction (e.g., single direction/single blow at a specified force or energy). There may be a plurality of settings for each type of liner such as poly, ceramic, oxinium, or other materials. Furthermore, the powered impaction device may offer settings for different bone quality based on preoperative testing/imaging/knowledge and/or intraoperative assessment by the surgeon. In some embodiments, the powered impactor device may have a dual function. For example, the powered impactor device not only could provide reciprocating motion to provide an impact force, but also could provide reciprocating motion for a broach or rasp.

In some embodiments, the powered impaction device includes feedback sensors that gather data during instrument use, and send data to a computing device such as a controller within the device or the Surgical Computer 150. This computing device can then record the data for later analysis and use. Examples of the data that may be collected include, without limitation, sound waves, the predetermined resonance frequency of each instrument, reaction force or rebound energy from patient bone, location of the device with respect to imaging (e.g., fluoro, CT, ultrasound, MRI, etc.) registered bony anatomy, and/or external strain gauges on bones.

Once the data is collected, the computing device may execute one or more algorithms in real-time or near real-time to aid the surgeon in performing the surgical procedure. For example, in some embodiments, the computing device uses the collected data to derive information such as the proper final broach size (femur); when the stem is fully seated (femur side); or when the cup is seated (depth and/or orientation) for a THA. Once the information is known, it may be displayed for the surgeon's review, or it may be used to activate haptics or other feedback mechanisms to guide the surgical procedure.

Additionally, the data derived from the aforementioned algorithms may be used to drive operation of the device. For example, during insertion of a prosthetic acetabular cup with a powered impaction device, the device may automatically extend an impaction head (e.g., an end effector) moving the implant into the proper location, or turn the power off to the device once the implant is fully seated. In one embodiment, the derived information may be used to automatically adjust settings for quality of bone where the powered impaction device should use less power to mitigate femoral/acetabular/pelvic fracture or damage to surrounding tissues.

Robotic Arm

In some embodiments, the CASS 100 includes a robotic arm 105A that serves as an interface to stabilize and hold a variety of instruments used during the surgical procedure. For example, in the context of a hip surgery, these instruments may include, without limitation, retractors, a sagittal or reciprocating saw, the reamer handle, the cup impactor, the broach handle, and the stem inserter. The robotic arm 105A may have multiple degrees of freedom (like a Spider device), and have the ability to be locked in place (e.g., by a press of a button, voice activation, a surgeon removing a hand from the robotic arm, or other method).

In some embodiments, movement of the robotic arm 105A may be effectuated by use of a control panel built into the robotic arm system. For example, a display screen may include one or more input sources, such as physical buttons or a user interface having one or more icons, that direct movement of the robotic arm 105A. The surgeon or other healthcare professional may engage with the one or more input sources to position the robotic arm 105A when performing a surgical procedure.

A tool or an end effector 105B may be attached or integrated into a robotic arm 105A which may include, without limitation, a burring device, a scalpel, a cutting device, a retractor, a joint tensioning device, or the like. In embodiments in which an end effector 105B is used, the end effector 105B may be positioned at the end of the robotic arm 105A such that any motor control operations are performed within the robotic arm system. In embodiments in which a tool is used, the tool may be secured at a distal end of the robotic arm 105A, but motor control operation may reside within the tool itself.

The robotic arm 105A may be motorized internally to both stabilize the robotic arm, thereby preventing it from falling and hitting the patient, surgical table, surgical staff, etc., and to allow the surgeon to move the robotic arm without having to fully support its weight. While the surgeon is moving the robotic arm 105A, the robotic arm may provide some resistance to prevent the robotic arm from moving too fast or having too many degrees of freedom active at once. The position and the lock status of the robotic arm 105A may be tracked, for example, by a controller or the Surgical Computer 150.

In some embodiments, the robotic arm 105A can be moved by hand (e.g., by the surgeon) or with internal motors into its ideal position and orientation for the task being performed. In some embodiments, the robotic arm 105A may be enabled to operate in a "free" mode that allows the surgeon to position the arm into a desired position without being restricted. While in the free mode, the position and orientation of the robotic arm 105A may still be tracked as described above. In one embodiment, certain degrees of freedom can be selectively released upon input from user (e.g., surgeon) during specified portions of the surgical plan tracked by the Surgical Computer 150. Designs in which a robotic arm 105A is internally powered through hydraulics or motors or provides resistance to external manual motion through similar means can be described as powered robotic arms, while arms that are manually manipulated without power feedback, but which may be manually or automatically locked in place, may be described as passive robotic arms.

A robotic arm 105A or end effector 105B can include a trigger or other means to control the power of a saw or drill. Engagement of the trigger or other means by the surgeon can cause the robotic arm 105A or end effector 105B to transition from a motorized alignment mode to a mode where the saw or drill is engaged and powered on. Additionally, the CASS 100 can include a foot pedal (not shown) that causes the system to perform certain functions when activated. For example, the surgeon can activate the foot pedal to instruct the CASS 100 to place the robotic arm 105A or end effector 105B in an automatic mode that brings the robotic arm or end effector into the proper position with respect to the patient's anatomy in order to perform the necessary resections. The CASS 100 can also place the robotic arm 105A or end effector 105B in a collaborative mode that allows the surgeon to manually manipulate and position the robotic arm or end effector into a particular location. The collaborative mode can be configured to allow the surgeon to move the robotic arm 105A or end effector 105B medially or laterally, while restricting movement in other directions. As discussed, the robotic arm 105A or end effector 105B can include a cutting device (saw, drill, and burr) or a cutting guide or jig 105D that will guide a cutting device. In other embodiments, movement of the robotic arm 105A or robotically controlled end effector 105B can be controlled entirely by the CASS 100 without any, or with only minimal, assistance or input from a surgeon or other medical professional. In still other embodiments, the movement of the robotic arm 105A or robotically controlled end effector 105B can be controlled remotely by a surgeon or other medical professional using a control mechanism separate from the robotic arm or robotically controlled end effector device, for example, using a joystick or interactive monitor or display control device.

The examples below describe uses of the robotic device in the context of a hip surgery; however, it should be understood that the robotic arm may have other applications for surgical procedures involving knees, shoulders, etc. One example of use of a robotic arm in the context of forming an anterior cruciate ligament (ACL) graft tunnel is described in PCT/US2019/048502 filed Aug. 28, 2019 and entitled "Robotic Assisted Ligament Graft Placement and Tensioning," the entirety of which is incorporated herein by reference.

A robotic arm 105A may be used for holding the retractor. For example in one embodiment, the robotic arm 105A may be moved into the desired position by the surgeon. At that point, the robotic arm 105A may lock into place. In some embodiments, the robotic arm 105A is provided with data regarding the patient's position, such that if the patient moves, the robotic arm can adjust the retractor position accordingly. In some embodiments, multiple robotic arms may be used, thereby allowing multiple retractors to be held or for more than one activity to be performed simultaneously (e.g., retractor holding & reaming).

The robotic arm 105A may also be used to help stabilize the surgeon's hand while making a femoral neck cut. In this application, control of the robotic arm 105A may impose certain restrictions to prevent soft tissue damage from occurring. For example, in one embodiment, the Surgical Computer 150 tracks the position of the robotic arm 105A as it operates. If the tracked location approaches an area where tissue damage is predicted, a command may be sent to the robotic arm 105A causing it to stop. Alternatively, where the robotic arm 105A is automatically controlled by the Surgical Computer 150, the Surgical Computer may ensure that the robotic arm is not provided with any instructions that cause it to enter areas where soft tissue damage is likely to occur. The Surgical Computer 150 may impose certain restrictions on the surgeon to prevent the surgeon from reaming too far into the medial wall of the acetabulum or reaming at an incorrect angle or orientation.

In some embodiments, the robotic arm 105A may be used to hold a cup impactor at a desired angle or orientation during cup impaction. When the final position has been achieved, the robotic arm 105A may prevent any further seating to prevent damage to the pelvis.

The surgeon may use the robotic arm 105A to position the broach handle at the desired position and allow the surgeon to impact the broach into the femoral canal at the desired orientation. In some embodiments, once the Surgical Computer 150 receives feedback that the broach is fully seated, the robotic arm 105A may restrict the handle to prevent further advancement of the broach.

The robotic arm 105A may also be used for resurfacing applications. For example, the robotic arm 105A may stabilize the surgeon's hand while using traditional instrumentation and provide certain restrictions or limitations to allow for proper placement of implant components (e.g., guide wire placement, chamfer cutter, sleeve cutter, plan cutter, etc.). Where only a burr is employed, the robotic arm 105A may stabilize the surgeon's handpiece and may impose restrictions on the handpiece to prevent the surgeon from removing unintended bone in contravention of the surgical plan.

The robotic arm 105A may be a passive arm. As an example, the robotic arm 105A may be a CIRQ robot arm available from Brainlab AG. CIRQ is a registered trademark of Brainlab AG, Olof-Palme-Str. 9 81829, München, FED REP of GERMANY. In one particular embodiment, the robotic arm 105A is an intelligent holding arm as disclosed in U.S. patent application Ser. No. 15/525,585 to Krinninger et al., U.S. patent application Ser. No. 15/561,042 to Nowatschin et al., U.S. patent application Ser. No. 15/561, 048 to Nowatschin et al., and U.S. Pat. No. 10,342,636 to Nowatschin et al., the entire contents of each of which is herein incorporated by reference.

Surgical Procedure Data Generation and Collection

The various services that are provided by medical professionals to treat a clinical condition are collectively referred to as an "episode of care." For a particular surgical intervention the episode of care can include three phases: pre-operative, intra-operative, and post-operative. During each phase, data is collected or generated that can be used to analyze the episode of care in order to understand various aspects of the procedure and identify patterns that may be used, for example, in training models to make decisions with minimal human intervention. The data collected over the episode of care may be stored at the Surgical Computer 150 or the Surgical Data Server 180 (shown in FIG. 2C) as a complete dataset. Thus, for each episode of care, a dataset exists that comprises all of the data collectively pre-operatively about the patient, all of the data collected or stored by the CASS 100 intra-operatively, and any post-operative data provided by the patient or by a healthcare professional monitoring the patient.

As explained in further detail, the data collected during the episode of care may be used to enhance performance of the surgical procedure or to provide a holistic understanding of the surgical procedure and the patient outcomes. For example, in some embodiments, the data collected over the episode of care may be used to generate a surgical plan. In one embodiment, a high-level, pre-operative plan is refined intra-operatively as data is collected during surgery. In this way, the surgical plan can be viewed as dynamically changing in real-time or near real-time as new data is collected by the components of the CASS 100. In other embodiments, pre-operative images or other input data may be used to develop a robust plan preoperatively that is simply executed during surgery. In this case, the data collected by the CASS 100 during surgery may be used to make recommendations that ensure that the surgeon stays within the pre-operative surgical plan. For example, if the surgeon is unsure how to achieve a certain prescribed cut or implant alignment, the Surgical Computer 150 can be queried for a recommendation. In still other embodiments, the pre-operative and intra-operative planning approaches can be combined such that a robust pre-operative plan can be dynamically modified, as necessary or desired, during the surgical procedure. In some embodiments, a biomechanics-based model of patient anatomy contributes simulation data to be considered by the CASS 100 in developing preoperative, intraoperative, and post-operative/rehabilitation procedures to optimize implant performance outcomes for the patient.

Aside from changing the surgical procedure itself, the data gathered during the episode of care may be used as an input to other procedures ancillary to the surgery. For example, in some embodiments, implants can be designed using episode of care data. Example data-driven techniques for designing, sizing, and fitting implants are described in U.S. patent application Ser. No. 13/814,531 filed Aug. 15, 2011 and entitled "Systems and Methods for Optimizing Parameters for Orthopaedic Procedures"; U.S. patent application Ser. No. 14/232,958 filed Jul. 20, 2012 and entitled "Systems and Methods for Optimizing Fit of an Implant to Anatomy"; and U.S. patent application Ser. No. 12/234,444 filed Sep. 19, 2008 and entitled "Operatively Tuning Implants for Increased Performance," the entire contents of each of which are hereby incorporated by reference into this patent application.

Furthermore, the data can be used for educational, training, or research purposes. For example, using the network-based approach described below in FIG. 2C, other doctors or students can remotely view surgeries in interfaces that allow them to selectively view data as it is collected from the various components of the CASS 100. After the surgical procedure, similar interfaces may be used to "playback" a surgery for training or other educational purposes, or to identify the source of any issues or complications with the procedure.

Data acquired during the pre-operative phase generally includes all information collected or generated prior to the surgery. Thus, for example, information about the patient may be acquired from a patient intake form or electronic medical record (EMR). Examples of patient information that may be collected include, without limitation, patient demographics, diagnoses, medical histories, progress notes, vital signs, medical history information, allergies, and lab results. The pre-operative data may also include images related to the anatomical area of interest. These images may be captured, for example, using Magnetic Resonance Imaging (MRI), Computed Tomography (CT), X-ray, ultrasound, or any other modality known in the art. The pre-operative data may also comprise quality of life data captured from the patient. For example, in one embodiment, pre-surgery patients use a mobile application ("app") to answer questionnaires regarding their current quality of life. In some embodiments, preoperative data used by the CASS 100 includes demographic, anthropometric, cultural, or other specific traits about a patient that can coincide with activity levels and specific patient activities to customize the surgical plan to the patient. For example, certain cultures or demographics may be more likely to use a toilet that requires squatting on a daily basis.

Figure 2A:
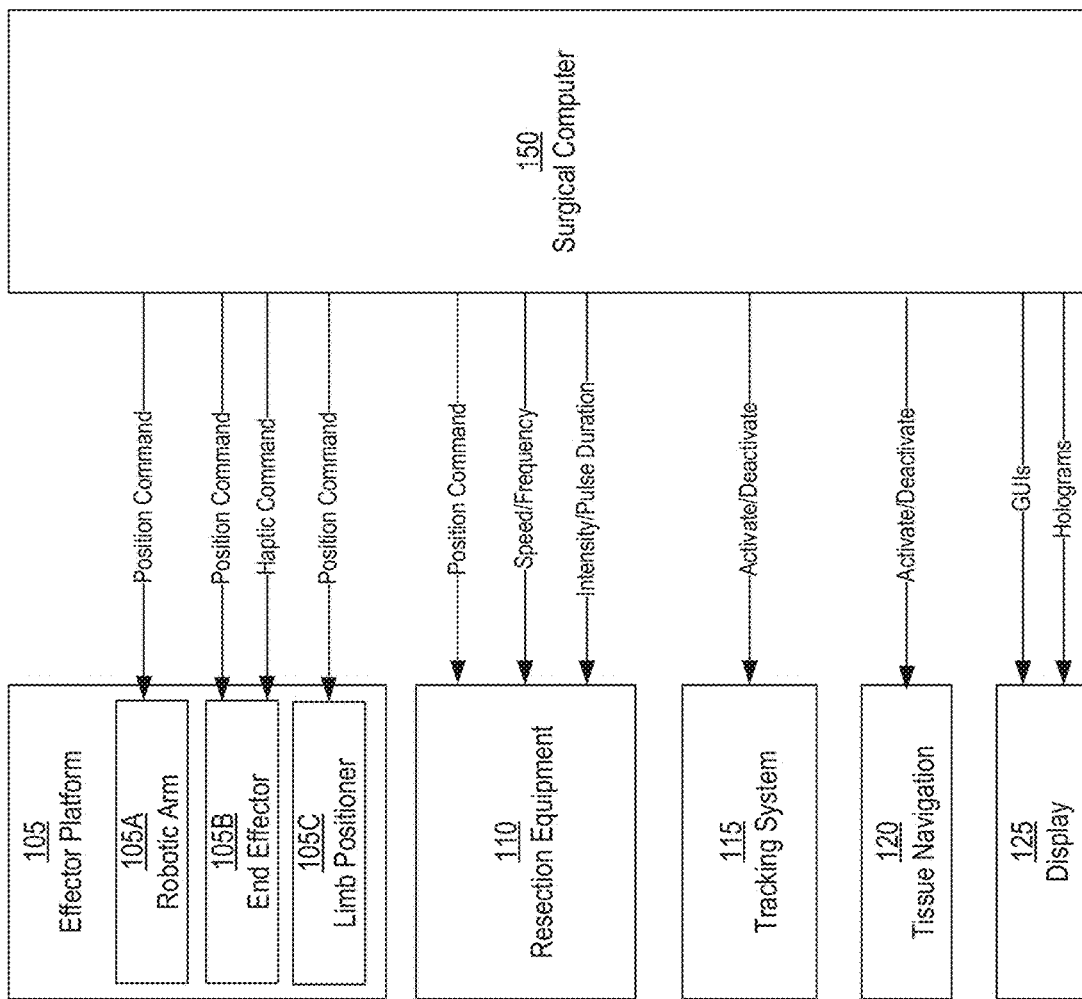
FIG. 2A illustrates examples of some of the control instructions that may be used by a surgical computer, in accordance with some embodiments.
Figure 2B:
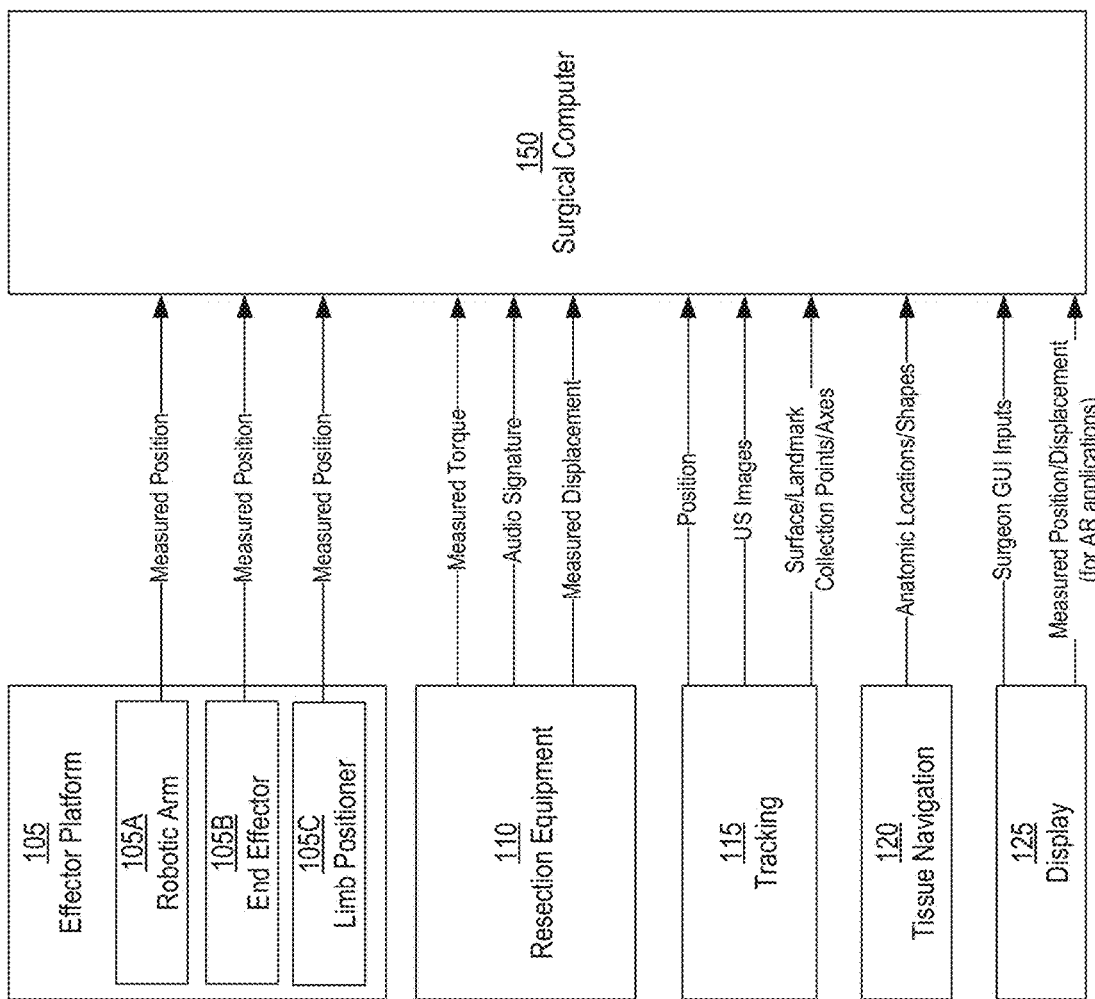
FIG. 2B illustrates examples of some of the data that may be used by a surgical computer, in accordance with some embodiments.

FIGS. 2A and 2B provide examples of data that may be acquired during the intra-operative phase of an episode of care. These examples are based on the various components of the CASS 100 described above with reference to FIG. 1; however, it should be understood that other types of data may be used based on the types of equipment used during surgery and their use.

FIG. 2A shows examples of some of the control instructions that the Surgical Computer 150 provides to other components of the CASS 100, according to some embodiments. Note that the example of FIG. 2A assumes that the components of the Effector Platform 105 are each controlled directly by the Surgical Computer 150. In embodiments where a component is manually controlled by the Surgeon 111, instructions may be provided on the Display 125 or AR HMD 155 (as shown in FIG. 1) instructing the Surgeon 111 how to move the component.

The various components included in the Effector Platform 105 are controlled by the Surgical Computer 150 providing position commands that instruct the component where to move within a coordinate system. In some embodiments, the Surgical Computer 150 provides the Effector Platform 105 with instructions defining how to react when a component of the Effector Platform 105 deviates from a surgical plan. These commands are referenced in FIG. 2A as "haptic" commands. For example, the End Effector 105B may provide a force to resist movement outside of an area where resection is planned. Other commands that may be used by the Effector Platform 105 include vibration and audio cues.

In some embodiments, the end effectors 105B of the robotic arm 105A are operatively coupled with cutting guide 105D (as shown in FIG. 1). In response to an anatomical model of the surgical scene, the robotic arm 105A can move the end effectors 105B and the cutting guide 105D into position to match the location of the femoral or tibial cut to be performed in accordance with the surgical plan. This can reduce the likelihood of error, allowing the vision system and a processor utilizing that vision system to implement the surgical plan to place a cutting guide 105D at the precise location and orientation relative to the tibia or femur to align a cutting slot of the cutting guide with the cut to be performed according to the surgical plan. Then, a surgeon can use any suitable tool, such as an oscillating or rotating saw or drill to perform the cut (or drill a hole) with perfect placement and orientation because the tool is mechanically limited by the features of the cutting guide 105D. In some embodiments, the cutting guide 105D may include one or more pin holes that are used by a surgeon to drill and screw or pin the cutting guide into place before performing a resection of the patient tissue using the cutting guide. This can free the robotic arm 105A or ensure that the cutting guide 105D is fully affixed without moving relative to the bone to be resected. For example, this procedure can be used to make the first distal cut of the femur during a total knee arthroplasty. In some embodiments, where the arthroplasty is a hip arthroplasty, cutting guide 105D can be fixed to the femoral head or the acetabulum for the respective hip arthroplasty resection. It should be understood that any arthroplasty that utilizes precise cuts can use the robotic arm 105A and/or cutting guide 105D in this manner.

The Resection Equipment 110 is provided with a variety of commands to perform bone or tissue operations. As with the Effector Platform 105, position information may be provided to the Resection Equipment 110 to specify where it should be located when performing resection. Other commands provided to the Resection Equipment 110 may be dependent on the type of resection equipment. For example, for a mechanical or ultrasonic resection tool, the commands may specify the speed and frequency of the tool. For Radiofrequency Ablation (RFA) and other laser ablation tools, the commands may specify intensity and pulse duration.

Some components of the CASS 100 do not need to be directly controlled by the Surgical Computer 150; rather, the Surgical Computer 150 only needs to activate the component, which then executes software locally specifying the manner in which to collect data and provide it to the Surgical Computer 150. In the example of FIG. 2A, there are two components that are operated in this manner: the Tracking System 115 and the Tissue Navigation System 120.

The Surgical Computer 150 provides the Display 125 with any visualization that is needed by the Surgeon 111 during surgery. For monitors, the Surgical Computer 150 may provide instructions for displaying images, GUIs, etc., using techniques known in the art. The display 125 can include various aspects of the workflow of a surgical plan. During the registration process, for example, the display 125 can show a preoperatively constructed 3D bone model and depict the locations of the probe as the surgeon uses the probe to collect locations of anatomical landmarks on the patient. The display 125 can include information about the surgical target area. For example, in connection with a TKA, the display 125 can depict the mechanical and anatomical axes of the femur and tibia. The display 125 can depict varus and valgus angles for the knee joint based on a surgical plan, and the CASS 100 can depict how such angles will be affected if contemplated revisions to the surgical plan are made. Accordingly, the display 125 is an interactive interface that can dynamically update and display how changes to the surgical plan would impact the procedure and the final position and orientation of implants installed on bone.

As the workflow progresses to preparation of bone cuts or resections, the display 125 can depict the planned or recommended bone cuts before any cuts are performed. The surgeon 111 can manipulate the image display to provide different anatomical perspectives of the target area and can have the option to alter or revise the planned bone cuts based on intraoperative evaluation of the patient. The display 125 can depict how the chosen implants would be installed on the bone if the planned bone cuts are performed. If the surgeon 111 choses to change the previously planned bone cuts, the display 125 can depict how the revised bone cuts would change the position and orientation of the implant when installed on the bone.

The display 125 can provide the surgeon 111 with a variety of data and information about the patient, the planned surgical intervention, and the implants. Various patient-specific information can be displayed, including real-time data concerning the patient's health such as heart rate, blood pressure, etc. The display 125 can also include information about the anatomy of the surgical target region including the location of landmarks, the current state of the anatomy (e.g., whether any resections have been made, the depth and angles of planned and executed bone cuts), and future states of the anatomy as the surgical plan progresses. The display 125 can also provide or depict additional information about the surgical target region. For a TKA, the display 125 can provide information about the gaps (e.g., gap balancing) between the femur and tibia and how such gaps will change if the planned surgical plan is carried out. For a TKA, the display 125 can provide additional relevant information about the knee joint such as data about the joint's tension (e.g., ligament laxity) and information concerning rotation and alignment of the joint. The display 125 can depict how the planned implants' locations and positions will affect the patient as the knee joint is flexed. The display 125 can depict how the use of different implants or the use of different sizes of the same implant will affect the surgical plan and preview how such implants will be positioned on the bone. The CASS 100 can provide such information for each of the planned bone resections in a TKA or THA. In a TKA, the CASS 100 can provide robotic control for one or more of the planned bone resections. For example, the CASS 100 can provide robotic control only for the initial distal femur cut, and the surgeon 111 can manually perform other resections (anterior, posterior and chamfer cuts) using conventional means, such as a 4-in-1 cutting guide or jig 105D.

The display 125 can employ different colors to inform the surgeon of the status of the surgical plan. For example, un-resected bone can be displayed in a first color, resected bone can be displayed in a second color, and planned resections can be displayed in a third color. Implants can be superimposed onto the bone in the display 125, and implant colors can change or correspond to different types or sizes of implants.

The information and options depicted on the display 125 can vary depending on the type of surgical procedure being performed. Further, the surgeon 111 can request or select a particular surgical workflow display that matches or is consistent with his or her surgical plan preferences. For example, for a surgeon 111 who typically performs the tibial cuts before the femoral cuts in a TKA, the display 125 and associated workflow can be adapted to take this preference into account. The surgeon 111 can also preselect that certain steps be included or deleted from the standard surgical workflow display. For example, if a surgeon 111 uses resection measurements to finalize an implant plan but does not analyze ligament gap balancing when finalizing the implant plan, the surgical workflow display can be organized into modules, and the surgeon can select which modules to display and the order in which the modules are provided based on the surgeon's preferences or the circumstances of a particular surgery. Modules directed to ligament and gap balancing, for example, can include pre- and post-resection ligament/gap balancing, and the surgeon 111 can select which modules to include in their default surgical plan workflow depending on whether they perform such ligament and gap balancing before or after (or both) bone resections are performed.

For more specialized display equipment, such as AR HMDs, the Surgical Computer 150 may provide images, text, etc., using the data format supported by the equipment. For example, if the Display 125 is a holography device such as the Microsoft HoloLens™ or Magic Leap One™, the Surgical Computer 150 may use the HoloLens Application Program Interface (API) to send commands specifying the position and content of holograms displayed in the field of view of the Surgeon 111.

In some embodiments, one or more surgical planning models may be incorporated into the CASS 100 and used in the development of the surgical plans provided to the surgeon 111. The term "surgical planning model" refers to software that simulates the biomechanics performance of anatomy under various scenarios to determine the optimal way to perform cutting and other surgical activities. For example, for knee replacement surgeries, the surgical planning model can measure parameters for functional activities, such as deep knee bends, gait, etc., and select cut locations on the knee to optimize implant placement. One example of a surgical planning model is the LIFEMOD™ simulation software from SMITH AND NEPHEW, INC. In some embodiments, the Surgical Computer 150 includes computing architecture that allows full execution of the surgical planning model during surgery (e.g., a GPU-based parallel processing environment). In other embodiments, the Surgical Computer 150 may be connected over a network to a remote computer that allows such execution, such as a Surgical Data Server 180 (see FIG. 2C). As an alternative to full execution of the surgical planning model, in some embodiments, a set of transfer functions are derived that simplify the mathematical operations captured by the model into one or more predictor equations. Then, rather than execute the full simulation during surgery, the predictor equations are used. Further details on the use of transfer functions are described in PCT/US2019/046995 filed Aug. 19, 2019 entitled "Patient Specific Surgical Method and System," the entirety of which is incorporated herein by reference.

FIG. 2B shows examples of some of the types of data that can be provided to the Surgical Computer 150 from the various components of the CASS 100. In some embodiments, the components may stream data to the Surgical Computer 150 in real-time or near real-time during surgery. In other embodiments, the components may queue data and send it to the Surgical Computer 150 at set intervals (e.g., every second). Data may be communicated using any format known in the art. Thus, in some embodiments, the components all transmit data to the Surgical Computer 150 in a common format. In other embodiments, each component may use a different data format, and the Surgical Computer 150 is configured with one or more software applications that enable translation of the data.

In general, the Surgical Computer 150 may serve as the central point where CASS data is collected. The exact content of the data will vary depending on the source. For example, each component of the Effector Platform 105 provides a measured position to the Surgical Computer 150. Thus, by comparing the measured position to a position originally specified by the Surgical Computer 150, the Surgical Computer can identify deviations that take place during surgery.

The Resection Equipment 110 can send various types of data to the Surgical Computer 150 depending on the type of equipment used. Example data types that may be sent include the measured torque, audio signatures, and measured displacement values. Similarly, the Tracking Technology 115 can provide different types of data depending on the tracking methodology employed. Example tracking data types include position values for tracked items (e.g., anatomy, tools, etc.), ultrasound images, and surface or landmark collection points or axes. The Tissue Navigation System 120 provides the Surgical Computer 150 with anatomic locations, shapes, etc., as the system operates.

Although the Display 125 generally is used for outputting data for presentation to the user, it may also provide data to the Surgical Computer 150. For example, for embodiments where a monitor is used as part of the Display 125, the Surgeon 111 may interact with a GUI to provide inputs which are sent to the Surgical Computer 150 for further processing. For AR applications, the measured position and displacement of the HMD may be sent to the Surgical Computer 150 so that it can update the presented view as needed.

During the post-operative phase of the episode of care, various types of data can be collected to quantify the overall improvement or deterioration in the patient's condition as a result of the surgery. The data can take the form of, for example, self-reported information reported by patients via questionnaires. For example, in the context of a knee replacement surgery, functional status can be measured with an Oxford Knee Score questionnaire, and the post-operative quality of life can be measured with a EQSD-5L questionnaire. Other examples in the context of a hip replacement surgery may include the Oxford Hip Score, Harris Hip Score, and WOMAC (Western Ontario and McMaster Universities Osteoarthritis index). Such questionnaires can be administered, for example, by a healthcare professional directly in a clinical setting or using a mobile app that allows the patient to respond to questions directly. In some embodiments, the patient may be outfitted with one or more wearable devices that collect data relevant to the surgery. For example, following a knee surgery, the patient may be outfitted with a knee brace that includes sensors that monitor knee positioning, flexibility, etc. This information can be collected and transferred to the patient's mobile device for review by the surgeon to evaluate the outcome of the surgery and address any issues. In some embodiments, one or more cameras can capture and record the motion of a patient's body segments during specified activities postoperatively. This motion capture can be compared to a biomechanics model to better understand the functionality of the patient's joints and better predict progress in recovery and identify any possible revisions that may be needed.

The post-operative stage of the episode of care can continue over the entire life of a patient. For example, in some embodiments, the Surgical Computer 150 or other components comprising the CASS 100 can continue to receive and collect data relevant to a surgical procedure after the procedure has been performed. This data may include, for example, images, answers to questions, "normal" patient data (e.g., blood type, blood pressure, conditions, medications, etc.), biometric data (e.g., gait, etc.), and objective and subjective data about specific issues (e.g., knee or hip joint pain). This data may be explicitly provided to the Surgical Computer 150 or other CASS component by the patient or the patient's physician(s). Alternatively or additionally, the Surgical Computer 150 or other CASS component can monitor the patient's EMR and retrieve relevant information as it becomes available. This longitudinal view of the patient's recovery allows the Surgical Computer 150 or other CASS component to provide a more objective analysis of the patient's outcome to measure and track success or lack of success for a given procedure. For example, a condition experienced by a patient long after the surgical procedure can be linked back to the surgery through a regression analysis of various data items collected during the episode of care. This analysis can be further enhanced by performing the analysis on groups of patients that had similar procedures and/or have similar anatomies.

In some embodiments, data is collected at a central location to provide for easier analysis and use. Data can be manually collected from various CASS components in some instances. For example, a portable storage device (e.g., USB stick) can be attached to the Surgical Computer 150 in order to retrieve data collected during surgery. The data can then be transferred, for example, via a desktop computer to the centralized storage. Alternatively, in some embodiments, the Surgical Computer 150 is connected directly to the centralized storage via a Network 175 as shown in FIG. 2C.

Figure 2C:
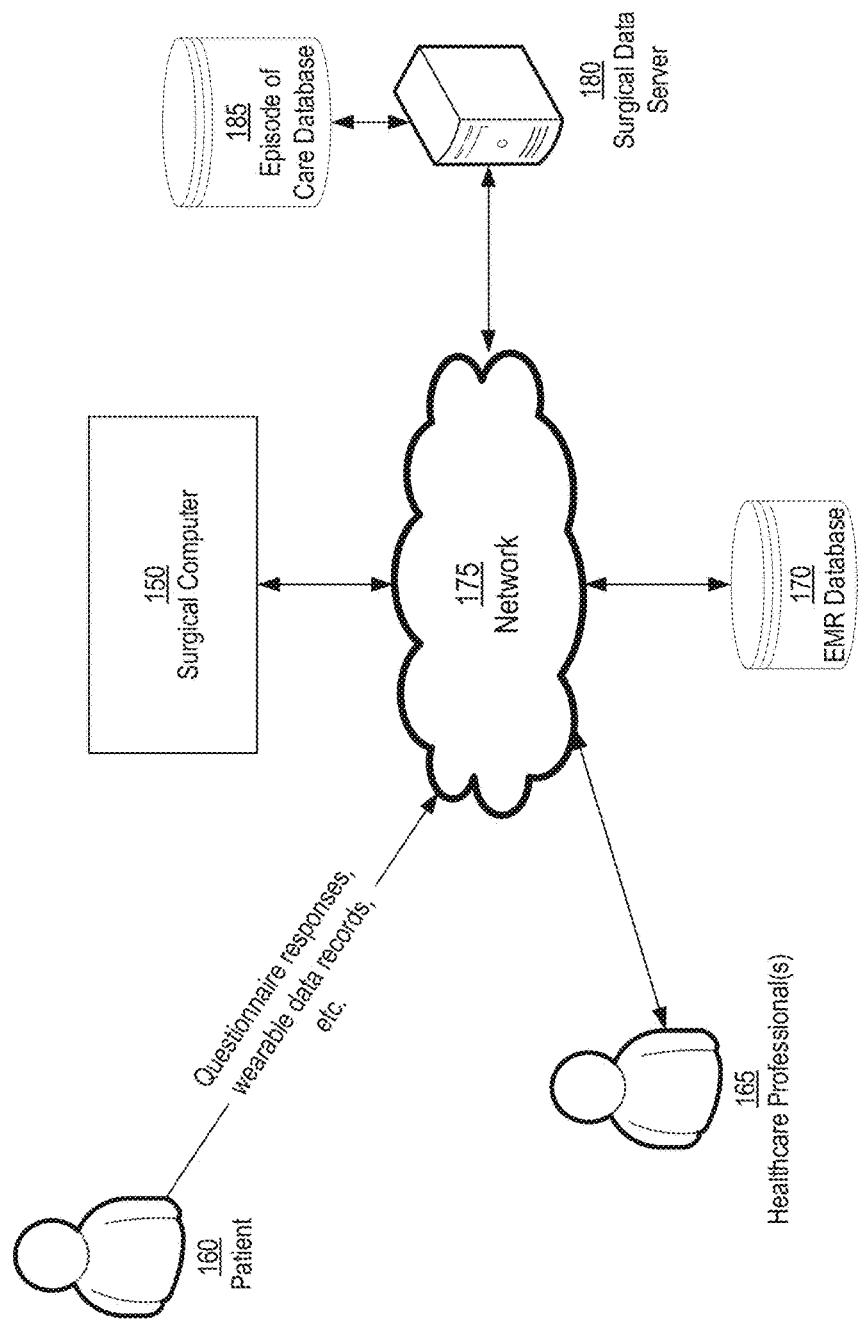
FIG. 2C is a system diagram illustrating an example of a cloud-based system used by a surgical computer, in accordance with some embodiments.

FIG. 2C illustrates a "cloud-based" implementation in which the Surgical Computer 150 is connected to a Surgical Data Server 180 via a Network 175. This Network 175 may be, for example, a private intranet or the Internet. In addition to the data from the Surgical Computer 150, other sources can transfer relevant data to the Surgical Data Server 180. The example of FIG. 2C shows 3 additional data sources: the Patient 160, Healthcare Professional(s) 165, and an EMR Database 170. Thus, the Patient 160 can send pre-operative and post-operative data to the Surgical Data Server 180, for example, using a mobile app. The Healthcare Professional(s) 165 includes the surgeon and his or her staff as well as any other professionals working with Patient 160 (e.g., a personal physician, a rehabilitation specialist, etc.). It should also be noted that the EMR Database 170 may be used for both pre-operative and post-operative data. For example, assuming that the Patient 160 has given adequate permissions, the Surgical Data Server 180 may collect the EMR of the Patient pre-surgery. Then, the Surgical Data Server 180 may continue to monitor the EMR for any updates post-surgery.

At the Surgical Data Server 180, an Episode of Care Database 185 is used to store the various data collected over a patient's episode of care. The Episode of Care Database 185 may be implemented using any technique known in the art. For example, in some embodiments, an SQL-based database may be used where all of the various data items are structured in a manner that allows them to be readily incorporated in two SQL's collection of rows and columns. However, in other embodiments a No-SQL database may be employed to allow for unstructured data, while providing the ability to rapidly process and respond to queries. As is understood in the art, the term "No-SQL" is used to define a class of data stores that are non-relational in their design. Various types of No-SQL databases may generally be grouped according to their underlying data model. These groupings may include databases that use column-based data models (e.g., Cassandra), document-based data models (e.g., MongoDB), key-value based data models (e.g., Redis), and/or graph-based data models (e.g., Allego). Any type of No-SQL database may be used to implement the various embodiments described herein and, in some embodiments, the different types of databases may support the Episode of Care Database 185.

Data can be transferred between the various data sources and the Surgical Data Server 180 using any data format and transfer technique known in the art. It should be noted that the architecture shown in FIG. 2C allows transmission from the data source to the Surgical Data Server 180, as well as retrieval of data from the Surgical Data Server 180 by the data sources. For example, as explained in detail below, in some embodiments, the Surgical Computer 150 may use data from past surgeries, machine learning models, etc., to help guide the surgical procedure.

In some embodiments, the Surgical Computer 150 or the Surgical Data Server 180 may execute a de-identification process to ensure that data stored in the Episode of Care Database 185 meets Health Insurance Portability and Accountability Act (HIPAA) standards or other requirements mandated by law. HIPAA provides a list of certain identifiers that must be removed from data during de-identification. The aforementioned de-identification process can scan for these identifiers in data that is transferred to the Episode of Care Database 185 for storage. For example, in one embodiment, the Surgical Computer 150 executes the de-identification process just prior to initiating transfer of a particular data item or set of data items to the Surgical Data Server 180. In some embodiments, a unique identifier is assigned to data from a particular episode of care to allow for re-identification of the data if necessary.

Although FIGS. 2A-2C discuss data collection in the context of a single episode of care, it should be understood that the general concept can be extended to data collection from multiple episodes of care. For example, surgical data may be collected over an entire episode of care each time a surgery is performed with the CASS 100 and stored at the Surgical Computer 150 or at the Surgical Data Server 180. As explained in further detail below, a robust database of episode of care data allows the generation of optimized values, measurements, distances, or other parameters and other recommendations related to the surgical procedure. In some embodiments, the various datasets are indexed in the database or other storage medium in a manner that allows for rapid retrieval of relevant information during the surgical procedure. For example, in one embodiment, a patientcentric set of indices may be used so that data pertaining to a particular patient or a set of patients similar to a particular patient can be readily extracted. This concept can be similarly applied to surgeons, implant characteristics, CASS component versions, etc.

Further details of the management of episode of care data is described in PCT/US2019/067845, filed Dec. 20, 2019 and entitled "Methods and Systems for Providing an Episode of Care," the entirety of which is incorporated herein by reference.

Open Versus Closed Digital Ecosystems

In some embodiments, the CASS is designed to operate as a self-contained or "closed" digital ecosystem. Each component of the CASS is specifically designed to be used in the closed ecosystem and data is generally not accessible to devices outside of the digital ecosystem. For example, in some embodiments, each component includes software or firmware that implements proprietary protocols for activities such as communication, storage, security, etc. The concept of a closed digital ecosystem may be desirable for a company that wants to control all components of the CASS to ensure that certain compatibility, security, and reliability standards are met. For example, the CASS can be designed such that a new component cannot be used with the CASS unless it is certified by the company.

In other embodiments, the CASS is designed to operate as an "open" digital ecosystem. In these embodiments, the components may be produced from a variety of different companies, and components implement standards for activities, such as communication, storage, and security. Thus, by using these standards, any company can freely build an independent, compliant component of the CASS platform. Data may be transferred between components using publicly available application programming interfaces (APIs) and open, shareable data formats.

CASS Queries and CASS Recommendations

Simple joints, such as the ball and socket joint (e.g., hip and shoulder) or the pivot joint (e.g., elbow), or more complex joints, such as the condylar joint (e.g., knee joint), are incredibly intricate systems whose performance can be significantly affected by various factors. Procedures for replacing, resurfacing, or otherwise repairing these joints are common, such as in response to damage or other degradation of the joint. For instance, TKA, which replaces the articular surfaces of the femur, tibia and/or patella with artificial implants, is a common procedure for patients suffering from degradation or trauma to the knee joint.

Selecting the optimal parameters for performing joint surgery is challenging. To continue with the example of knee replacement surgery, a surgeon can place a first prosthesis on the distal end of the femur and a second prosthesis at the proximal end of the tibia, or the surgeon can install the prostheses in the opposite order. The surgeon seeks to optimally place the prostheses with respect to various parameters, such as the gap between the prostheses throughout a range of motion. Misplacement of an implant could have a negative impact on the patient's quality of life post-surgery. For example, if the gap between the tibia and the femur is too small at any time during the range of motion, the patient can experience painful binding. On the other hand, if the gap is too large, the knee joint is too loose and can become unstable.

In some embodiments, the CASS (or preoperative planning application) 100 is configured to generate recommendations based on queries received from the surgeon or the surgical staff. Examples of recommendations that may be provided by the CASS 100 include, without limitation, optimization of one or more surgical parameters, optimization of implant position and orientation relative to a reference point or points, such as an anatomical or mechanical axis, a modification of the surgical plan, or a description of how to achieve a particular result. As noted above, the various components of the CASS 100 generate various types of data that collectively define the state of the system. Additionally, the CASS 100 may have access to various types of pre-operative data (e.g., patient demographics, pre-operative images, etc.), historical data (e.g., from other surgeries performed by the same or a different surgeon), and simulation results. Based on all of this data, the CASS 100 can operate in a dynamic manner and allow the surgeon to intelligently modify the surgical plan on-the-fly as needed. In some embodiments, these modifications are performed before surgery (e.g., before printing cutting guides). In some embodiments, where custom cutting guides are not used (e.g., a selection of non-patient specific cutting guides are available that can be selected and placed by a CASS), modifications can be made during surgery by the CASS. Thus, for example, in some embodiments, the CASS 100 notifies the surgeon via a display 125 of a modified surgical plan or an optimization based on a condition that was not detected pre-operatively.

In some embodiments, a surgical plan can be created prior to surgery using preoperative images and data. These images can include x-ray, CT, MRI, and ultrasound images. Data can include characteristics of the patient including joint geometry, age, weight, activity level, and the like, and data about the prosthetic to be implanted. This plan can then be modified based on additional information gathered intraoperatively. For example, additional medical images can be taken during the surgical procedure and may be used to modify the surgical plan based on additional physiological details gleaned from such images. In some embodiments, the surgical plan is based on patient information, without the need to capture three-dimensional images, such as via a CT or MIII scan of the patient. Additional optical or x-ray images can be taken during the procedure to provide additional detail and alter the surgical plan, allowing the surgical plan to be developed and modified without the need for expensive medical imaging preoperatively.

The processor of the CASS 100 can recommend any aspect of the surgical plan and modify this recommendation based on new data collected during surgery. For example, the processor of the CASS 100 can optimize anteversion and abduction angles for hip cup placement (in hip arthroplasty) or the depth and orientation of the distal and posterior femoral cut planes and patella configuration (in PKA/TKA), in response to images captured before or during surgery. Once an initial default plan is generated, a surgeon can ask for a recommendation on a particular aspect of the surgery and may deviate from the initial surgical plan. Requests for a recommendation can result in a new plan, partial deviation from the initial or default plan, or confirmation and approval of the initial plan. Accordingly, by using a data-driven approach using a processor of the CASS 100, the surgical plan can be updated and optimized as the procedure transpires. These optimizations and recommendations, as explained throughout, can be generated by a processor before or during a procedure based on a statistical model of patient anatomy from a plurality of simulations or a transfer function that is informed by the simulations and specific details of the patient anatomy being operated upon. Accordingly, any additional data collected about patient anatomy can be used to update the statistical model for that patient to optimize implant characteristics to maximize performance criteria of the expected outcome of the procedure from the surgical plan.

Figure 3A:
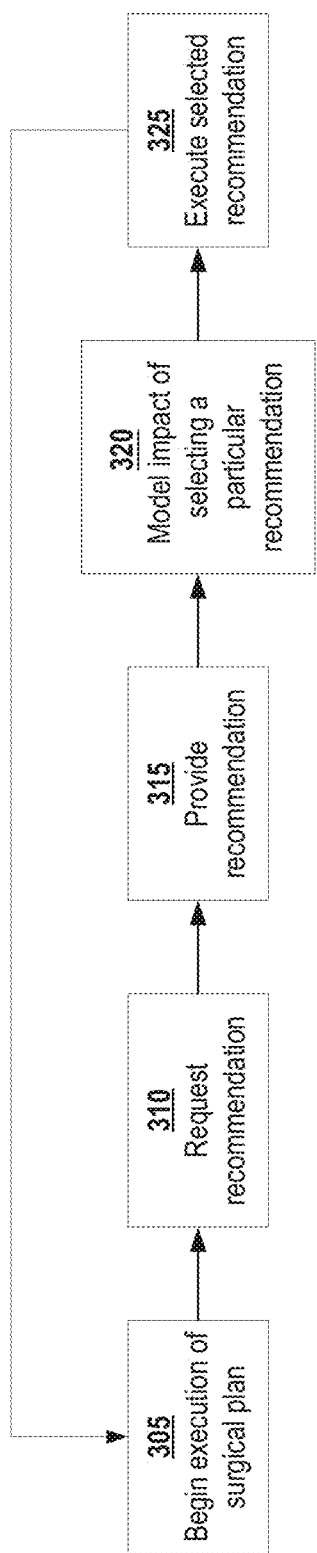
FIG. 3A provides a high-level overview of how recommendations can be generated by a surgical computer, in accordance with some embodiments.

FIG. 3A provides a high-level overview of how recommendations can be generated. This workflow begins at 305 with the surgical staff executing the surgical plan. This surgical plan could be the original plan generated based on pre-operative or intra-operative imaging and data, or the plan could be a modification of the original surgical plan. At 310, the surgeon or a member of the surgical staff requests a recommendation of how to address one or more issues in the surgical procedure. For example, the surgeon may request a recommendation for how to optimally align an implant based on intra-operative data (e.g., acquired using a point probe or new images). In some embodiments, the request may be made by manually entering a specific request into a GUI or voice interface of the CASS 100. In other embodiments, the CASS 100 includes one or more microphones that collect verbal requests or queries from the surgeon that are translated into formal requests (e.g., using natural language processing techniques).

Continuing with reference to FIG. 3A, at 315 the recommendation is provided to the surgeon. Various techniques can be used to provide the recommendation. For example, where the recommendation provides a recommended cut to be made or a recommended implant orientation alignment, a graphical representation of the recommendation may be depicted on a display 125 of the CASS 100. In one embodiment, the recommendation may be overlaid on the patient's anatomy in an AR HMD 155. The resulting performance characteristics (such as medial and lateral condylar gaps and patellar groove tracking for various flexions and curves showing ligament tension for a range of motion, for a PKA/TKA or plots of range of motion and center of pressure and edge loading stresses between femoral head and acetabular for THA) can be presented. In some embodiments, the information can be conveyed via a display 125 (which could include an HMD 155) to a user in the form of a plot, number, or by changing a color or an indicator. For example, in a PKA/TKA an image of the patella (overlaid on a patient image, for example) could glow red or flash when a change to the plan or the patient data indicates via the statistical model that the patella will encounter tracking problems relative to the patella groove or overstrain patellar ligaments without additional changes. For a THA, a portion of the acetabular cup can glow to indicate where there is an increased edge loading or dislocation risk. In some embodiments, the interface can then invite the user to click for a recommended solution, such as patellar stuffing, ligament release, or changes to the pose of a patellar implant or the femoral implant (PKA/TKA) or acetabulare cup anteversion and abduction angles (THA) to optimize performance.

Aside from the recommendation, in some embodiments, the CASS/planning system 100 may also provide a rationale for the recommendation. For example, for a recommended alignment or orientation of an implant, the CASS 100 may provide a listing of patient-specific features or activities that influenced the recommendation. The CASS-recommended alignment or orientation of an implant may further refer to a reference frame or point, such as an anatomical or mechanical axis or a distance from a bone or bone landmark. Additionally, as shown in 320, the CASS may model how selecting a particular recommendation will impact the rest of the surgical procedure. For example, prior to surgery, a default cutting guide may be generated based on preoperative 3-dimensional CT or MM scans. During surgery, the surgeon may acquire high-resolution data of the patient's anatomy from an Mill or using a point probe or optical camera once an incision is made. The CASS 100 may use such data to create a new or updated plan or recommendation regarding the resection of bone tissue using a resection tool or cutting guide. At step 320, the impact of this revised plan or recommendation may be presented in the form of revised alignment instructions, etc. The surgeon may also be presented with a plurality of recommendations and view the impact of each on the surgical plan. For example, two viable recommended bone resection plans or recommendations could be generated, and the surgeon can decide which one to execute based on the impact each recommendation has on the subsequent steps of the surgery. The surgeon may also be presented with animations of range of motion or dynamic activities (such as walking or ascending stairs etc.) that are a functional consequence of each recommendation to allow the surgeon to better understand how the recommendation will affect patient motion characteristics. In some embodiments, the surgeon has the ability to select individual data items or parameters (e.g., alignment, tension and flexion gaps, etc.) for optimization recommendations. Finally, once the surgeon selects a particular recommendation, it is executed at step 325. For example, in embodiments where a custom cutting guide is manufactured prior to surgery, step 325 can be executed by printing and delivering the cutting guide to the surgeon for use during surgery. In embodiments where a robot arm holds a cutting guide at a specific predetermined location, the commands to place the cutting guide can be sent to the robot arm as part of the CASS workflow. In embodiments that do not use a cutting guide, the CASS can receive instructions to assist the surgeon and resecting the femoral components and tibia in accordance with the recommendation.

The CASS 100 can present recommendations to the surgeon or the surgical staff preoperatively or at any time during surgery. In some instances, the surgeon may expressly request the recommendation as discussed above with respect to FIG. 3A. In other embodiments, the CASS 100 may be configured to execute recommendation algorithms as a background process while the surgery is proceeding based on the available data. When a new recommendation is generated, the CASS 100 may notify the surgeon with one or more notification mechanisms. For example, a visual indicator may be presented on a display 125 of the CASS 100. Ideally, a notification mechanism should be relatively unobtrusive such that it does not interfere with surgery. For example, in one embodiment, as the surgeon navigates through the surgical plan, different text colors could be used to indicate that a recommendation is available. In some embodiments, where an AR or VR headset 155 is used, the recommendation may be provided into the user's visual field and highlighted to draw the user's attention to either the recommendation or the fact that a recommendation is available. The user (e.g., a surgeon or technician) can then interact with the recommendation or solicitation for recommendation in the AR or VR user interface using any of the means described below. In these embodiments, the CASS 100 can treat user headsets 155 as additional displays and communicate information to be displayed thereon using any conventional means used to communicate with displays.

To illustrate one type of recommendation that may be performed with the CASS 100, a technique for optimizing surgical parameters is disclosed below. The term "optimization" in this context means selection of parameters that are optimal based on certain specified criteria. In an extreme case, optimization can refer to selecting optimal parameter(s) based on data from the entire episode of care, including any pre-operative data, the state of CASS data at a given point in time, and post-operative goals. Moreover, optimization may be performed using historical data, such as data generated during past surgeries involving, for example, the same surgeon, past patients with physical characteristics similar to the current patient, or the like.

The optimized parameters may depend on the portion of the patient's anatomy to be operated on. For example, for knee surgeries, the surgical parameters may include positioning information for the femoral and tibial components including, without limitation, rotational alignment (e.g., varus/valgus rotation, external rotation, flexion rotation for the femoral component, posterior slope of the tibial component), resection depths (e.g., varus knee, valgus knee), and implant type, size and position. The positioning information may further include surgical parameters for the combined implant, such as overall limb alignment, combined tibiofemoral hyperextension, and combined tibiofemoral resection. Additional examples of parameters that could be optimized for a given TKA femoral implant by the CASS 100 include the following:

| Parameter | Reference | Exemplary Recommendation (s) |
|---|---|---|
| Size | Posterior | The largest sized implant that does not overhang medial/lateral bone edges or overhang the anterior femur. A size that does not result in overstuffing the patella femoral joint |
| Implant Position-Medial Lateral | Medial/lateral cortical bone edges | Center the implant evenly between the medial/lateral cortical bone edges |
| Resection Depth-Varus Knee | Distal and posterior lateral | 6 mm of bone |
| Resection Depth-Valgus Knee | Distal and posterior medial | 7 mm of bone |
| Rotation-Varus/Valgus | Mechanical Axis | 1° varus |
| Rotation-External | Transepicondylar Axis | 1° external from the transepicondylar axis |
| Rotation-Flexion | Mechanical Axis | 3° flexed |

Additional examples of parameters that could be optimized for a given TKA tibial implant by the CASS include the following:

| Parameter | Reference | Exemplary Recommendation (s) |
|---|---|---|
| Size | Posterior | The largest sized implant that does not overhang the medial, lateral, anterior, and posterior tibial edges |
| Implant Position | Medial/lateral and anterior/posterior cortical bone edges | Center the implant evenly between the medial/lateral and anterior/posterior cortical bone edges |
| Resection Depth-Varus Knee | Lateral/Medial | 4 mm of bone |
| Resection Depth-Valgus Knee | Lateral/Medial | 5 mm of bone |
| Rotation-Varus/Valgus | Mechanical Axis | 1° valgus |
| Rotation-External | Tibial Anterior Posterior Axis | 1° external from the tibial anterior paxis |
| Posterior Slope | Mechanical Axis | 3° posterior slope |

For hip surgeries, the surgical parameters may comprise femoral neck resection location and angle, cup inclination angle, cup anteversion angle, cup depth, femoral stem design, femoral stem size, fit of the femoral stem within the canal, femoral offset, leg length, and femoral version of the implant.

Shoulder parameters may include, without limitation, humeral resection depth/angle, humeral stem version, humeral offset, glenoid version and inclination, as well as reverse shoulder parameters such as humeral resection depth/angle, humeral stem version, Glenoid tilt/version, glenosphere orientation, glenosphere offset and offset direction.

Various conventional techniques exist for optimizing surgical parameters. However, these techniques are typically computationally intensive and, thus, parameters often need to be determined pre-operatively. As a result, the surgeon is limited in his or her ability to make modifications to optimized parameters based on issues that may arise during surgery. Moreover, conventional optimization techniques typically operate in a "black box" manner with little or no explanation regarding recommended parameter values. Thus, if the surgeon decides to deviate from a recommended parameter value, the surgeon typically does so without a full understanding of the effect of that deviation on the rest of the surgical workflow, or the impact of the deviation on the patient's post-surgery quality of life.

To address these and other drawbacks of conventional optimization technology, in some embodiments, optimization may be performed during the surgical workflow using a button or other component in the GUIs presented to the surgeon (e.g., on the Display 125 or the AR HMD 155). For the purposes of the following discussion, a surgeon or other healthcare professional may invoke a request for a recommendation or input from the CASS 100 using any means such as an oral request/command or a manual input (e.g., using a touch screen or button). For purposes of this application, these types of queries or requests for a recommended course of action, a recommended parameter optimization, or other feedback to be provided to the surgeon or medical professional in response to such query or request are referred to as a CASS Recommendation Request or "CASSRR." A CASS Recommendation Request may be invoked or activated by the surgeon or healthcare professional at any time during surgery. For example, for a TKA, a CASSRR may be invoked during the femoral implant planning stage, the tibial implant planning stage, and/or the gap planning stage. In a THA surgery, a CASSRR may be used during femoral neck resection, acetabular implant placement, femoral implant placement, and implant selection (e.g., size, offset, bearing type, etc.). A CASSRR may be invoked, for example, by pushing the button or by speaking a particular command (e.g., "optimize gap"). As noted above, the recommendation system can be configured to offer or prompt the surgeon for a recommendation or optimization at any time during surgery.

Figure 3B:
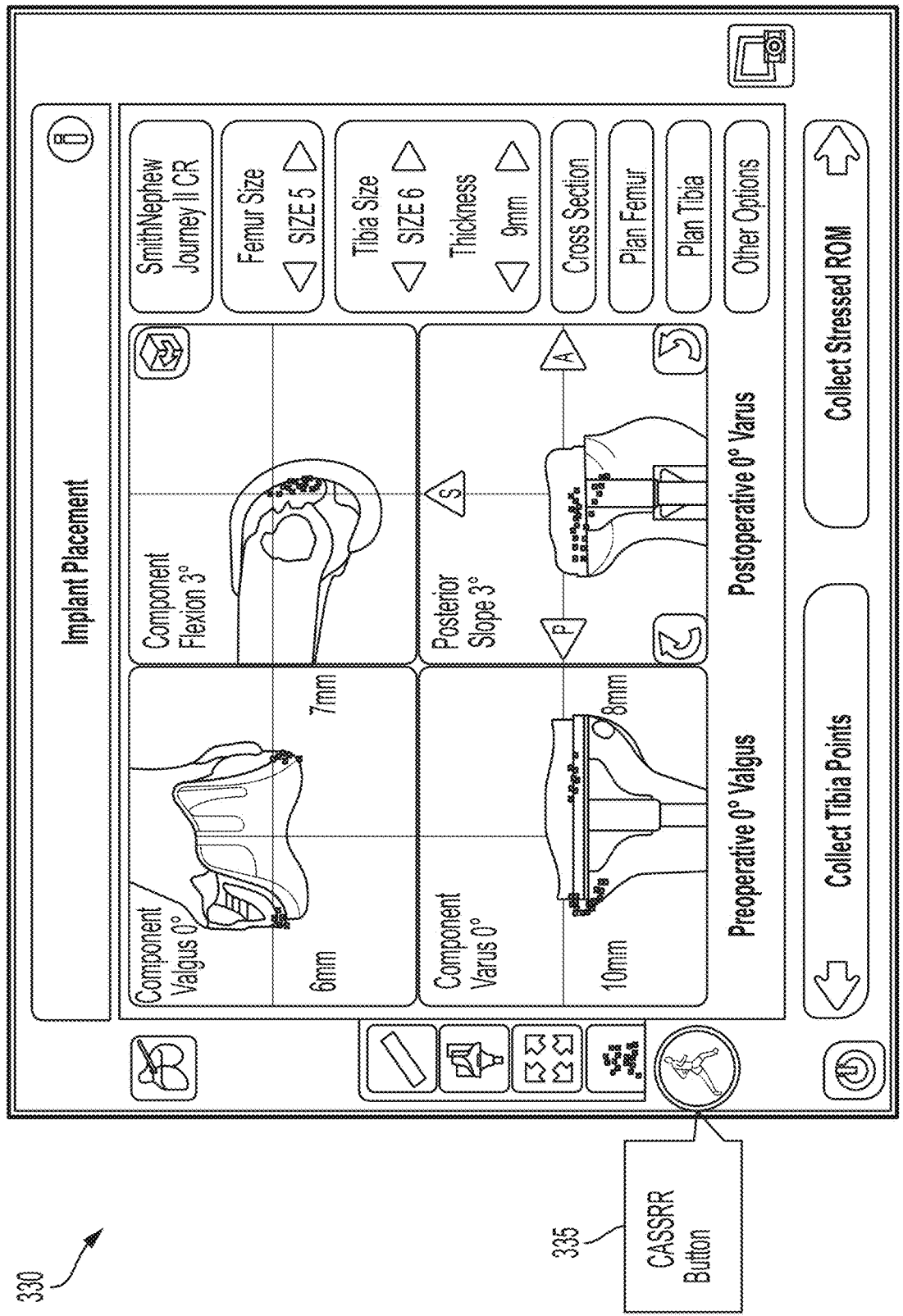
FIG. 3B shows an exemplary Implant Placement Interface, in accordance with some embodiments.
Figure 3C:
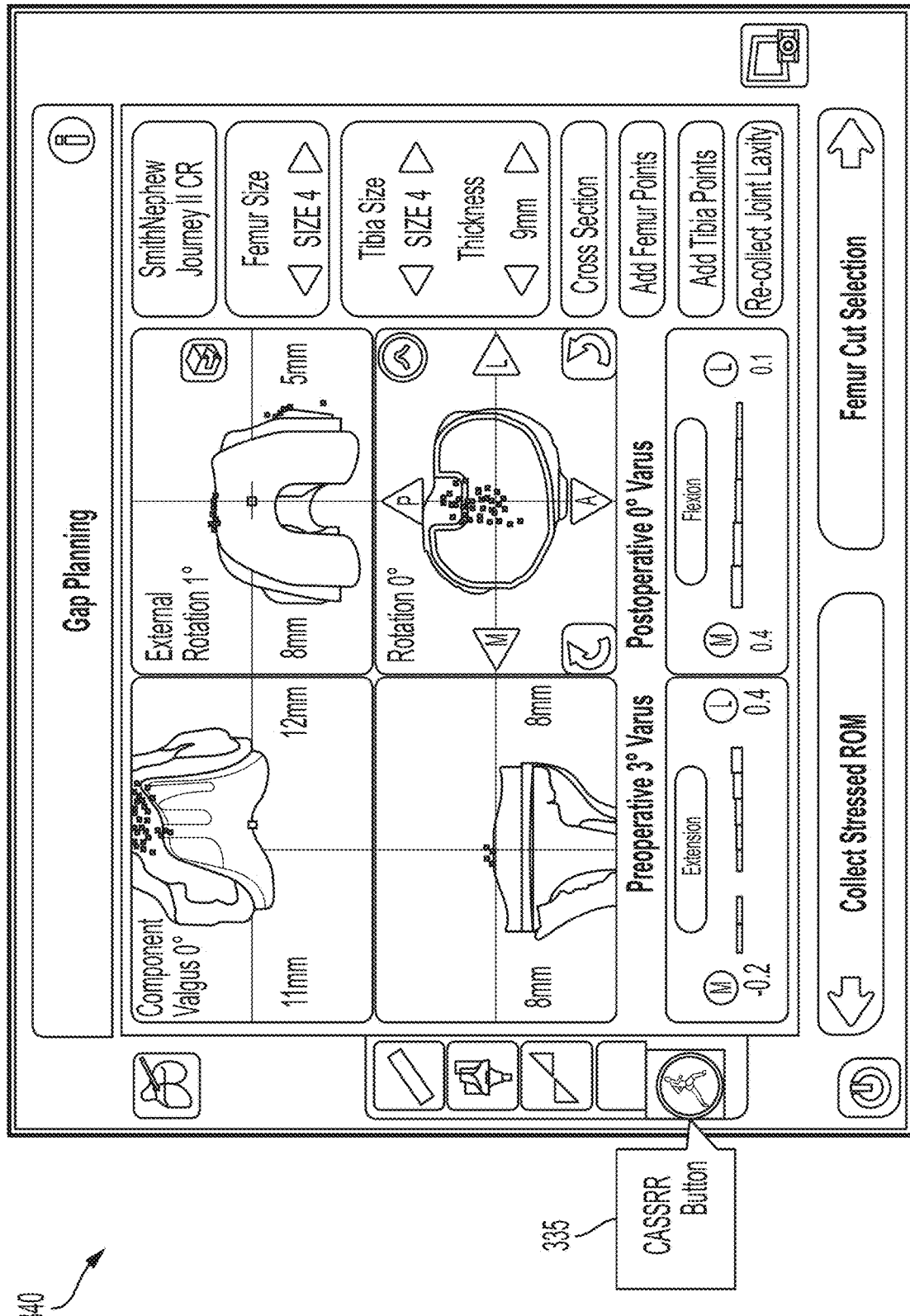
FIG. 3C shows an exemplary Gap Planning Interface, in accordance with some embodiments.

FIGS. 3B-3E show examples of GUIs that may be used during the surgical workflow using a CASS/planning app, such as the one depicted in FIG. 1. These GUIs may be displayed, for example, on the Display 125 of the CASS 100 or on a workstation during the planning stages for an upcoming surgery. In each example, an AI-driven recommendation request may be invoked using a button that is presented as a visual component of the interface. Specifically, FIG. 3B shows an example Implant Placement Interface 330 where a recommendation button 335 (labeled as a CASSRR in this example) is shown in the lower left hand corner. Similarly, FIG. 3C shows an example Gap Planning Interface 340 with the Button 335.

Figure 3D:
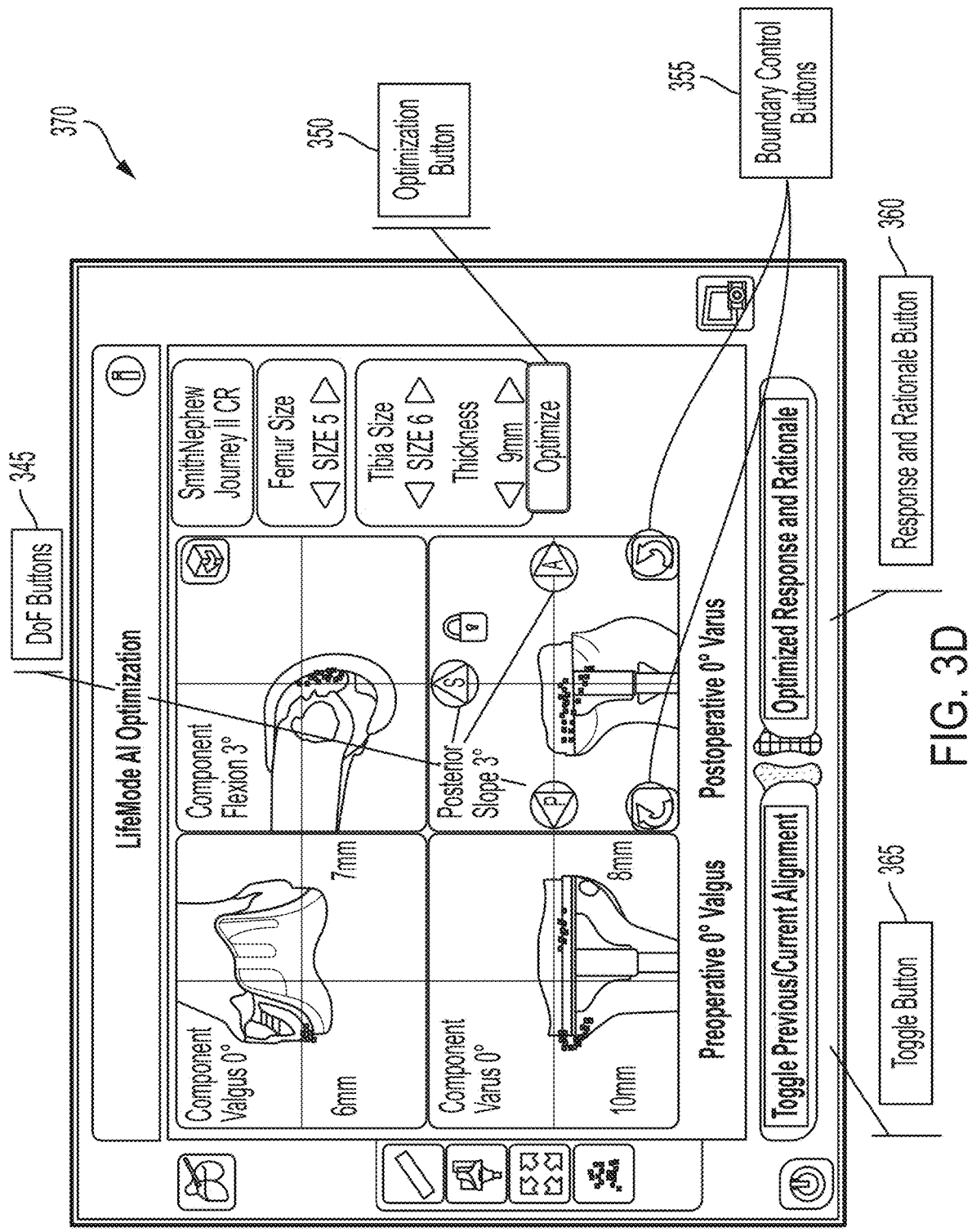
FIG. 3D shows an exemplary Optimization Parameterization Interface, in accordance with some embodiments.

Invoking a CASSRR may cause an Optimization Parameterization Interface 370 to be displayed as shown in FIG. 3D when a user requests a recommendation. In the example of FIG. 3D, a CASSRR/recommendation request is invoked using a button that has been activated on the Implant Placement Interface 330 (shown in FIG. 3B). The Optimization Parameterization Interface 370 includes Degree of Freedom (DoF) Buttons 345 related to movement of the implant (e.g., translation, rotation, etc.). Activation of any of the DoF Buttons 345 "locks" a corresponding degree of freedom during the optimization analysis. For example, if the surgeon is satisfied with the anterior or posterior positioning, the surgeon may activate the "A" Button or the "P" Button to lock the anterior position or the posterior position, respectively. In some embodiments, the locked buttons change color or provide a different type of visual indicator when toggled into the locked position. In the example of FIG. 3D, the "S" button (corresponding to superior positioning) has been locked as shown by the graphical depiction of a lock to the right of the button. It should be noted that the use of buttons for locking positions is but one example of how the surgeon can interface with the CASS 100; in other embodiments, for example, the surgeon may verbally request locking of a particular position (e.g., "lock superior positioning") or, in the VR context, gestures may be employed. The values that can be fixed may depend on available optimization factors and the surgeon's comfort level with optimizing different aspects of the surgery. For example, it has been assumed thus far that the optimization is performed from a wholly functional kinematic perspective. Thus, the optimizing system does not truly understand how the implant interacts with bone. This may be addressed, for example, by adding an image-based analysis to the optimization. However, for embodiments where such analysis is not performed, the surgeon may want to constrain matters based on how he/she views the bone fit. For example, regarding the femoral component of the implant in a TKA surgery, when the optimization is performed, the anterior overhang may not be known. That would imply that the surgeon may want to adjust the A-P position of the femoral component because he or she is viewing the implant in terms of bone fit and not as a function of a kinematic performance. Thus, the surgeon may determine the A-P position, the rotation, and possibly the joint line used in determining the final implant position, orientation and location. In this way, the surgeon can supplement the knowledge provided from a computer-generated optimization run allowing the surgical plan that is implemented by surgeon to deviate from a computational recommendation.

Buttons may also be used to provide boundary controls for a given parameter used for optimization. In the example of FIG. 3D, there are two Boundary Control Buttons 355 for the posterior slope. These can be used to set minimum or maximum values for the relevant parameters that will bound the parameters in an optimization. If the right Boundary Control Button 355 is locked, the optimization can be configured to produce a value above the current value specified for the posterior slope. Conversely, if only the left Boundary Control Button 355 is locked, the optimization can be configured to produce values below the current value specified for posterior slope. If both Boundary Control Buttons 355 are locked, then the optimization is configured such that it does not change the specified posterior slope value. On the other hand, if neither Boundary Control Buttons 355 is locked, then optimization is free to change values (within device specifications).

The Optimization Parameterization Interface 370 includes an Optimization Button 350 that, when activated, causes the implant placement parameters to be optimized using any of the data-drive/AI approaches described herein. It should be noted that this general concept is not limited to implant placement; rather, in general, any surgical parameter, or group of parameters, can be optimized using similar interfaces and techniques. This optimization process is further detailed below. Following optimization, the surgeon may be returned to the Implant Placement Interface 330 (as shown in FIG. 3B) to continue the surgery with the optimal parameters.

A Toggle Button 365 allows the surgeon to toggle between any two views or aspects of the surgical procedure or surgical procedure plan. For example, the Toggle Button 365 can provide the surgeon with the current bone condition and a future bone condition based on the partial or complete execution of the surgical plan or the current planned implant position and an alternative (e.g., recommended) implant position. The Toggle Button 365 could also provide the surgeon with alternative future conditions of the bone and/or implant depending on whether the surgeon elects to take one course of action as opposed to an alternative course of action. Activation of this button causes the various images and data presented on the Optimization Parameterization Interface 370 to be updated with current or previous alignment information. Thus, the surgeon can quickly view the impact of any changes. For example, the toggle feature may allow the surgeon to visualize the prosthesis positioning changes that are suggested by the optimizer relative to their previous notion of proper implant placement. In one embodiment, during initial use of the system, the user may choose to plan the case without optimization, and wish to visualize the impact of automation. Similarly, the user may wish to visualize the impact of 'locking' various aspects of planning.

Figure 3E:
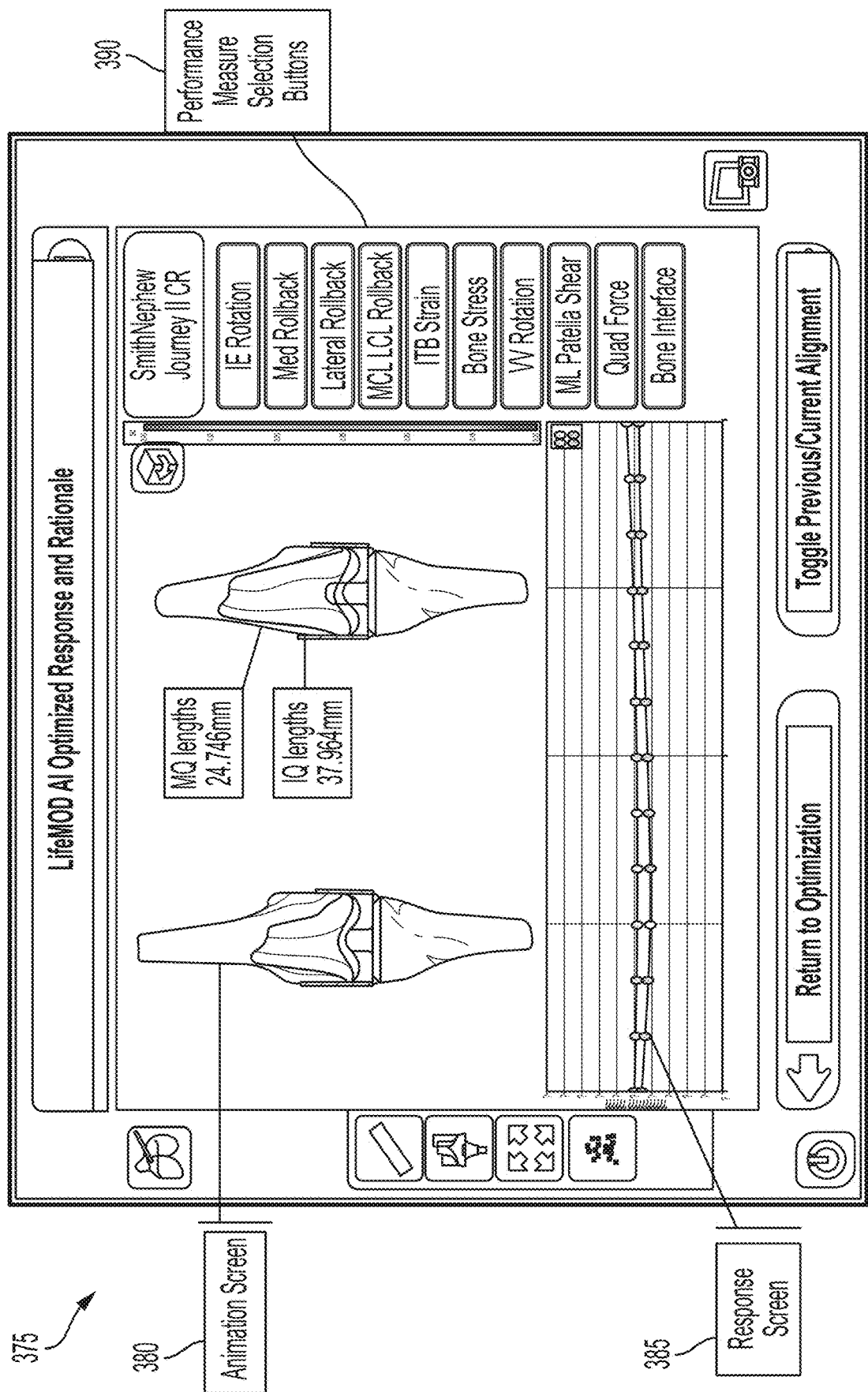
FIG. 3E shows an exemplary Response and Rationale Interface, in accordance with some embodiments.

If the surgeon wishes to understand the rationale behind the optimization, the Response and Rationale Button 360 on the Optimization Parameterization Interface 370 may be activated to display the Response and Rationale Interface 375 shown in FIG. 3E. This interface 375 includes an Animation Screen 380 that provides an animation of the anatomy of interest during the performance measurement activity (e.g., deep knee bend). This animation may be provided as an output of the anatomical modeling software performing the optimization (e.g., LIFEMOD™) or, alternatively, separate software may be used to generate the animation based on the output of the optimization software. The animation may be depicted, for example, using an animated GIF file or a small video file. In embodiments where an AR HMD 155 is used, a hologram of the animation can be provided over the relevant anatomy to provide further contextualization of the simulated behavior.

The Response and Rationale Interface 375 also includes a Response Screen 385 that displays plots for various performance or condition measures (e.g., measure v flexion angle). A set of Performance Measure Selection Buttons 390 on the right-hand side of the Response and Rationale Interface 375 allows the surgeon to select various relevant performance measures and update the plot shown in the Response Screen 385. In the example of FIG. 3E, these performance measures include internal-external (IE) rotation, medial and lateral rollback, MCL and LCL strain, iliotibial band (ITB) strain, bone stress, varus-valgus (V-V) rotation, medial-lateral (ML) patella shear, quayd force, and bone interface forces. The example shown in screen 385 depicts the lateral and medial gaps throughout the range of flexion, which is a traditional estimate of TKA performance. Traditionally, the lateral and medial gaps have only been considered at two degrees of flexion.

In order to support the various interfaces described above, the algorithms supporting a CASSRR/recommendation button should preferably be performed as quickly as possible to ensure that the surgical workflow is not disrupted. However, the calculations involved with performing optimization can be computationally intensive. Thus, to simplify the required processing, a set of predictor equations can be generated based on a training dataset and simulated performance measurements in some embodiments. These predictor equations provide a simplified form of the parameter space that can be optimized in near real-time. These processes can be executed locally or on a remote server, e.g., in the cloud.

Figure 4:
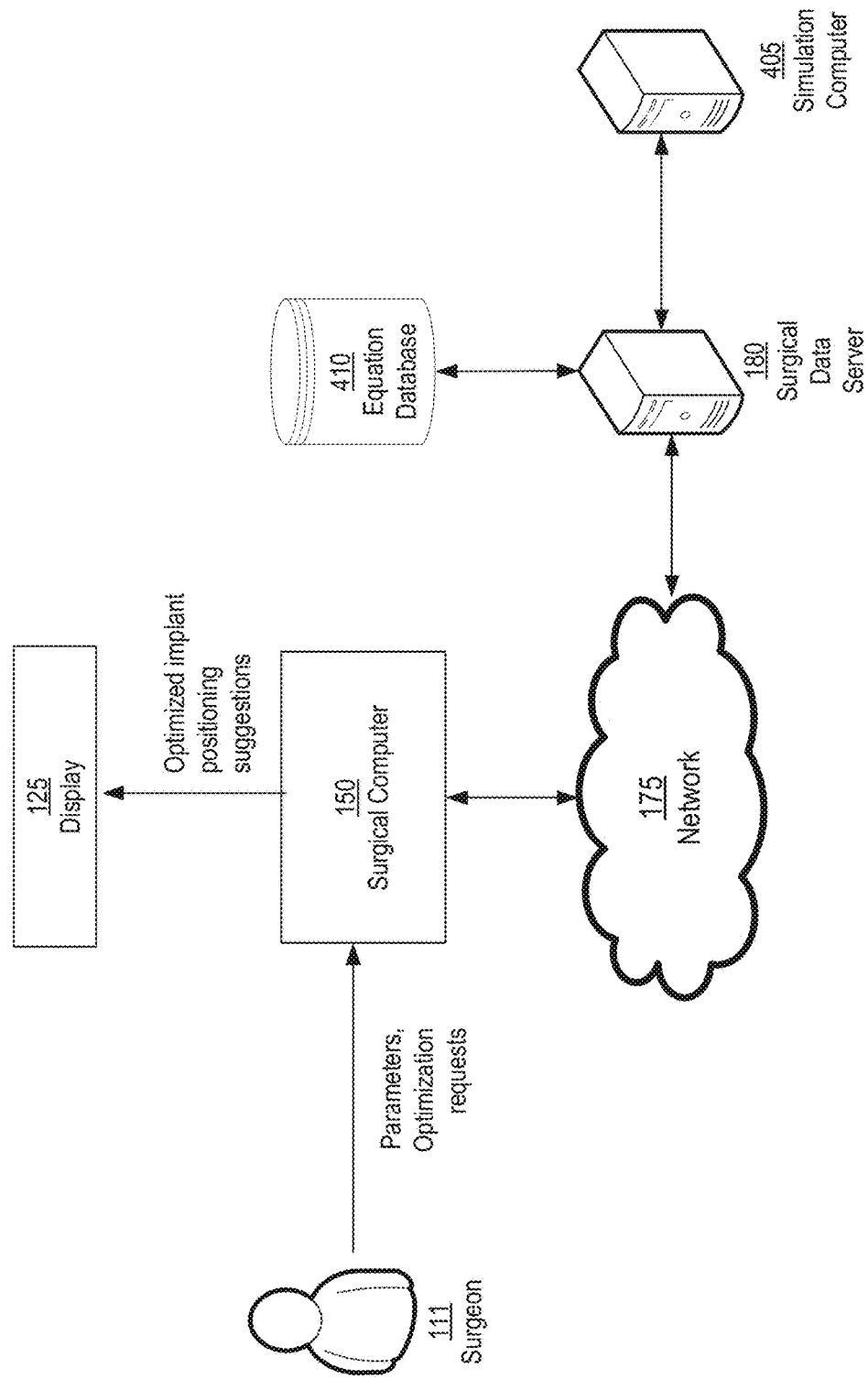
FIG. 4 provides a system diagram illustrating how optimization of surgical parameters can be performed, according to some embodiments.

FIG. 4 provides a system diagram illustrating how optimization of surgical parameters can be performed, according to some embodiments. This optimization can be performed during a preoperative planning stage, such as in embodiments where a custom cutting guide is created before surgery, or intraoperatively, such as in embodiments where a CASS can adjust the exact pose of resection planes robotically or through other practical means, such as haptic feedback. Briefly, the Surgeon 111 provides certain patient-specific parameters and parameters related to the implant to the Surgical Computer 150 (via a GUI presented on the Display 125). The Surgeon 111 requests that optimization be performed. The Surgical Computer 150 uses the parameters to retrieve a set of predictor equations from an Equation Database 410 stored on the Surgical Data Server 180. In embodiments where a cloud-based architecture is not used, this Equation Database 410 may be stored directly on the Surgical Computer 150. Optimization of the equation set provides the desired optimization (e.g., optimal implant alignment and positioning). This information can then be presented to the Surgeon 111 via the Display 125 of the CASS 100 (see, e.g., FIGS. 3D and 3E).

As explained in greater detail below, each equation dataset provides kinematic and kinetic responses for a group of parameters. In some embodiments, the Equation Database 410 is populated using equation datasets derived by a Simulation Computer 405 based on a set of training data. The training dataset comprises surgical datasets previously collected by the CASS 100 or another surgical system. Each surgical dataset may include, for example, information on the patient's geometry, how the implant was positioned and aligned during surgery, ligament tensions, etc. Data may be gathered using any technique known in the art. For example, for ligament tension, a robotic assisted technique may be employed as described in PCT/US2019/067848, filed Dec. 20, 2019, entitled "Actuated Retractor with Tension Feedback," the entirety of which is incorporated herein by reference. An additional example is provided by PCT/US2019/045551 and PCT/US2019/045564, filed Aug. 7, 2019 and entitled "Force-Indicating Retractor Device and Methods of Use," the entirety of which is incorporated herein by reference.

For each surgical dataset, a Simulation Computer 405 executes an anatomical simulation on the surgical dataset to determine a set of kinematic and kinetic responses. Non-limiting examples of suitable anatomical modeling tools that may be used include LIFEMOD™ or KNEESIM™ (both available from LIFEMODELER, INC. of San Clemente, Calif., a subsidiary of SMITH AND NEPHEW, INC.). Additional examples for using biomechanical modeling during surgery are described in U.S. Pat. No. 8,794,977 entitled "Implant Training System"; U.S. Pat. No. 8,712,933 entitled "Systems and methods for determining muscle force through dynamic gain optimization of a muscle PID controller for designing a replacement prosthetic joint"; and U.S. Pat. No. 8,412,669 entitled "Systems and methods for determining muscle force through dynamic gain optimization of a muscle PID controller"; the entire contents of which are incorporated herein by reference.

In addition to determining the responses for the surgical dataset, the Simulation Computer 405 may also be used to supplement the real-world surgical datasets with artificially generated surgical datasets that fill in any gaps in the training dataset. For example, in one embodiment, Monte Carlo analysis is performed using small permutations of various factors in the training set to see how they affect the response. Thus, a relatively small set of real-world surgical data (e.g., 1,000 datasets) can be essentially extrapolated to produce an exponentially larger dataset covering various patient anatomies, implant geometries, etc. Once the dataset has been populated, one or more equation fitting techniques generally known in the art may be used to derive the equation datasets stored in the Equation Database 410.

In order to determine the kinematic and kinetic responses used in each equation dataset, the simulation executed by the Simulation Computer 405 may model and simulate various activities that stress the anatomy of interest. For example, in the context of TKA or other knee surgeries, a weighted deep knee bend may be used. During a deep knee bend, the knee flexes down at various angles (e.g., 120°, 130°, etc.) under a certain load and returns to an erect position. During the deep knee bend, loads occur on the extensors of the leg (i.e., quadriceps), the flexors of the leg (i.e., hamstrings), the passive ligaments in the knee, etc. As such, the deep knee bend stresses the anterior cruciate ligament (ACL), posterior cruciate ligament (PCL), lateral collateral ligament (LCL) and medial collateral ligament (MCL). Additionally, the deep knee bend allows the measurement of various kinematics (e.g., how the patella is moving in relation to the femoral component, how the femur is moving with respect to the tibia, etc.). It should be noted that this is one example of a performance measurement that may be applied and various other measurements may be used as a supplement or alternative to the deep knee bend. The knee kinematics can further be simulated using the model of the knee to perform approximately real-world motions associated with dynamic activities, such as walking up or down stairs or swinging a golf club. Other joints can be simulated in the body as simple ideal components while the individual ligaments of concern and implant components can be simulated in detail performing the motion under exemplary loads associated with each activity being considered.

Figure 5A:
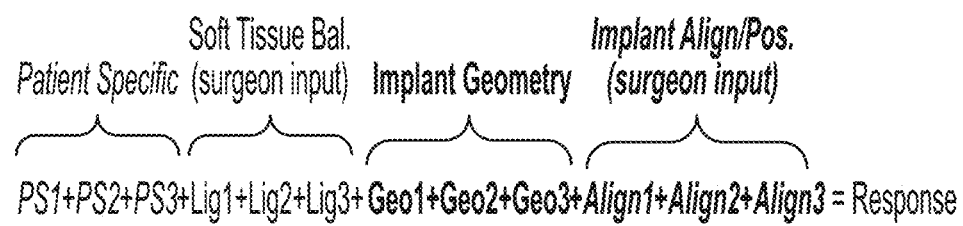

FIGS. 5A-5F describe an exemplary joint predictor equation that may be used in an equation dataset in some embodiments. While these figures will be described with respect to knee arthroplasty, these concepts apply equally to other arthroplasties, such as hip. Regardless of the arthroplasty being performed, the basic categories can be the same, with the specific data in each category relevant to the surgery being performed. FIG. 5A provides an overview of the knee predictor equation. As will be explained below, the terms of this equation are simplified to allow for understanding of the various terms. Thus, it should be understood that the exact mathematical constructs may differ from those shown in the figures.

In these predictor equations, the terms on the left-hand side are referred to as "factors," while the terms on the right-hand side are referred to as "responses." The responses and factors may be associated with specific numerical values, although, in at least some embodiments, at least some may be represented as a probability distribution (such as a bell curve) or in another manner reflecting uncertainty about the actual value of the factor or response. As such, the equations may account for uncertainty in certain aspects of this process. For instance, in at least some embodiments, it may be difficult to identify soft tissue attachment locations with certainty, and, accordingly, uncertainty information may be used reflecting a probability distribution of where such soft tissue attachment locations are actually located based on estimated locations identified during image processing. Similarly, in at least some embodiments, rather than determining an exact optimal position and orientation for the orthopedic implant, it may be desirable to determine optimal position and orientation in the context of potential for variability in where the implant will actually be positioned and oriented (e.g., to account for tolerances in manufacturing custom cutting guide instrumentation, variability in surgeons' surgical techniques, etc.).

FIG. 5B illustrates the patient-specific parameters used in the knee predictor equation. These parameters may be measured by the surgical staff based on pre-operative or intra-operative data. As shown in the example of FIG. 5B, an X-Ray measurement tool may be used to measure various anatomical features in images. Examples of patient-specific parameters that may be utilized include load-bearing access (LBA), pelvis width, femoral ML width, tibial ML width, femur length, etc.

Figure 5C:
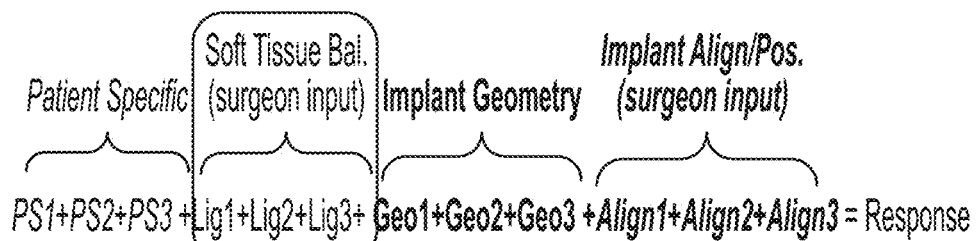

FIG. 5C shows the soft tissue balance parameters that are included in the knee predictor equations. The soft tissue balance parameters may be derived from multiple sources. For example, by default, the parameters may be derived from an atlas of landmarks based on the patient's bone geometry. This may be supplemented with the results of an anterior drawer test, varus-valgus stability measurements, tissue attachment estimates, and tissue condition measurements (e.g., stiffness), etc. Data may also be supplemented with intra-operatively acquired data, such as joint distraction tests, instrumented tibial inserts, force sensing gloves, etc.

Figure 5D:
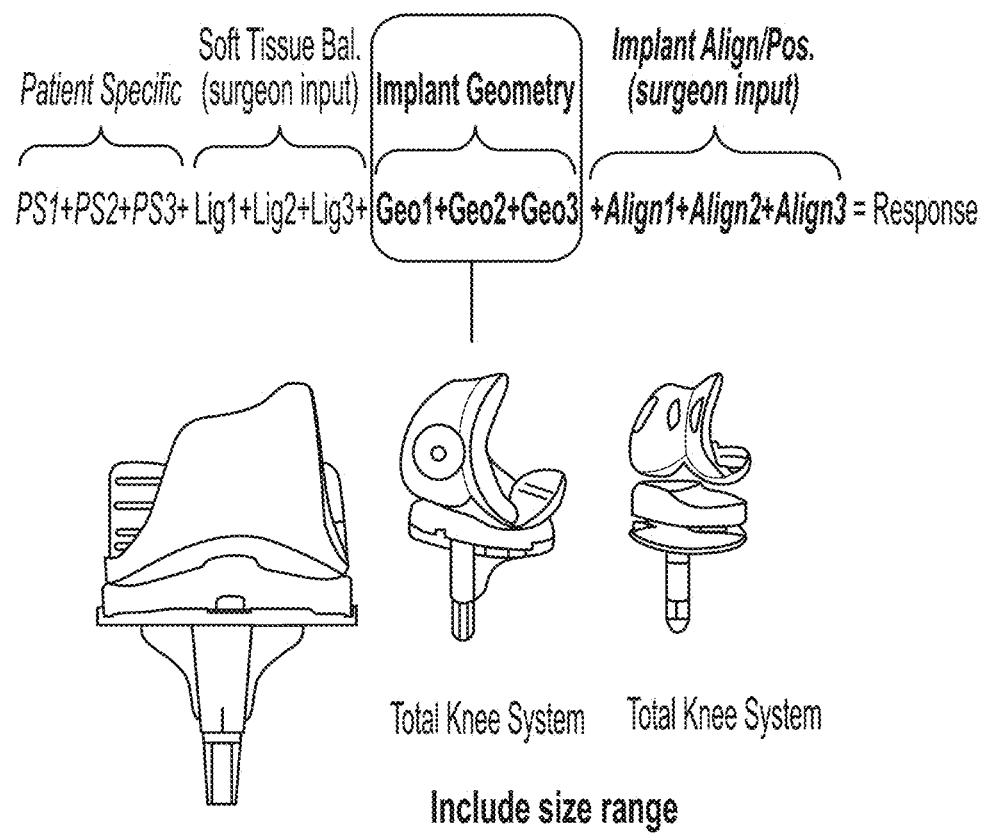

FIG. 5D shows the implant geometry parameters of the knee predictor equation. These parameters may include, for example, the femoral and tibial gaps, the distal or posterior radii, patellar geometry and alignment or stuffing, and the femoral anterior-posterior/lateral-medial placement of the implant. It should be noted that there may be a number of possible implants for a given patient (e.g., models, sizes, etc.). As such, different knee predictor equations may be designed with the same patient-specific and tissue balance parameters, but different implant geometry parameters. For example, a range of sizes may be represented by a set of key predictor equations. In some embodiments, the implant geometry can be determined programmatically using anatomical modeling software such as LIFEMOD™. Example techniques for optimizing parameters relating to the anatomic and biomechanical fit of an implant or implant system implanted into the patient's joint are described in U.S. patent application Ser. No. 13/814,531, which was previously incorporated herein by reference.

Figure 5E:
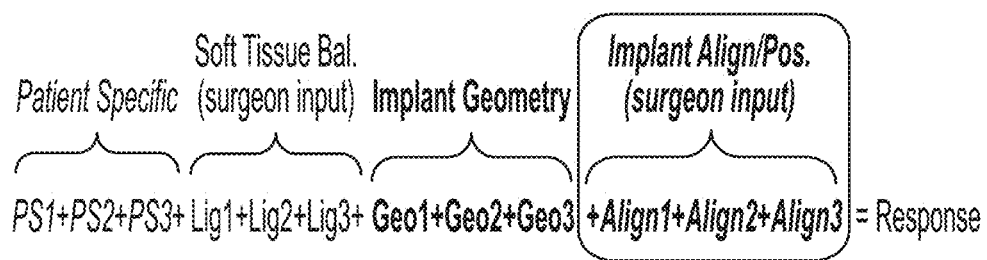

FIG. 5E shows the implant alignment and positioning parameters that may be used in the knee predictor equation. As noted above, these may be used as variables during the optimization. As shown in FIG. 5E, example parameters include the femoral superior-inferior (S-I) position, the femoral anterior-posterior (A-P) position, the femoral varus-valgus (V-V) position, the femoral internal-external (I-E) position, the tibial posterior slope, the tibial V-V position, the tibial I-E position, and the tibial depth as determined by the extension gap.

FIG. 5F shows the response portion of the knee predictor equation. The response may include a dataset comprising kinematics data and kinetics data related to the knee. The kinematics data provides a measurement of how the kinematics of a specific patient and component set compared to a specified goal. For example, the kinematics may measure the internal-external rotation of the femoral component with respect to the tibia, and what that signature looks like over the flexion history of a deep knee bend event. This can then be compared to a goal measurement of the internal-external rotation. This concept can be extended to the patella and other anatomy related to knee motion. The kinetics data provides a measure of the loads on the various components of the knee (e.g., LCL, MCL, etc.). As shown in FIG. 5F, the simulation derives this data for several different degrees of knee flexion (e.g., 30, 60, 90, 120, etc.). Thus, for a given set of parameters on the left-hand side of the equation, a set of equations may be specified with different response values.

Figure 6:
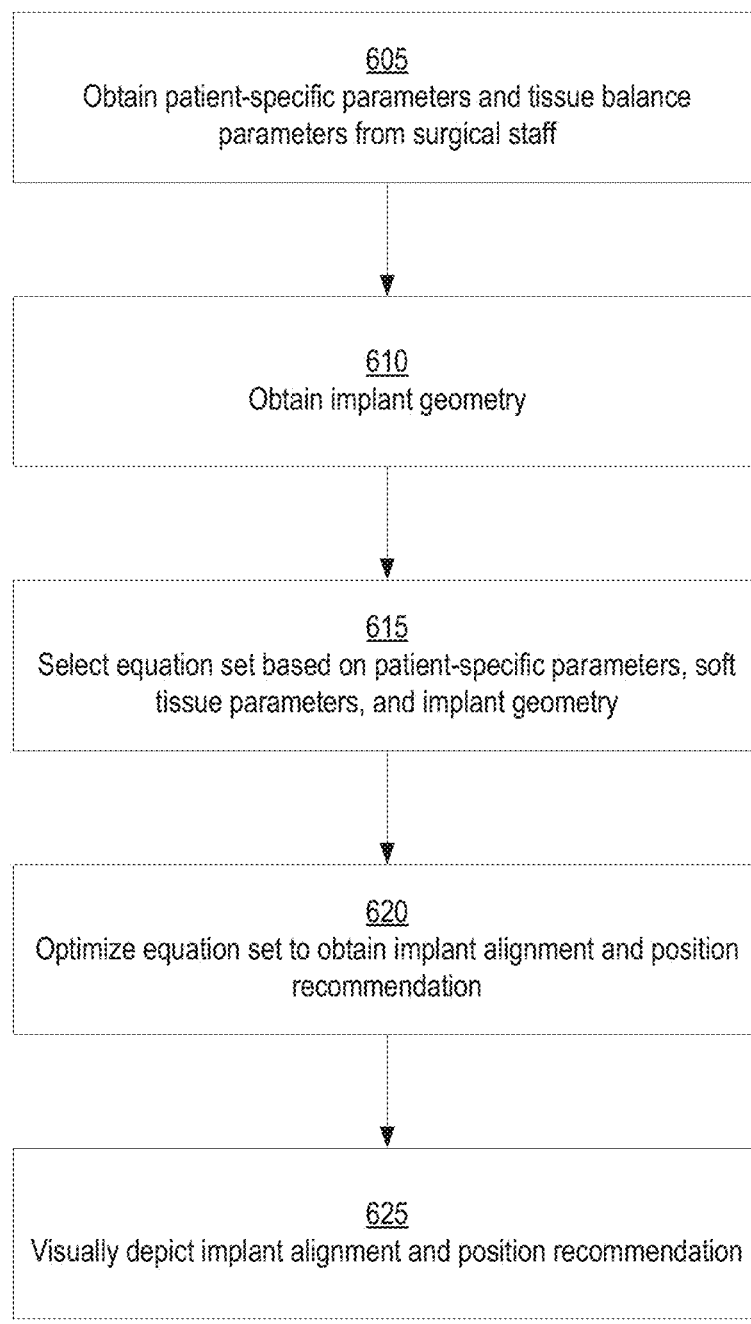
FIG. 6 is a flow chart illustrating a process by which the optimization of an equation set may be performed, according to some embodiments.

FIG. 6 illustrates a process by which the optimization of the equation set may be performed, according to some embodiments. Starting at step 605, the patient-specific parameters and the soft tissue balance parameters are entered by the surgical staff. As noted above, the patient-specific parameters may be derived based on any combination of pre-operative and intra-operative data. The tissue balance parameters are measured by the surgeon (or default values may be used). At step 610, the implant geometry or implant make, model, and manufacturer and product ID are entered by the surgical staff. In some embodiments, the surgical staff may manually enter each of the implant geometry parameters. In other embodiments, the surgical staff may specify a particular implant make, model, and/or size (e.g., SMITH & NEPHEW, GENESIS® II left femoral implant, size 6) and the appropriate implant parameters (e.g., geometry, dimensions, or other implant characteristics) can be retrieved from a local or remote database.

Continuing with reference to FIG. 6, at step 615, the equation set is selected based on the patient-specific parameters, soft tissue parameters and implant geometry. The equation set includes one or more predictor equations with each equation providing a different response value. Next, at step 620, the equation set is optimized to obtain the implant alignment and position recommendation. In at least some embodiments, it may not be possible to perfectly solve all of the equations because the factors may impact on the various responses in different ways. As such, in some embodiments, the responses may be associated with weighted values such that the optimization process accords greater weight to certain responses than others. These weighted values may act as desirability factors or functions quantifying the relative importance of the various responses. For example, in some embodiments, the optimization is performed using a Goal Programming (GP) algorithm in which the weights of response variables are obtained through a Group Decision Making (GDM) process. Finally, at step 625, the implant alignment and position recommendation are visually depicted, for example, on the Display 125 of the CASS 100.

In some embodiments, the relationship(s) between the factors and responses may be defined by a set of trained neural networks rather than a series of equations. Similar statistical and modeling tools to those described above may be used to define and train the neural networks and the factors used therein. In some embodiments, tools such as NEUROSOLUTIONS 6.0, available from NEURODIMENSIONS, INC. of Gainesville, Fla., may further facilitate the development and training of the neural networks. In some embodiments, a database of information collected from previous orthopedic procedures or studies may be used to train the neural networks, and, as additional data is collected over time, the neural networks may be further refined to enhance the optimization processes described herein. In some embodiments, kernel methods may be used to explore the relationship(s) between the factors and responses. Kernel-based learning algorithms may be used to solve complex computational problems, to detect and exploit complex patterns in the data by clustering, classifying, etc.

In some embodiments, the relationship(s) between the factors and responses may be defined by one or more trained support vector machines. Like some neural networks, a support vector machine may be trained to recognize patterns in existing data, such as data collected from previous orthopedic procedures or studies, and, once trained, used to predict responses for an orthopedic procedure for a particular patient based on settings for certain factors.

Although the discussion above was directed to recommendations in the context of knee surgeries, the factors and responses used in the predictor equations can be modified as needed based on the anatomy that is the subject of the surgical procedure. For example, surgeries to repair a torn or injured anterior cruciate ligament ("ACL") could benefit from the use of the CASS and CASSRR concepts described above. The application of robotic surgical systems to ACL surgeries are described in PCT/US2019/048502, entitled "Robotic Assisted Ligament Graft Placement and Tensioning", and filed on Aug. 28, 2019, which was previously incorporated by reference in its entirety.

Another surgical intervention that could benefit from the use of the CASS and CASSRR concepts described above is a high tibial osteotomy ("HTO") procedure. In a HTO procedure, a cut in the tibia is made and a wedge of bone may be removed from or added to the cut in the tibia to better align the tibia and femur in the knee joint. For example, CASSRR could be used to optimize the amount of bone that is added or removed to achieved the desired kinetic response (i.e., unload the affected compartment to delay further cartilage damage). Additionally, changes in tibial slope, which are difficult to plan, can be simulated and robotically implemented.

In the context of a THA procedure, the "implant alignment/position" factors discussed above with respect to FIG. 5E can be replaced with parameters such as cup inclination, cup anteversion, cup size, cup depth, bearing type (traditional, ceramic on ceramic, dual mobility, resurfacing, etc.), femoral stem design, femoral stem version, combined anteversion, femoral stem size, femoral stem offset (STD, HIGH), and femoral head offset. Another component of implant alignment/position could be screw placement. The software may make recommendations for how many screws should be used, the length and trajectory of each screw, as well as problem areas to avoid (soft tissue, blood vessels, etc.) For a hip revision surgery, the "implant geometry" factors can be modified to make recommendations for which type of acetabular or femoral components would best fill in the missing anatomy.

Furthermore, although the recommendation system was discussed above with respect to the generation of intraoperative recommendations, it should be noted that recommendations may also be applied during the pre-operative and post-operative stages of the episode of care. For example, based on pre-operative data and historical data, a recommended surgical plan can be developed. Similarly, if a surgical plan is already generated, recommendations may be generated based on changed circumstances that occurred after the pre-operative data was generated. Post-surgery, the data gathered during the earlier stages of the episode of care can be used to generate a recommended post-operative rehabilitation protocol (e.g., goals, exercises, etc.). Examples of data that can affect the rehab protocol include, without limitation, implant make and size, operative time, tourniquet time, tissue release, and the intraoperative flexion. Aside from the activities of the rehab protocol, the devices used for rehab and recovery could also be customized based on the episode of care data. For example, in one embodiment, the episode of care data is used to generate designs for custom shoe inserts that can be 3D printed for the patient. In addition to generating post-operative recommendations for the patient, the post-operative episode of care data can also be used as a feedback mechanism into the CASSRR to further refine the machine learning models used to provide recommendations for performing surgical procedures on other patients.

Slider Interfaces for Providing Interactive Anatomical Modeling Data

Figures 1, 7A:
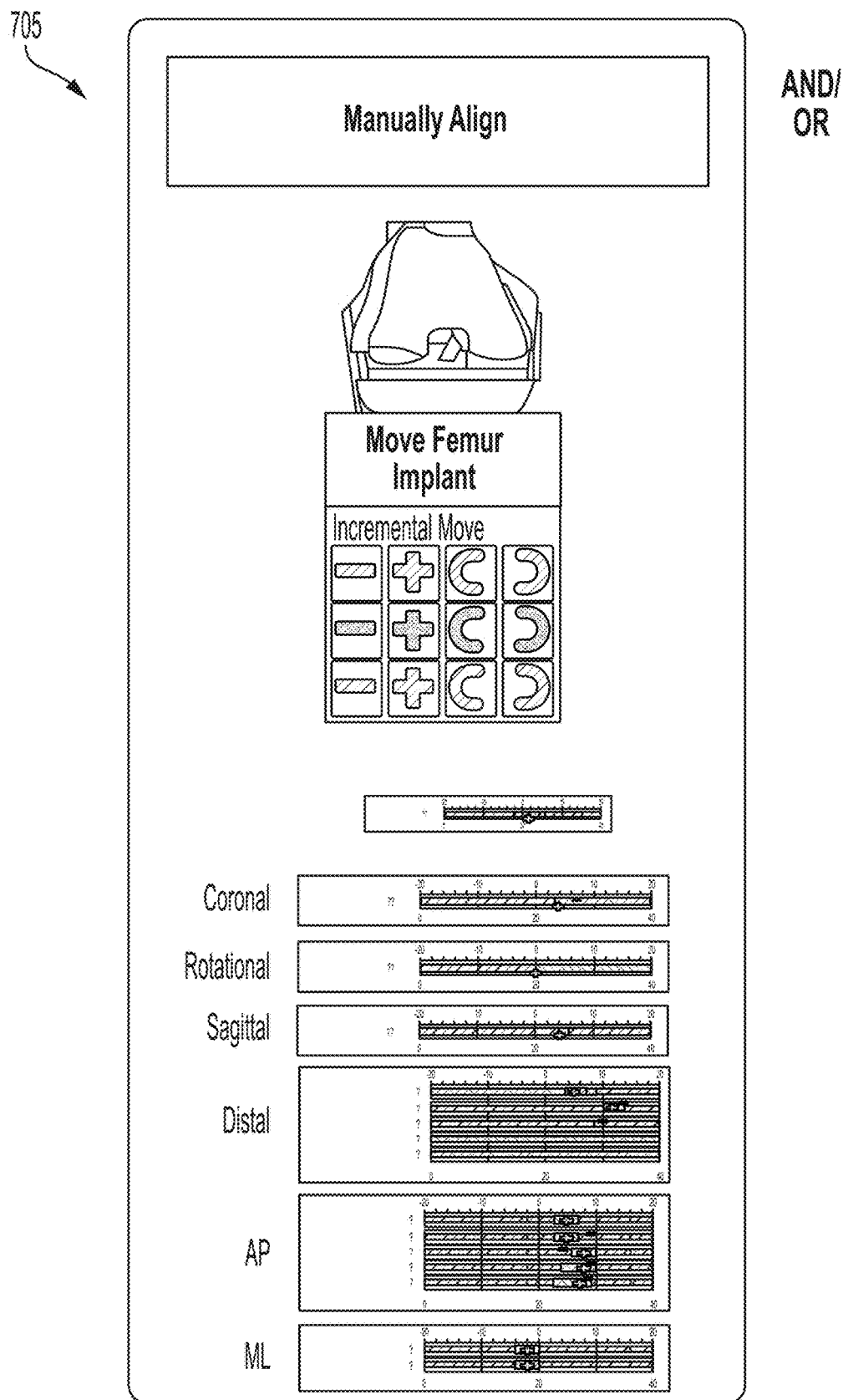

In some embodiments, as an alternative or supplement to the interfaces described above, dynamic sliders can be used to depict various measurements as shown in FIG. 7A. While FIG. 7A continues with the example of knee implant alignment, it should be understood that the general concept illustrated in FIG. 7A can be applied to various types of measurements performed during surgery or a preoperative stage. As depicted in FIG. 7A, the surgeon either manually aligns the implant (as depicted in image 705) or uses the optimization process described above (shown in image 710) to manipulate the implant on the display screen to produce the responses 715. In this case, the responses 715 are shown as a plurality of sliders with settings corresponding to a plurality of flexion angles (30, 60, 90, and 120 degrees). These sliders are "dynamic" in the sense that they are updated in real-time as the surgeon changes the alignment. Thus, for example, if the surgeon makes a manual movement 705 of the implant, the responses 715 would be recalculated, and each slider would be updated accordingly.

Figures 2, 7A:
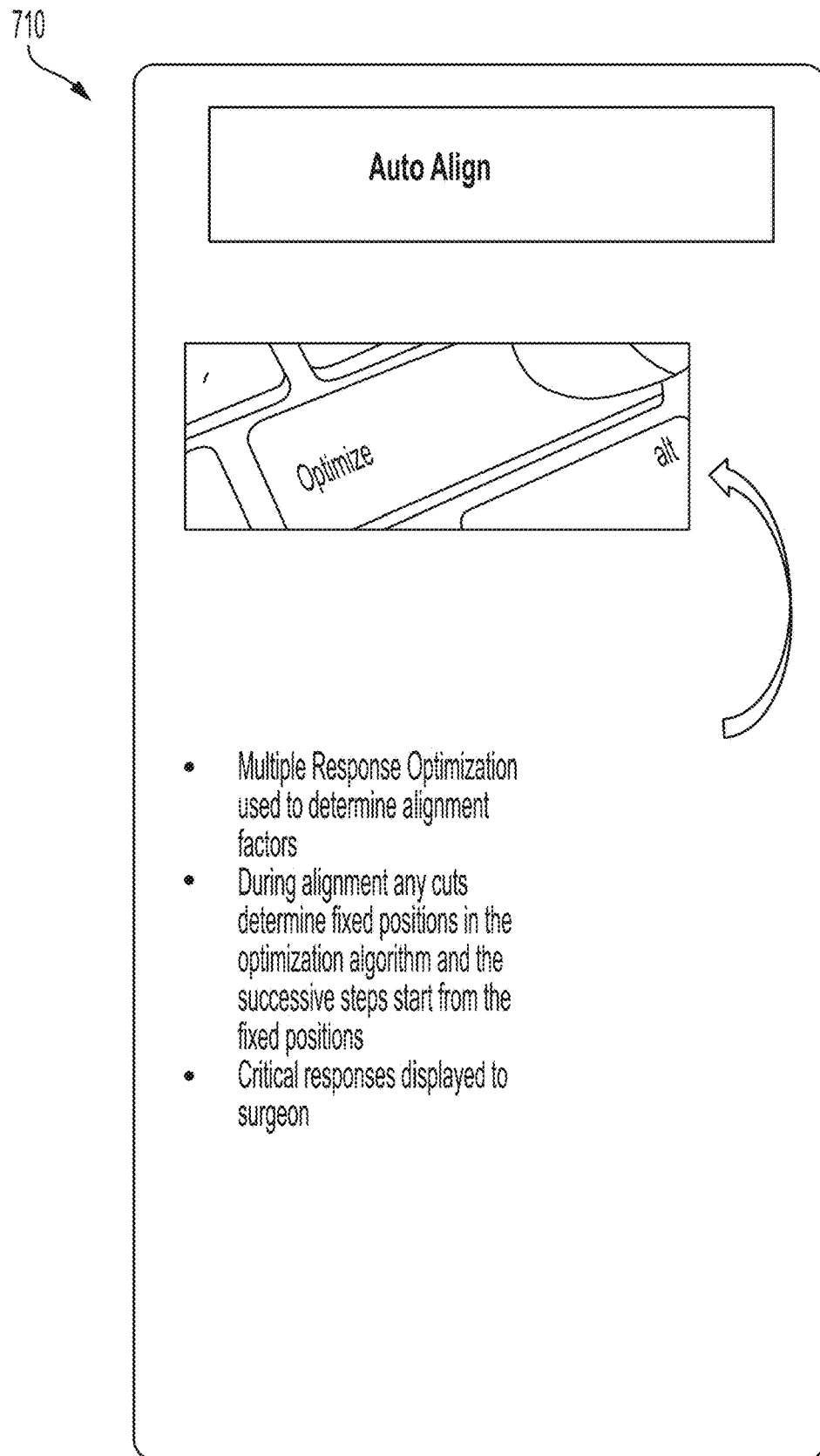
Figures 3, 7A:
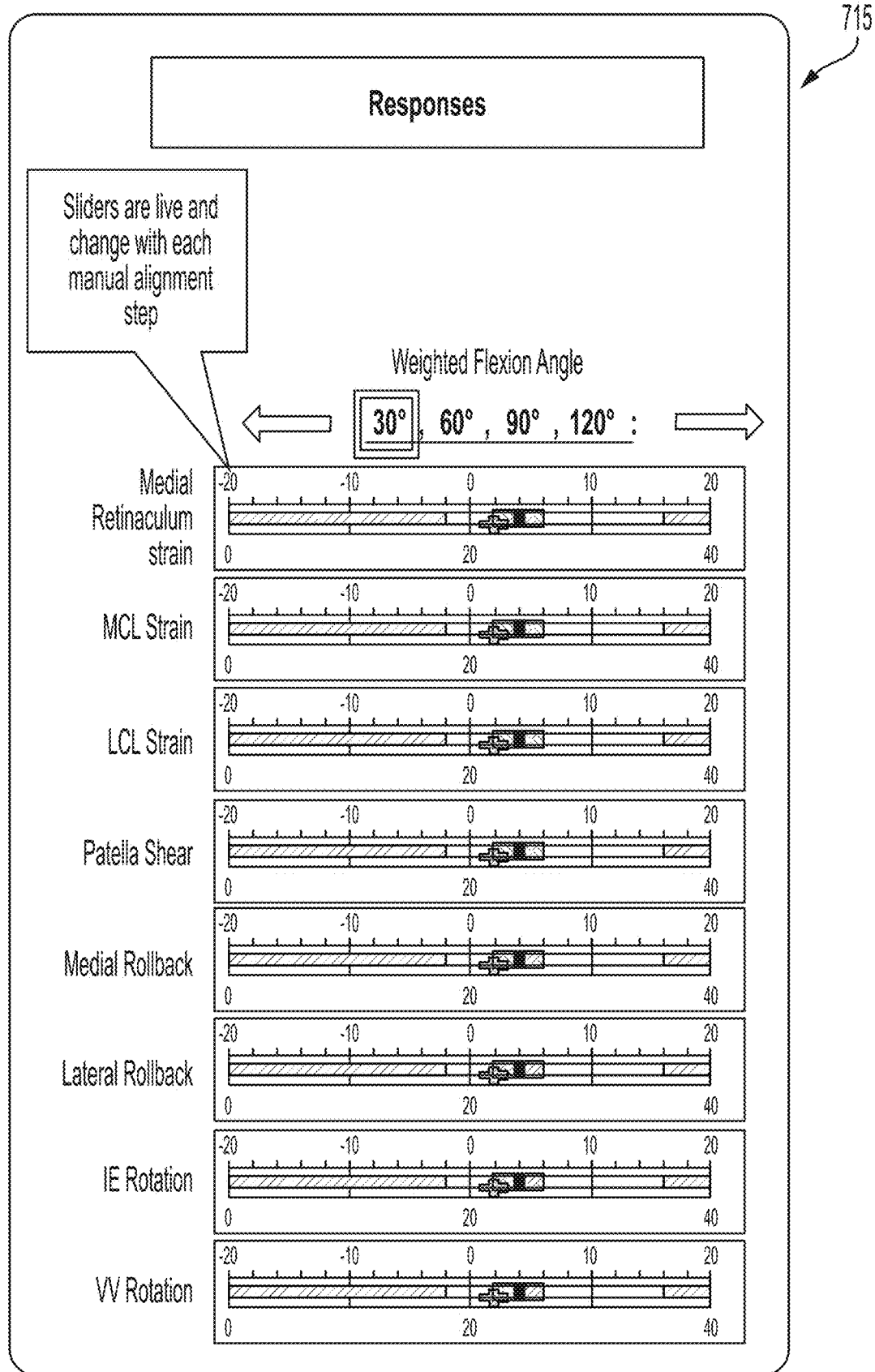
Figure 7B:
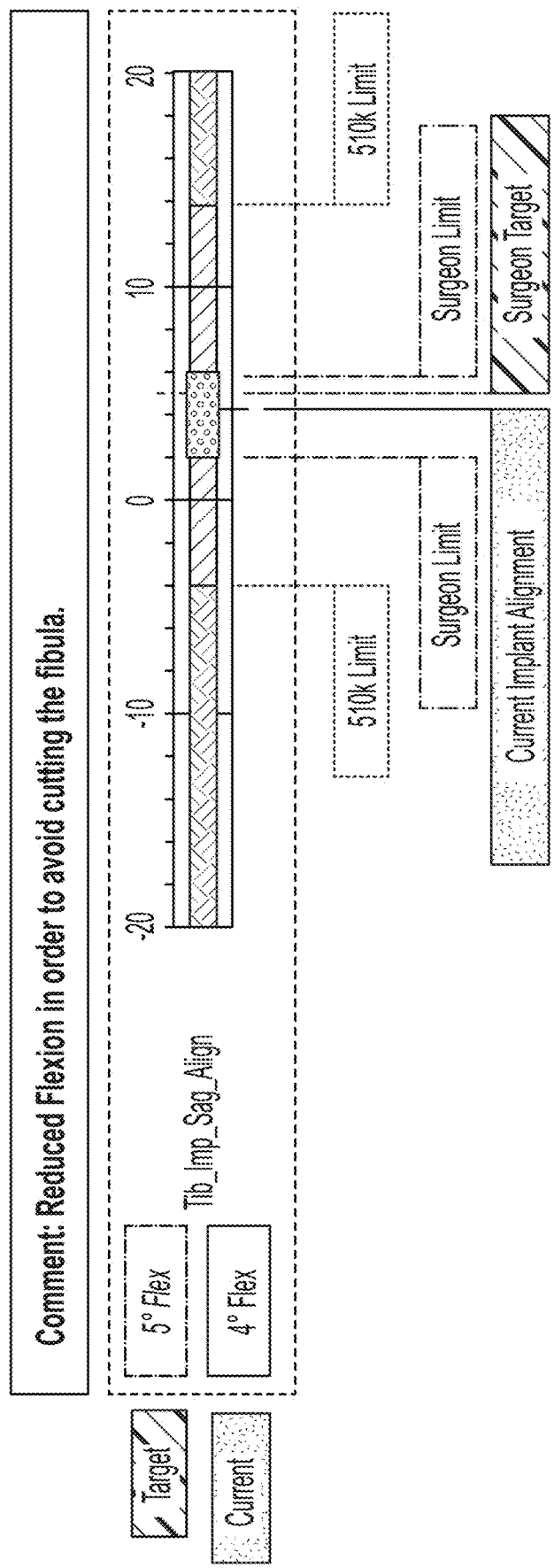

FIG. 7B provides further illustration of the contents of the slider showing the tibial implant sagittal alignment response. As depicted in FIG. 7B, the desired or preferred alignment configuration is 5 degree flexion but the current flexion measurement is only 4 degrees. An indication, prompt, or comment may be provided to indicate that flexion should be altered (e.g., reduced or increased) in order to avoid cutting the fibula. The current implant alignment is depicted with a tick mark on the lower portion of the slider, while the surgeon's target of 5 degrees is shown as a tick mark on the upper portion of the slider. FDA 510(k) limits (which define the allowable parameters to comply with FDA regulations) are shown with an outer bar overlaid on the slider.

In the example of FIG. 7B, the slider also includes an inner bar overlaid on the slider showing the surgeon's limits for the response value. These limits can be derived or ascertained either by review and analysis of certain historical data accessible from the CASS (i.e., limits from past surgeries) or the surgical staff or other technician may input this information prior to surgery. In some embodiments, each limit is not provided explicitly; rather, the limit is derived from a general set of instructions provided by the surgeon. For example, in one embodiment, the surgeon or the surgeon's staff provides a textual description of the surgeon's preferences. Then, a natural language processing algorithm is applied to extract relevant information from the text. Based on the extracted text, the rules for generating the text are generated. The following table provides an example set of rules generated based on the shown input text.

| Input Text | Rules |
|---|---|
| Wants to align to the neutral mechanical axis. Keep between 3 and 7 degrees. Let surgeon decide if a collet is necessary. "Have a gravitational pull towards 5 degrees" but does not necessarily want a 5 degree collet. He said if it measures 9 degrees, make it 7 degrees. If it measures 7 degrees, make it 6 degrees. If measured femur valgus angle is less than 5 degrees, match raster. If femur valgus angle is out of the ordinary (less than 3 degrees, more than 7 degrees) contact surgeon. | Fem Imp Val Ang Targ = Fem Imp Val Ang LSL IF (Fem Val Ang Meas < Fem Imp Val Ang LSL)<br>Fem Imp Val Ang Targ = Fem Val Ang Meas IF AND ( Fem Val Ang Meas ≥ Fem Imp Val Ang LSL, Fem Val Ang Meas ≤ 5° valgus)<br>Fem Imp Val Ang Targ = 7° valgus IF AND (Fem Val Ang Meas > 7° valgus, Fem Val Ang Meas ≤ 7° valgus + 3° valgus)<br>Fem Imp Val Ang Targ = Fem Val Ang Meas + 1° varus IF (Fem Val Ang Meas > 5.9° valgus, Fem Val Ang Meas ≤ 7° valgus)<br>Fem Imp Val Ang Targ = Fem Val Ang Meas + 3° varus IF (Fem Val Ang Meas > 7° valgus + 3° valgus)<br>Fem Imp Val Ang LSL = 3° valgus<br>Fem Imp Val Ang USL = EMPTY |

Operative Patient Care System

Figure 8:
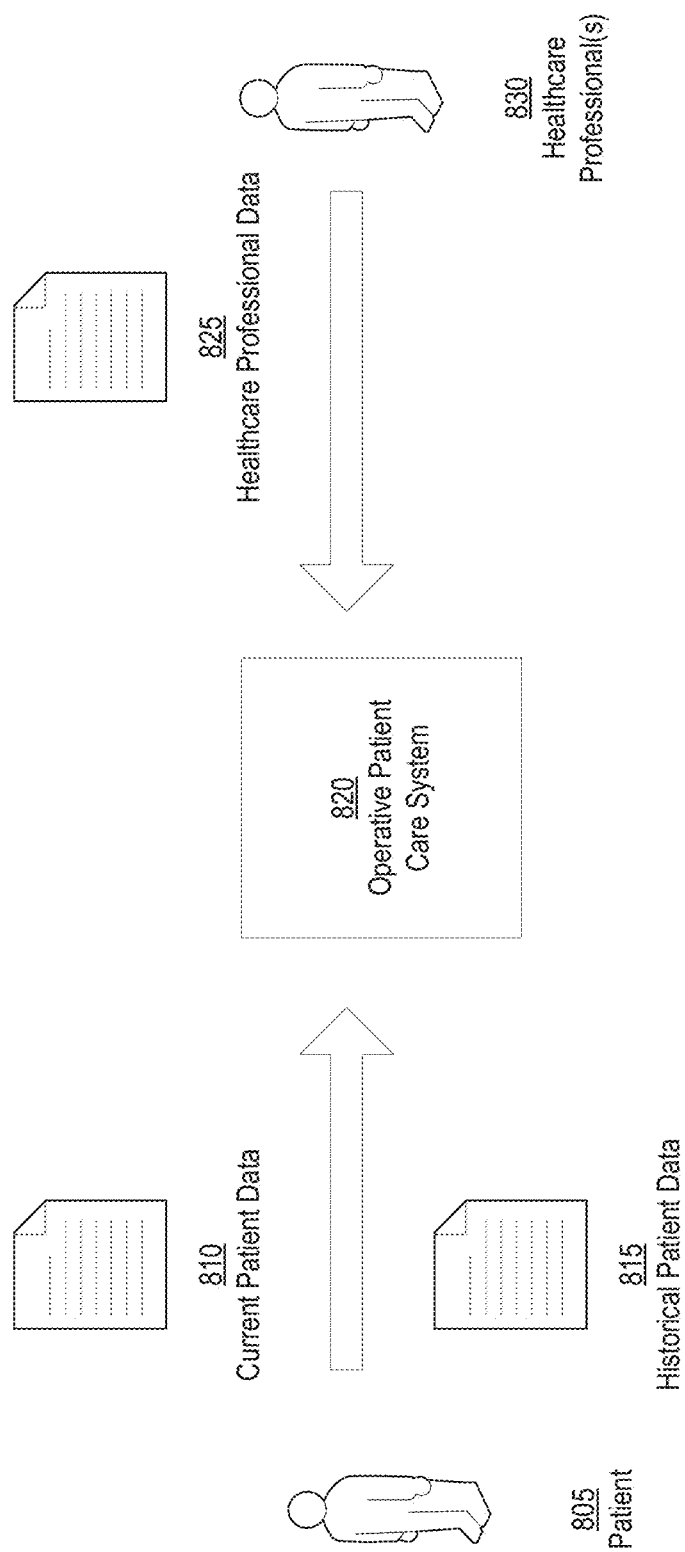
FIG. 8 provides an overview of an exemplary Operative Patient Care System, for use with some embodiments.

The general concepts of optimization may be extended to the entire episode of care using an Operative Patient Care System 820 that uses the surgical data, and other data from the Patient 805 and Healthcare Professionals 830 to optimize outcomes and patient satisfaction as depicted in FIG. 8.

Conventionally, pre-operative diagnosis, pre-operative surgical planning, intra-operative execution of a prescribed plan, and post-operative management of total joint arthroplasty are based on individual experience, published literature, and training knowledge bases of surgeons (ultimately, tribal knowledge of individual surgeons and their 'network' of peers and journal publications) and their native ability to make accurate intra-operative tactile discernment of "balance" and accurate manual execution of planar resections using guides and visual cues. This existing knowledge base and execution is limited with respect to the outcomes optimization offered to patients needing care. For example, limits exist with respect to accurately diagnosing a patient to the proper, least-invasive prescribed care; aligning dynamic patient, healthcare economic, and surgeon preferences with patient-desired outcomes; executing a surgical plan resulting in proper bone alignment and balance, etc.; and receiving data from disconnected sources having different biases that are difficult to reconcile into a holistic patient framework. Accordingly, a data-driven tool that more accurately models anatomical response and guides the surgical plan can improve the existing approach.

The Operative Patient Care System 820 is designed to utilize patient specific data, surgeon data, healthcare facility data, and historical outcome data to develop an algorithm that suggests or recommends an optimal overall treatment plan for the patient's entire episode of care (preoperative, operative, and postoperative) based on a desired clinical outcome. For example, in one embodiment, the Operative Patient Care System 820 tracks adherence to the suggested or recommended plan, and adapts the plan based on patient/care provider performance. Once the surgical treatment plan is complete, collected data is logged by the Operative Patient Care System 820 in a historical database. This database is accessible for future patients and the development of future treatment plans. In addition to utilizing statistical and mathematical models, simulation tools (e.g., LIFEMOD®) can be used to simulate outcomes, alignment, kinematics, etc., based on a preliminary or proposed surgical plan, and reconfigure the preliminary or proposed plan to achieve desired or optimal results according to a patient's profile or a surgeon's preferences. The Operative Patient Care System 820 ensures that each patient is receiving personalized surgical and rehabilitative care, thereby improving the chance of successful clinical outcomes and lessening the economic burden on the facility associated with near-term revision.

In some embodiments, the Operative Patient Care System 820 employs a data collecting and management method to provide a detailed surgical case plan with distinct steps that are monitored and/or executed using a CASS 100. The performance of the user(s) is calculated at the completion of each step and can be used to suggest changes to the subsequent steps of the case plan. Case plan generation relies on a series of input data that is stored on a local or cloud-storage database. Input data can be related to both the current patient undergoing treatment and historical data from patients who have received similar treatment(s).

A Patient 805 provides inputs such as Current Patient Data 810 and Historical Patient Data 815 to the Operative Patient Care System 820. Various methods generally known in the art may be used to gather such inputs from the Patient 805. For example, in some embodiments, the Patient 805 fills out a paper or digital survey that is parsed by the Operative Patient Care System 820 to extract patient data. In other embodiments, the Operative Patient Care System 820 may extract patient data from existing information sources, such as electronic medical records (EMRs), health history files, and payer/provider historical files. In still other embodiments, the Operative Patient Care System 820 may provide an application program interface (API) that allows the external data source to push data to the Operative Patient Care System. For example, the Patient 805 may have a mobile phone, wearable device, or other mobile device that collects data (e.g., heart rate, pain or discomfort levels, exercise or activity levels, or patient-submitted responses to the patient's adherence with any number of pre-operative plan criteria or conditions) and provides that data to the Operative Patient Care System 820. Similarly, the Patient 805 may have a digital application on his or her mobile or wearable device that enables data to be collected and transmitted to the Operative Patient Care System 820.

Current Patient Data 810 can include, but is not limited to, activity level, preexisting conditions, comorbidities, prehab performance, health and fitness level, pre-operative expectation level (relating to hospital, surgery, and recovery), a Metropolitan Statistical Area (MSA) driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels of pain or discomfort, care infrastructure information (payer coverage type, home health care infrastructure level, etc.), and an indication of the expected ideal outcome of the procedure.

Historical Patient Data 815 can include, but is not limited to, activity level, preexisting conditions, comorbidities, prehab performance, health and fitness level, pre-operative expectation level (relating to hospital, surgery, and recovery), a MSA driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels or pain or discomfort, care infrastructure information (payer coverage type, home health care infrastructure level, etc.), expected ideal outcome of the procedure, actual outcome of the procedure (patient reported outcomes [PROs], survivorship of implants, pain levels, activity levels, etc.), sizes of implants used, position/orientation/alignment of implants used, soft-tissue balance achieved, etc.

Healthcare Professional(s) 830 conducting the procedure or treatment may provide various types of data 825 to the Operative Patient Care System 820. This Healthcare Professional Data 825 may include, for example, a description of a known or preferred surgical technique (e.g., Cruciate Retaining (CR) vs Posterior Stabilized (PS), up- vs down-sizing, tourniquet vs tourniquet-less, femoral stem style, preferred approach for THA, etc.), the level of training of the Healthcare Professional(s) 830 (e.g., years in practice, fellowship trained, where they trained, whose techniques they emulate), previous success level including historical data (outcomes, patient satisfaction), and the expected ideal outcome with respect to range of motion, days of recovery, and survivorship of the device. The Healthcare Professional Data 825 can be captured, for example, with paper or digital surveys provided to the Healthcare Professional 830, via inputs to a mobile application by the Healthcare Professional, or by extracting relevant data from EMRs. In addition, the CASS 100 may provide data such as profile data (e.g., a Patient Specific Knee Instrument Profile) or historical logs describing use of the CASS during surgery.

Information pertaining to the facility where the procedure or treatment will be conducted may be included in the input data. This data can include, without limitation, the following: Ambulatory Surgery Center (ASC) vs hospital, facility trauma level, Comprehensive Care for Joint Replacement Program (CJR) or bundle candidacy, a MSA driven score, community vs metro, academic vs non-academic, postoperative network access (Skilled Nursing Facility [SNF] only, Home Health, etc.), availability of medical professionals, implant availability, and availability of surgical equipment.

These facility inputs can be captured by, for example and without limitation, Surveys (Paper/Digital), Surgery Scheduling Tools (e.g., apps, Websites, Electronic Medical Records [EMRs], etc.), Databases of Hospital Information (on the Internet), etc. Input data relating to the associated healthcare economy including, but not limited to, the socioeconomic profile of the patient, the expected level of reimbursement the patient will receive, and if the treatment is patient specific may also be captured.

These healthcare economic inputs can be captured by, for example and without limitation, Surveys (Paper/Digital), Direct Payer Information, Databases of Socioeconomic status (on the Internet with zip code), etc. Finally, data derived from simulation of the procedure is captured. Simulation inputs include implant size, position, and orientation. Simulation can be conducted with custom or commercially available anatomical modeling software programs (e.g., LIFE-MOD®, AnyBody, or OpenSIM). It is noted that the data inputs described above may not be available for every patient, and the treatment plan will be generated using the data that is available.

Prior to surgery, the Patient Data 810, 815 and Healthcare Professional Data 825 may be captured and stored in a cloud-based or online database (e.g., the Surgical Data Server 180 shown in FIG. 2C). Information relevant to the procedure is supplied to a computing system via wireless data transfer or manually with the use of portable media storage. The computing system is configured to generate a case plan for use with a CASS 100. Case plan generation will be described hereinafter. It is noted that the system has access to historical data from previous patients undergoing treatment, including implant size, placement, and orientation as generated by a computer-assisted, patient-specific knee instrument (PSKI) selection system, or automatically by the CASS 100 itself. To achieve this, case log data is uploaded to the historical database by a surgical sales rep or case engineer using an online portal. In some embodiments, data transfer to the online database is wireless and automated.

Historical data sets from the online database are used as inputs to a machine learning model such as, for example, a recurrent neural network (RNN) or other form of artificial neural network. As is generally understood in the art, an artificial neural network functions similar to a biologic neural network and is comprised of a series of nodes and connections. The machine learning model is trained to predict one or more values based on the input data. For the sections that follow, it is assumed that the machine learning model is trained to generate predictor equations. These predictor equations may be optimized to determine the optimal size, position, and orientation of the implants to achieve the best outcome or satisfaction level.

Figure 9:
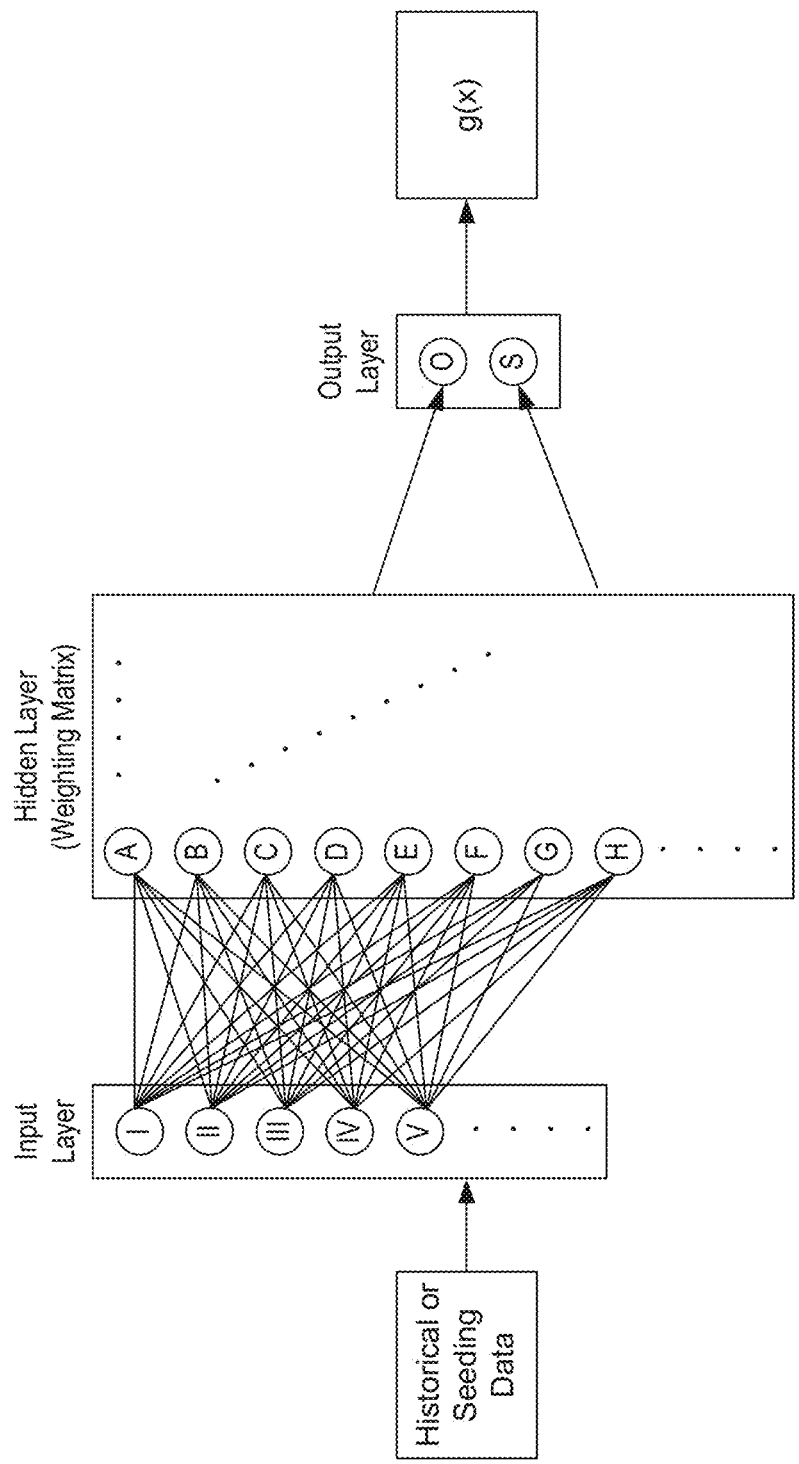
FIG. 9 provides an overview of or a machine learning algorithm, for use with some embodiments.

FIG. 9 shows an example of using seeding data to determine the predictor equation from machine learning according to some embodiments. Input signals comprising information from the online database (described previously) are introduced to the system as input nodes. Each input node is connected to a series of downstream nodes for calculation in the hidden layer. Each node is generally represented by a real number (typically between 0 and 1), but the connections between nodes also have weighting values that change as the system 'learns'. To train the system, a set of seeding or training data is supplied with associated known output values. Seeding data is iteratively passed to the system and the inter-node weighting values are altered until the system provides a result that matches the known output. In this embodiment, the weighting values in the hidden layer of the network are captured in a weighting matrix that can be used to characterize the performance of the surgery. The weighting matrix values are used as coefficients in a predictor equation that relates database inputs to outcomes and satisfaction. Initially, the RNN will be trained with seeding data developed through clinical studies and registry data. Once a sufficient number of cases have been established in the database, the system will use historical data for system improvement and maintenance. Note that the use of a RNN will act as a filter to determine which input data have a large effect on outputs. The system operator may choose a sensitivity threshold so that input data that does not have a significant effect on output can be disregarded and no longer captured for analysis.

Figure 10:
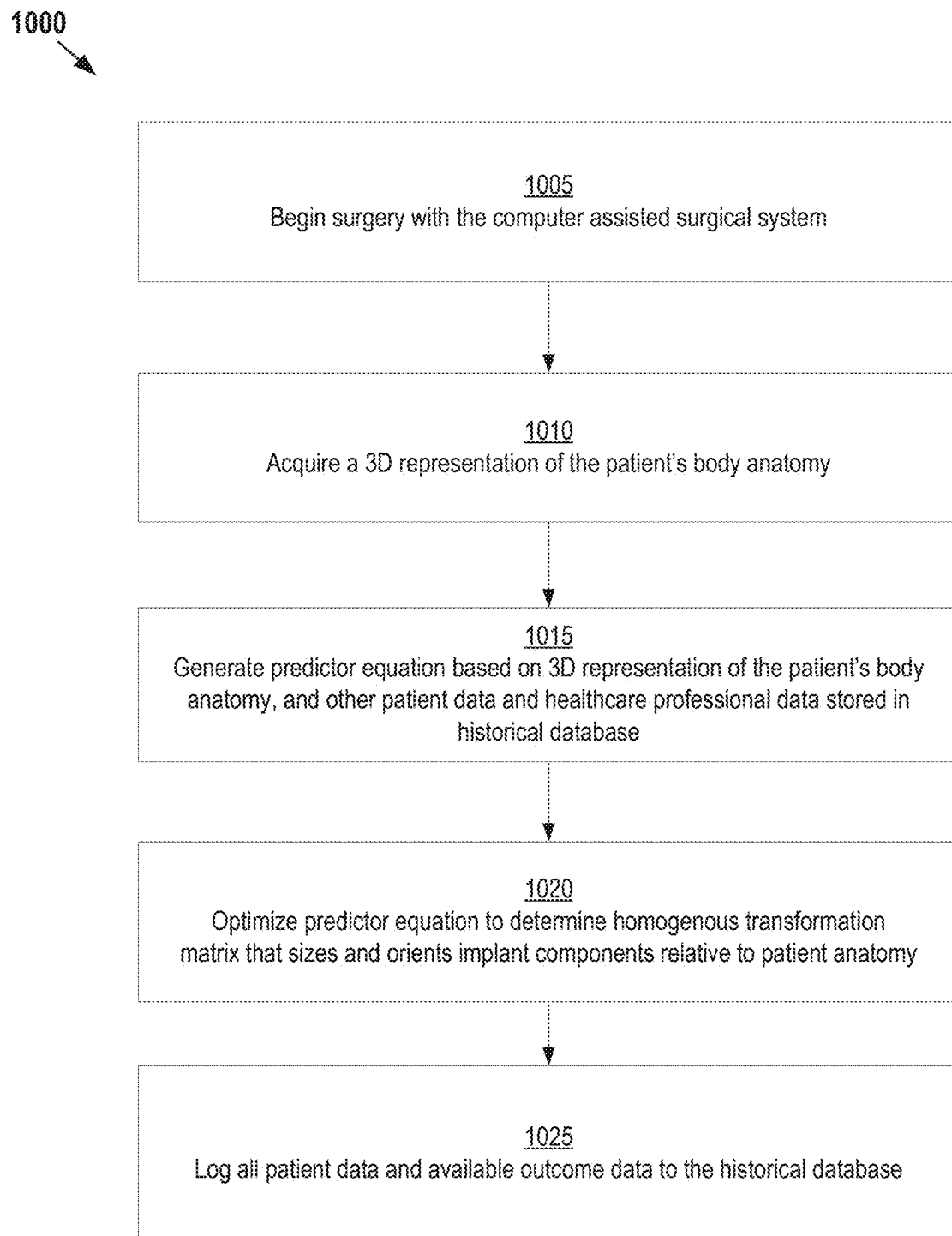
FIG. 10 is a flow chart illustrating operation of an exemplary Operative Patient Care System, for use with some embodiments.

FIG. 10 shows embodiments 1000 of how the Operative Patient Care System 820 can be used in surgery, according to some embodiments. Starting at step 1005, the surgical staff begins the surgery with the CASS. The CASS may be an image-based or imageless system, as is generally understood in the art. Regardless of the type of system employed, at step 1010, the surgical staff can access or acquire a 3D representation of the patient's relevant body anatomy (traditional probe painting, 3D imaging mapped with references, visual edge detection, etc.). In many cases, the 3D representation of the anatomy can be mathematically accomplished by capturing a series of Cartesian coordinates that represent the tissue surface. Example file formats include, without limitation, .stl, .stp, .sur, .igs, .wrl, .xyz, etc. The 3D representation of the patient's relevant body anatomy may be generated pre-operatively based on image data, for example, or the 3D representation can be generated intraoperatively using the CASS.

Certain input data for the current patient can be loaded on a computing system, for example, through wireless data transfer or the use of portable storage media. The input file is read into the neural network and a resulting predictor equation is generated at step 1015. Next, at step 1020, global optimization of the predictor equation (e.g., using direct Monte-Carlo sampling, stochastic tunneling, parallel tempering, etc.) is conducted to determine the optimal size, position, and orientation of the implants to achieve the best outcome or satisfaction level and determine the corresponding resections to be performed based on the implant size, position, and orientation. During the optimization phase, the system operator may choose to ignore aspects of the equation. For example, if the clinician feels that inputs relating to the patient's economic status are not relevant, the coefficients related to these inputs can be removed from the equation (e.g., based on input provided through a GUI of the CASS 100).

In some embodiments, the predictor equation is not calculated using a RNN, but instead with a design of experiments (DOE) method. A DOE will provide sensitivity values relating each of the input values to an output value. Significant inputs are combined in a mathematical formula that was previously described as a predictor equation.

Regardless of how the predictor equation is configured or determined, optimization of this equation can provide recommended, preferred or optimized implant positioning, for example, in the form of a homogenous transformation matrix. The transform mathematically sizes and orients the implant components relative to the patient anatomy. Boolean intersection of the implant geometry and patient anatomy creates a volumetric representation of the bone to be removed. This volume is defined as the "cutting envelope." In many commercially available orthopedic robotic surgical systems, the bone removal tool is tracked relative to the patient anatomy (with optical tracking and other methods). Using position feedback control, the speed or depth of the cutting tool is modulated based on the tool's position within the cutting envelope (i.e., the cutting tool will spin when the position of the tool end is within the cutting envelope and will stop or retract when its position is outside of the cutting envelope).

Once the procedure is complete, at step 1025, all patient data and available outcome data, including the implant size, position and orientation determined by the CASS, are collected and stored in the historical database. Any subsequent calculation of the target equation via the RNN will include the data from the previous patient in this manner, allowing for continuous improvement of the system.

In addition to, or as an alternative to determining implant positioning, in some embodiments, the predictor equation and associated optimization can be used to generate the resection planes for use with a PSKI system. When used with a PSKI system, the predictor equation computation and optimization are completed prior to surgery. Patient anatomy is estimated using medical image data (x-ray, CT, MRI). Global optimization of the predictor equation can provide an ideal size and position of the implant components. Boolean intersection of the implant components and patient anatomy is defined as the resection volume. PSKI can be produced to remove the optimized resection envelope. In this embodiment, the surgeon cannot alter the surgical plan intraoperatively.

The surgeon may choose to alter the surgical case plan at any time prior to or during the procedure. If the surgeon elects to deviate from the surgical case plan, the altered size, position, and/or orientation of the component(s) is locked, and the global optimization is refreshed based on the new size, position, and/or orientation of the component(s) (using the techniques previously described) to find the new ideal position of the other component(s) and the corresponding resections needed to be performed to achieve the newly optimized size, position and/or orientation of the component(s). For example, if the surgeon determines that the size, position and/or orientation of the femoral implant in a TKA needs to be updated or modified intraoperatively, the femoral implant position is locked relative to the anatomy, and the new optimal position of the tibia will be calculated (via global optimization) considering the surgeon's changes to the femoral implant size, position and/or orientation. Furthermore, if the surgical system used to implement the case plan is robotically assisted (e.g., as with NAVIO® or the MAKO Rio), bone removal and bone morphology during the surgery can be monitored in real time. If the resections made during the procedure deviate from the surgical plan, the subsequent placement of additional components may be optimized by the processor taking into account the actual resections that have already been made.

Figure 11A:
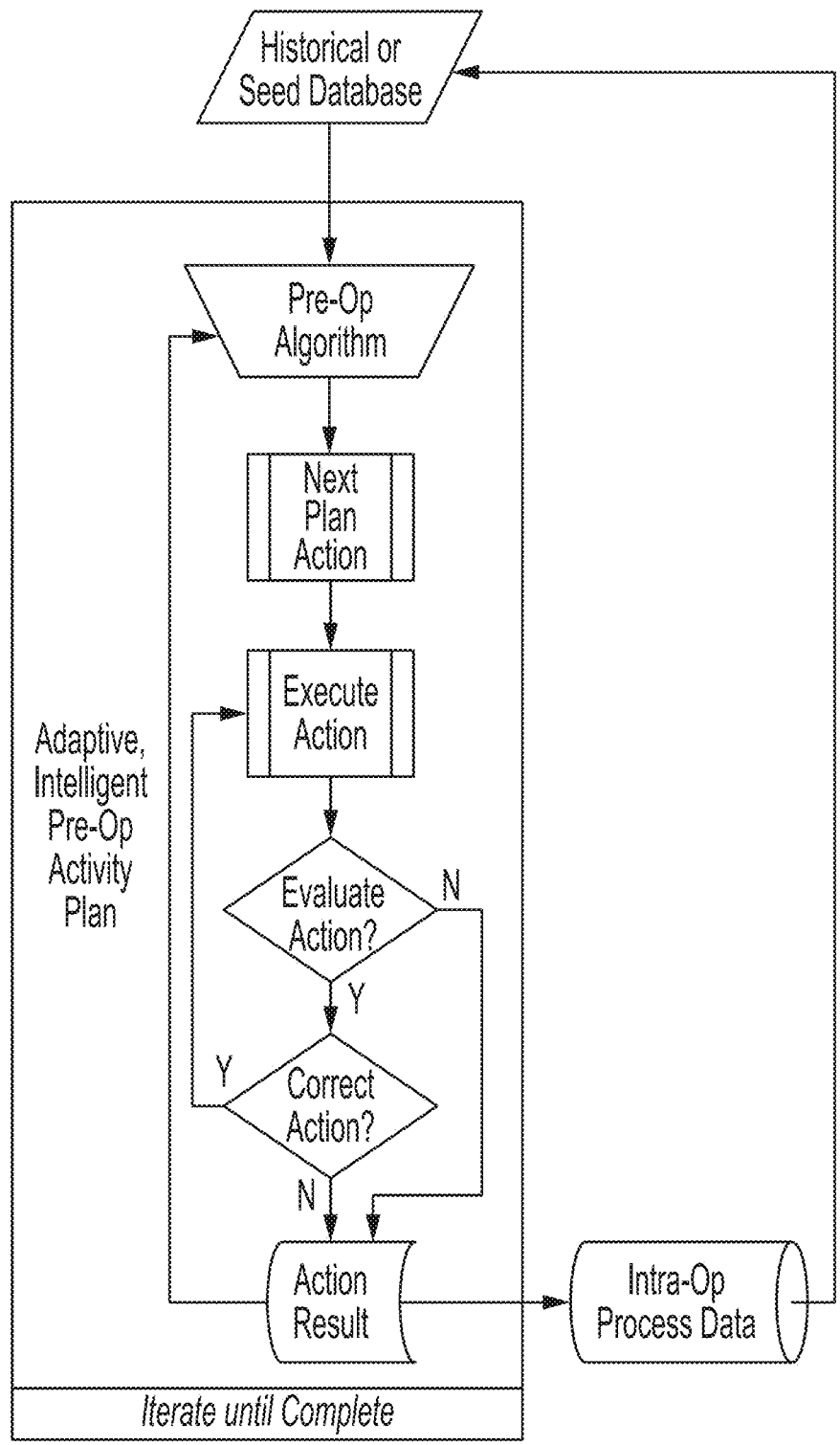
FIGS. 11A-B are flow charts illustrating operation of an exemplary Operative Patient Care System, for use with some embodiments.
Figure 11B:
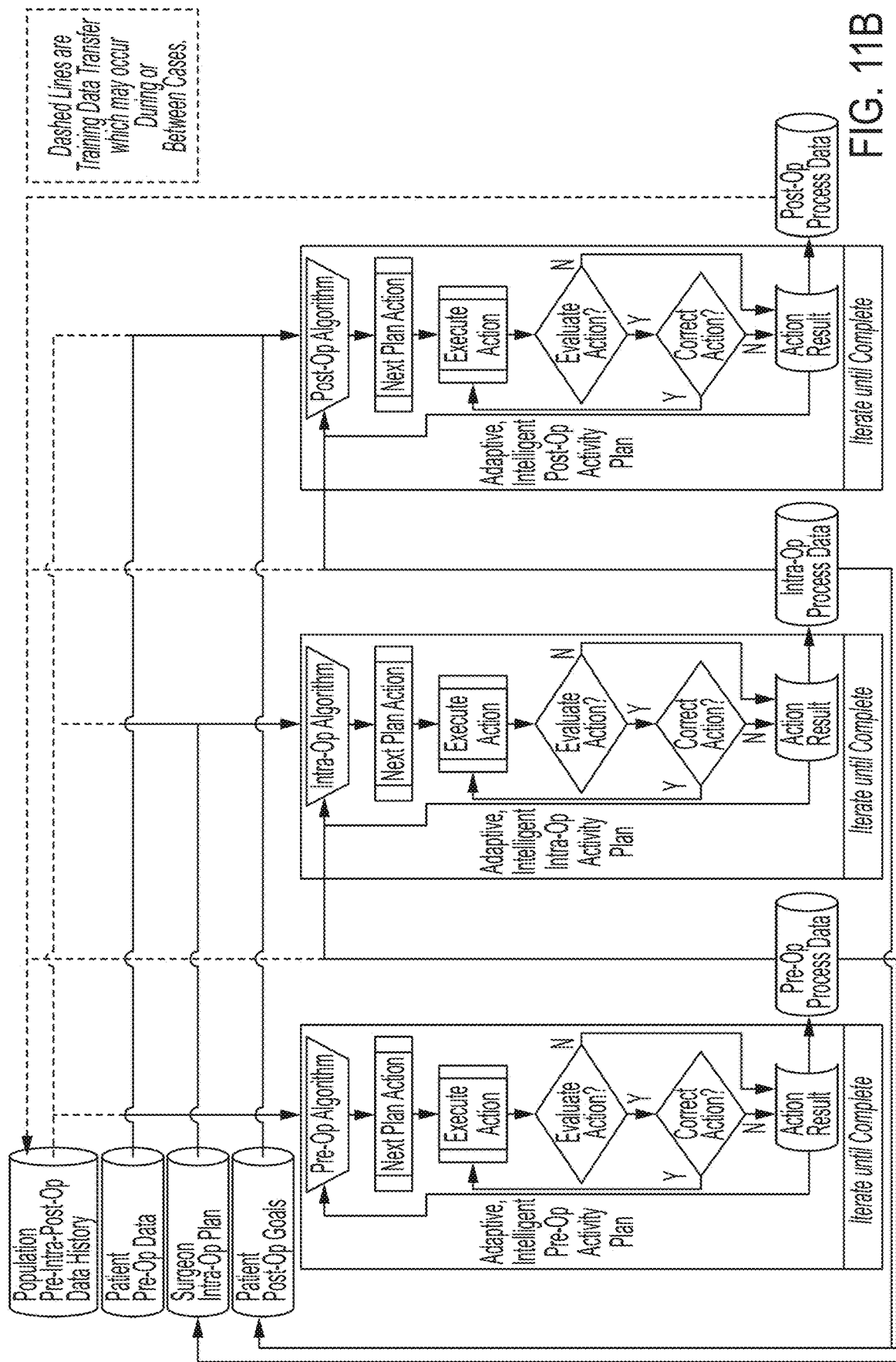

FIG. 11A illustrates how the Operative Patient Care System 820 (FIG. 8) can be adapted for performing case plan matching services. In this example, data 810 is captured relating to the current patient 805 and is compared to all or portions of a historical database of patient data and associated outcomes 815. For example, the surgeon may elect to compare the plan for the current patient against a subset of the historical database. Data in the historical database can be filtered to include, for example, only data sets with favorable outcomes, data sets corresponding to historical surgeries of patients with profiles that are the same or similar to the current patient profile, data sets corresponding to a particular surgeon, data sets corresponding to a particular aspect of the surgical plan (e.g., only surgeries where a particular ligament is retained), or any other criteria selected by the surgeon or medical professional. If, for example, the current patient data matches or is correlated with that of a previous patient who experienced a good outcome, the case plan from the previous patient can be accessed and adapted or adopted for use with the current patient. The predictor equation may be used in conjunction with an intra-operative algorithm that identifies or determines the actions associated with the case plan. Based on the relevant and/or preselected information from the historical database, the intra-operative algorithm determines a series of recommended actions for the surgeon to perform. Each execution of the algorithm produces the next action in the case plan. If the surgeon performs the action, the results are evaluated. The results of the surgeon's performing the action are used to refine and update inputs to the intra-operative algorithm for generating the next step in the case plan. Once the case plan has been fully executed, all data associated with the case plan, including any deviations performed from the recommended actions by the surgeon, are stored in the database of historical data. In some embodiments, the system utilizes preoperative, intraoperative, or postoperative modules in a piecewise fashion, as opposed to the entire continuum of care. In other words, caregivers can prescribe any permutation or combination of treatment modules including the use of a single module. These concepts are illustrated in FIG. 11B and can be applied to any type of surgery utilizing the CASS 100.

Surgery Process Display

As noted above with respect to FIGS. 1-2C, the various components of the CASS 100 generate detailed data records during surgery. The CASS 100 can track and record various actions and activities of the surgeon during each step of the surgery and compare actual activity to the pre-operative or intraoperative surgical plan. In some embodiments, a software tool may be employed to process this data into a format where the surgery can be effectively "played-back." For example, in one embodiment, one or more GUIs may be used that depict all of the information presented on the Display 125 during surgery. This can be supplemented with graphs and images that depict the data collected by different tools. For example, a GUI that provides a visual depiction of the knee during tissue resection may provide the measured torque and displacement of the resection equipment adjacent to the visual depiction to better provide an understanding of any deviations that occurred from the planned resection area. The ability to review a playback of the surgical plan or toggle between different aspects of the actual surgery vs. the surgical plan could provide benefits to the surgeon and/or surgical staff, allowing such persons to identify any deficiencies or challenging aspects of a surgery so that they can be modified in future surgeries. Similarly, in academic settings, the aforementioned GUIs can be used as a teaching tool for training future surgeons and/or surgical staff. Additionally, because the data set effectively records many aspects of the surgeon's activity, it may also be used for other reasons (e.g., legal or compliance reasons) as evidence of correct or incorrect performance of a particular surgical procedure.

Over time, as more and more surgical data is collected, a rich library of data may be acquired that describes surgical procedures performed for various types of anatomy (knee, shoulder, hip, etc.) by different surgeons for different patients. Moreover, aspects such as implant type and dimension, patient demographics, etc., can further be used to enhance the overall dataset. Once the dataset has been established, it may be used to train a machine learning model (e.g., RNN) to make predictions of how surgery will proceed based on the current state of the CASS 100.

Training of the machine learning model can be performed as follows. The overall state of the CASS 100 can be sampled over a plurality of time periods for the duration of the surgery. The machine learning model can then be trained to translate a current state at a first time period to a future state at a different time period. By analyzing the entire state of the CASS 100 rather than the individual data items, any causal effects of interactions between different components of the CASS 100 can be captured. In some embodiments, a plurality of machine learning models may be used rather than a single model. In some embodiments, the machine learning model may be trained not only with the state of the CASS 100, but also with patient data (e.g., captured from an EMR) and an identification of members of the surgical staff. This allows the model to make predictions with even greater specificity. Moreover, it allows surgeons to selectively make predictions based only on their own surgical experiences if desired.

Figures 1, 11C:
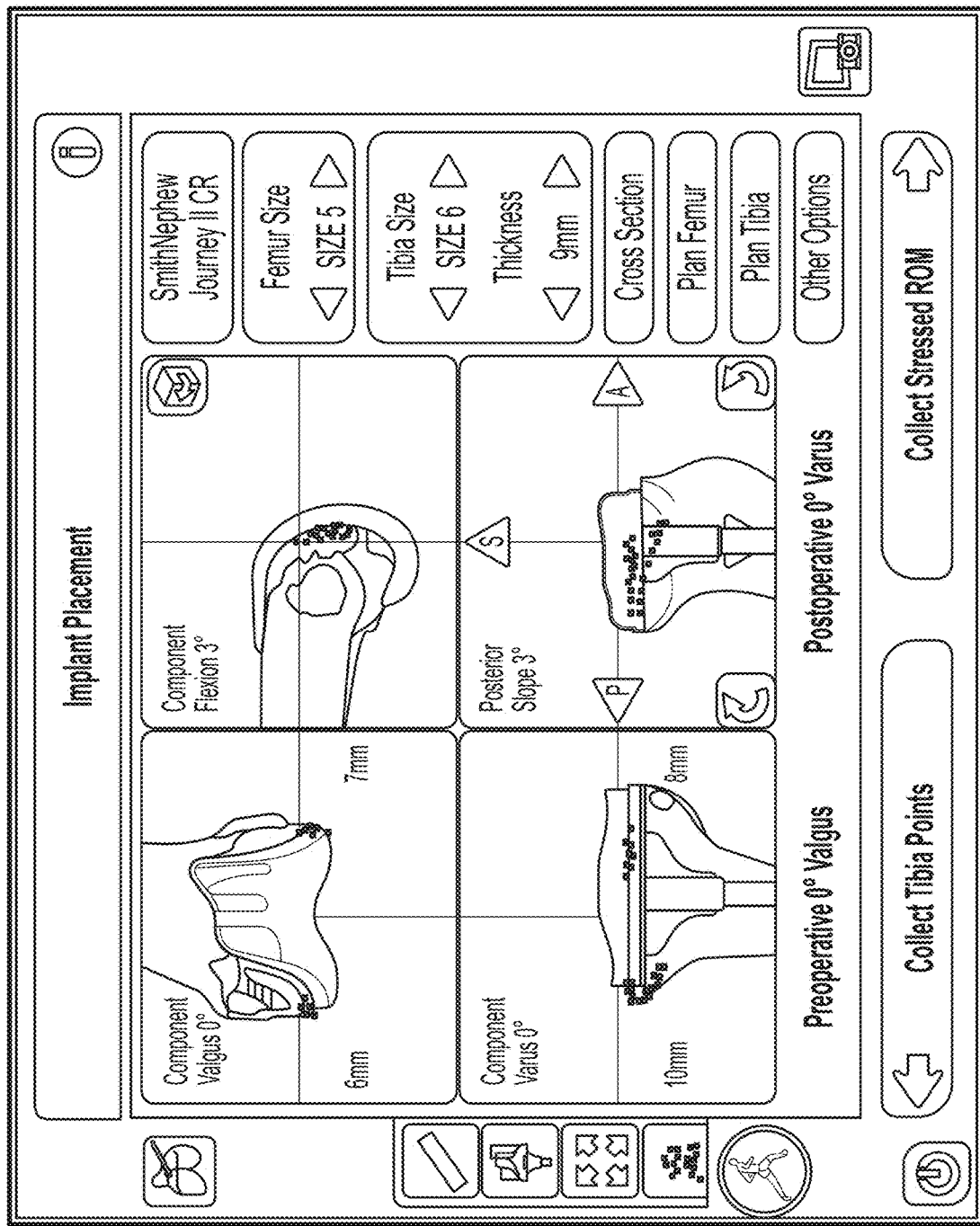
Figures 2, 11C:
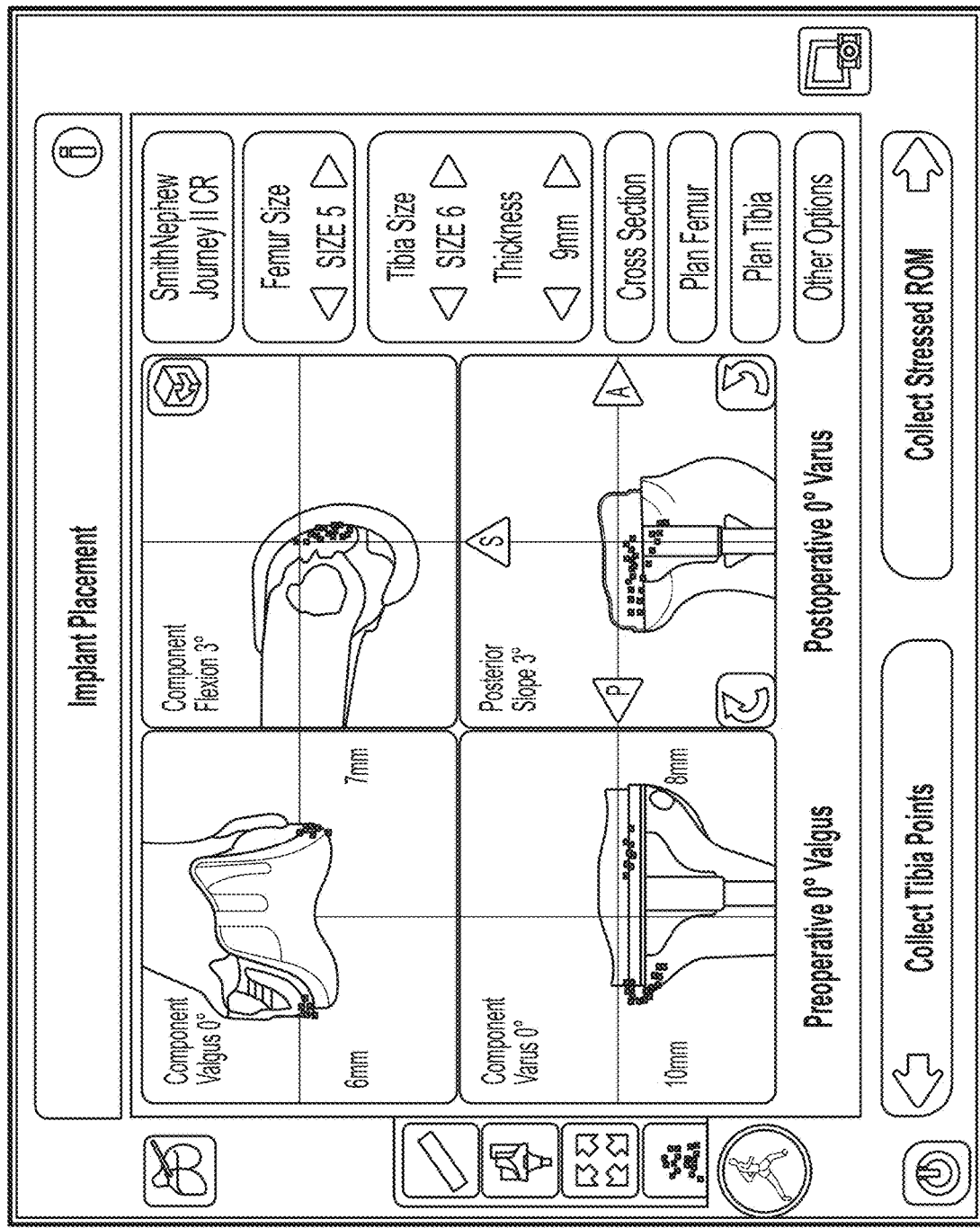
Figures 3, 11C:
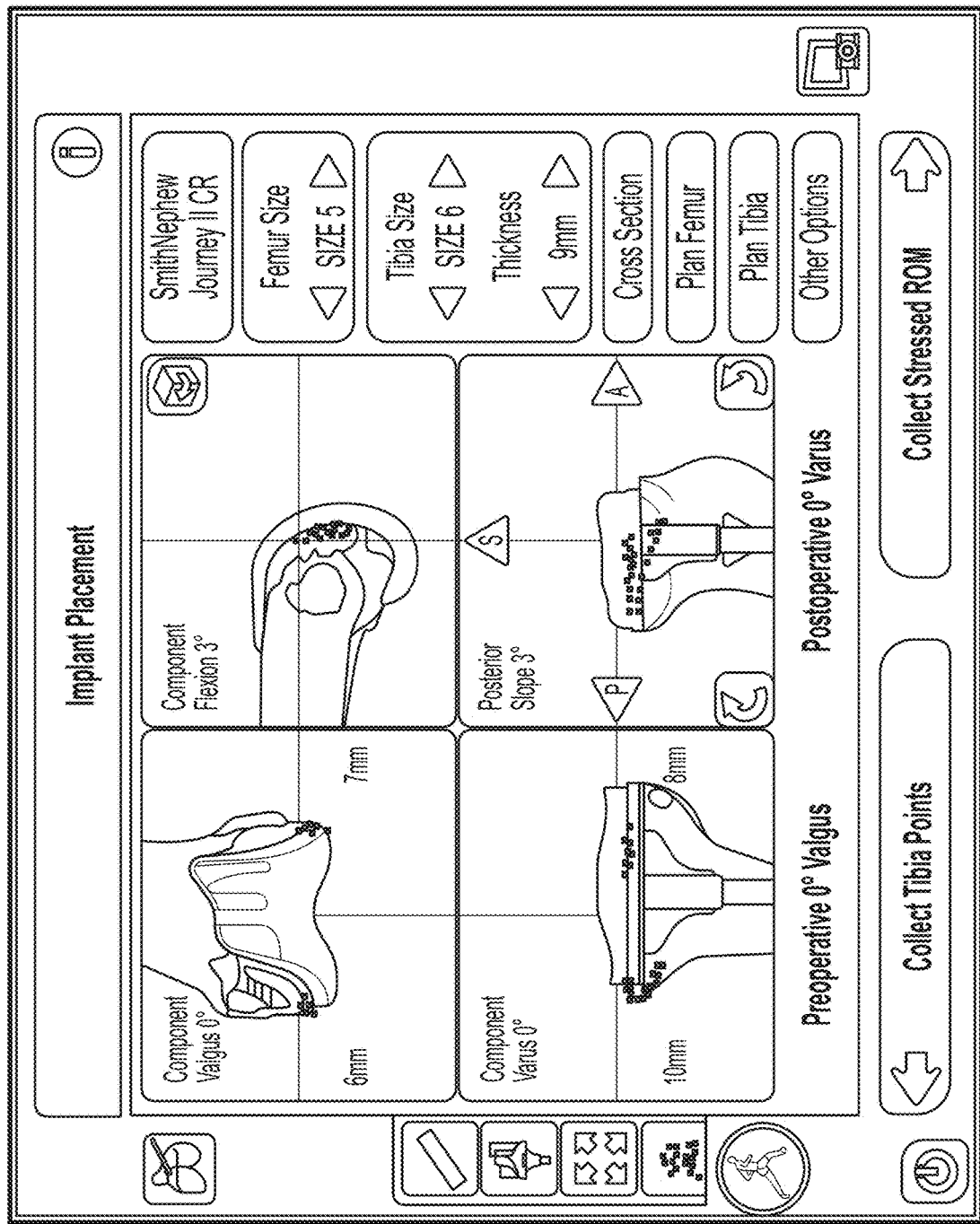

In some embodiments, predictions or recommendations made by the aforementioned machine learning models can be directly integrated into the surgical workflow. For example, in some embodiments, the Surgical Computer 150 may execute the machine learning model in the background making predictions or recommendations for upcoming actions or surgical conditions. A plurality of states can thus be predicted or recommended for each period. For example, the Surgical Computer 150 may predict or recommend the state for the next 5 minutes in 30 second increments. Using this information, the surgeon can utilize a "process display" view of the surgery that allows visualization of the future state. For example, FIG. 11C depicts a series of images that may be displayed to the surgeon depicting the implant placement interface. The surgeon can cycle through these images, for example, by entering a particular time into the display 125 of the CASS 100 or instructing the system to advance or rewind the display in a specific time increment using a tactile, oral, or other instruction. In one embodiment, the process display can be presented in the upper portion of the surgeon's field of view in the AR HMD. In some embodiments, the process display can be updated in real-time. For example, as the surgeon moves resection tools around the planned resection area, the process display can be updated so that the surgeon can see how his or her actions are affecting the other aspects of the surgery.

In some embodiments, rather than simply using the current state of the CASS 100 as an input to the machine learning model, the inputs to the model may include a planned future state. For example, the surgeon may indicate that he or she is planning to make a particular bone resection of the knee joint. This indication may be entered manually into the Surgical Computer 150 or the surgeon may verbally provide the indication. The Surgical Computer 150 can then produce a film strip showing the predicted effect of the cut on the surgery. Such a film strip can depict over specific time increments how the surgery will be affected, including, for example, changes in the patient's anatomy, changes to implant position and orientation, and changes regarding surgical intervention and instrumentation, if the contemplated course of action were to be performed. A surgeon or medical professional can invoke or request this type of film strip at any point in the surgery to preview how a contemplated course of action would affect the surgical plan if the contemplated action were to be carried out.

It should be further noted that, with a sufficiently trained machine learning model and robotic CASS, various aspects of the surgery can be automated such that the surgeon only needs to be minimally involved, for example, by only providing approval for various steps of the surgery. For example, robotic control using arms or other means can be gradually integrated into the surgical workflow over time with the surgeon slowly becoming less and less involved with manual interaction versus robot operation. The machine learning model in this case can learn what robotic commands are required to achieve certain states of the CASS-implemented plan. Eventually, the machine learning model may be used to produce a film strip or similar view or display that predicts and can preview the entire surgery from an initial state. For example, an initial state may be defined that includes the patient information, the surgical plan, implant characteristics, and surgeon preferences. Based on this information, the surgeon could preview an entire surgery to confirm that the CASS-recommended plan meets the surgeon's expectations and/or requirements. Moreover, because the output of the machine learning model is the state of the CASS 100 itself, commands can be derived to control the components of the CASS to achieve each predicted state. In the extreme case, the entire surgery could thus be automated based on just the initial state information.

Using Anatomical Modeling Software for Pre-Operative Planning

In some embodiments, anatomical modeling software, such as LIFEMOD™, can be used to develop a pre-operative or intraoperative plan to guide surgery. For example, in the context of hip surgery, if the anatomical modeling software has knowledge of relationship between the spine and the pelvis throughout a variety of functional activities, then the software can better predict an optimal implant position. Studies have shown that individuals who have limited or abnormal spino-pelvic mobility are at a higher risk for dislocation. For these patients, surgeons recommend taking lateral radiographs in several positions (e.g., standing, sitting, flexed-standing) in order to understand how the spine and pelvis interact during a variety of activities. These images can feed into a 3D biomechanical simulation to better predict the optimal implant positions and orientations. Additionally, as an alternative to the manual process of taking radiographs, the anatomical modeling software may also be used to simulate the positions of the lumbar spine and pelvis throughout a range of activities. In the context of knee surgery, if the anatomical modeling software has knowledge of the relationship among the mechanical axes of the joint, the condylar axis, and the central axes of the femur and tibia, and the existing flexion and extension gaps, the software can better determine how changes in the size and pose (position and orientation) of the implant components can affect the mechanics of the replacement knee. More specifically, if the software incorporates the relationship between these variables throughout the range of motion and exemplary forces of a given patient activity, the implant performance can be modeled.

Figure 12A:
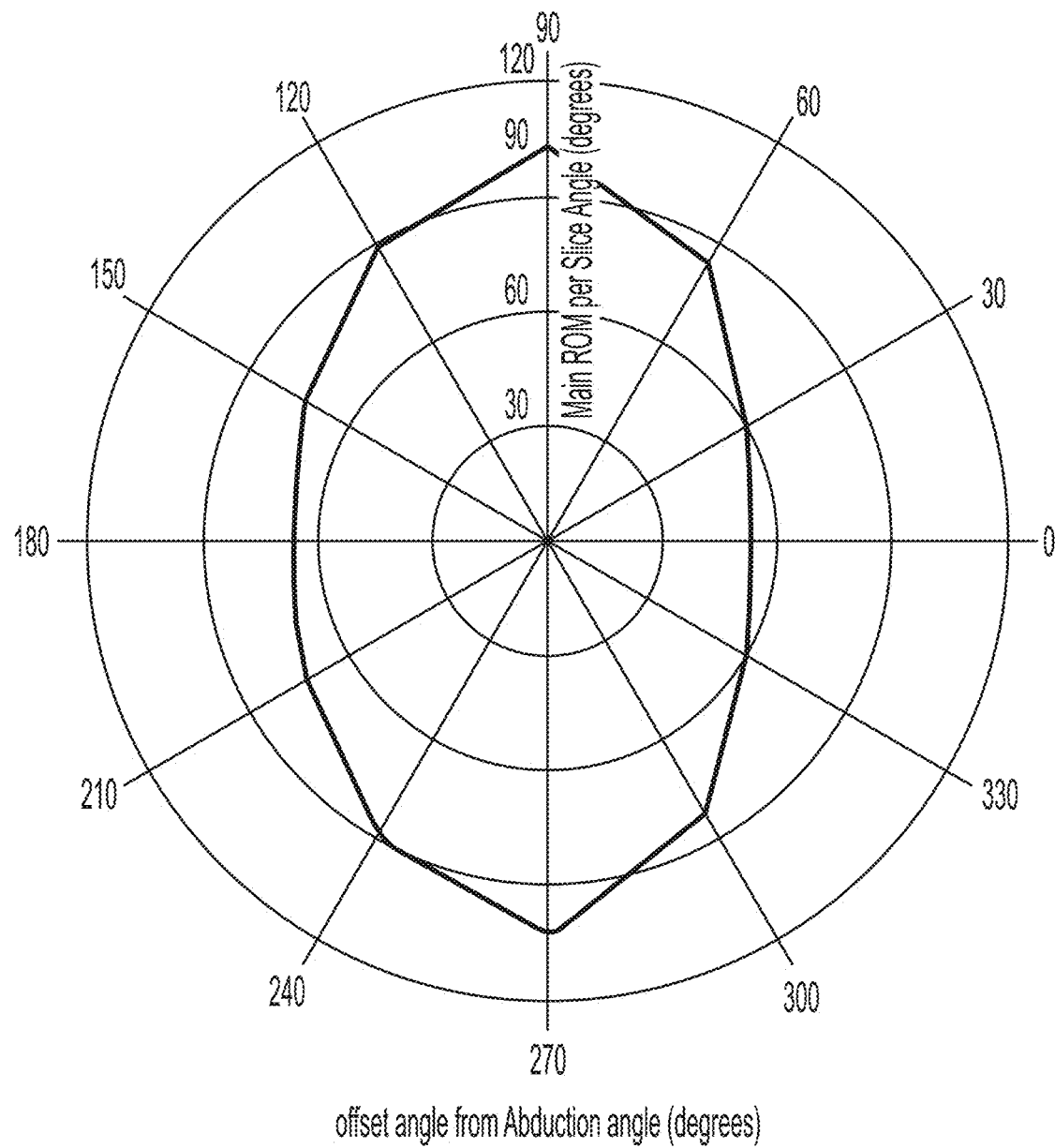
FIGS. 12A-12C provide some outputs that the anatomical modeling software may use to visually depict the results of modeling hip activity, for use with some embodiments.
Figure 12B:
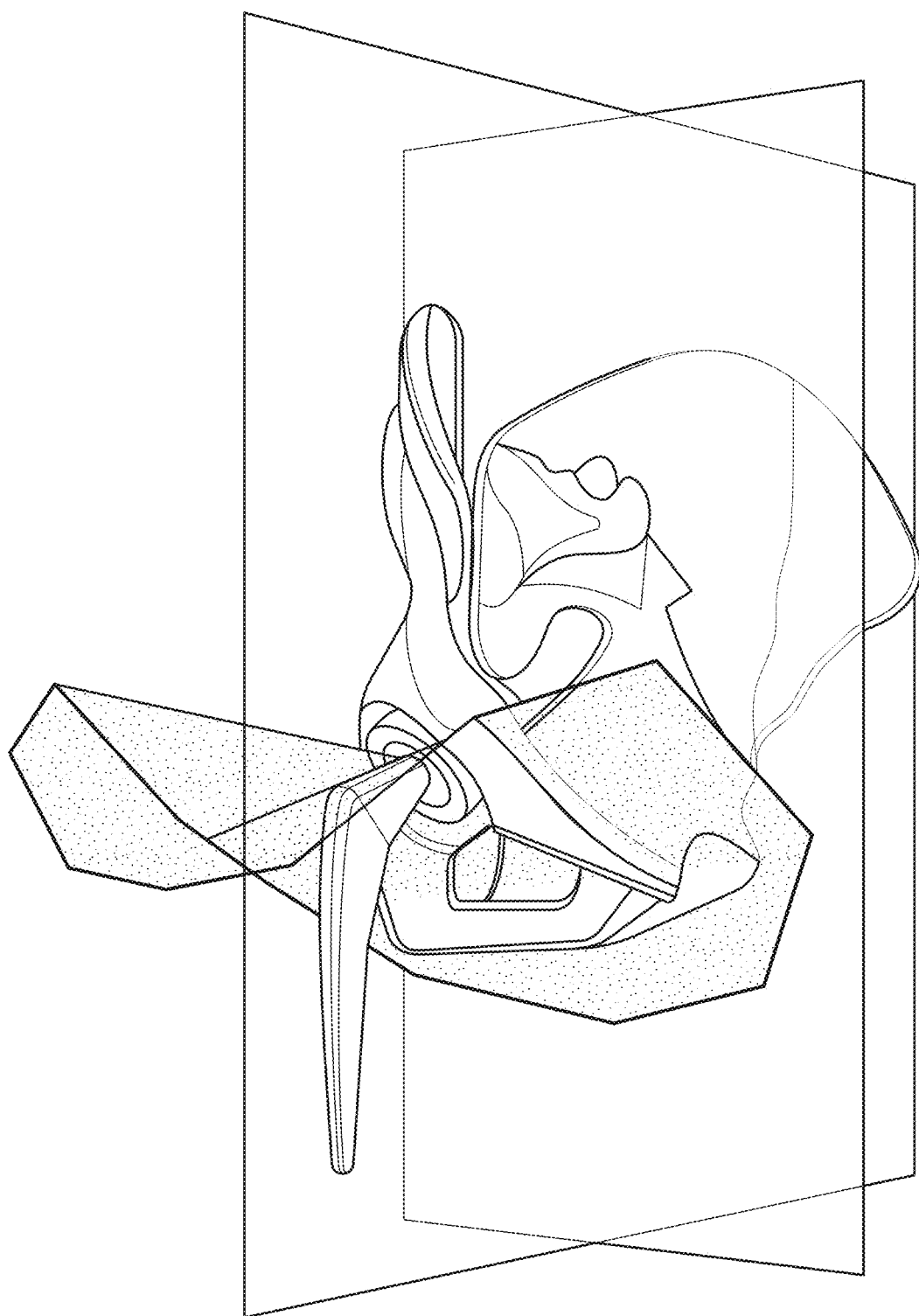
Figure 12C:
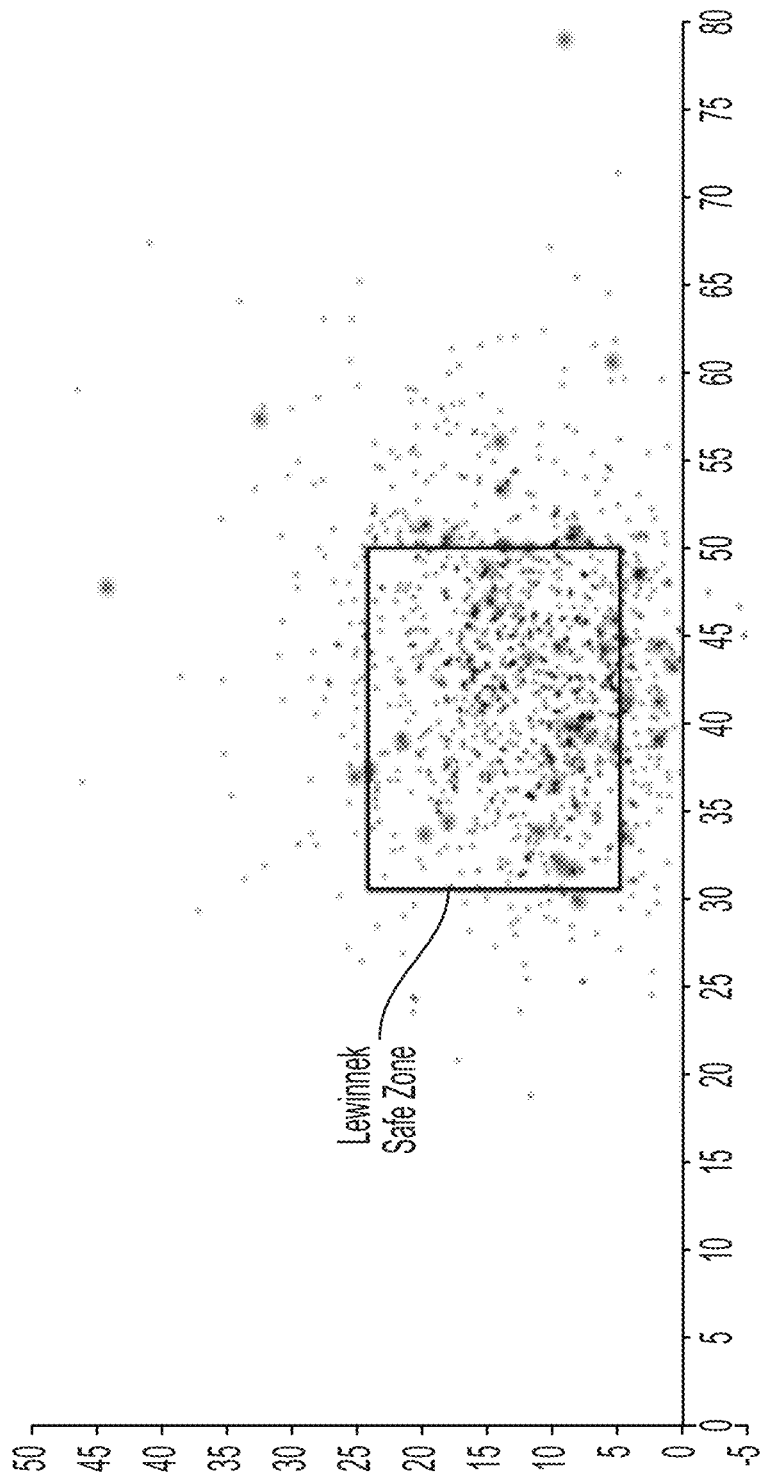

FIGS. 12A-12C provide some outputs that the anatomical modeling software may use to visually depict the results of modeling hip activity with the anatomical modeling software. FIGS. 12A and 12B show hip range of motion (ROM) plots. In this case, the anatomical modeling software may be employed to perform a ROM "exam" by placing the patient in various positions and modeling movement of the hip when the patient's leg moves in different positions. For example, the software can virtually simulate the positions and orientation of the implants in relation to bony anatomy throughout a variety of activities that a patient may experience post-surgery. These may include the standard stability checks that are performed during a total hip procedure, or could even include activities that pose a high risk for impingement and dislocation (crossing legs while seated, deep flexion while sitting, hyperextension while standing, etc.). Following performance of the exam, the collected ROM data can be presented on a ROM plot as shown in FIG. 12A. Additionally, the anatomical modeling software may identify any impinged ROM where abnormal and wearing contact exists between the patient's anatomy and the implant components. As shown in FIG. 12B, after the unimpinged ROM is determined, it may be graphically overlaid on a 3D model of the patient's anatomy.

FIG. 12C shows 2D graphs that demonstrate a recommendation for a desirable or "safe" range of positions for seating a hip implant in the acetabulum. In this case, the anatomical modeling software may be used to identify a safe range of placement locations by modeling functional activities to the point of failure. For example, initially, the anatomical modeling software may assume that the implant can be placed at any location within a large bounding box surrounding the anatomy of interest. Then, for each possible implant position, the anatomical modeling software may be used to test whether the position creates a failure of the anatomy or implant under normal functional activities. In the event of failure, a position is discarded. Once all the possible points have been evaluated, the remaining points are considered "safe" for implant placement. As shown in FIG. 12B, for hip surgeries the safe positions may be indicated by a graph of abduction versus anteversion. In this case, the Lewinnek Safe Zone is superimposed on the graph. As is commonly understood in the art, the Lewinnek Safe Zone is based on the clinical observation that dislocation is less likely to occur if the acetabular cup is placed within 30 degrees-50 degrees of abduction and 5-25 degrees of anteversion. However, in this case, some of the patient's "safe" positions (depicted in "red") fall outside the Lewinnek Safe Zone. Thus, the surgeon is given more flexibility to deviate from standard recommendations based on the features of the patient's anatomy.

An additional output of the anatomical modeling software may be 3D renderings that display the final implant components in relation to the bone. In some embodiments, the 3D rendering may be displayed in an interface that allows the surgeon to rotate around the entire image and view the rendering from different perspectives. The interface may allow the surgeon to articulate the joint to visualize how implants will perform and identify where impingement, misalignment, excessive strain, or other problems may occur. The interface may include functionality that allows the surgeon to hide certain implant components or anatomical features in order to best visualize certain areas of the patient anatomy. For example, for a knee implant, the interface may allow the surgeon to hide the femoral component and only show the bearing surface and tibial component in the visualization. FIG. 12D provides an exemplary visualization in the context of a hip implant.

In some embodiments, the anatomical modeling software may provide an animation that shows the positions of the implants and bone as the patient performs different physical activities. For example, in the context of a knee surgery, a deep knee bend can be presented. For a hip surgery, the spine and pelvis can be shown during walking, sitting, standing, and other activities that may represent a challenge to the implants.

Revision hip or knee arthroplasty surgery involves the removal of one or more existing hip/knee implants and replacing the removed implants with new implants in a single surgical procedure. In some embodiments, the preoperative planning stage can anticipate handling of osteophytes or other tasks beyond planar resections needed to receive a new implant. For example, in some embodiments, for a revision surgery, an output of the anatomical modeling software may be a 3D image or bone map showing the placement of each of the components, as well as problem areas that may require special preparation by the surgeon. Areas that would prevent implants from being fully seated may be highlighted by the software in the surgical plan to show the surgeon which areas will require bone to be removed. This software may be interactive, allowing the surgeon to virtually "ream" or "burr" bone away in order to optimally prepare the bone to receive the implants. This may be performed, for example, by allowing the surgeon/engineer to selectively remove individual pixels or groups of pixels from an X-ray image or a 3D representation by touching the area or using a "virtual burr" component of the interface. In some embodiments, images of mixed modalities can be registered and overlaid to provide a view of the structure of the anatomical area of interest, the anatomy, etc. In some embodiments, the anatomical modeling software may provide a recommended area for burring away the bone. For example, a machine learning model may be trained to identify areas for burring based on how the surgeon (or other surgeons) performed burring in the past. Then, using the x-ray image or other patient measurements as input, the machine learning model can input the recommended burring area for review by the surgeon during the virtual burring procedure. In some embodiments, the virtual burring process can be performed interactively with other aspects of the anatomical modeling discussed above. This burring process may also be used with primary arthroplasty.

Using the Point Probe to Acquire High-Resolution of Key Areas During Hip Surgeries Use of the point probe is described in U.S. patent application Ser. No. 14/955,742 entitled "Systems and Methods for Planning and Performing Image Free Implant Revision Surgery," the entirety of which is incorporated herein by reference. Briefly, an optically tracked point probe may be used to map the actual surface of the target bone that needs a new implant. Mapping is performed after removal of the defective or worn-out implant, as well as after removal of any diseased or otherwise unwanted bone. A plurality of points is collected on the bone surfaces by brushing or scraping the entirety of the remaining bone with the tip of the point probe. This is referred to as tracing or "painting" the bone. The collected points are used to create a three-dimensional model or surface map of the bone surfaces in the computerized planning system. The created 3D model of the remaining bone is then used as the basis for planning the procedure and necessary implant sizes. An alternative technique that uses X-rays to determine a 3D model is described in U.S. patent application Ser. No. 16/387,151, filed Apr. 17, 2019 and entitled "Three Dimensional Guide with Selective Bone Matching," the entirety of which is incorporated herein by reference.

For hip applications, the point probe painting can be used to acquire high resolution data in key areas such as the acetabular rim and acetabular fossa. This can allow a surgeon to obtain a detailed view before beginning to ream. For example, in one embodiment, the point probe may be used to identify the floor (fossa) of the acetabulum. As is well understood in the art, in hip surgeries, it is important to ensure that the floor of the acetabulum is not compromised during reaming so as to avoid destruction of the medial wall. If the medial wall were inadvertently destroyed, the surgery would require the additional step of bone grafting. With this in mind, the information from the point probe can be used to provide operating guidelines to the acetabular reamer during surgical procedures. For example, the acetabular reamer may be configured to provide haptic feedback to the surgeon when he or she reaches the floor or otherwise deviates from the surgical plan. Alternatively, the CASS 100 may automatically stop the reamer when the floor is reached or when the reamer is within a threshold distance.

As an additional safeguard, the thickness of the area between the acetabulum and the medial wall could be estimated. For example, once the acetabular rim and acetabular fossa has been painted and registered to the pre-operative 3D model, the thickness can readily be estimated by comparing the location of the surface of the acetabulum to the location of the medial wall. Using this knowledge, the CASS 100 may provide alerts or other responses in the event that any surgical activity is predicted to protrude through the acetabular wall while reaming.

The point probe may also be used to collect high resolution data of common reference points used in orienting the 3D model to the patient. For example, for pelvic plane landmarks like the ASIS and the pubic symphysis, the surgeon may use the point probe to paint the bone to represent a true pelvic plane. Given a more complete view of these landmarks, the registration software has more information to orient the 3D model.

The point probe may also be used to collect high-resolution data describing the proximal femoral reference point that could be used to increase the accuracy of implant placement. For example, the relationship between the tip of the Greater Trochanter (GT) and the center of the femoral head is commonly used as a reference point to align the femoral component during hip arthroplasty. The alignment is highly dependent on proper location of the GT; thus, in some embodiments, the point probe is used to paint the GT to provide a high resolution view of the area. Similarly, in some embodiments, it may be useful to have a high-resolution view of the Lesser Trochanter (LT). For example, during hip arthroplasty, the Don Classification helps to select a stem that will maximize the ability of achieving a press-fit during surgery to prevent micromotion of femoral components post-surgery and ensure optimal bony ingrowth. As is generally understood in the art, the Dorr Classification measures the ratio between the canal width at the LT and the canal width 10 cm below the LT. The accuracy of the classification is highly dependent on the correct location of the relevant anatomy. Thus, it may be advantageous to paint the LT to provide a high-resolution view of the area.

In some embodiments, the point probe is used to paint the femoral neck to provide high-resolution data that allows the surgeon to better understand where to make the neck cut. The navigation system can then guide the surgeon as they perform the neck cut. For example, as understood in the art, the femoral neck angle is measured by placing one line down the center of the femoral shaft and a second line down the center of the femoral neck. Thus, a high-resolution view of the femoral neck (and possibly the femoral shaft as well) would provide a more accurate calculation of the femoral neck angle.

High-resolution femoral head neck data could also be used for a navigated resurfacing procedure where the software/hardware aids the surgeon in preparing the proximal femur and placing the femoral component. As is generally understood in the art, during hip resurfacing, the femoral head and neck are not removed; rather, the head is trimmed and capped with a smooth metal covering. In this case, it would be advantageous for the surgeon to paint the femoral head and cap so that an accurate assessment of their respective geometries can be understood and used to guide trimming and placement of the femoral component.

Registration of Pre-Operative Data to Patient Anatomy Using the Point Probe

As noted above, in some embodiments, a 3D model is developed during the pre-operative stage based on 2D or 3D images of the anatomical area of interest. In such embodiments, registration between the 3D model and the surgical site is performed prior to the surgical procedure. The registered 3D model may be used to track and measure the patient's anatomy and surgical tools intraoperatively.

During the surgical procedure, landmarks are acquired to facilitate registration of this pre-operative 3D model to the patient's anatomy. For knee procedures, these points could comprise the femoral head center, distal femoral axis point, medial and lateral epicondyles, medial and lateral malleolus, proximal tibial mechanical axis point, and tibial A/P direction. For hip procedures these points could comprise the anterior superior iliac spine (ASIS), the pubic symphysis, points along the acetabular rim and within the hemisphere, the greater trochanter (GT), and the lesser trochanter (LT).

In a revision surgery, the surgeon may paint certain areas that contain anatomical defects to allow for better visualization and navigation of implant insertion. These defects can be identified based on analysis of the pre-operative images. For example, in one embodiment, each pre-operative image is compared to a library of images showing "healthy" anatomy (i.e., without defects). Any significant deviations between the patient's images and the healthy images can be flagged as a potential defect. Then, during surgery, the surgeon can be warned of the possible defect via a visual alert on the display 125 of the CASS 100. The surgeon can then paint the area to provide further detail regarding the potential defect to the Surgical Computer 150.

In some embodiments, the surgeon may use a non-contact method for registration of bony anatomy intra-incision. For example, in one embodiment, laser scanning is employed for registration. A laser stripe is projected over the anatomical area of interest and the height variations of the area are detected as changes in the line. Other non-contact optical methods, such as white light inferometry or ultrasound, may alternatively be used for surface height measurement or to register the anatomy. For example, ultrasound technology may be beneficial where there is soft tissue between the registration point and the bone being registered (e.g., ASIS, pubic symphysis in hip surgeries), thereby providing for a more accurate definition of anatomic planes.

Surgical Navigation with Mixed Reality Visualization

In some embodiments, a surgical navigation system utilizes an augmented reality (AR) or mixed reality (MR) visualization system to further assist a surgeon during robotically-assisted surgery. Conventional surgical navigation can be enhanced with AR by using graphical and informational overlays (e.g., holographic or heads up displays/HUD) to guide surgical execution. An exemplary system allows for the implementation of multiple headsets to share the same mixed or different reality experience in real-time. In a multi-user use scenario, multiple user profiles can be implemented for selective AR display. This can allow headsets to work together or independently, displaying different subsets of information to each user.

Embodiments utilizing AR/MR include a surgical system for operating in a surgical environment to enhance surgery through vision tracking that includes head mounted displays (HMDs) worn by one or more individuals performing operational functions. For example, a surgeon may have an HMD and some or all of the nurses or lab technicians assisting the surgeon (or residents, other surgeons etc.) may have their own HMD. By using HMDs, a surgeon can view information pertaining to the surgery, including information traditionally associated with robotic surgical enhancement, without requiring the surgeon to shift his vision field away from the patient. This can make the surgery faster because the surgeon does not need to context switch between the display and the patient. In some embodiments, a surgeon can selectively be shown a virtual holographic monitor that mirrors the display of a conventional cart-mounted LCD screen during surgery. The HMD interface can allow the surgeon to move the holographic monitor to appear fixed in space at any location in space she chooses, such as next to exposed patient tissue in front of surgical drapes.

A variety of types of HMDs can be used in some embodiments. Generally, an HMD includes a headpiece that is worn on a user's head and a communication interface. The communication interface can be wired, such as USB, serial port, SATA, or proprietary communication interfaces, or preferably wireless, such as Wi-Fi or Bluetooth (but timing and bandwidth constraints can restrict practical choices to some of the faster conventional communication interfaces, such as Wi-Fi or USB 3.0). An exemplary HMD also has a power source (such as battery or hardwired power connector), an onboard computer (including a processor, GPU, RAM, and non-volatile data and instruction memory), and one or more displays for superimposing information into the user's field of view. An exemplary HMD may also include an array of cameras (which may include optical and IR sensors and illumination sources) that capture 3-D imagery of the environment. In some embodiments, the HMD or an external processor may create a model of the user's environment using image processing algorithms that identify important features of the environment and by processing stereoscopic or IR data to create a 3D model of the environment. By calibrating the HMD's display to the user's field of view, information displayed on a holographic display (e.g., using direct retinal or semi-reflective projection) can be reliably superimposed onto the user's field of view to augment the user's view of the environment.

The HMDs worn by surgical staff can include commercially available, off-the-shelf HMDs, such as the Oculus Rift™, Microsoft HoloLens™, Google Glass™, Magic Leap One™, or custom designed hardware for the surgical environment. In some embodiments, supplemental hardware is added to a commercially available HMD to enhance it for the surgical environment using off-the-shelf HMD components and custom hardware. In some embodiments, HMD hardware can be integrated into traditional surgical hoods and face shields allowing the HMD to serve as personal protective equipment and to allow information to be displayed by reflecting light off of a face shield that a surgeon already is familiar with wearing. HMD technology on the market has a variety of approaches to providing a mixed reality environment for a user. For example, virtual-reality headsets, such as the Oculus Rift™, HTC Vive™, Sony PlayStation VR™, or Samsung Gear VR™, obstruct the user's natural vision, replacing the entire visual field of the user with a stereoscopic screen to create a 3D environment. These systems can use one or more cameras to recreate an enhanced version of the three-dimensional environment to be displayed to the user. This allows the natural environment to be captured and redisplayed to the user with mixed reality components. Other AR headsets, such as Google Glass™ and Microsoft HoloLens™ augment reality by providing supplemental information to a user that appear as holograms within the user's visual field. Because the user views the environment either directly or through a clear lens, the additional displayed information, which is projected off of a reflective surface in front of the user's eyes or directly onto the user's retina, appears semi-transparent to the user.

Commercially available HMDs typically include one or more outward facing cameras to collect information from the environment. These cameras can include visible light cameras and IR cameras. The HMDs may include illumination sources that assist the cameras in collecting data from the environment. Most HMDs include some form of user interface that a user can use to interact with the processor via the display of the HMD. In some systems, the user interface can be a handheld remote control used to select and engage displayed menus. This may not be ideal for a surgical environment due to sterilization issues and fluid-covered hands. Other systems, such as the Microsoft HoloLens™ and Google Glass™, use one or more cameras to track gestures or MEMS accelerometers to detect motion by the user's head. A user can then use gestures to interact with a virtual interface. For example, a virtual keyboard may be holographically displayed, and a camera may track the user's finger movements to allow the user to type on a virtual floating keyboard. Some HMDs may also have a voice interface. In addition to the display, the headset may provide haptic feedback through actuators or audio signals to the user through an earpiece or speakers. Other onboard sensors of an HMD can include gyroscopes, magnetometers, laser or optical proximity sensors. In some embodiments, an HMD may also have a laser or other projecting device that allows information to be projected onto the environment, rather than holographically to the user.

While AR headsets can provide a more natural feel to a user than VR, because most of the image the user sees is natural, it can be difficult to properly superimpose and align displayed information with the user's viewpoint. There have been many software initiatives in the industry that address this issue, spearheaded by AR headset manufacturers. Therefore, AR headsets and VR headsets typically come with the software tools necessary to superimpose information into the user's visual field to align that information with what the user sees in the environment.

In some embodiments, information similar to that displayed on a traditional cart-mounted display is provided to the surgeon as part of a robotic assistive surgery system, such as the NAVIO surgical system. In some embodiments, different HMDs worn by different people in the surgical theatre can display different information at any time. For example, a surgeon can see information relating to what is in his current field of view, while an HMD worn by a surgical resident can display camera footage of what the attending surgeon sees and any enhancements that the attending surgeon sees. In some embodiments, the resident may see additional patient information that may be helpful for the resident to learn or to convey to the surgeon, such as pre-operative imaging, patient files, information from the manufacturer of a tool or medical device, etc.

HMDs include one or more cameras that capture the field-of-view (or a wider or narrower version thereof) of the wearer and provide the images to a processor, thereby allowing the processor to resolve the two-dimensional image captured by the HMD and its relation to a 3D model of the surgical theatre. For example, one or more tracking cameras of the HMD can capture the presence of fiducial marks of patient bones and/or tools to determine how the wearer's perspective relates to a 3D model of the patient and/or the tools. This can allow an image processor to extract features from the captured image, such as bone/tissue and tools, and use the information to display enhanced information over the image being viewed by the wearer. For example, when a surgeon is operating on a knee, a camera on the surgeon's HMD can capture what the surgeon sees, allowing image processing software to determine where in the three-dimensional space the surgeon is looking and to determine specific patient features that the surgeon is looking at. Those specific patient features can be located in the two-dimensional image by image processing software using pattern matching or machine learning techniques informed by the location of the surgeon's view in the surgical scene.

For example, the surgeon may be looking at the tibial plateau and femoral condyles. The camera on her HMD will capture this image in real time (which includes practical processing and communication delays) and send this image to image processing software. Image processing software may identify the object being viewed as the tibial plateau and femoral condyles (or may receive a hint based on the perspective) and look for patterns in the image to identify the extent of these features within the surgeon's field of view. Information about the tibial plateau and femoral condyles can then be overlaid with the image that the surgeon sees. Software may be able to accurately locate the two-dimensional image relative to a three-dimensional model of the surgical scene if fiducial marks are available in the image (or recent images) or the surgeon's HMD includes fiducial marks that are captured by a robotic vision system or by the cameras of other HMDs in the room to allow calculation of the pose of the surgeon's HMD cameras.

Figure 13:
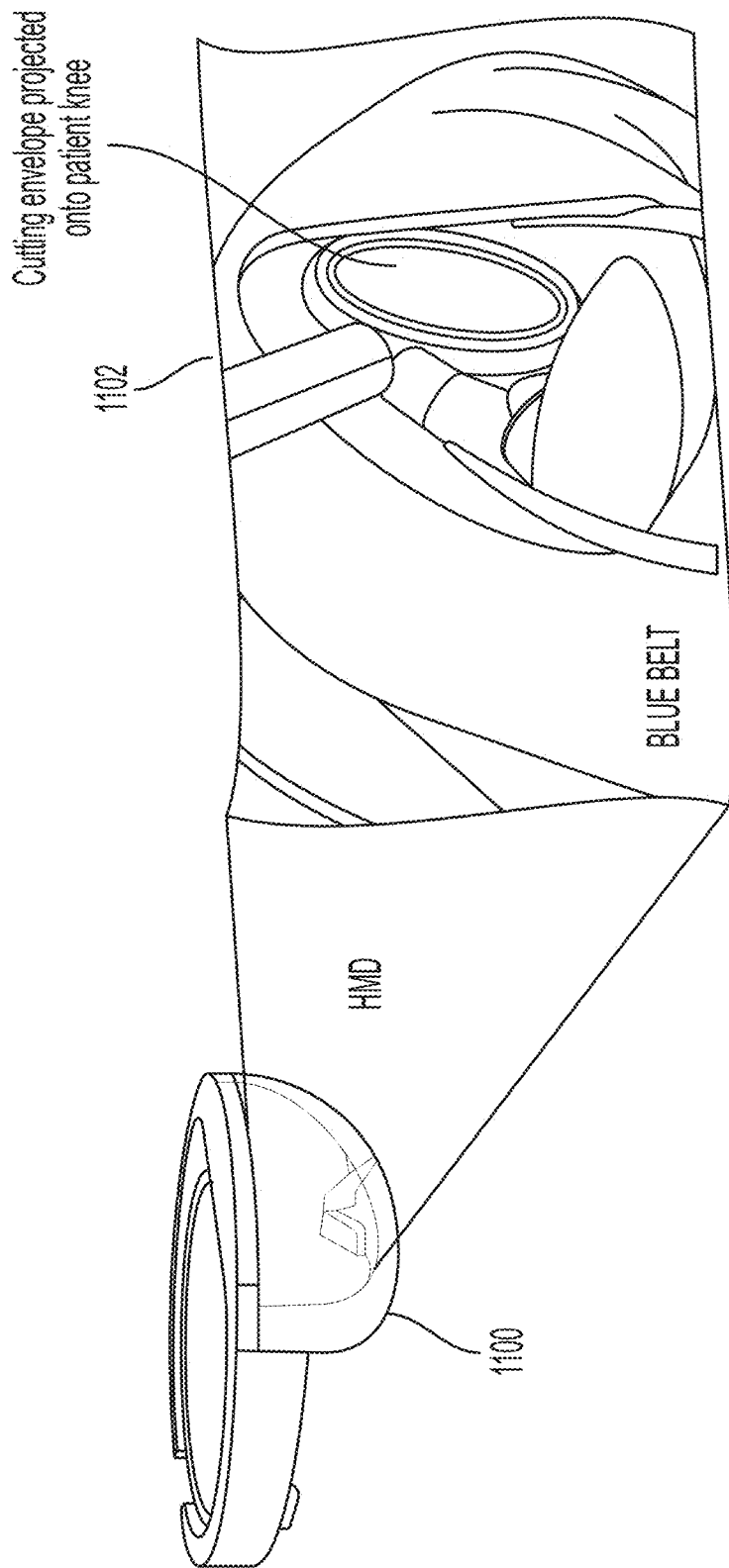
FIG. 13 provides an example of an augmented reality visualization in some embodiments.

In some embodiments, information is overlaid in the user's visual field holographically. In some embodiments, information can be digitally projected from the HMD onto the environment. For example, a laser array MEMS mirror coupled to the headset can project an image directly onto a surface in the environment. Because this projection comes from approximately the same location as the user's eyes, this projection can be easily collocated with the user's field-of-view, overlaying the information onto the environment in a more robust manner than presenting a floating hologram to the user. For example, as shown in FIG. 13, HMD 1100 projects a computer-generated image of a cutting envelope onto a portion of a patient's knee 1102 to indicate to the wearer exactly where on a bone in the knee she should cut without distracting the wearer or interfering with her peripheral vision.

Figure 14:
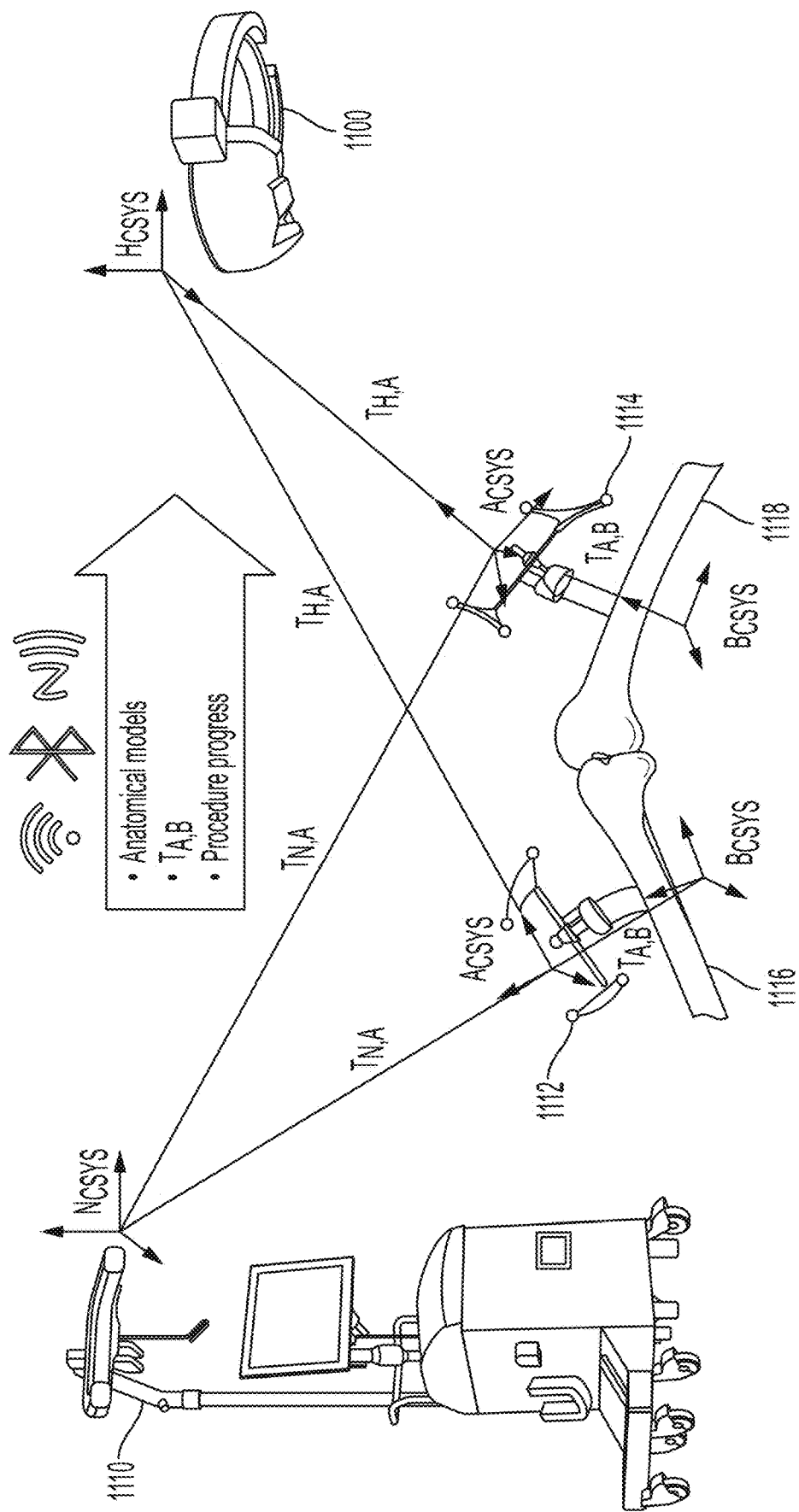
FIG. 14 is a system diagram illustrating an augmented reality visualization system, for use with some embodiments.

Surgical systems using an optical tracking modality, such as the NAVIO system, can be well-suited for use with HMDs. The one or more cameras included in an HMD make it especially convenient to adapt the HMD for use in the surgical theatre. As shown in FIG. 14, one or more cameras 1110 that are mounted to carts or fixed in the surgical environment use optical and IR tracking to capture the location of fiducial markers 1112 and 1114 mounted to tools and patient bones. Adding one or more HMDs 1100 to this environment can supplement this tracking system by providing additional perspectives for optical or IR tracking. In some embodiments, multiple HMDs 1100 can be used simultaneously in the operating room, thereby providing a variety of perspectives to aid in tracking the fiducial marks of tools and patient anatomy. In some embodiments, the use of multiple HMDs provides a more robust tracking modality because additional perspectives can be compared, weighted, correlated, etc., in software to verify and refine a 3D model of the environment. In some embodiments, permanently mounted cameras in the OR (to a wall, cart, or surgical light) can utilize higher-quality IR and optical components than those in the HMDs. Where there is a disparity in the quality of components, 3D model refinement using multiple perspectives can assign heuristic weights to the different camera sources, allowing refinement with deference to higher-quality components or more reliable perspectives.

Given the rapid development of optical sensor technology spurred by the mobile device market, HMD optical sensor technology is rapidly evolving. In some embodiments, a cart-mounted camera array is unnecessary for the optical tracking modality. Optical and IR sensors on HMDs worn by surgeons, residents, and nurses can provide sufficient perspectives for tracking fiducial marks on a patient and tools without the need for a standalone cart. This can mitigate the cost of adding HMDs to conventional tracking modalities or reduce the overall system cost. HMD prices for off-the-shelf components are rapidly declining as they become accepted in the consumer market. In some embodiments, cart or wall-mounted cameras can be added to the system using lower quality optical and IR sensors than traditional cart-mounted tracking systems to supplement embodiments that otherwise rely entirely on IR and optical sensors of HMDs. (Optical sensors include IR sensors/cameras and optical sensors/cameras, and may be described generically as cameras, but these components may be listed separately for clarity; embodiments may include any subset of available optical sensors.)

As shown in FIG. 14, each camera array (of a cart-mounted tracking system 1110 and of each HMD 1100) has a camera pose that defines the frame of reference for the camera system. In the case of cart- or wall-mounted cameras, the camera pose may be fixed throughout the operation. In the case of HMD cameras, the camera pose will often change during the operation as a user moves her head. Accordingly, some embodiments, where HMDs work along with cart- or wall-mounted tracking systems to supplement the tracking information, use fiducial marks to identify at least the location of the other camera systems in the environment. In some embodiments, fiducial marks can be rigidly applied to these camera systems to enable other camera systems to identify the location and pose of each other camera system. This can be useful in calculating camera perspectives to determine a robust 3D model of the surgical environment. It should be appreciated that as a user moves in HMD, the field-of-view may lose sight of other camera systems, but fiducial marks on the systems allow the camera system to quickly identify other cameras and their poses once they move back into the field-of-view.

Once cameras has identified the location and/or the pose of other cameras in the environment, the cameras can identify the location and orientation of fiducial marks that are affixed to patient bones or tools. Where two cameras have the same fiducial markers in their field-of-view, a central processor or peer-to-peer processing can correlate the location and orientation of those marks relative to each camera to create a model of the 3D environment that includes the location and pose of each camera and the location and pose of each operable bone of a patient. In the example shown in FIG. 14, the fiducial markers 1112 and 1114 mounted to each patient bone include four reflective points with known geometry. Each of these fiducial markers 1112 and 1114 has a pose defined in three-dimensional space. Because this geometry is known, this pose can be correlated through a registration process to define a frame of reference for each bone that is a transfer function of the pose of the corresponding fiducial mark. Thus, when the pose can be determined by a processor from camera information, the pose of each bone 1116 and 1118 relative to each camera's field-of-view can be calculated. In this example, headset 1100 and cart-mounted tracking systems 1110 communicate with one another or with a central processor wirelessly.

The robustness of the 3D model is improved by the number of fiducial marks that multiple cameras observe. Because cameras capture an analog world with digital signals and are limited to the quality of optical components, the precision with which each camera can locate fiducial markers in space includes some degree of error. The use of multiple camera systems or HMDs can reduce this error, thereby creating a more robust 3D model with a level of precision unachievable with a single cart mounted tracking modality. Any method of computing a 3D model of an environment from pose information captured by multiple cameras that is known in the art may be adapted to a multi-HMD operating room environment.

Figure 15:
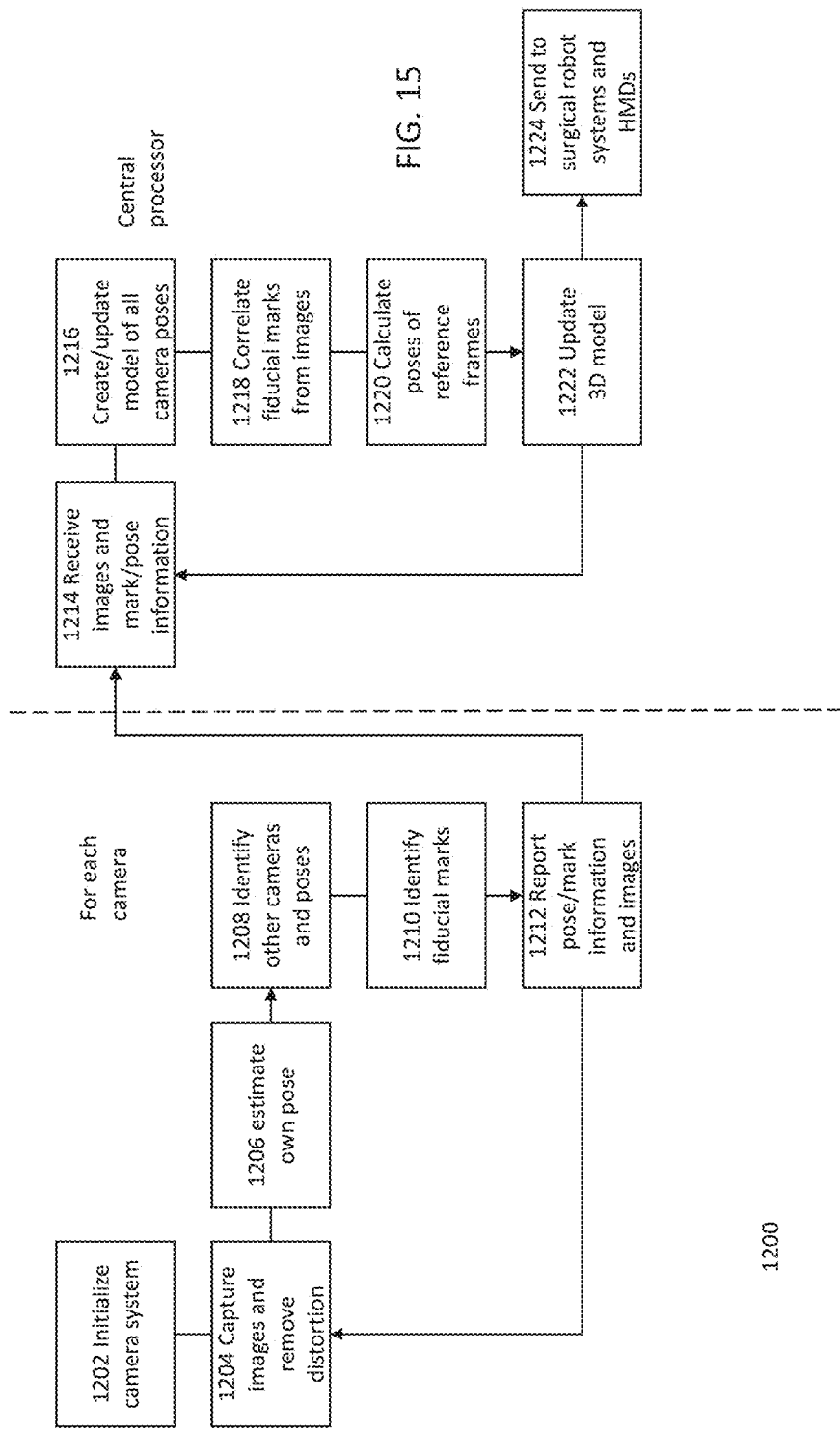
FIG. 15 is a flow chart illustrating operation of an augmented reality system, for use with some embodiments.

FIG. 15 shows an exemplary method 1200 for using AR headsets in the surgical environment where fiducial marks are used on patients and tools. Each camera system in the operating room, which may include cameras on HMDs and fixed cameras, such as cameras mounted to carts or walls, may perform steps 1202 through 1212. Each camera system may be initialized at step 1202. This can include any startup procedures and calibrations needed to prepare the camera for operation during surgery. At step 1204, the camera system captures images and applies any techniques to prepare those images for processing, including removing distortion or any image preprocessing. At step 1206, each camera system can optionally estimate its own pose. This can include gyroscopic sensors, accelerometer sensors, magnetic sensors, or compasses and models based on previous poses that are updated based on image information. At step 1208, each camera system attempts to identify any other camera systems that are in its field-of-view. This can be useful for determining the geometric relationships between various camera systems. In some embodiments, this identification step looks for certain markers in the visual field that can include fiducial marks that are placed on cameras or IR beacons or the like. At step 1210, each camera system identifies fiducial marks in the images captured. Fiducial marks may be physical markers placed on or affixed to the patient's anatomy, tools, other cameras, or landmarks in the environment. The processor associated with each camera system can determine pose information based on these fiducial marks. This pose information can include the pose of that camera system and/or the pose of objects in the environment. For example, a tool may have a plurality of IR/UV-reflective or uniquely colored or patterned markers placed on it such that the location and orientation of that tool can be identified from one or more images. Similarly, a camera may have a plurality of fiducial markers placed upon it to allow the camera's position and orientation to be calculated by other camera systems. This information about the position and orientation of other objects in the environment may be reported wirelessly or through a hard wired network to a central processor that manages the system, at step 1212. The above-listed steps (1204-1212) may be repeated as each camera system continuously captures images and prepares them for analysis.

A central processor receives the image data and the pose or fiducial mark information from each camera system at step 1214. At step 1216, the central processor creates or updates a model of all camera systems in the environment and their poses relative to an environment reference frame. At step 1218, the central processor identifies fiducial marks in the received images to correlate marks captured by multiple camera systems. By capturing such marks in multiple fields of view, different perspectives of an object can be used to refine the determination of the position and orientation of the object in the environment. Once correlated, at step 1220, the central processor can calculate the position and orientation of each object having fiducial marks, such as tools, environmental landmarks, other HMDs or camera systems, and patient anatomy. At step 1222, this information is used to update a 3D model of the environment, calculating a position and orientation of objects relative to a fixed reference frame, as well as identifying the pose of reference frames defined by each object. For example, a patient's femur has a given pose based on the way the patient is laying within the operating room. That femur also has its own reference frame, which is useful when correlating preoperative imaging with the structure of the patient's femur and identifying the portions of that femur that may need to be resected during surgery. At step 1224, the central processor can use the updated 3D model to send information about the environment to a surgical robotic system and any HMDs in the operating room. The central processor continues to receive images and update models of the environment. In some embodiments, this process can be enhanced via other sensors, such as accelerometers, compasses, etc., for any objects within the operating room. Once this 3D model is generated, the central processor is free to interact with individual HMDs in accordance with numerous software applications described herein.

Figure 16:
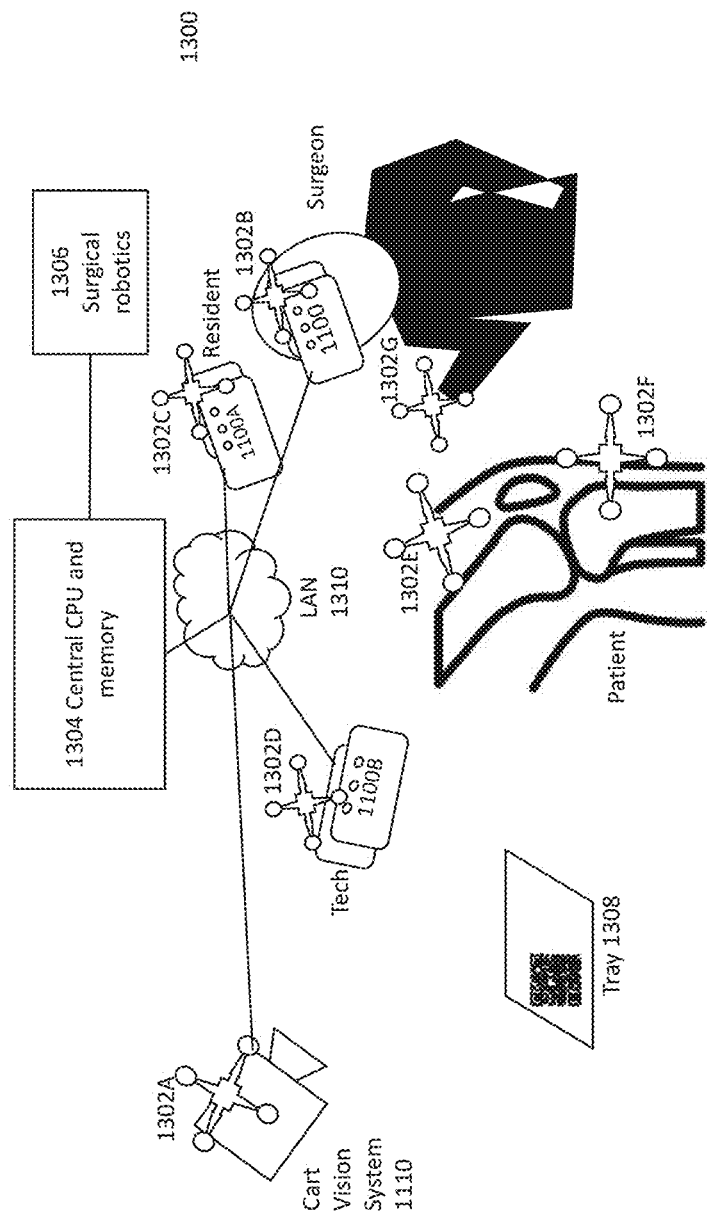
FIG. 16 is a system diagram illustrating an augmented reality visualization system, for use with some embodiments.

FIG. 16 is a system diagram of an augmented reality system 1300 for use during surgery. In this example, fiducial markers 1302A-G are placed on each HMD and camera system, as well as a patient's femur and tibia. In this example, a partial or total knee replacement is being performed. A cart-mounted camera system 1110 (such as that available with the NAVIO surgical system) is placed with a view of the surgical scene. Fiducial markers 1302E-F having a plurality of fiducial marks (such as three or more spherical IR reflective marks) are temporarily, mechanically affixed to the patient's femur and tibia. This allows cart-mounted camera system 1110 to track the pose and motion of the tibia and femur. This can be used to determine the pivot center between these bones, as well as other information about the patient's anatomy during motion. A surgical robot 1306 may also use this information to determine the ideal placement of cuts and replacement knee parts. The cart-mounted camera system 1110 communicates via a local area network (e.g., a secure Wi-Fi network) with a central processor 1304 that includes software and memory sufficient to process the images from the cart-mounted camera to determine an environmental model and to calculate any information that may be useful to the surgical robot 1306 to assist the surgeon in the operation. In some embodiments, central processor 1304 is part of the cart that supports the camera system. In these embodiments, cart-mounted camera system 1110 may communicate directly with central processor 1304. Central processor 1304 then communicates with any robotic systems 1306 that are used during the procedure.

In addition to this traditional robotic surgery system, a plurality of HMDs 1100, 1100A, and 1100B are worn by doctors and house staff during the procedure. Each HMD has an identifier that allows that HMD to be identified in the visual plane of the cart-mounted camera system 1110. In some embodiments, the identifier includes an IR emitter that sends a binary modulated code identifying the specific HMD or wearer.

In this embodiment, each HMD 1100-1100B has an array of cameras (IR and/or visible spectrum) that capture the visual field of the user (or subsection or wider angle, thereof) from multiple positions, creating a stereoscopic (or higher order) view of the scene for image processing. This allows each headset to capture image data sufficient to provide three-dimensional information about the scene. Each HMD captures a different prospective of the surgical scene. As explained in FIG. 15, the camera arrays of each HMD capture images of the scene, estimates the current pose of the HMD (which can be by non-optical sensors as well), and identifies other cameras in the field-of-view and any fiducial marks. In some embodiments, HMDs have an IR emitter to illuminate reflective fiducial marks. These captured images can then be processed onboard the HMD or sent to the central processor for more powerful image processing. In some embodiments, a preprocessing step is performed on each HMD to identify fiducial marks and other cameras and to estimate poses for fiducial markers and other cameras. Each HMD can communicate with other HMDs or with the central processor 1304 over local network 1310, such as a secure Wi-Fi network. The central processor 1304 receives the image information from each HMD and further refines the 3D model of the surgical space.

Based on the images captured from each HMD, central processor 1304 can determine which objects in the three-dimensional model of the surgical theatre correspond to reference features in the two-dimensional image plane of each HMD. This information can then be communicated back to the HMD over the network 1310. In some embodiments, each HMD receives information about the three-dimensional model at regular intervals, but uses onboard image processing to track objects based on the three-dimensional model information received from the central processor. This allows the headset to accurately track objects within the field-of-view in real time without delays caused by network communication.

In some embodiments, an HMD 1100 receives information about objects from the central processor 1304 and processes current and recent images to identify the salient features of an object corresponding to the three-dimensional model information received from the central processor. The HMD 1100 uses local image processing to track those features (and the associated objects) in the visual plane. This allows the HMD 1100 to have reference pixel locations to overlay information related to objects.

For example, a surgeon's HMD 1100 can capture fiducial marks 1302E and 1302F relating to the tibia and femur. Based on communication with the central processor 1304 to identify a three-dimensional model of the tibia and femur, the surgeon's HMD 1100 can identify which features in the two-dimensional images correspond to features of the tibial plateau and femoral condyles. By tracking the fiducial marks on these bones or by tracking the image features identified as the tibial plateau or femoral condyles, the surgeon's HMD 1100 can track these features of the bones in real time (taking into account any processing and memory delays) without worrying about network lag. If software running on HMD 1100 wishes to overlay visual indicators of where to cut on the tibial plateau, the HMD can track the tibial plateau as the surgeon's head moves or the patient's leg moves. The surgeon's HMD 1100 can accurately estimate where the reference points of that bone feature are and where to display the augmented holographic feature.

In some embodiments, HMDs 1100-1100B can communicate directly to assist one another in updating any positional models. Using peer-to-peer communication, HMDs 1100-1100B can present their models of the environment to other HMDs allowing them to rectify their own models using arbitration rules.

In some embodiments, objects within the surgical space can include QR codes or other visual indicators that can be captured by a camera on a HMD 1100 to convey information about that object to the HMD directly. For example a surgical tray 1308 having tools for a given surgery can have a QR code indicating the identity of the tray. By consulting a database, the HMD 1100 capturing a QR code can identify exactly which objects and surgical tools are on that tray prior to the start of the surgery. This can allow the HMD 1100 to identify important objects relating to the surgery, such as various knives, cutting tools, sponges, or implantable devices. Then, the HMD 1100 can track these objects within the surgical space taking into account the last known location of those objects. In some embodiments, HMDs 1100-1100B can share information about the last known location of objects in the surgical theatre to make it faster or easier for each headset to identify objects that come into the field of view of each HMD. This can assist the surgeon in quickly identifying which tool or object to grab for the next step of the surgery. For example, a tray may include a series of cutting guides that are used in various surgeries. However, each patient may only need a single cutting guide used on his femur. HMD 1100 can identify the cutting guides in the tray based on the tray's QR code and an initial layout and track the individual cutting guides. The holographic display of the HMD 1100 can superimpose an indicator to the surgeon of which cutting guide to use for a given step in the procedure.

Figure 17A:
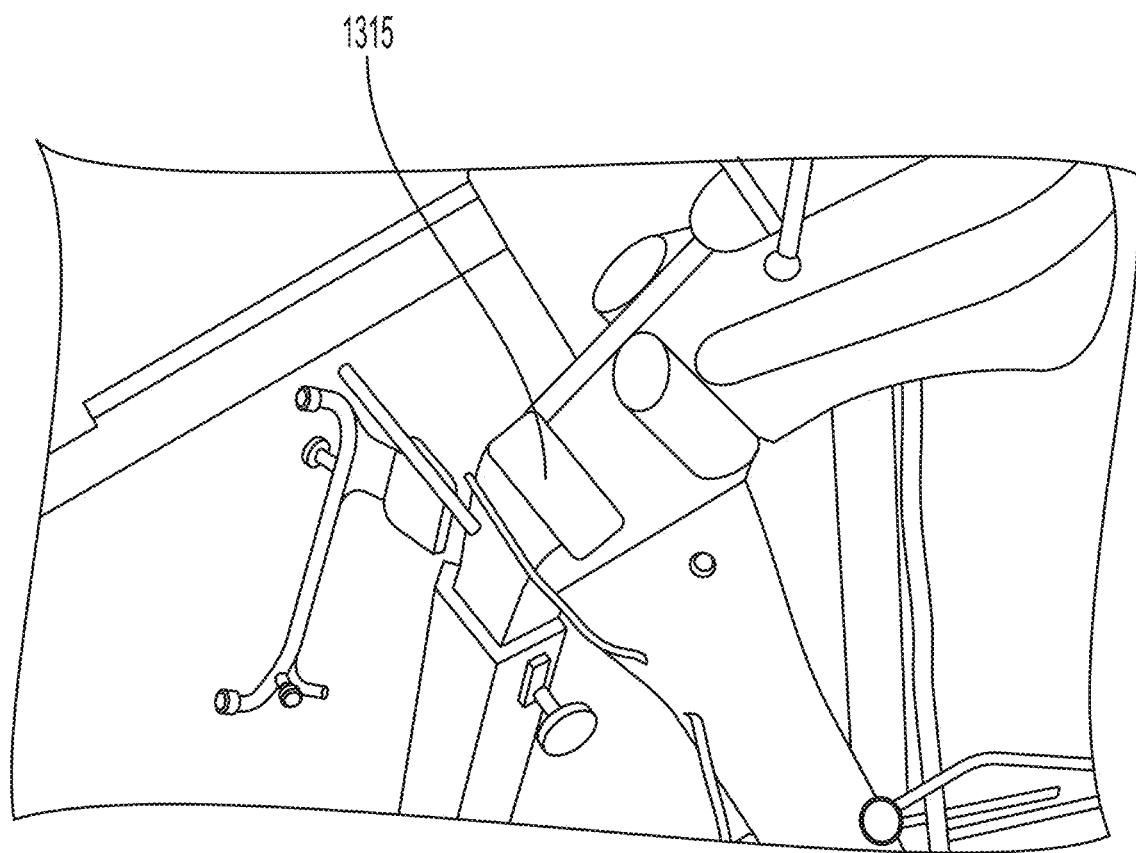
FIG. 17A provides an example of an augmented reality visualization in some embodiments.

In different embodiments, various information can be displayed to a user of an HMD. For example, in FIG. 17A, a user is presented with a holographic superimposition 1315 of a resection area on a femoral condyle to indicate exactly where a surgeon should remove tissue for seating a replacement knee part that will be cemented and affixed to that femoral head. FIG. 17A is the view that the surgeon sees, including the natural scene and a superimposed shape that is placed holographically onto the surface of the bone. In some embodiments, rather than using a hologram as part of a conventional AR display, a laser or projector mounted to the HMD can project this information directly onto the surface of the bone. Cameras on the HMD can provide a feedback loop to ensure proper and consistent placement of the projection onto the bone.

Figure 17B:
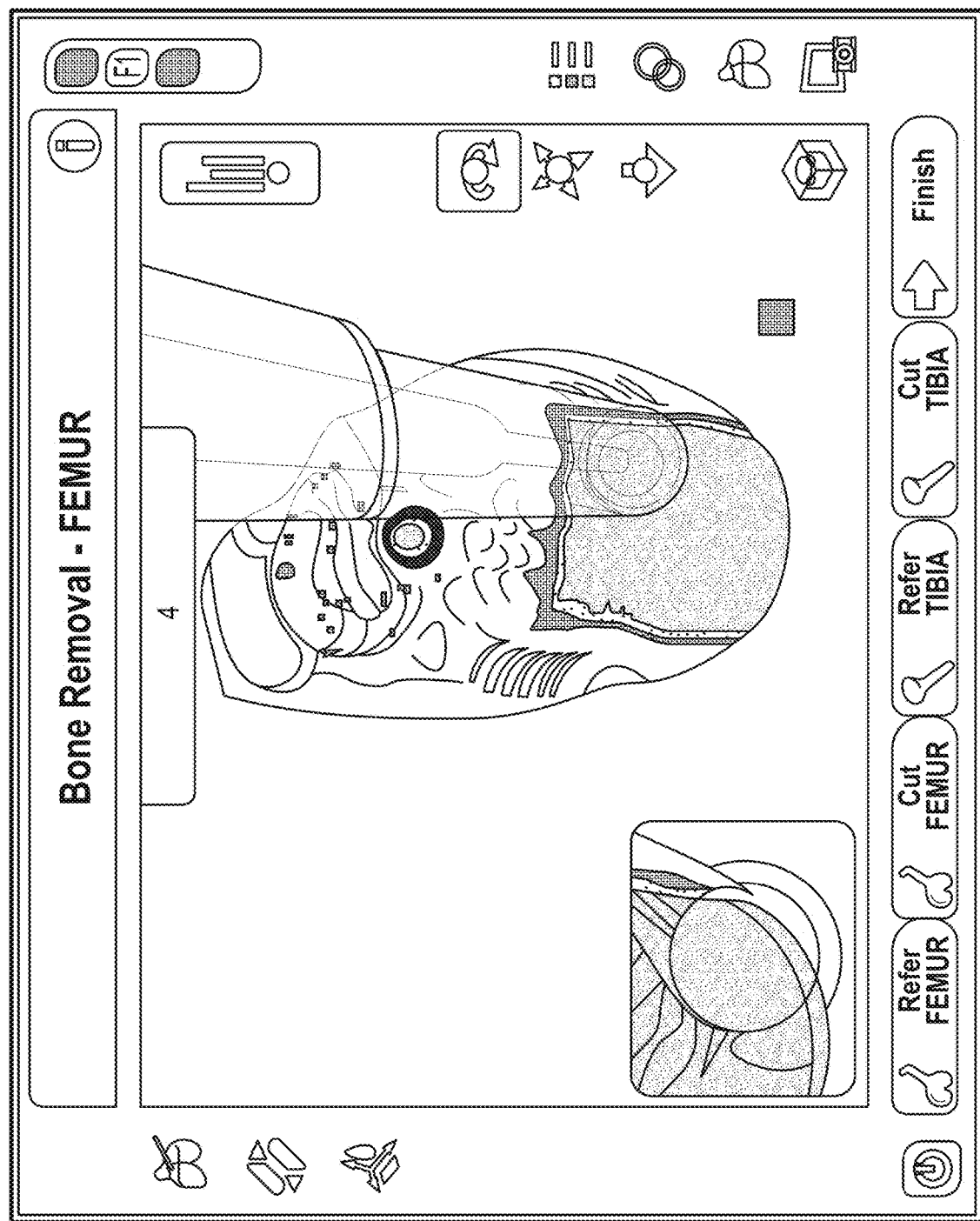
FIG. 17B provides an example of a three-dimensional visualization in some embodiments.

In FIG. 17B, an exemplary display of the three-dimensional model is shown. Conventionally, this display might appear on a computer screen for robotic surgery system. It indicates on the three-dimensional model exactly where the surgeon's tool should go and where the tool should cut the bone. This information can be adapted for an AR display, overlaying a part of the three-dimensional model of the bone holographically onto the bone, allowing the resection area to be displayed to the user who looks at the real-world bone. In some embodiments, only the three-dimensional model of the resection area is displayed, while a three-dimensional model of the bone is compared to the visual field of the HMD to ensure proper placement of the holographically displayed three-dimensional model of the resection area. In addition, any of the menus or additional information shown in FIG. 17B can be displayed as a holographic menu to the user of the HMD, allowing the user to select certain user interface menus for additional information or views through the standard AR user interface.

Figure 18A:
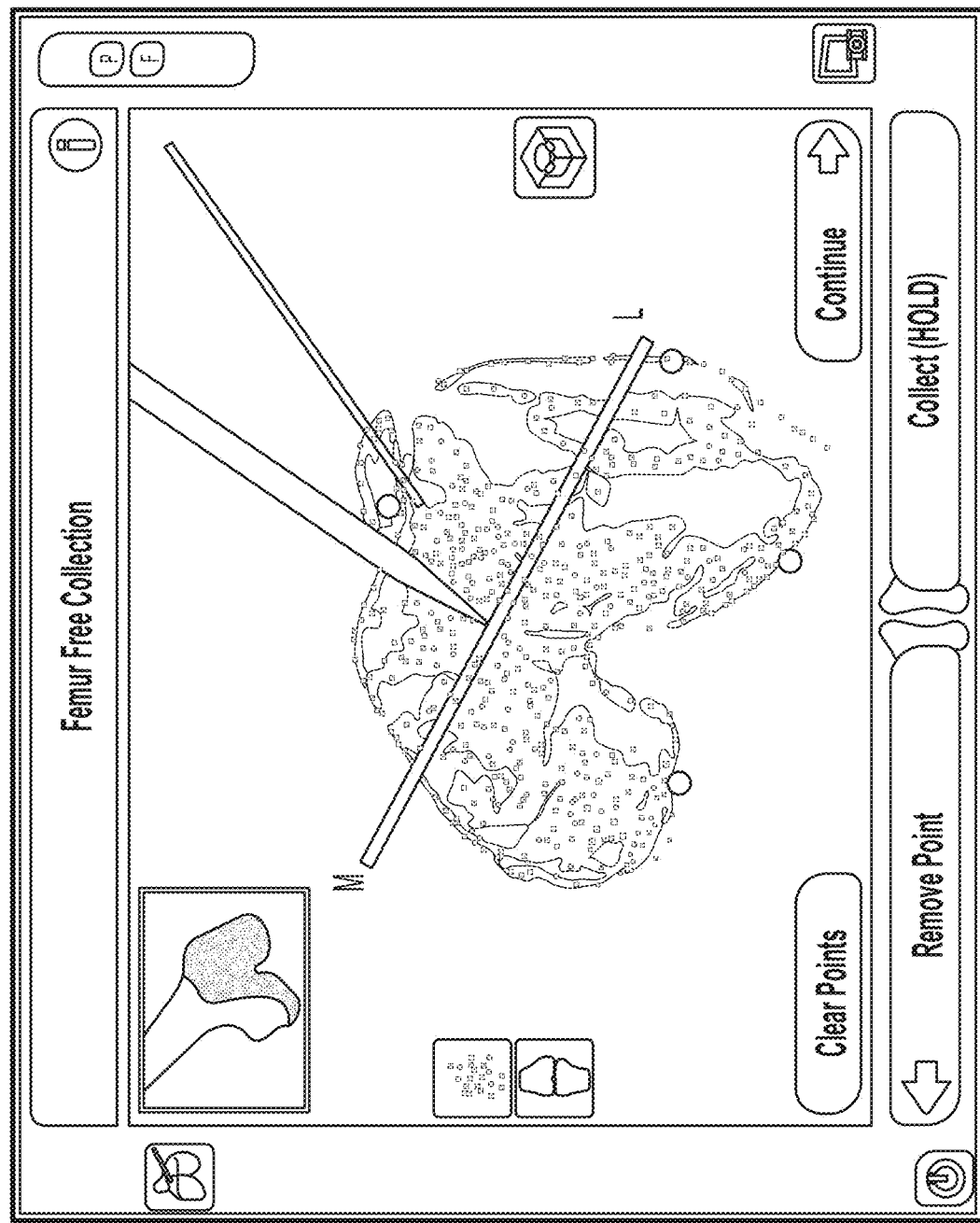
FIG. 18A provides an example of a three-dimensional visualization in some embodiments.

FIG. 18A shows an additional three-dimensional model view that can be displayed to a user. FIG. 18A depicts points identified by a point probe in a femoral head mapping process. Such information can be displayed to a surgeon via a holographic image of the portions of bone that have been probed to identify the shape of the femoral head. In some embodiments, this information may be displayed on a resident's HMD. The image shown in FIG. 18A could be displayed on a conventional computer display within the operating room. Individual portions of a display, such as the three-dimensional model of the femoral head can be displayed holographically onto the bone using the AR display. Again, any of these menus shown can be displayed to the user's headset or can be displayed on the two-dimensional LCD-type display on a cart in the room. These menus can be selected by a user of an HMD to change views or get additional information. The user of an AR HMD can make a selection of the menu using any conventional AR selection means, such as air clicks or head/hand gestures that can be detected by sensors or cameras in the HMD. In some embodiments, where robotic cutting tools are used, this display may indicate where a robot is to cut, allowing visual confirmation by the surgeon before cutting begins.

Figure 18B:
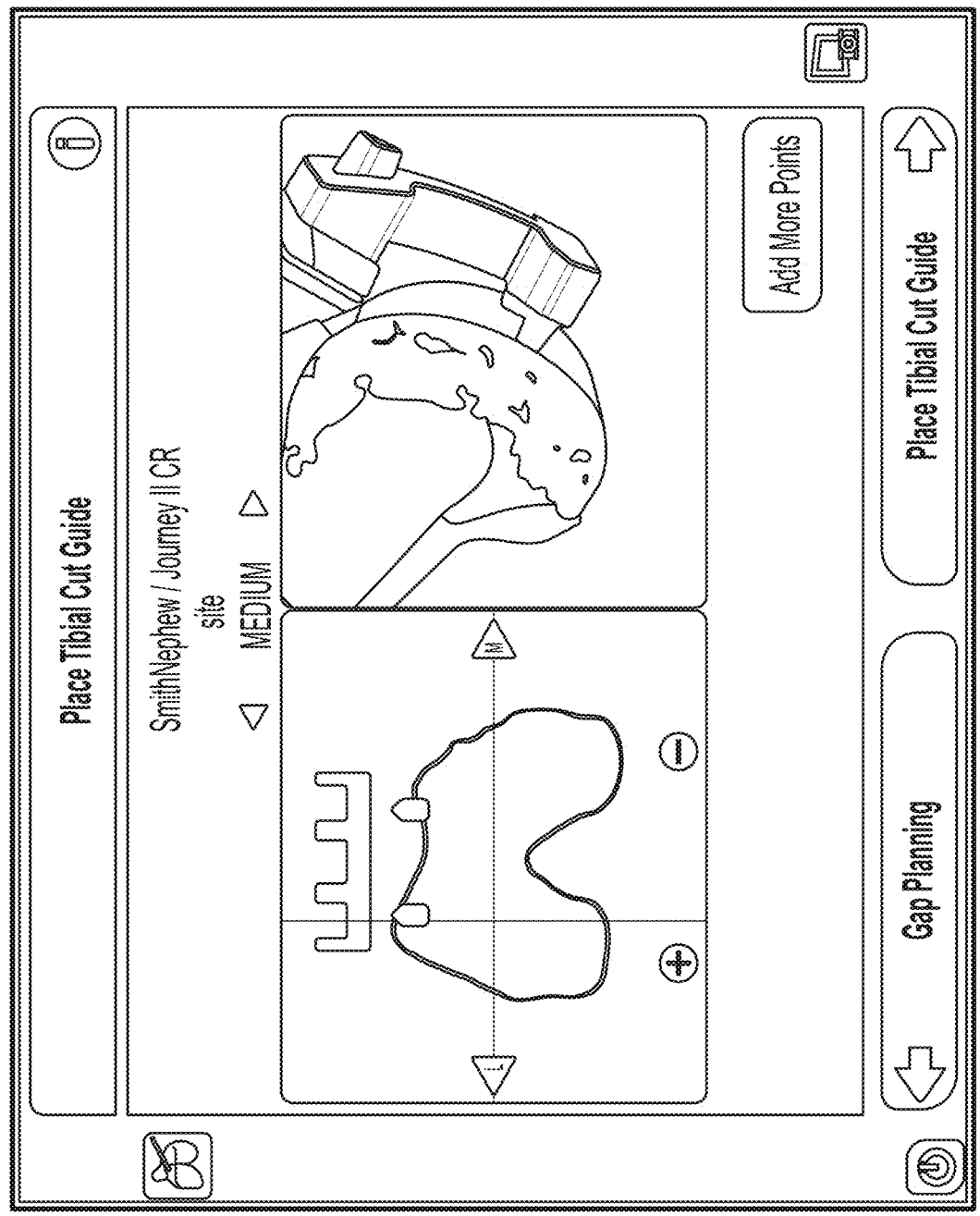
FIG. 18B provides an example of a three-dimensional visualization in some embodiments.

FIG. 18B shows another three-dimensional model of the femur that shows proper placement of the femoral cutting guide. This can be displayed to a surgeon holographically to indicate exactly where the femoral cutting guide should be placed. During alignment of the cutting guide, a surgeon can consult this holographic superimposition to ensure that the placement is approximately correct. Robotic vision systems within the room can provide a final confirmation before mounting the cut guide. In a hip procedure, this same technology could be used to aid the surgeon with placing a custom femoral neck cut guide, or an acetabular jig used to help with cup placement. In some embodiments, the display in FIG. 18B can be selected from menus in FIG. 18A, allowing a surgeon to switch between a history of steps and a model of the next steps that can be accomplished. This can allow a user to effectively rewind and fast-forward the procedure, seeing steps to be performed in the future and the steps that have already been performed.

In some embodiments, a user may also select and modify proposed cutting angles, allowing a processor to calculate using a model of anatomy, such as LIFEMOD™ by SMITH AND NEPHEW, INC., how changes in the cutting angles may affect the geometry of the replacement knee. Displayed information can include static and dynamic forces that will occur to ligaments and tissue of a patient if cutting geometry is altered. This can allow surgeon to modify the replacement knee procedure on the fly to ensure proper placement of replacement knee parts during the procedure to optimize the patient's outcome.

Figure 19:
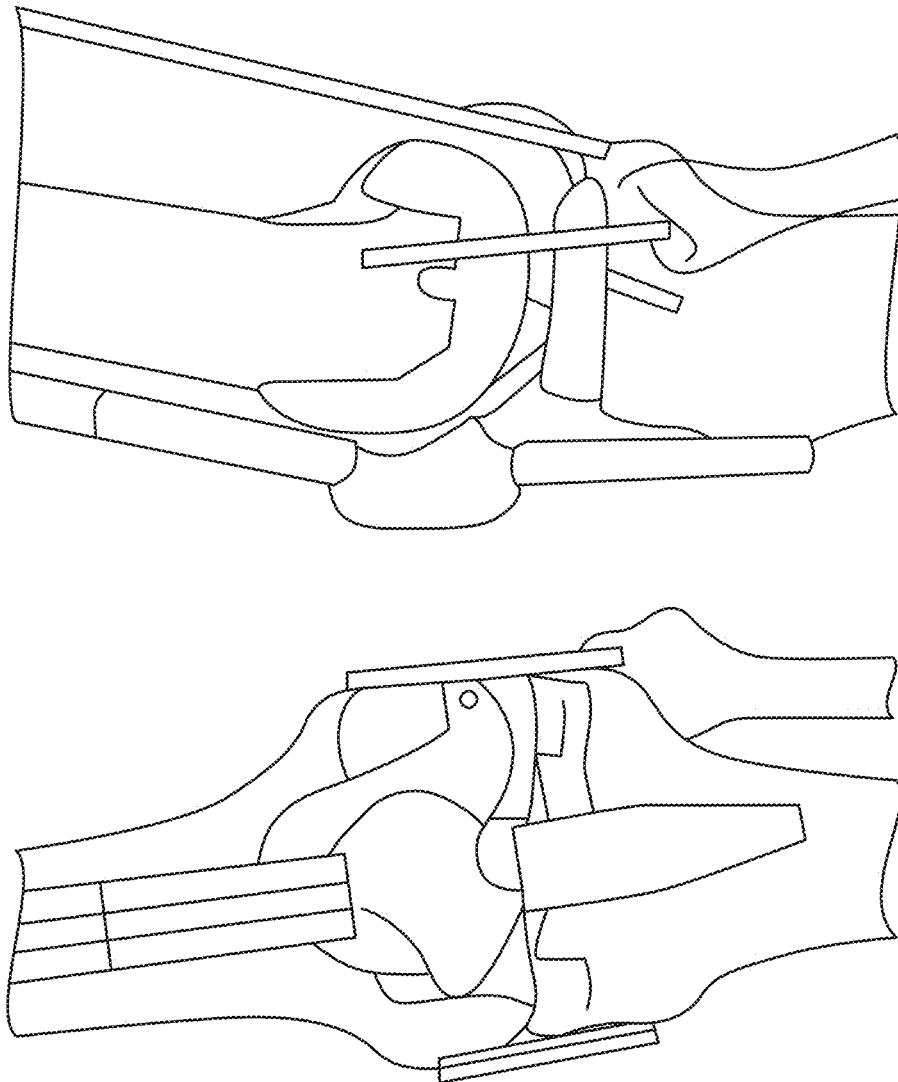
FIG. 19 provides an example of a three-dimensional model of a knee components visualization, for use with some embodiments.

FIG. 19 shows a three-dimensional model of a complete replacement knee system including a model of ligament and tendon forces. A portion of this model can be displayed holographically to a surgeon during operation if the surgeon wishes to see how cutting decisions during the procedure can affect hinge geometry and resulting stresses on ligaments and tendons. Exemplary modeling of the placement of an implant and of other parameters for an arthroplasty procedure is described in U.S. patent application Ser. No. 13/814,531, which was previously incorporated herein by reference. A surgeon can change parameters of the arthroplasty via the AR interface to create hypothetical results that may be displayed via the headset, such as whether a parameter change during a total knee arthroplasty (TKA) cause a patient's gait to become more varus or valgus or how a patella will track. Optimized parameters can also be modeled and displayed to the surgeon the procedure holographically.

In some embodiments, the wearer of an HMD can selectively request display of patient history information including preoperative scans of patient tissue. In some embodiments, the display of the scans can be holographically overlaid to the existing patient tissue observed in the scene by aligning features from the imaging to features found in the patient. This can be useful for guiding a surgeon to determine the proper resection area during a procedure.

In some embodiments, video of a three-dimensional model of data can be recorded, logged, and time stamped. Playback of the video can be performed after the procedure or the video could be called up on an HMD display during the procedure to review one or more steps. This may be a valuable teaching tool for residents or for a surgeon wishing to see when a certain cut or step was undertaken. Playback may be a useful tool to create a change of surgical plan during the procedure based on events during the procedure. Head or hand gestures by an operator of the HMD can rewind or advance the virtual viewing of video or 3-D model information.

Exemplary Use Cases

By adding AR to an operating theater using HMDs, many improvements to the operative flow in various surgeries can be achieved. The following are some examples of the ways in which AR can be utilized in various surgical procedures.

Software can utilize the HMD camera and display to determine (with the assistance of preoperative plan and processor) the ideal starting location for an incision. Through holographic overlay (or by projecting directly onto patient skin), the line defining the extents of an incision location can be displayed to a surgeon looking at the patient. The exact location can consider the specific patient anatomy and intraoperative point registration, where a user registers patient geometry with the system more accurately.

Soft tissue dissection can utilize built-in cameras of the HMD and the model of the patient to highlight certain muscle groups, ligaments of a joint, such as a hip capsule or knee, nerves, vascular structures, or other soft tissues to aid the surgeon during dissection to get to the hip joint or knee. The augmented display can display indicators to a surgeon of the location of these soft tissues, such as by holographically displaying a 3D model or preoperative imaging.

During a hip replacement or repair, software may superimpose a line across the proximal femur that indicates the ideal neck cut based on the pre-operative plan. This can define a precise location for cutting the bone to place a replacement femoral head prosthesis. Similar to the above examples, during acetabular reaming, the heads-up display can show the amount of bone that needs to be removed by overlaying different colors onto the patient's acetabulum. This allows the surgeon to know when he/she is getting close to the floor of the acetabulum. In some embodiments, the extent of the resection area used for reaming the acetabulum can be superimposed onto the patient bone. A color indicator, such as green, yellow, and red, can indicate to a surgeon (based on the location of his/her tool) how deep the reaming has gone relative to the predetermined resection area. This provides a simple indicator during surgery to avoid removing too much bone. In some embodiments, the heads-up display may superimpose an image of a reamer handle (or other tool) to indicate the proper inclination and anteversion from the pre-operative plan (or from surgeon input). It may also display the actual inclination/anteversion of the reamer/tool handle to allow the surgeon to correct their approach angle.

During a cup impaction step for hip replacement, similar to reaming, the inclination and anteversion values can be displayed on the heads-up unit, along with the values that were determined from the pre-operative plan. A superimposed image of a cup impactor (or a long axis) may be displayed to aid the surgeon with positioning the implant. The HMD can also display an indication of how far away the cup is from being fully seated. For example, a measurement value or a change of a color of a superimposed cup or impactor can be used to indicate whether the cup is fully seated or overlaying a model of the final ideal location of the cup that highlights the difference from what the surgeon currently sees.

An HMD can highlight screw holes that should be used to affix any hardware to a bone. While using a drill and a drill guide, the heads up display may superimpose an "ideal" axis for screw insertion to aid with positioning of the screw within the screw hole.

During femoral canal preparation, an HMD can superimpose an image of a broach in the proper orientation (corresponding to the pre-operative plan) while the surgeon is inserting the broach into the femoral canal. Additionally, there can be an indication superimposed onto the scene to give the surgeon information related to final broach seating. This can be shown by a changing of color around the broach or by a percentage or number that indicates to the surgeon if the broach is fully seated and whether or not that size is the correct "final" component size.

A surgeon performing a trial reduction can be given the option to display a combination of leg length and offset increases based on the implant sets being used (e.g., in chart form). For example, the chart can list a combination of leg length and offset changes for each of the implant combinations. Alternatively, there may be an option to have the proposed/changed components superimposed on the patient's anatomy to show the surgeon what the resultant implant positioning would be if they were to change the neck offset/femoral head length (e.g., changing from STD to High offset neck, +0 to +4 femoral head). The surgeon can select the appropriate implants from a first trial and perform the implantation step. Multiple trialing steps, a conventional standard of care, would likely be unnecessary.

Resurfacing techniques can also be improved through AR. When performing a resurfacing procedure, the HMD can superimpose an axis that indicates the ideal position and orientation of a guide wire. In some embodiments, software allows the surgeon to adjust this axis, and the HMD can superimpose a cross-sectional or other view of the femoral neck to display to the surgeon how thick the bone would be if the implant were inserted at the position (one of the most common complications from resurfacing surgery is inserting the component in varus, which can lead to femoral neck fracture). Giving the surgeon the ability to adjust this axis may enable optimization of the performance of the implants in-vivo.

In some embodiments, this traditional femoral resurfacing technique can be replaced by a burr-only technique. In this exemplary technique, a surgeon prepares the proximal femur entirely by burring. The bone map can be superimposed onto the bone to indicate how much bone is left to be removed. This can also be indicated by color on the map. A variety of cutting instruments can be made available to the surgeon to reduce the overall amount of time required to cut the bone to the desired shape.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, a tri-scopic, quad-scopic, etc., imaging. In addition to the camera array, which in some embodiments is affixed to a cart, additional cameras can be placed throughout the surgical theatre. For example, hand-held tools or headsets worn by operators/surgeons can include imaging capability that can communicate images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in QR codes or barcodes. This can be helpful in identifying specific objects not manually registered with the system.

In some embodiments, specific objects can be manually registered by a surgeon with the system preoperatively or during operation. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one or two dimensional optical codes (barcode, QR code, etc.) can be affixed to objects in the theater to provide passive identification that can occur based on image analysis. If these codes are placed asymmetrically on an object, they can also be used to determine orientation of an object bay comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality headsets can be worn by surgeons and other staff, providing additional camera angles and tracking capabilities.

In addition to optical tracking, certain features of objects can be tracked by registering physical properties of that object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

Figure 20:
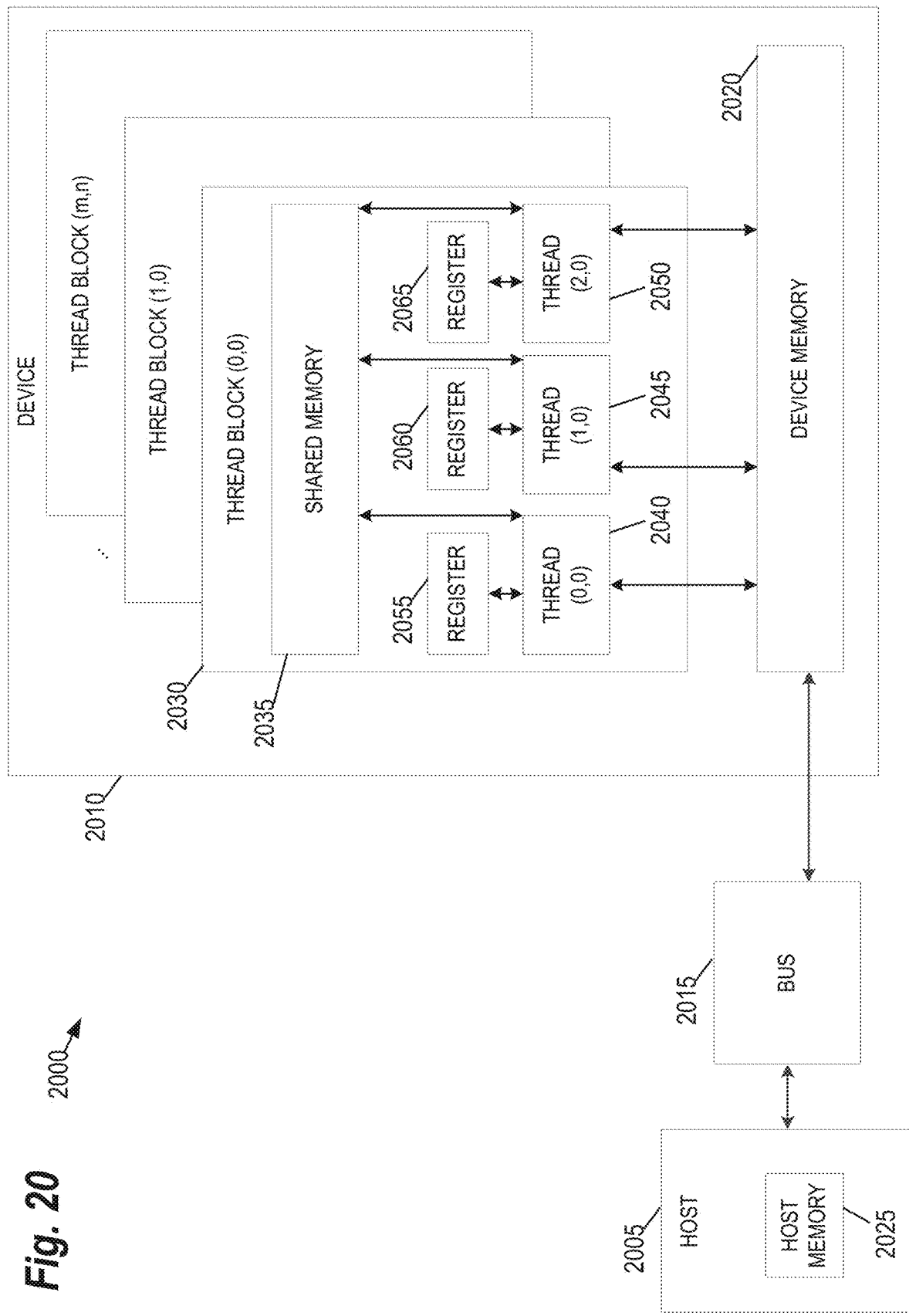
FIG. 20 is a system diagram illustrating an exemplary computational system, for use with some embodiments.

FIG. 20 provides an example of a parallel processing platform 2000 that may be utilized to implement the Surgical Computer 150, the Surgical Data Server 180, or other computing systems used in accordance with the present invention. This platform 2000 may be, for example, used in embodiments in which machine learning and other processing-intensive operations benefit from parallelization of processing tasks. This platform 2000 may be implemented, for example, with NVIDIA CUDA™ or a similar parallel computing platform. The architecture includes a host computing unit ("host") 2005 and a graphics processing unit (GPU) device ("device") 2010 connected via a bus 2015 (e.g., a PCIe bus). The host 2005 includes the central processing unit, or "CPU" (not shown in FIG. 20), and host memory 2025 accessible to the CPU. The device 2010 includes the graphics processing unit (GPU) and its associated memory 2020, referred to herein as device memory. The device memory 2020 may include various types of memory, each optimized for different memory usages. For example, in some embodiments, the device memory includes global memory, constant memory, and texture memory.

Parallel portions of a big data platform and/or big simulation platform may be executed on the platform 2000 as "device kernels" or simply "kernels." A kernel comprises parameterized code configured to perform a particular function. The parallel computing platform is configured to execute these kernels in an optimal manner across the platform 2000 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by a grid of thread blocks (described in greater detail below). Using concurrent kernel execution, streams, and synchronization with lightweight events, the platform 2000 (or similar architectures) may be used to parallelize portions of the machine learning-based operations performed in training or utilizing the smart editing processes discussed herein. For example, the parallel processing platform 2000 may be used to execute multiple instances of a machine learning model in parallel.

The device 2010 includes one or more thread blocks 2030 which represent the computation unit of the device 2010. The term thread block refers to a group of threads that can cooperate via shared memory and synchronize their execution to coordinate memory accesses. For example, threads 2040, 2045 and 2050 operate in thread block 2030 and access shared memory 2035. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, the thread block 2030 may be organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints.

Continuing with reference to FIG. 20, registers 2055, 2060, and 2065 represent the fast memory available to thread block 2030. Each register is only accessible by a single thread. Thus, for example, register 2055 may only be accessed by thread 2040. Conversely, shared memory is allocated per thread block, so all threads in the block have access to the same shared memory. Thus, shared memory 2035 is designed to be accessed, in parallel, by each thread 2040, 2045, and 2050 in thread block 2030. Threads can access data in shared memory 2035 loaded from device memory 2020 by other threads within the same thread block (e.g., thread block 2030). The device memory 2020 is accessed by all blocks of the grid and may be implemented using, for example, Dynamic Random-Access Memory (DRAM).

Each thread can have one or more levels of memory access. For example, in platform 2000, each thread may have three levels of memory access. First, each thread 2040, 2045, 2050, can read and write to its corresponding register 2055, 2060, and 2065. Registers provide the fastest memory access to threads because there are no synchronization issues and the register is generally located close to a multiprocessor executing the thread. Second, each thread 2040, 2045, 2050 in thread block 2030, may read and write data to the shared memory 2035 corresponding to that block 2030. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 2010 to read and/or write to the device memory 2020. Device memory requires the longest time to access because access must be synchronized across the thread blocks operating on the device.

The embodiments of the present disclosure may be implemented with any combination of hardware and software. For example, aside from the parallel processing architecture presented in FIG. 20, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

Applying Statistical Models to Optimize Pre-Operative or Intra-Operative Planning by Patient Activity There is a need for simple and processor efficient planning tools for patient-specific preoperative or intraoperative planning by surgical staff. The preoperative planning stage for arthroplasty should be computationally and labor efficient due to the volume of surgeries and limitations on the time of engineers and surgeons, while the intraoperative planning stage places more computational limitations on any simulation data because there is no time to wait for simulations in the surgical theater. With the rise of cheap tablet or mobile devices (lower powered computational systems in general, such as cart work stations in a surgical theater) there is an opportunity to provide low processor overhead applications that can assist surgical staff in gathering data and planning surgical procedures that utilizes more powerful systems that are interfaced across a network that maintain data stores of simulation or real-world data from past patient cases. These backend systems can maintain, manipulate, create, and mine large amounts of data, allowing lower powered devices in a surgical office or to take advantage of this trove of information. An ideal planning application should assist surgical staff in gathering data and planning surgical procedures and access data stores of simulation or real-world data from past patient cases.

For example, in some embodiments, in-theater or mobile devices with an intuitive touchscreen interface, wireless networking ability, and cameras lend themselves particularly well to assisting creation or modification of a surgical plan that can be used with a CASS, either in a pre-operative phase or during an operation. Their interface can be helpful gathering and interacting with new information (e.g., imaging or force characteristics of a joint captured during surgery) that can be used to improve a surgical plan. Devices such as tablets, laptops, or cart-based computers often lack powerful processors, which can be improved by utilizing a server or a database of past simulation or clinical results to give devices in a surgical theater or office the advantages of patient-specific simulation without the need to run simulations locally or on-demand. Some embodiments of the surgical planning tool utilize a network interface to allow remote databases or server processors to offload some of the data storage or processing from the in-theater or mobile device. By looking up or learning from past, similar simulations, these databases provide an opportunity for efficient, on-the-fly estimations of simulation results for given patient data that lend themselves particularly well to low processor overhead applications.

Some embodiments recognize that patient goals for a surgery are often unique and personal. One patient may want simply to get back to a pain-free, rather sedentary life, while another might hope to get back to an active life of golf and biking or running. By utilizing a large store of data of similar patient simulations or past results, preoperative data can assist a surgeon in optimizing a surgical plan toward these specific activity-based goals. Each of a variety of common activities (e.g., walking, stairclimbing, squatting, bending over, golf, etc.) can be characterized by a motion profile that accounts for the actual motion that a joint will undergo during an exemplary repetitive motion associated with that activity and the expected stresses on an implant and soft tissue. Simulations of the repetitive motion profile for each activity can be done for a variety of patient joint geometries to populate the database of simulation results. The CASS or an application on a user's computing device can then solicit selection of the activities for which the patient surgical plan is optimized. The surgical plan can then focus on the simulation results relevant to those motion profiles while ignoring or weighting less heavily simulation results that are relevant to unselected activities.

An exemplary embodiment of a surgical application or CASS that utilizes past simulation results is a knee replacement planning tool. It should be noted that these techniques can also be applied to other resection surgeries, such as partial knee replacement, hip replacement, shoulder replacement, ankle replacement, spinal resection, etc., or any procedure where patient geometry impacts performance of the prosthetic implant. In the example of the knee replacement planning tool, the planning tool can assist the surgeon in selecting the proper size of the implants, the proper position and orientation, and the type of implants to be used when implanting the prosthesis to maximize mobility and minimize the chance of failure due to premature wear, impingement, dislocation, or unnecessary loading of the implant or ligaments during expected activity.

In the context of THA, existing guidelines (e.g., those that use the Lewinnek "safe zone") that utilize a rule of thumb ranges for abduction and anteversion angles for acetabular cup placement may not be enough to minimize the risk of hip dislocation once the patient has recovered. For example, recent studies have shown that more than 50% of postoperative dislocations occur in implants that were installed within the Lewinnek "safe zone." Studies have also shown that spinal pelvic mobility of the patient may directly influence proper acetabular cup placement, which may not be considered in traditional guidelines. Accordingly, proper implant position and orientation can benefit from a planning tool that utilizes simulation results to account for patient specific risk factors.

An embodiment of a surgical planning tool can be an application that runs on a desktop, server, laptop, a tablet computer, mobile phone, or cart-based workstations. The exemplary applications consider primarily geometry data within x-rays (or other medical image data such as CT, MII, ultrasound, etc.) which can minimize the impact of x-ray/image distortion. In some embodiments, image processing software can estimate the location of salient points and distances within the image, or a touchscreen (or other) interface may allow a user to easily manipulate these points and measurements by dragging them around on the image until the surgeon is satisfied with the accuracy of placement relative to patient anatomy. For example, in PKA/TKA, anatomical axes for femur and tibia can be extracted from an image to determine varus/valgus angle; center points and radii for the distal and posterior portions of the medial and lateral condyles can be extracted; medial and lateral gaps between the tibial plateau and respective condyles can be measured from images at various degrees of flexion. The shape of the patellar groove can be determined from anterior/posterior images of various degrees of flexion, while depth can be determined from lateral images or MRI. A surgeon can also estimate tension or laxity of ligaments by applying forces to the knee at predetermined degrees of flexion to supplement image data. Some embodiments use a combination of an estimate of the location of these points (which may be learned from past interactions with surgeon users, as they place these points on the image) done through automatic image processing (guided by searching for salient features as learned by a training set of past human selections) and refinement by a user using the touchscreen or computer. In some embodiments, images of an extended and a flexed knee (e.g., lateral and AP x-ray or an MRI) in two or more positions are considered. In some embodiments, an x-ray (or other image) of the patient standing and an x-ray (or other image, such as an MRI) of them sitting are considered. This can give the system an estimate of the change in pelvic tilt between standing and sitting, which can be utilized in estimating patient mobility issues. In other embodiments, an x-ray of the patient in a challenging position, such as a flex-seated position or hyper-extension while standing, may be considered. Some embodiments also utilize motion capture systems to provide information regarding existing joint mobility of the patient, such as pelvic mobility limitations.

Once images are landmarked to identify geometric features and relationships of patient anatomy (automatically through image analysis or manually through touchscreen/UI manipulation), the simulation model can also include any additional patient conditions, such as spinal or hip mobility concerns. (For example, in the case of THA, conditions may include a specific range of motion in the sagittal plane as well as a measure of stiffness. This can be important for the positioning of an implant device in a patient to reduce the incidences of edge loading and dislocation for the patient's expected activity level.) The planning application can then perform a lookup of previously performed anatomical simulation results or perform a calculation based on a transfer function extracted from a multitude of past anatomical simulation results (of various patient geometries and attributes) to create a profile of the ligament impingement risks, ligament stresses, and condylar compartment gaps, and patellar tracking (for PKA/TKA) or center of pressure and range of motion between the femoral head and the acetabular cup (THA) throughout the range of motion during the repetitive motion profile for each of various selected activities. In some embodiments, various activities to consider can be guided by the patient's lifestyle and activity level and the aggregate results of the simulations for each activity. The user can then be presented with a simple user interface option to change position and orientation of the distal and posterior cuts, and patellar attachment points/stuffing (for PKA/TKA) or abduction and anteversion angles (THA) to see how implant position and orientation affects these characteristics of the resulting joint. The user may also be presented with different implant options that affect the performance of the resulting joint, such as target gap size, artificial cartilage thickness, implant size and model, tibial and femoral implant depth, laxity, etc. For THA, these may include, but are not limited to: femoral head diameter, liner type (neutral, hooded, anteverted, ceramic, constrained, dual mobility, or resurfacing), standard/high offset, femoral head offset, implant style/family (i.e., flat tapered wedge vs fit & fill), implant depth in bone, implant size, etc. Because the results can be generated quickly through table look up or algorithmically using a transfer function from past simulation results, the user gets seemingly instantaneous feedback in the interface about the effects of his or her choices in implant type and position/orientation. This can be especially helpful in the surgical theater when new information about a patient is gathered (such as force loading of a joint, soft tissue laxity, etc.) or when a surgeon requests changes to an existing preoperative plan, and provides rapid feedback on how the changes or new information affects expected outcome and joint performance.

In some embodiments, a user is also presented with a button that allows the system to automatically suggest optimized distal and posterior cut planes, tibial implant depth, patellar pose and stuffing, as well as implant type and size to minimize deviation in tibial-condyle gaps, and ligament tension and laxity throughout a range of activities, while also minimizing the amount of ligament release needed during surgery to achieve acceptable balance (for TKA/PKA). The results of these choices or optimization can then be easily added to the surgical plan of the CASS or shared between colleagues with at-a-glance information about range of motion and center of pressure. The optimization can occur by using any suitable algorithm, such as by incrementally adjusting the angles or implant types and re-running the database search or transfer function calculation until a local or global maximum is achieved. In some embodiments, the optimization occurs beforehand for each possible combination of patient geometries (or within each combination in a reasonable range), searching for the distal and posterior cut poses or implant types for that combination that minimizes the deviation in the compartment gaps or strain/laxity of ligaments (PKA/TKA) or the anteversion and abduction angles or implant types for that combination that minimizes the risk of edge loading or dislocation (for THA).

In some embodiments, all reasonable combinations or a subset of all combinations of patient geometry are simulated to create a simulation database to be used for subsequent real-world patient implantation plans. Once a sufficiently large number of simulations are performed, an algorithm can search for a transfer function that approximates the results of these simulations, allowing interpolation of simulation maps for different combinations of implant types and positions/ orientations without actively simulating every combination. Because each anatomical simulation can take several minutes to perform, determining a transfer function from all or a subset of such past simulations can speed the process of determining a plan for a particular patient. In some embodiments, a subset of implant orientations can be simulated and the implantation angles optimized to populate a results database. A suitable machine learning algorithm can then be applied to create a learned results model that can be applied to estimate results for additional combinations of parameters. This allows dynamic creation of a good estimate of flexion and extension gaps and ligament tension (PKA/ TKA) or edge loading or dislocation stresses (THA) for various activities and implant orientations by the results model without fully simulating the motion using an anatomical model (which is processor intensive each time) for every combination. Exemplary algorithms that can be applied alone or in combination to develop and train a learned results model or to optimize selection of angles include, for example, linear or logistics regression, neural networks, decision tree, random forest, K-means clustering, K nearest neighbor, or suitable deep learning open source libraries. The transfer function can be identified through regression analysis, neural net creation, or any suitable AI/analysis algorithm that can estimate the parameters of the transfer function.

By running many different simulations for different implant orientations and types for each activity and simulating loads, stresses, and ranges of motion in a joint, the database or model created from analyzing these results can act as a statistical model that describes the output of a multi-body system for a given combination of outputs for each activity. This can be accomplished through simulating all possible inputs for models with only a few degrees of freedom, as a transfer function for fitting a multi-dimension expression that closely estimates the response of the system after mining hundreds or thousands of simulations of a subset of possible parametric combinations, or by applying conventional machine-learning software systems to create an AI-driven model that approximates the system response of a multi-body model of the joint, based on a large number of simulations. Any of these statistical models can be used in different embodiments to model joint behavior in a way that approaches the accuracy of an on-demand simulation of a patient-specific model for a given activity without the performance impracticalities of on-demand simulation of a detailed multi-body model of a patient joint.

These same concepts can be applied to the selection of position and orientation for other implantable devices, such as total or partial knee replacement, allowing user to easily markup x-ray/image data to manipulate implantation position and orientation of the hardware and be given fast, at-a-glance feedback on how those positions and orientations affects risk factors associated with the implant based on a patient's activity level and to easily create or modify a surgical plan. Each anatomical simulation uses a specific patient anatomical geometry with specific implantation position and orientation performing a given repetitive motion associated with a given activity, such as stair climbing. Each simulation creates a data point in the database that can be accessed when attempting to later optimize an implantation plan for a similar patient. By repeating this simulation for hundreds to thousands of other geometric combinations and activities, the database can be used for a wide combination of native patient geometries, implantation poses and selectable activities.

Figure 21:
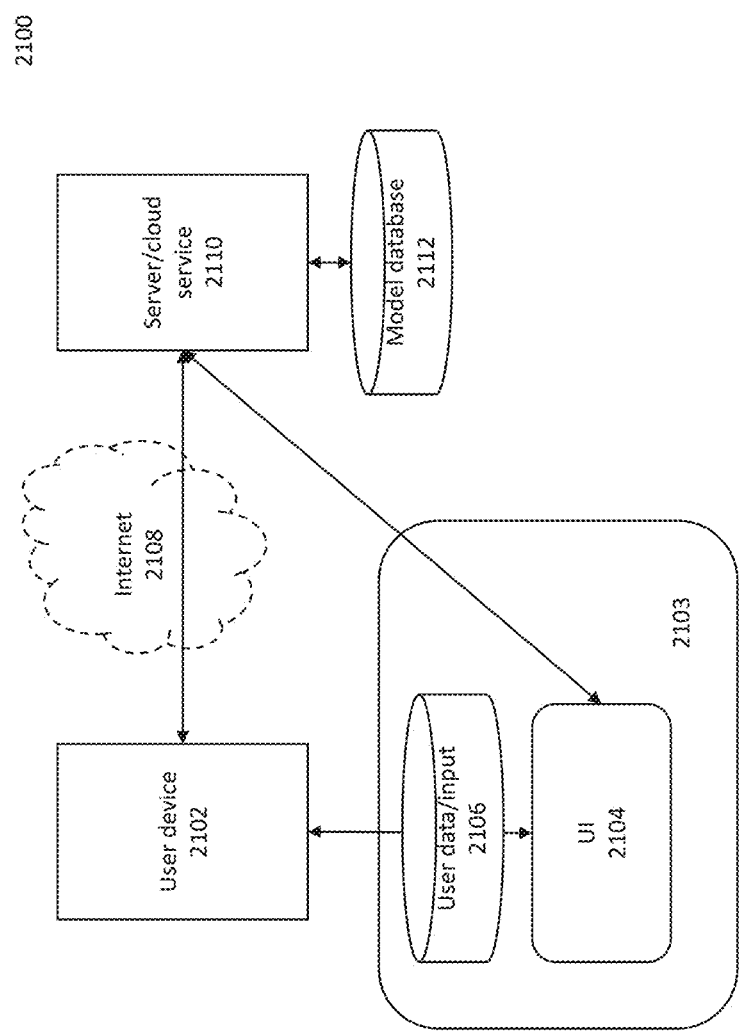
FIG. 21 is a system diagram illustrating an exemplary computational system, for use with some embodiments.

FIG. 21 is a system diagram for a system 2100 that implements an exemplary embodiment of a surgical planning tool that can be used in a standalone system or as part of a CASS to create or modify a surgical plan. In some embodiments, a low computational overhead client-server approach that uses a pre-populated data store of complex simulation results allows for on-the-fly optimization and tweaking by a surgeon, thereby allowing selection of various post-operative patient activities and changes to implantation factors. In this case of hip arthroplasty, this can include acetabular cup anteversion and abduction angles, bearing type (polyethylene, hard on hard, dual mobility, constrained, resurfacing), femoral head size and offset, femoral stem offset (std., high, valgus), femoral stem style, femoral stem depth and orientation (version). In the case of knee arthroplasty, the implantation factors include anterior-posterior/ lateral-medial placement or cut angles, distal depth, the specific orientation of the distal and posterior cuts for the condyles to ensure that the compartment gaps are consistent throughout a range of motion occurring during selected activities and that ligaments are neither too strained nor too lax, and geometry of patella relative to femoral features (PKA/TKA). User device 2102 can be a personal computing device, such as a mobile device, tablet, surgical workstation/ cart or laptop/desktop computer. For purposes of this example, user device 2102 may be described as a tablet device. In general, user device 2102 is assumed to have low processing abilities relative to a computer that might otherwise be used to run simulations of patient anatomy. System 2100 is particularly suitable for a system in which it would computationally impractical to perform an on-the-fly simulation of a given patient geometry and implant orientation and position for each selected activity. Within the memory of user device 2102 resides application 2103 that guides the surgical planning process. Application 2103 includes a user interface (UI) 2104 and a data store of user data and inputs 2106. Application 2103 solicits certain inputs about a given patient from a user. In some embodiments, application 2103 may communicate with the medical records server that includes patient records to supply some of this information.

Exemplary information that application 2103 solicits via UI 2104 and stores in database 2106 includes using the camera of user device 2102 to snap a picture of one or more images of the patient's x-ray/medical images (or provides a means by which a user can upload previously captured x-rays/CT/MRI images from medical records or concurrently captured images during a surgery if using the application during surgery), entering vital information about the patient, such as height, weight, age, physical build and activity level. In some embodiments, X-rays are the primary medical images, but MRI, CT, or ultrasound images can be used in some embodiments. The UI also allows the user to select information about the prosthesis to be implanted and to select various activities that the patient would like to participate in postoperatively (e.g., running, golf, stair climbing, etc.). In some embodiments, the ability of the user to enter this information using the touchscreen of the UI and the camera of the device simplifies the application so that it does not need to communicate with electronic medical records, which may present additional regulatory issues and require additional security and software modules or the like.

User device 2102 communicates across the Internet 2108 with a server or cloud service 2110. Server 2110 provides backend processing and resources to user device 2102 allowing application 2103 to be a lightweight app and user device 2102 to be virtually any available user device, such as a tablet or existing surgical workstation. Server 2110 maintains a model database 2112 that contains simulation results for various implant impatient geometries carrying out predetermined motion profiles associated with each patient activity. Database 2112 can be pre-populated or continuously updated with additional simulations via suitable processor, such as a multicore processor of server 2110. In some embodiments, an additional computer or cluster (not shown) populates this model database, allowing server 2110 to handle incoming requests from multiple user devices.

In addition to simulation results, model database 2112 can also include guidelines to assist user in understanding suitable ranges that for selecting appropriate implantation poses. In the case of TKA/PKA, this can include selecting appropriate stuffing for the patella, as well as other implant characteristics. For THA, this can include various spinal pelvic motions or sacral tilt angles to assist the user in selecting appropriate anteversion and abduction angles, as well as other implant characteristics. Model database 2112 can also include optimal recommended implantation information, such as optimal implant pose for a given patient geometry and activity, optimal implant sizes or types or an optimal range that will work with a given patient anatomical geometry performing a given activity. In some embodiments, simulation results also include simulations with patients having a given geometry and additional handicaps, such as orthopedic or neurological conditions not fully captured in viewing seated and standing images.

Once a user has uploaded x-ray images (or other medical images) and manipulated those images to identify certain points and angles within those images (or image processing software has automatically identified or estimated these angles from the images), patient characteristics, desired patient activities, and optionally starting point implant characteristics (e.g., starting poses, implant sizes, bearing type, etc.), server 2110 can consult model database 2112 to find the entry that best matches the user input and medical imaging geometry. In some embodiments, a large number of independently adjustable variables can make having a complete database of all possible combinations impractical. In these embodiments, the database can include a subset of possible combinations of patient characteristics, x-ray/imaging geometries, and implant characteristics and server 2110 can interpolate a specific result from surrounding entries that are the nearest match to a specific user choice. In some embodiments, the nearest match may be provided as the result, without interpolation.

In some embodiments, once a variety of simulations have been performed for various combinations of patient characteristics and geometries, the processor can optimize a transfer function to closely match the results of the simulation using any conventional means, as described above. By fitting a transfer function to the results of many simulations, the transfer function may be provided to server 2110 for quick calculation of results for various activities given user inputs for x-ray and implant characteristics and patient characteristics, regardless of whether that specific combination has been simulated before. This can enable server 2110 to rapidly handle requests for multiple users without having to run potentially tens of thousands of combinations or more in simulation to populate model database 2112. Model database 2112 may be used to store the transfer function, allowing server 2110 to calculate the result rather than searching model database 2112. In some embodiments, a learning algorithm is used to train a model of patient response to each activity for a given geometry to allow quick estimation of response and determination of optimized implant position and orientation at the server, similar to the use of a transfer function.

Exemplary simulations can utilize various simulation tools, including LIFEMOD™ anatomical modeling software available from LIFEMODELER INC., a subsidiary of SMITH AND NEPHEW, INC., of Memphis, Tenn. Exemplary simulations are explained in concurrently owned U.S. patent application Ser. No. 12/234,444 to Otto, et al, which is incorporated herein by reference. Anatomical modeling software can utilize a multi-body physics model of human anatomy that includes bone and soft tissue elements that accurately model human joints of a given geometry. The specific physics-based biomechanical model can be customized to the specific information from the patient, such as height, weight, age, gender, bone segment lengths, range of motion and stiffness profile for each joint, balance, posture, prior surgeries, lifestyle expectations, etc. A design of test is created to simulate a variety of anatomical geometries and implantation angles performing a variety of predetermined motions, each relating to a different selectable activity.

FIG. 22 shows the various theoretical angles that can be extracted from x-ray imaging using a model of hip geometry. Model 2120 is a model of the geometry of a hip in standing position, while model 2122 is a model of a hip in a sitting position. Various angles that can be extracted from the geometry of these models include a dynamic sacral tilt or slope (ST, 45° in standing, 20° in sitting), a static pelvic incidence (PI, 55° in standing and in sitting), a dynamic pelvic femoral angle (PFA, 180° in standing, 125° in sitting), a dynamic ante-inclination angle (AI 35° in standing, 60° in sitting). A theoretical angle not shown in FIG. 22 that may be extracted and used may include the combined sagittal index, defined as the sum of ante-inclination and pelvic femoral angle. Not shown in this model is also a static sacral acetabular angle (SAA) at the intersection of the lines that make the ST and AI angles as explained below.

Figure 23A:
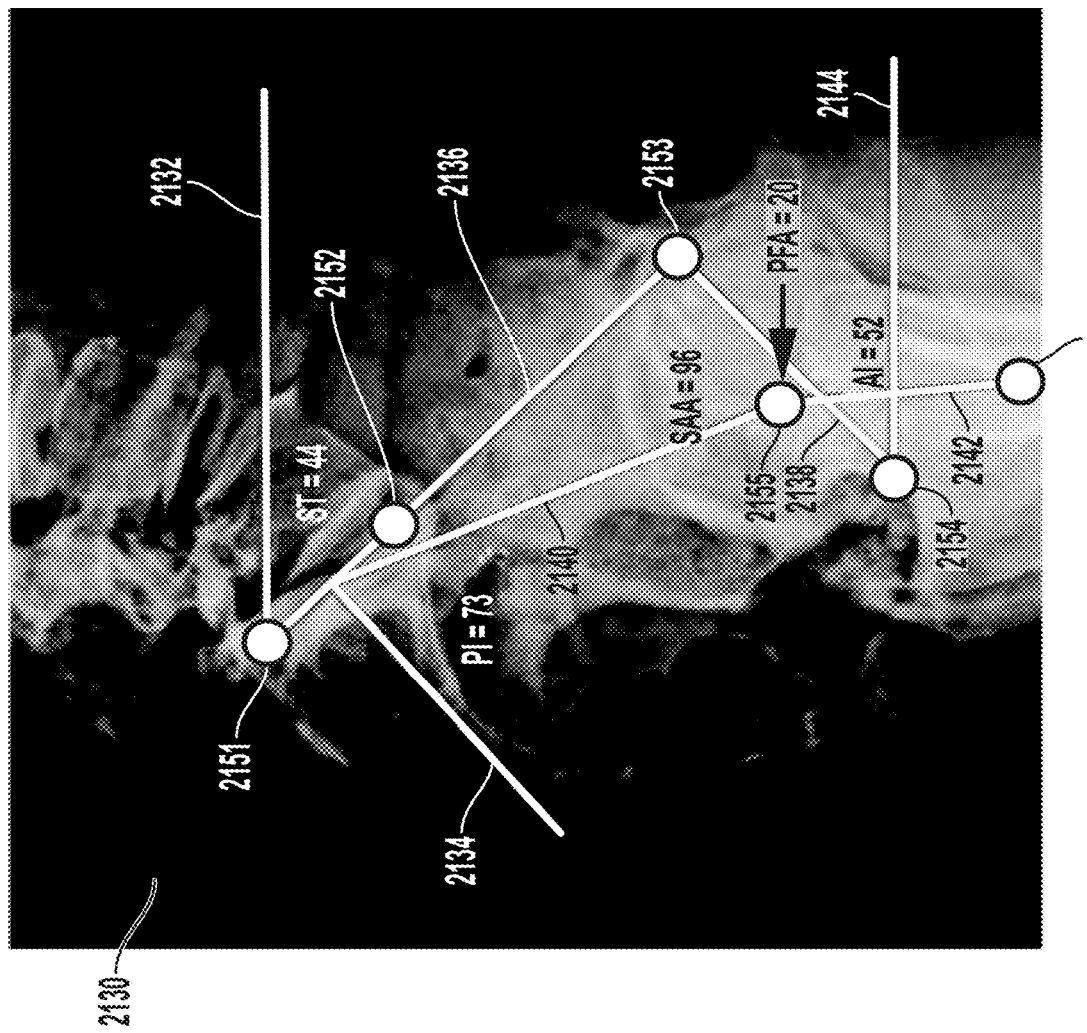
FIGS. 23A-B are diagrams of hip geometry within an x-ray image that may be used in some embodiments.

FIG. 23A is an x-ray of the various points, lines, and angles that can be extracted from an x-ray image 2130 of the hip of a person standing. A user can manipulate points 2151 through 2156 using the user interface/touchscreen, or these points may be automatically generated through an image processing algorithm that can be improved by machine learning of multiple iterations of user input as the application is developed and used by real world users. Note that in some embodiments, other image types can be used, including MRI, CT or ultrasound image data. Once points 2151 through 2156 are placed in the image, lines 2132 through 2144 can be automatically placed on the image allowing the various angles described with respect to FIG. 22 to be automatically calculated by the processor of the user device. Points include superior/posterior S1 endplate 2151, inferior/anterior S1 endplate 2152, the center point between hip centers 2153, posterior acetabulum 2154, interior acetabulum 2155, and femoral axis point 2156.

Lines include a horizontal line 2132 originating at point 2151, line 2136 (which runs between superior/posterior S1 endplate point 2151 and inferior/anterior S1 endplate point 2152), line 2134 (which is automatically generated to be perpendicular to line 2136 at the bisection of points 2152 and 2151), line 2138 (defined by the location of points 2153 and 2155), line 2140 (defined by the intersection point between lines 2134 and 2136 and point 2155), and line 2142 (defined by points 2155 and 2156), and horizontal line 2144 (running from point 2154). These lines can be automatically generated once points 2151 through 2156 are added or extracted from the image. This allows the processor to determine the ST (between lines 2132 and 2136), PI (between lines 2134 and 2140), SAA (between lines 2136 and 2138), PFA (between lines 2140 and 2142), and AI (between lines 2138 and 2144) angles.

Figure 23B:
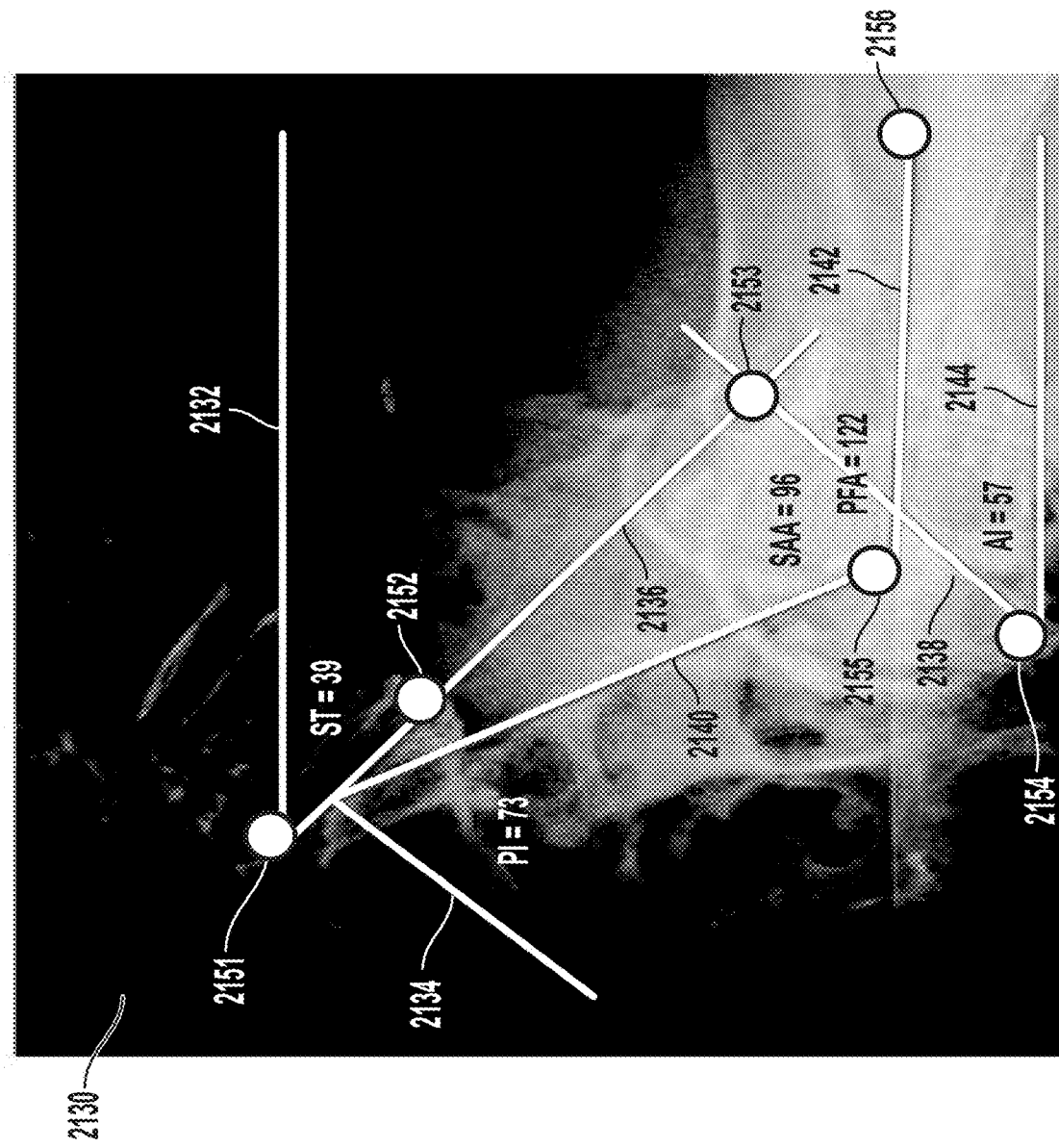

As shown in FIG. 23B, the various points 2151 through 2156 (discussed in FIG. 23A) can be manipulated and extracted from an x-ray image 2158 of a patient hip in a sitting position. From these points, lines 2132-2144 can be extracted by the processor of the user device/tablet. Once these lines are extracted, the various angles can be calculated. If static PI and SAA angles disagree between sitting and standing, and average can be used. In some environments, a disagreement between these angles can result in an error or solicitation of additional input from the user. In some embodiments, a disagreement between these angles can be used to scale or adjust other angles or to refine the placement of points in the sitting and standing x-ray images. These angles can be used by the server to find appropriate simulation results, as these angles define the geometry of the anatomy of the patient.

Figure 24:
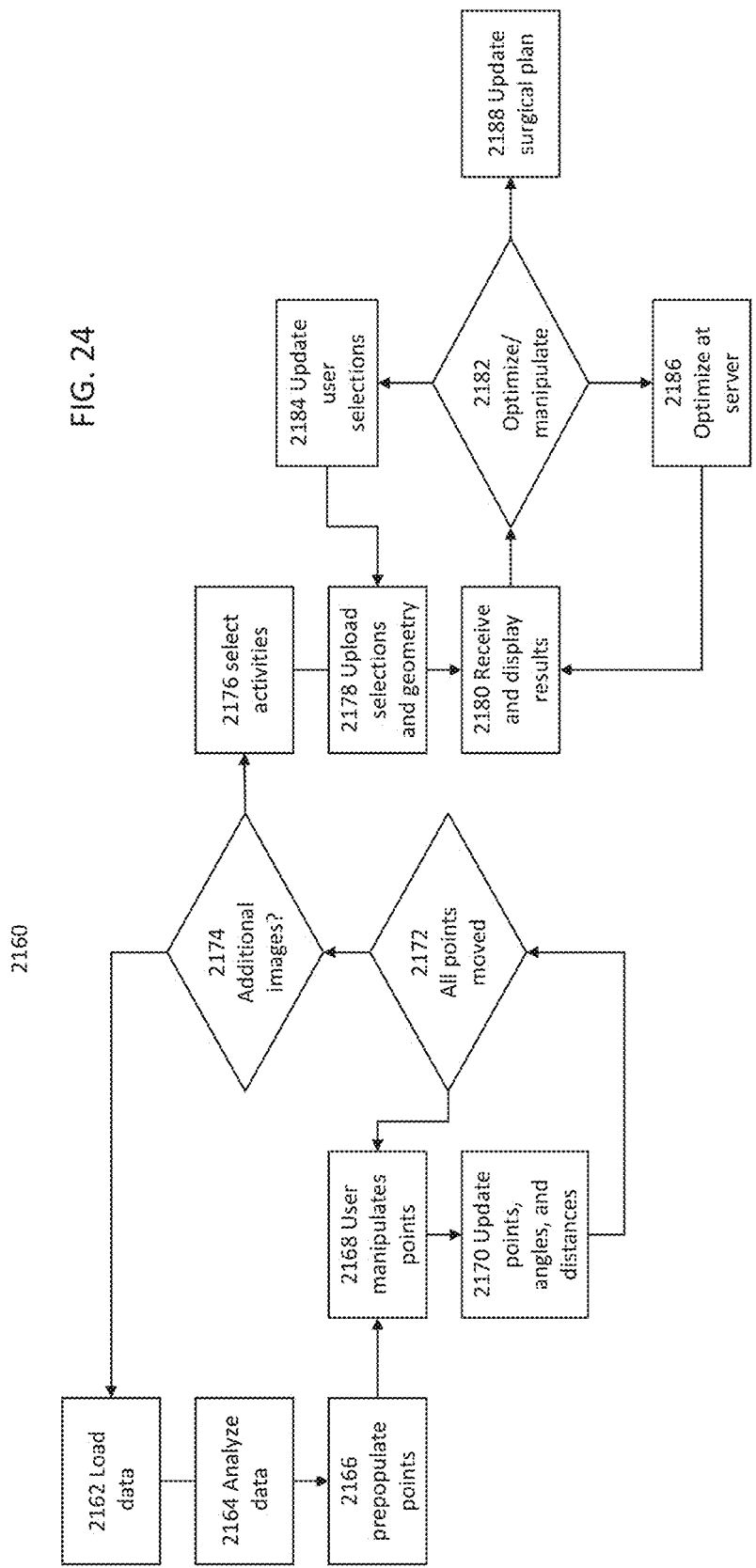
FIG. 24 is a flow chart illustrating an exemplary process to extract anatomical landmarks and determine a surgical plan based on modeled performance, for use with some embodiments.

FIG. 24 is a flowchart of an exemplary process 2160 by which a user manipulates landmarks in an x-ray (or other medical images) to determine the feature locations, sizes, angles, and spacing that will be used for the patient geometry to determine joint performance for various patient activities using a pre-populated statistical model of the behavior of the joint for each activity. This can typically be done during a preoperative phase, but can be done in response to images captured during a surgery or updated based on new data obtained during surgery, such as be capturing bone features and their relative locations using a probe that is tracked by a CASS. For example, for a knee arthroplasty, performance can include a measure of the variation of condyle or compartment gaps, degrees of tension or laxity and ligaments, and the degree to which the patella tracks in the patellar groove of the femur. At step 2162, the application on the user device loads an image of patient anatomy into memory. This can occur by using the camera to capture an image from a film or screen, by connecting to a stored image in a local data store or in a medical records system, or by using a local imaging device to create an image on the fly (such as an x-ray taken during surgery). In some embodiments, the image can be an x-ray, ultrasound, CT, MRI, or other medical images. The file format of this image can be any suitable file format, such as PDF, JPEG, BMP, TIF, raw image, etc. Once the user device loads this image, at step 2164, the image is displayed and optionally analyzed using image recognition software. This optional analysis step can utilize any common image processing software that identifies salient features in the image that can be useful for identifying landmarks. For example, image processing software may be trained to look for certain geographic features, geometric indicia, or may be trained through any suitable AI process to identify probable locations for landmarks that are used to determine patient geometry. At step 2166, the results of this analysis step are overlaid on the displayed image, placing the landmark points at pixel locations that the analysis software believes are most likely locations of these landmarks (such as those shown in FIGS. 23A-23B). It should be appreciated that this process described in steps 2162 through 2172 need not be limited to medical images and can be done automatically, without human interaction with the processor. During the operation, additional geometric and location data can be acquired in the CASS through various means, including images or by using a robot arm or surgeon manipulating a point probe to paint the surfaces of relevant features and register their location with the surgical tracking system. This provides an additional level of improvement of geometric extraction of relevant features that can be used to optimize the surgical plan beyond what may be possible from preoperative imaging alone.

In some embodiments, image recognition software is helpful, and can be a supplemental/partial or complete substitute for the analysis of an experienced surgeon or technician. In some embodiments, at step 2168, the user of the software is given the opportunity to manipulate the exact placement of anatomical features, such as femoral axis, sacral geometry, femoral head and neck characteristics, acetabular cup geometry, condylar centers and radii, the patellar groove, the patellar dome, and tendon and ligament contact points. The exact method by which the user manipulates these points will depend on the interface of the computing device. For example, on a tablet computing device having a touchscreen, a user can use his or her finger to manipulate and drag the exact placement of these points (which have been placed automatically at step 2166). In some embodiments, where suitable image processing software has not been trained, the user may create these points from scratch at step 2168 by tapping the location of these points on the image after being prompted by the system. In response to moving each point, at step 2170, the display creates and updates the model of anatomical geometry (such as the relationship of condylar features to tibial features and patellar features, as well as information suitable for determining strain on ligaments and tendons, such as the quadricep angle.) (In some embodiments the step may be held in abeyance until the user indicates that all points have been moved and the user is satisfied with their placement.) This process continues at step 2172 where the software and the user determine whether or not all points and distances have been properly manipulated and placed, and the manipulation is repeated for each point and distance.

Once all points have been moved and the user is satisfied, the user is given the option of selecting and loading additional images at step 2174. For example, when the surgical procedure being planned is a knee arthroplasty, suitable images can include anterior-posterior and medial-lateral images of a patient knee in a flexed position and an image in the extended position or any additional poses needed to determine the geometry of the relevant features. For hip arthroplasty, suitable images can include at least a lateral image of a patient in a standing position and an image in the sitting position. In a knee arthroplasty, suitable images may include a lateral or anterior view of a knee in both a full extension and bent at some predetermined angle, such as 90°. Additional images may include a patient in the flexed seated position or an extended position while standing. If additional images, such as posterior/anterior or medial/lateral views or a different position of the joint is available, that image can then be loaded again at step 2162.

Once all images have been loaded, and analyzed, the placement of landmark points can be manipulated by a user (or software image processing AI). The relevant angles and distances can be calculated from the positioning of these points and the method can proceed to step 2176. At step 2176, a user can select the appropriate activities that a patient would like to enjoy postoperatively. These activities can be governed, for example, by the relative activity level of the patient, age, other infirmities or mobility issues, of the patient. Exemplary activities may include standing, walking, climbing or descending stairs, biking, golfing, low-impact yoga, squatting, sitting cross-legged, gardening/kneeling, etc. It should be appreciated that some of these activities will likely be relevant to most or all patients, while some activities may only be relevant to younger or a select subset of patients. For example, a running activity may be available that will likely only be selected for younger or more active patients.

At step 2178, the selection of activities and the patient-specific geometry calculated from the manipulation of points on patient images can be uploaded to a server for (or placed into memory accessible to a processor that is suitable for) applying the statistical model created from pre-existing simulation data to calculate suitable results relevant to the surgical procedure. For example, for a hip arthroplasty, the results may include a map of the centers of pressure within the acetabular cup and range of motion of the joint expressed in a polar plot of the femoral head relative to the acetabular cup. For a knee arthroplasty, the results may include range of motion between the tibial plateau and the femoral condyle's, a contact point map, and stresses experienced by relevant ligaments, a graph mapping lateral and medial condylar compartment gaps and ligament tension for a range of flexion angles or for discrete angles, or a graph highlighting the strain on patellar tendons or ligaments during a range of motion, or how the patellar dome sits in the patellar groove during that range. For this first pass of step 2178, a default implementation characteristics of the prosthetic implant can be used, (e.g., a 3 degree varus angle and 9-10 mm condylar compartment gap). In some embodiments, before step 2178 is performed, the user also selects the starting implant position/orientation for a given implant for this initial calculation.

At step 2180, the processor that applies the statistical model to the anatomical information and selection of activities sends this result in the implantation variables used for the result to the user device for display. In embodiments using a client/server model, the step can include sending the results over a network to the user device. In some embodiments, the processor that performs the analysis using the statistical model can be the same processor as the user device. In these embodiments, the statistical model is generally refined enough to be stored and analyzed locally. The exact display of these results can be in any suitable graphical manner, such as those interfaces described in succeeding figures.

At step 2182, the user is given the opportunity to choose to manipulate the implant characteristics (position, orientation, and in some embodiments size and type) manually or to ask for a processor to automatically optimize the implantation geometry. In some cases, the user may select an automatic optimization by processor and then refine the exact resections used for implantation manually to suit the surgeon's preferences or to place a greater emphasis on certain activities over others. For example, a surgeon may attempt to optimize an implant so that the patient can return to golfing, but still place an emphasis on the patient's ability to perform everyday activities, such as climbing stairs and sitting comfortably. In some embodiments, a weighting of activities can be provided in a patient profile that can be used by the optimization algorithm to do this automatically.

At step 2186, if a user has requested processor optimization of implantation angles, an optimization algorithm is run by a processor (at the server or on the user device in non-client/server embodiments) based on the statistical model. This optimization algorithm can include any searching algorithm that searches through the statistical database to find a local or global maximum for the implementation angles that provide the best performance or an analysis of the extracted transfer function to find maximum or minimum results. Criteria used for this search can vary depending on the type of implant being implanted. For example, in a knee arthroplasty, the algorithm can target a reasonable range of condylar compartment gaps for medial and lateral compartments, identifying the most consistent gap through the flexion range, while maintaining ligament tension within a suitable range, in accordance with guidelines and identify the femoral implant pose and patella packing and attachment constraints that best allow the patella dome to track in the patellar groove with minimal soft tissue strain. For hip arthroplasty, anteversion and abduction angles that provide the center-of-pressure profiles and range-of-motion profiles that run the lowest risk of edge loading or dislocation can be identified by minimizing the amount of pressure near edges of the acetabular cup and minimizing the amount of range of motion that risks impinging on the edges of the cup for each of the selected activities.

In some embodiments, this optimization procedure can include iteratively changing resection placement and orientation until a suitable or best result is achieved. Once this optimization has been completed by the processor that handles the statistical model, the results can be received and displayed by the user device at step 2180. If the user wishes to manually alter the angles of implantation, the user will can update the selected angles of implantation through the user interface at step 2184. The selections can then be uploaded to the processor handling statistical model at step 2178. In some embodiments, the user can also change implant bearing type or liner options. For example, a user can switch from a 0 degree neutral XLPE liner to a 20 degree anteverted XLPE liner, allowing the user to experiment with range of motion and center of pressure. Similarly, a user can switch from a conventional bearing surface (XLPE) to a dual mobility system that offers increased head size and jump distance that allows for greater stability in the joint.

Once a user is satisfied with the results of manipulation or automatic optimization, at step 2188, the user device updates the surgical plan displayed to a user or within a CASS, allowing a robotic surgical system to prepare to implement the chosen implant locations and orientations based on method 2160. In embodiments where a cutting guide is used, step 2188 can include sending the surgical plan (that includes the specific map of relevant patient bone surfaces and the specific location of resection cuts relative to these surface) to a manufacturing system that manufactures patient-specific cutting guides and requesting that these are 3-D printed prior to the operation. In some embodiments, where a robotic arm will position or hold a non-patient specific cutting guide, the surgical plan can include requesting the appropriate cutting guide to be provided to the surgeon for the operation and programming the robotic arm to place the cutting guide at the specific predetermined location and orientation.

FIG. 25 is an exemplary table 2200 that can be displayed to a user to assist in understanding how pre-operative anatomy compares to expected ranges for a healthy patient. This can help guide a surgeon in understanding the appropriate surgical plan for use with a CAS system. Table 2200 shows the results of the calculation of various angles in sitting and standing images using image analysis or manipulation of points as described above for planning a hip arthroplasty. Column 2202 lists the various angles that are calculated for each image including ST, PI, PFA, and AI. Column 2204 shows the results of the analysis of the angles based on the points identified in a standing image. Column 2206 is an analysis to be performed by the server or the user device based on a list of acceptable ranges for these angles, such as guidelines shown in table 2114 in FIG. 21. In this example, the sacral tilt has been identified as normal, while pelvic incidence, the pelvic femoral angle, and anti-inclination angle have been identified as abnormal, being outside the normal range expected for a healthy patient. Column 2208 shows the angles that have been calculated based on the points identified in a seated x-ray image. Column 2210, like column 2206, is an identification of whether or not each angle is within an acceptable range for a healthy patient. Section 2212 is a comparison of various angles between standing and seated positions (2204 and 2208), including a difference in sacral tilt and anti-inclination. These deltas are then used for determining whether or not spinal-pelvic mobility falls within a normal range and where the spinal-pelvic balance lies. This information can be useful in guiding the selection of implantation orientation of a prosthesis to improve mobility and balance patient hip geometry. This information can be considered by the surgical user or can be available on demand as a teaching tool. As discussed, the angles for standing and sitting are used by the patient model database in conjunction with anteversion and abduction angles for the acetabular cup (or other implant characteristics) to determine range of motion and center of pressure results from the statistical database of simulated results.

Figure 26A:
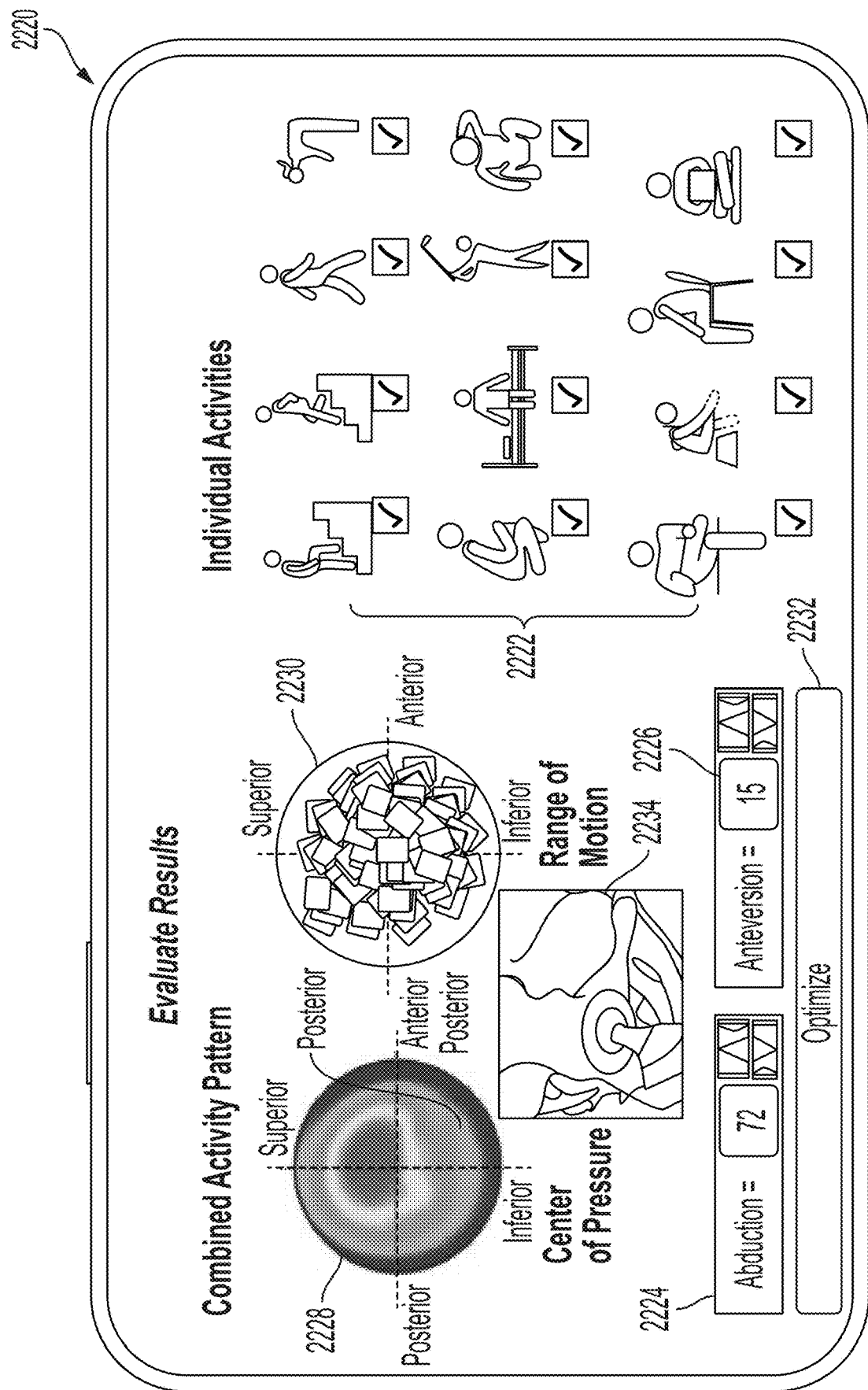
FIGS. 26A-D are exemplary user interfaces, for use with some embodiments.

FIG. 26A is an exemplary user interface 2220 for selecting individual activities that are relevant to a given patient and displaying the results from the statistical database based on previous user input about a patient, including x-ray landmark mapping for that patient. A user may select from various individual activities 2222 and can manipulate the abduction and anteversion angles 2224 and 2226 for the implant (note that these exemplary angles may vary from real-world values for given implants). A center-of-pressure heat map 2228 is an aggregate of all of the selected individual activities 2222 based on the patient geometry from x-ray imaging and the manipulation of abduction and anteversion angles 2224 and 2226. (Not shown are options to change liner and bearing characteristics, which may be available in some embodiments.) Manipulating abduction angle 2224 or anteversion angle 2226 will move the heat map relative to the circle, which represents the extent of the acetabular cup, based on the statistical model. Placing pressure too near any of the edges of the acetabular cup can result in edge loading that can lead to premature wear or failure of a hip implant or can lead to dislocation in some cases. Similarly, range of motion map 2230 is an aggregate of a patient's range of motion that is used in each individual activity and how that motion translates to the interaction between femoral head and acetabular cup. The extents of this range of motion should be confined to the circle that represents the extents of the acetabular cup. Any range of motion that falls outside of these extents will result in a high risk of hip dislocation or impingement that impedes the motion needed for that activity.

In some embodiments, an optimized button 2232 is presented to a user that allows the user device or server to automatically change abduction and anteversion angles such that it optimizes the placement of the center of pressure and range of motion within the circles. (In some embodiments, this automatic recommendation can include implant selection, such as implant size, bearing type, liner type, femoral head characteristics, etc.) This can be done iteratively using any suitable algorithm to adjust these angles to improve the area of the center pressure and range of motion that falls within the extents of the acetabular cup circle. Heuristics that are used can include maximizing the distance between pressure points and the edges of the acetabular cup for the center pressure and maximizing the distance between the extents of the range of motion in the edges of the acetabular cup circle, maximizing the mean distance, maximizing the minimum distance, etc.

In some environments, a diagram 2234 is presented to the user that changes as abduction and anteversion angles are manipulated, to provide visual feedback to a user on how these angles affect acetabular cup placement. Not shown in interface 2220 is a button that exists in some embodiments to finalize and save the abduction and anteversion angles and load these into the surgical plan of the CAS system.

Figure 26B:
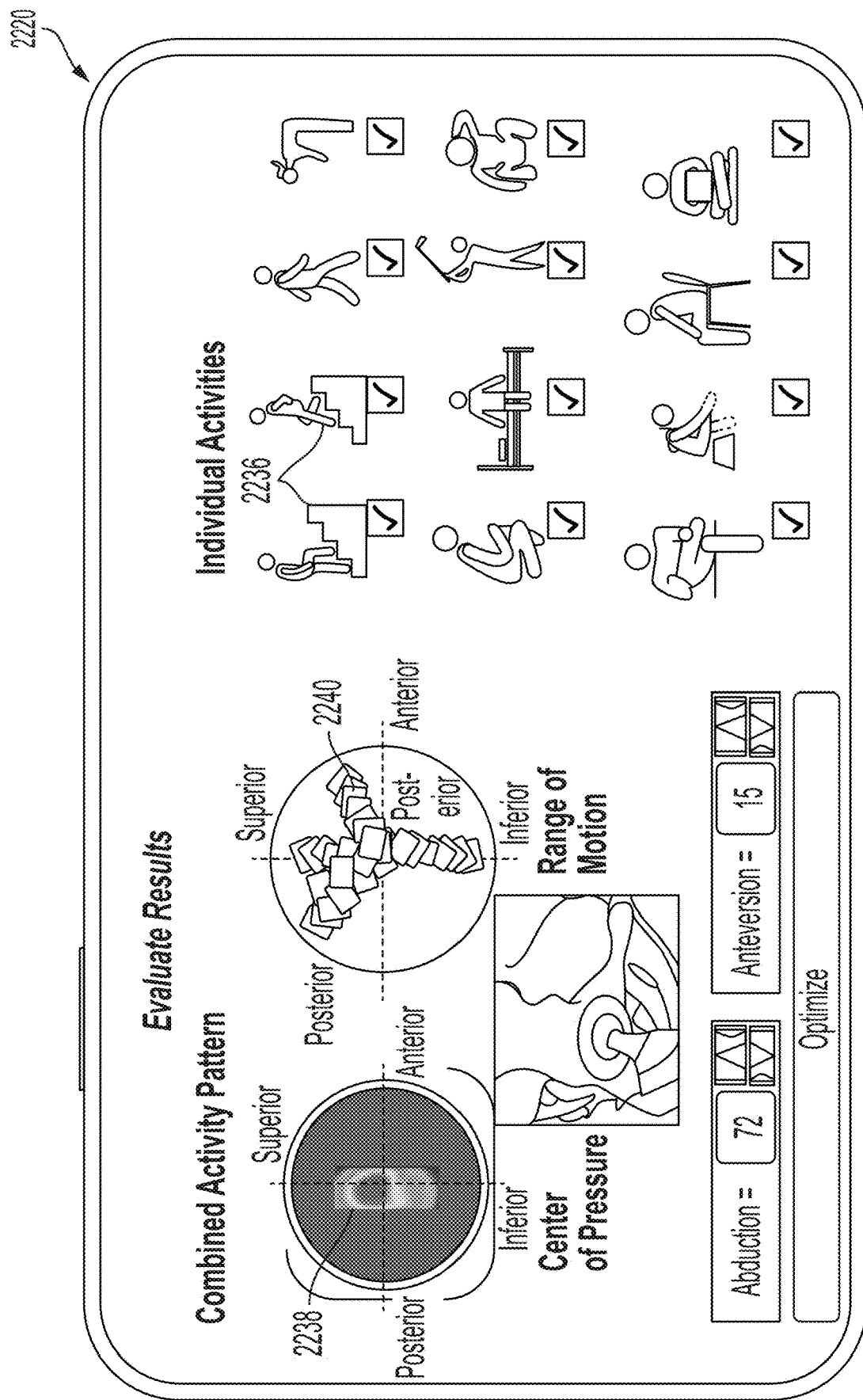

FIG. 26B shows how the user interface changes when only a subgroup of individual activities 2236 is selected. Rather than a large heat map or large variety of ranges of motion, the center-of-pressure map 2238 shows a more limited center of pressure that is attributed to just these activities. Similarly, range-of-motion map 2240 shows the range of motion used by just these activities. Contrast these maps to maps 2228 and 2230 (FIG. 26A), which illustrates the fact that a broader range of activities results in a broader heat map of the center of pressure and a bushier range of motion. For some patients, where mobility is limited by lifestyle or other factors, only certain activities may be important, allowing a user to more easily optimize implant selection and acetabular placement (in hip arthroplasty applications) to ensure that the user can successfully do these activities. With some patients, it may not be possible given other constraints to place an acetabular cup in such a way that all activities are possible. This can be due to abnormal hip geometry determined from the (x-ray) images or due to external mobility issues, such as spinal immobilization. In some embodiments, the surgeon or user is able to make recommendations to their patients on which activities or positions may pose a risk for impingement, dislocation, or excessive wear to their artificial hip.

Figure 26C:
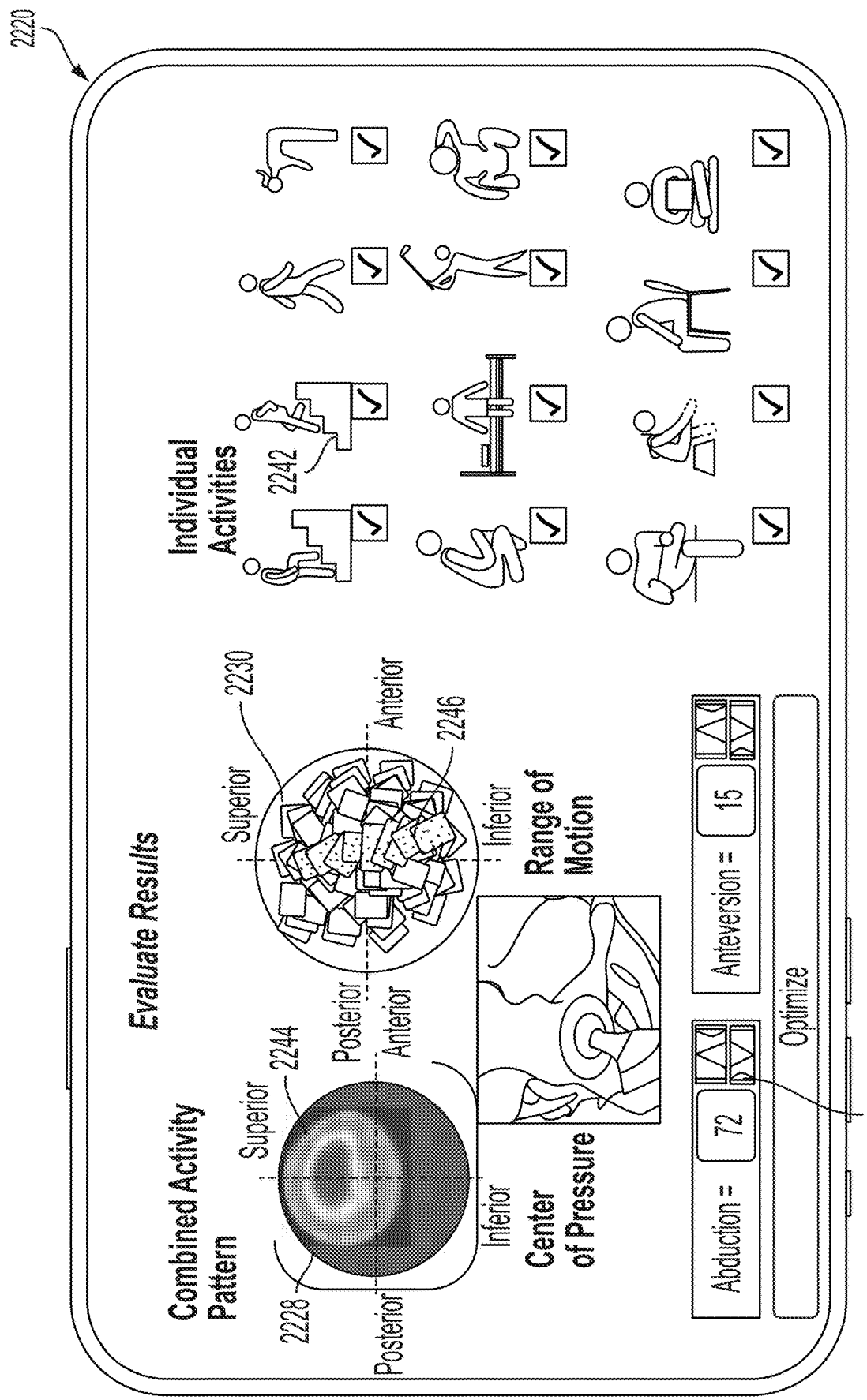

FIG. 26C is a user interface showing an embodiment whereby hovering over or otherwise temporarily selecting an individual activity 2242 amongst a group of activities can be used to highlight the contributions of that activity to the center-of-pressure map 2228 and range-of-motion map 2230. By selecting stair descent, the center of pressure map associate with that single activity and the range of motion map associated with that single activity can be highlighted within the respective maps. In this example, heat map 2244 is temporarily highlighted on center-of-pressure heat map 2228, showing the concentrated portion of the map that is attributable to stairclimbing descent. Similarly, a range of motion profile 2246 can be temporarily highlighted within range-of-motion map 2230 to show the contributions to the range-of-motion map that are attributable to this activity.

Figure 26D:
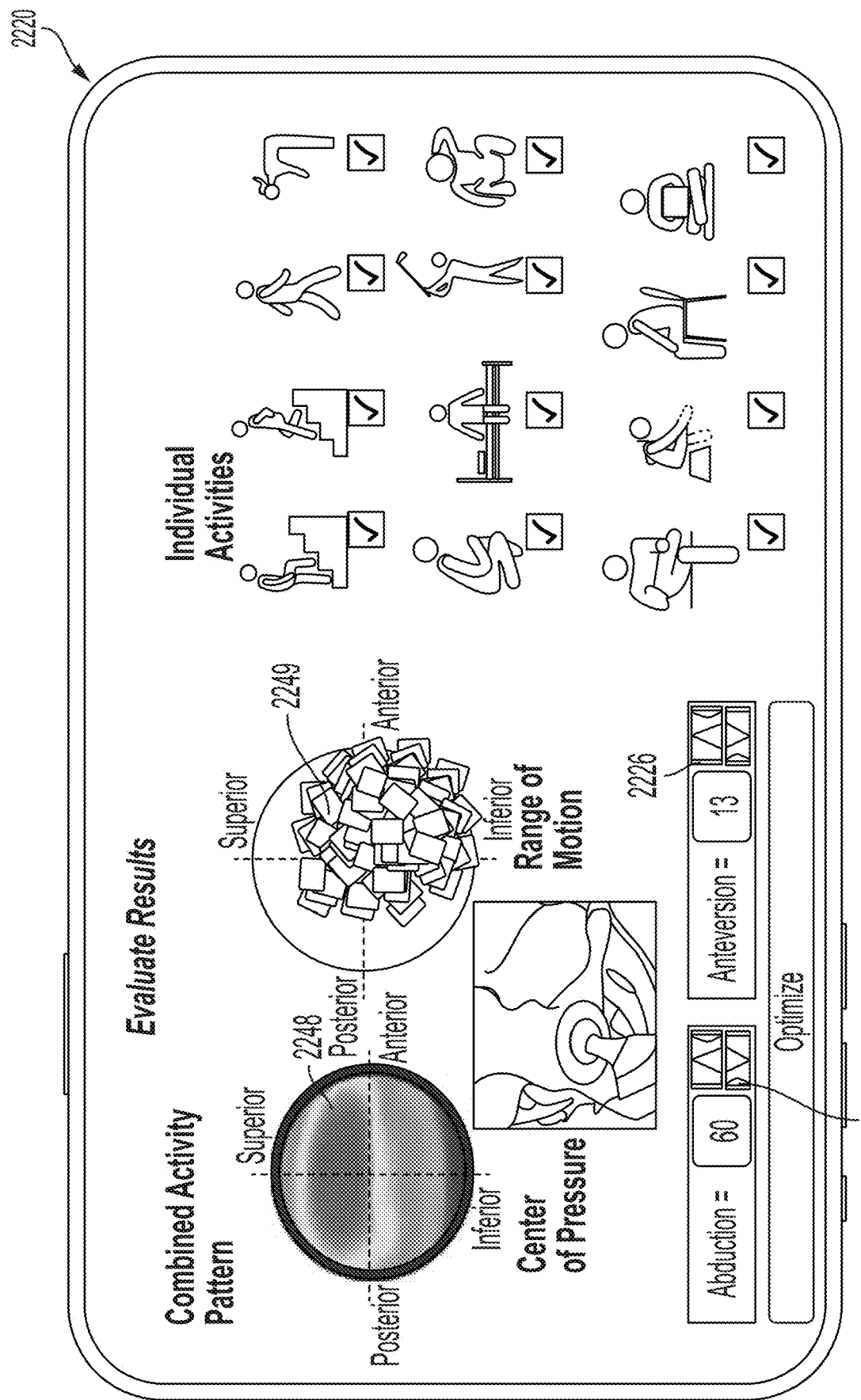

FIG. 26D is an illustration of how the user interface changes as abduction and anteversion angles 2224 and 2226 are manipulated. In this example, all activities are selected and the abduction angle is reduced by 12°, while the anteversion angle is reduced by 2°. This results in a broadened heat map 2248 of the center pressure, which creates an increased risk of edge loading of the acetabular cup, while at the same time shifting of the range of motion map 2249 of these activities away from the center of the acetabular cup, which creates a greater risk of dislocation or injury. The result in FIG. 26D is less desirable than the resultant FIG. 26A.

Figure 27:
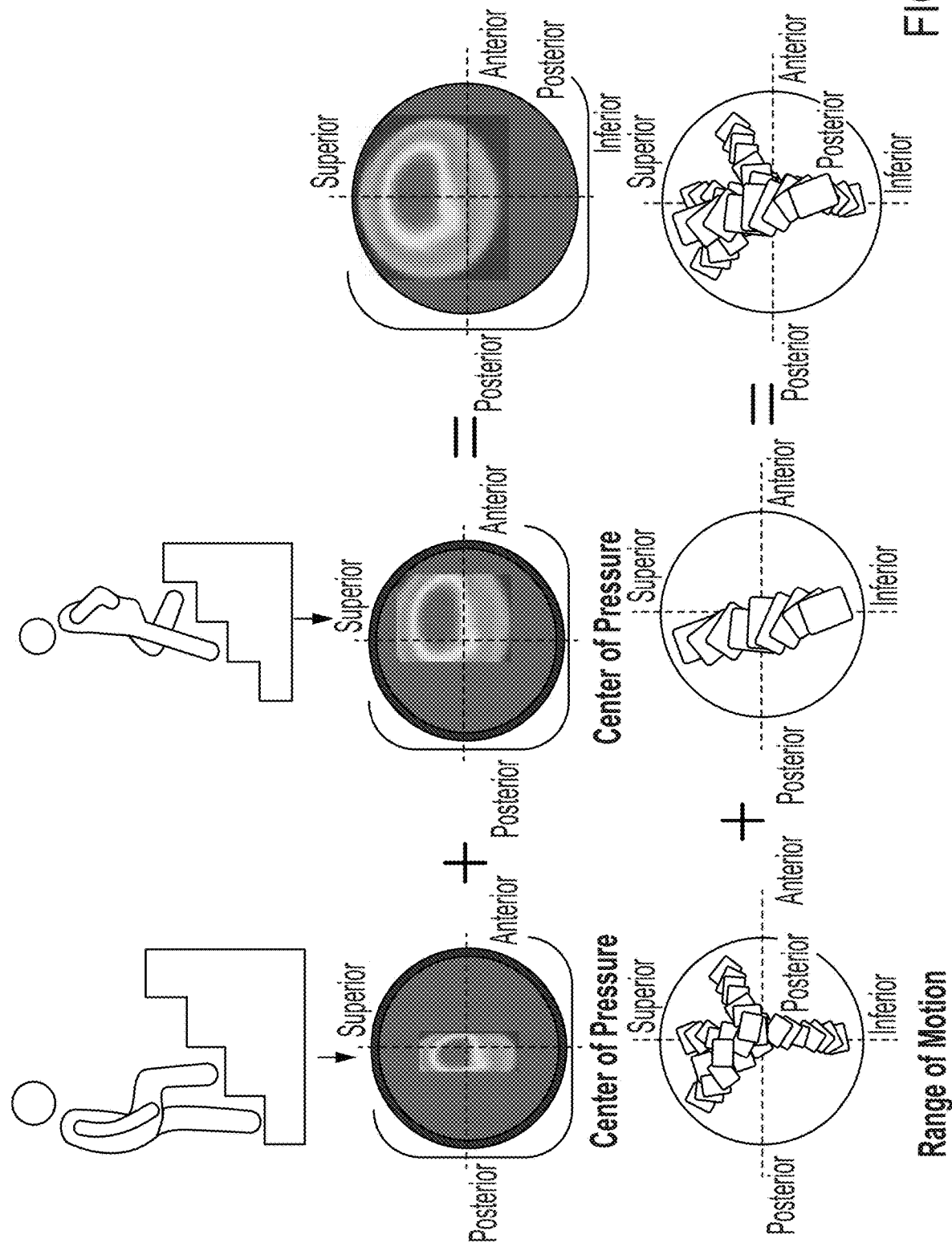
FIG. 27 depicts an exemplary combination of model results for different selected activities for a given geometry to display an aggregate result.

FIG. 27 shows the impact of adding multiple activities together to create an aggregate center of pressure heat map and range of motion map. In this example, stair climbing and stair decent result in a broader center of pressure and fuller range of motion than individual activity maps.

Figure 28:
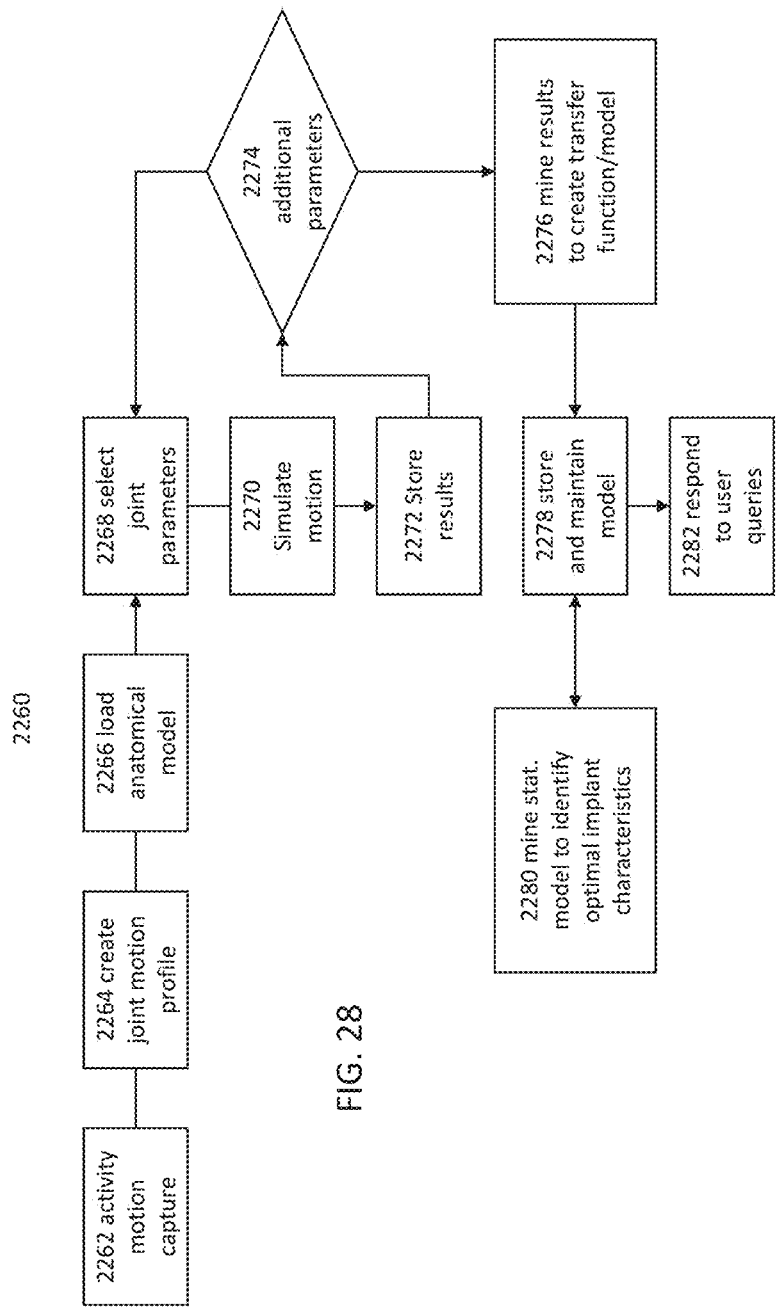
FIG. 28 is a flow chart illustrating an exemplary method for creating a statistical model database to help determine a surgical plan based on modeled performance, for use with some embodiments.

FIG. 28 is a flowchart illustrating an exemplary creation of a statistical model database that can be queried using patient anatomy and implant characteristics and a selection of patient activities to estimate performance of the implant. This statistical model database is created by performing (typically) hundreds to tens of thousands of simulations using a model of joint anatomy (such as a multi-body simulation) that models the behavior of each component of the joint as that joint is moved through a motion profile that is associated with at least one common motion that will occur in a patient joint when the patient participates in a given activity. In some embodiments, this motion profile may be modeled by using motion capture technology on a sample subject performing a given activity. By capturing the motion of that individual (or individuals) performing the activity, an accurate model of the motion that each joint will undergo during that activity can be created. The model of individual joint motion can then be reviewed to identify exemplary repetitive motions that a person will likely experience when performing an activity. This motion profile model can then be used to guide each individual simulation for that activity, where anatomical geometry and implant characteristics are varied to create a design of experiment that includes a range of anatomical geometry and implant characteristics.

In some embodiments, method 2260 begins at step 2262, where motion capture is used on an individual actor while that individual performs exemplary tasks associated with each activity to be modeled. For example, reflective marks can be placed on a model's body as he/she climbs and descends stairs in front of one or more cameras. At step 2264, a processor can then extract the motion that these marks undergo during the activity. By using a model of anatomy and where these marks relate to the individual's joints, the motion profile that each joint undergoes during this activity can be extracted. Any suitable conventional motion capture technology can be used for this step. For example, where a hip or knee motion profile is being created, at least two cameras can capture reflective marks on a model's leg, iliac crest, torso, femur, tibia, patella, malleolus, medial and lateral condyles, etc., as the individual moves. Hip and knee profiles can be created simultaneously with sufficient marks. As the individual moves her leg, lifting and placing her foot during the activity, the degree of motion and rotation within each degree of freedom can be calculated as the hip and knee move. This can then be used by the processor to estimate the degree of relative motion of the individual components of the joint.

At step 2266, a processor performing the simulation of anatomical models will load an anatomical model. An exemplary anatomical model can be a multibody model of bone and soft tissue components that accurately models the behavior of each of these components of an anatomical joint. By using a multibody model, simulation times can be expedited over finite element analysis models. In some embodiments, finite element analysis models can be used, as well. An exemplary multibody simulation tool for use with modeling joints includes the LIFEMOD™ software available from LIFEMODELER INC. This anatomical model, once loaded, can be customized to a given geometry. For example, component sizes can be adjusted to achieve any joint geometry to be simulated.

At step 2268, sample joint parameters (such as anatomical geometry and implant size, type, position, and orientation) are selected to be used for the next simulation. The selection of this joint geometry can be based on a preplanned design of experiment or randomly assigned in a Monte Carlo style simulation. Components in the model can then be sized appropriately to match the geometry for this given experimental simulation. For example, in the TKA context, the selected geometry can include any reasonable combination of distal and posterior cuts, as well as other implant features for the implantation of a sample prosthesis. In some embodiments, the geometry selected can include additional patient information, such as abnormal motion constraints due to other infirmities or deformities, or other common medical comorbidities. In some embodiments, age and weight can be added to the model to address changes in response of various components that may vary with the age or weight of the patient (e.g., less compliant or thinner soft tissue).

At step 2270, a simulation of the model that has been sized according to the experiment parameters is performed using the joint motion profile for a given activity. This results in several quantifiable results, such as soft tissue impressions and tensions, pressures between components such as femoral heads and acetabular cups (for hip arthroplasty) and condylar compartment gaps and patella tracking over a range of motion between components (in knee arthroplasty). The simulation profile used to run the simulation in step 2270 can define which of these results should be generated and recorded. At step 2272, once a simulation has completed, the results for that given combination of anatomical and implant characteristics and motion profile can be stored.

At step 2274, the processor determines whether additional parameters, such as anatomical geometry, implant design, orientation, and position, should be simulated. In many embodiments, a simulation profile that defines the design of experiment or extensive Monte Carlo simulation will define hundreds to tens of thousands of different simulations that should be carried out. Accordingly, the cycle of the steps 2268 through 2274 should be repeated many times. Once a sufficient number of simulations have been completed, method 2260 can proceed to step 2276, where the processor mines the results of these multiple simulations to create a transfer function or model of the behavior of the joint based on various geometries. This model or transfer function creates a statistical model for that activity and that joint that accurately estimates the performance as a function of geometries for the patient anatomy and implantation of a prostheses. This can be accomplished by performing a statistical fit of a polynomial function that maps input implant values to output values, in some embodiments. In some embodiments, a neural network or other AI strategy can be used to create a heuristic model of implant characteristics to performance output. Step 2276 can be repeated as additional simulation results are added to the database. In some embodiments, measured real-world performance values can be added to the database and mined similarly to simulated results, as additional implantation surgeries are performed and monitored clinically.

At step 2278, the processor stores and maintains the statistical model of joint performance as a function of anatomical geometry and implantation features (position, orientation, and types of implants selected). This stored model can be updated as additional simulation data becomes available. In some embodiments, the resulting model can be computationally lightweight (e.g., a transfer function), allowing mining and manipulation of this model to be performed by any processor in the system, at the server or on a user device. At step 2280, this statistical model is mined by the processor to identify optimal implant values that optimize performance based on predetermined heuristics. For example, in a model of hip arthroplasty, the maps of center of pressure and range of motion can be optimized to minimize the risk of edge loading or dislocation, minimizing the range of motion and degree of pressure that falls near the edges of the acetabular cup for a given activity. For example, in a model of knee arthroplasty, the heuristics can include gaps, patellar tracking, and ligament tensions being near normal anatomical values during a given simulated activity. This optimization can be through any statistical or AI approach, including finding a best fit that that best approximates an ideal anatomical model. These optimization values can then be added to the maintained model at step 2278.

Once the model has been stored and an optimization has been performed to assist in identifying optimal implantation features (position, orientation, implant type, implant size) for a given patient anatomy and activity, at step 2282, the model can be queried by a processor in response to user interaction, such as during a preoperative or intraoperative planning stage. This allows a surgical user to access the statistical database model to develop a surgical plan that can then be used by a CASS or displayed to the user.

Figure 29:
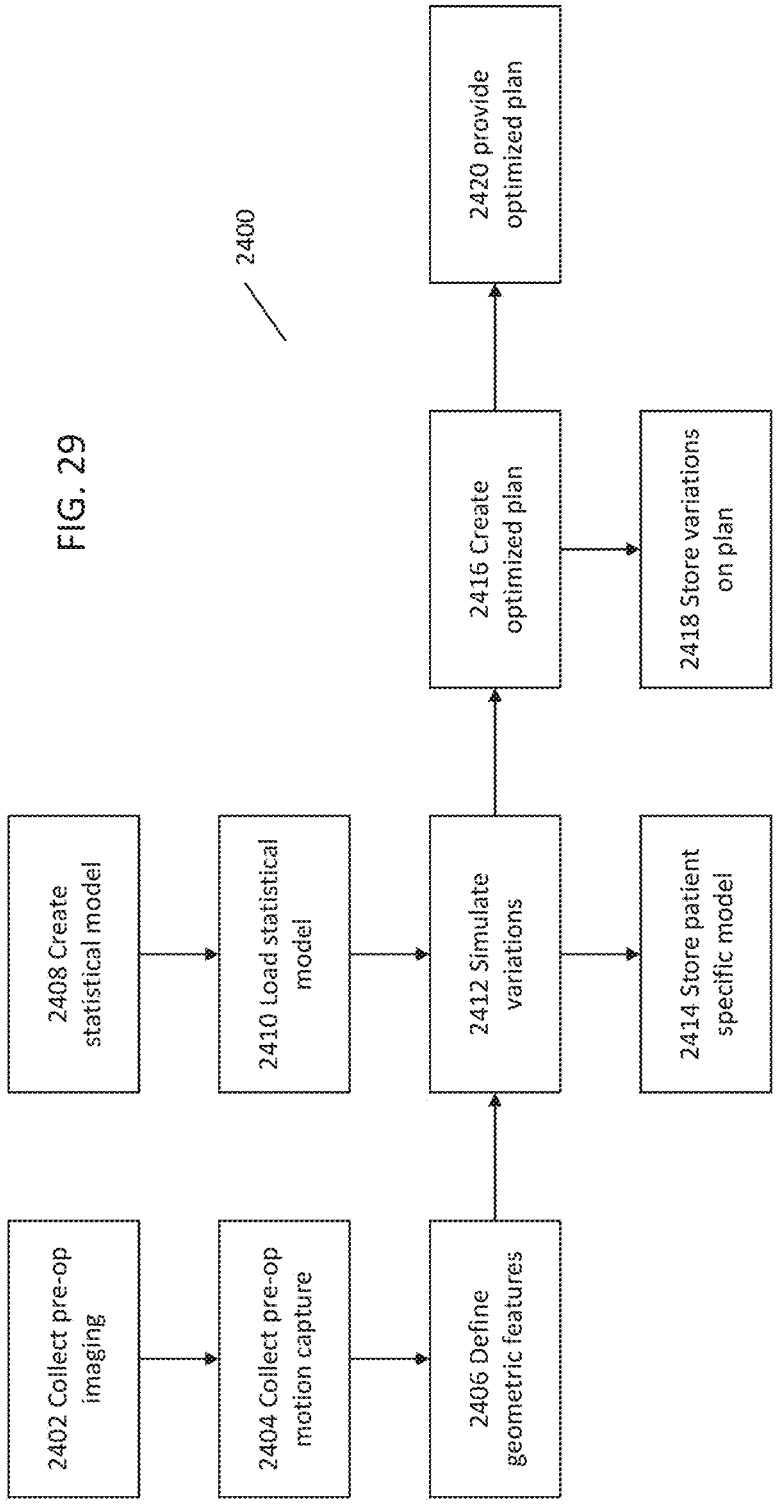
FIG. 29 is a flow chart illustrating an exemplary method for creating a surgical plan using a statistical model database based on modeled performance, for use with some embodiments.

FIG. 29 is a flow chart of an exemplary method 2400 for creating a preoperative plan using a simulation database and patient specific geometry extracted from images and (optionally) motion capture. The same method can be used to optimize a preoperative plan for hip (or other) arthroplasty, but will be discussed in the context of a knee arthroplasty. At step 2402, the surgical planning system collects preoperative imaging, such as MRIs, CT scans, x-rays, and ultrasound images. These can be done at any time in advance of the surgery. Image files can be loaded into a database specific to that patient for feature extraction. In some embodiments, at step 2404, motion capture techniques can be used in a preoperative visit to capture a patient's gait by affixing markers to various points on their leg and observing the relative motion of markers as the patient performs various motions. This can be used to provide supplemental detail about the geometry of the preoperative state of the patient's knee. At step 2406, imaging is analyzed using geometric techniques for image analysis (and any motion capture data is analyzed based on a motion model of human anatomy). Software performing the image analysis can use any suitable feature extraction technique to identify predetermined features in the patient images and create a three-dimensional model of the patient's knee based on a plurality of images that includes information such as sacral/pelvic geometry, femoral head/neck and acetabular cup geometry, femoral and tibial axes, condylar centers and sizes, existing condylar gaps, patella size, and its existing relationship with preoperative soft-tissue tensions.

In parallel, and typically prior to these steps, a statistical model is created at step 2408 that accounts for various possible patient geometries for a wide range of patients. Hundreds to hundreds of thousands of simulations for various possible patient geometries can be performed off-line to create the statistical model. The simulation data can then be mined to create a transfer function or simplified model for a given geometry, allowing performance to be determined or estimated for any given patient geometry. At step 2410, when an individual patient's anatomical geometry has been determined (step 2406), the statistical model is loaded.

At step 2412, the statistical model is used to explore possible corrections to a patient's given anatomical geometry. This can take on various suitable approaches as known in the art, such as applying artificial intelligence searching and matching algorithms to identify incremental improvements to implantation geometry to correct patient infirmities. For example, AI can be used to identify a design-of-test to identify likely candidate changes to improve the mechanics of the patient's joint. Similarly, a Monte Carlo simulation may be used to investigate random changes to implantation geometry using the statistical model to identify the best performing options for implanting a TKA prosthetic. In some embodiments, at step 2412, many (e.g., dozens or thousands) variations are used to identify the optimal solution to implantation. Because this step is preoperative, the processing time or overhead can be quite substantial, if needed. Various attributes can be changed, including the pose of tibial and femoral components, patellar packing and dome geometry, etc., to find a solution that optimizes performance of the patient knee that takes into account both the tibiofemoral and patellofemoral joints, rather than viewing of the patella as an afterthought, as is often the case with existing surgical plans. In some embodiments, the statistical model created at step 2408 can simply be queried for an optimal implantation pose based on the starting patient geometry, such as by using a transfer function with an AI model. In some embodiments, the simulation variations undertaken at step 2412 can be specific to different patient activities, allowing activity-specific optimization for an individual patient.

In some embodiments, the purpose of step 2412 is also to create a patient-specific model that takes into account the imprecise nature of preoperative data. For example, preoperative images and motion capture may create an estimate of patient geometry that is inexact. Data collected during a surgery can later be used to improve the model of patient anatomical geometry. By considering the plurality of variations on not only the implantation poses, but also the patient anatomical geometry (within a range), a patient-specific model can be created so that changes to the surgical plan can be made on-the-fly during surgery based on additional data or based on a request by a surgeon to alter the implantation plan, Once a plurality of variations on the patient geometry and implantation pose are considered, a patient specific model can be stored at step 2414. This model can be stored in non-volatile memory, allowing it to be accessed by the CASS during an operation. This will be discussed with respect to FIG. 30. Any suitable amount of information or format may be used, with the goal of simplifying any processing or simulation that is done during the patient operation, such that changes can be handled on-the-fly without slowing down the surgery.

At step 2416, the processor can create an optimized surgical plan based on an optimization of the implantation poses created at step 2412 and a patient profile. For PKA/TKA, this plan can include implantation poses for femoral and tibial components (including the resections needed to accomplish these poses), as well as a plan for packing the patella and any changes to the dome or patellar buttons that may be needed to achieve the relationship between patella and femoral components as part of the arthroplasty. At step 2420, this optimized preoperative plan is provided to the surgeon and to the CASS to prepare for surgery.

In some embodiments, an additional step, step 2418, can be undertaken, whereby variations of the preoperative plan are created to take into account possible variations in patient anatomical geometry that may be discovered during surgery, as well as any reasonable deviations from the surgical plan that may be undertaken by a surgeon during the operation. These variations can be associated with expected performance outcomes for the surgically modified joint. This can make it easier for the CASS to provide recommendations during surgery based on additional patient data observed in the surgical theater or based on requests by the surgeon. Effectively, this can create a very low computational load for providing recommendations or calculating expected performance impacts of additional data or decisions during surgery.

Figure 30:
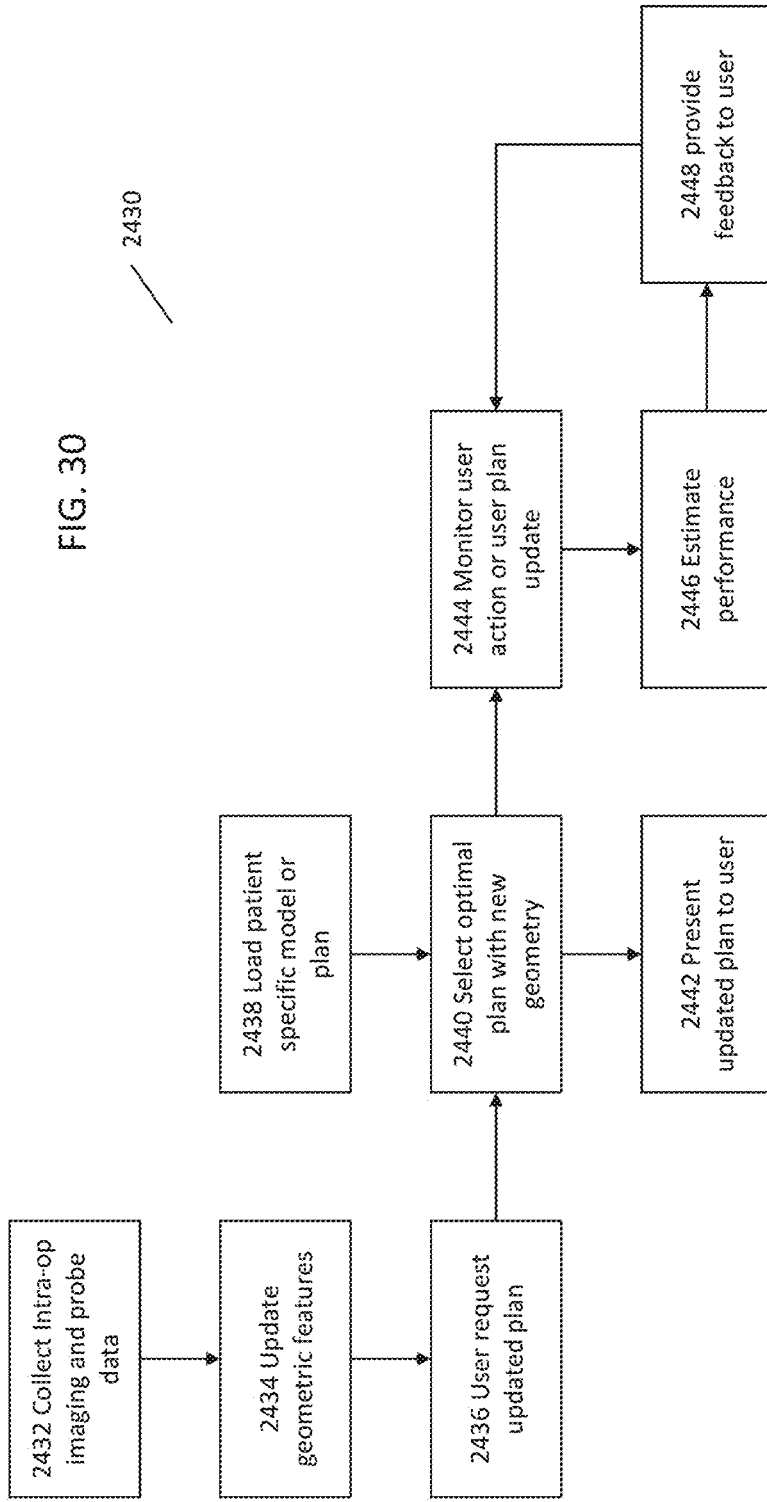
FIG. 30 is a flow chart illustrating an exemplary method for modifying a surgical plan using a statistical model database based on modeled performance, for use with some embodiments.

FIG. 30 shows an exemplary method 2430 for updating the surgical plan or for providing recommendations to a surgeon during a surgery. Once a preoperative plan is created, additional information may be gathered in the surgical theater that may be useful for updating this plan. Similarly, surgeons often rely on their own experience and expertise and may adapt the surgical plan based on what they find during the surgery or a disagreement with the AI-generated recommendation. At step 2432, the CASS collects intraoperative imaging and probe data. Intraoperative imaging may include any conventional medical imaging, such as ultrasound data. This intraoperative imaging can be in addition to preoperative imaging. This may provide additional detail or updates to a model of patient geometry. Similarly, once patient tissue is opened, a probe may be used to "paint" various surfaces of patient bone, as explained throughout. This can provide additional detail about the exact 3-D nature of patient tissue surfaces that may be more accurate than the model created from a two-dimensional or three-dimensional imaging. At step 2434, the processor analyzes intraoperative imaging and probe data to supplement the model of patient geometry by identifying specific features being observed in the surgical theater and comparing to the existing model. Once the geometric model of patient anatomy is updated, a surgical user can request an update to the plan at step 2436 (or forgo requesting an update, skipping to step 2444).

In response to this new data and user request, at step 2440, the processor selects the optimal plan based on the new anatomical geometry model. This is accomplished by first loading patient specific models or plans from memory at step 2438. Because of the time critical nature of intraoperative recommendations, the models and plans loaded at step 2438, in some embodiments, are patient specific, such as those created in FIG. 27. This limits the universe of possible geometric changes to the most relevant, based on a model of patient anatomy prior to surgery to expedite processing recommendations for changes to the plan. At step 2440, an optimal plan can be chosen via any conventional computational approach from the available plans and models, based on the observed patient anatomy. At step 2442, this updated recommendation to the plan can be presented to the user via a user interface of the CASS and to the CASS to update the plan it will assist in implementing.

At step 2444, the processor can begin monitoring user actions or requests by the user for plan updates. Monitoring of user actions can come via the CASS, such as by monitoring the actual resections that are undertaken by the surgeon. For example, a deviation from the surgical plan in the resection may necessitate a recommended change to other resections to limit the impact of the deviation. A user may also manually change the surgical plan, such as a surgeon intentionally deviating from a recommended plan, based on expertise and experience. These deviations to the plan will be noted by the processor, which will provide feedback to the user. If at any time, the user would like a recommendation for a change of plan, the user interface can be used to request a recommendation, which repeats step 2436.

At step 2446, the processor estimates the performance impacts of the deviation from the optimal plan provided at step 2440 and provides feedback to the user based on this estimate, at step 2448. For example, for a PKA/TKA a change to a patellar/implant pose that occurs during the surgery can necessitate changes to the patella. At step 2448, a GUI may cause an indicator of the patella to flash or change color to indicate a potential problem. For a hip revision/THA, hip components can flash or change color.

AI Enhanced Cutting Guides

Some embodiments utilize the simulation database and AI guided planning processes described herein to improve robotic or computer-enhanced surgical planning. However, such surgical systems may be limited or unavailable. Accordingly, in some embodiments custom, patient-specific cutting guides may be manufactured in accordance with the same concepts—their creation guided by applying a simulation database/statistical model to preoperative imaging, Some embodiments use these concepts to create a pre-surgical plan or adjust it on the fly intraoperatively, as more data is acquired in the surgical theater. In some embodiments this same process can be used with pre-operatively manufactured cutting guides. For TKA/PKA, once the ideal position and orientation of the distal and posterior cuts for a knee implant are identified, the surgical plan can then be sent to a computer assisted surgical system or other suitable system for implementation of the surgical plan. For example, in some embodiments, the preoperative plan can be used with a custom cutting guide system whereby images of the surfaces of patient femur and tibia are used to identify a patient matched surface to form the base of a 3-D printed cutting guide. The distal and posterior cuts, as well as any secondary cuts needed for fitment, can be added to this patient matched cutting guide. Once the cutting guide is printed (or otherwise manufactured), the cutting guides can be sent to the surgeon for use during implantation. Any suitable construction for a customized cutting guide can be used. Exemplary construction of a customized patient matched cutting guide can be seen in co-owned US Patent application publications US 2012/0116562 and US 2014/0018813, which are hereby incorporated by reference in their entirety. This can cut down on the risk of a surgeon imprecisely aligning the cuts in accordance with the preoperative surgical plan. In some embodiments, a cutting guide is less customized to patient surfaces and can be used with a computer-assisted surgical system. For example, a robot arm may precisely place and hold a non-patient matched cutting guide that is selected in accordance with the preoperative surgical plan. Once a robot arm places and holds the cutting guide in place, or once a patient-matched cutting guide is affixed to a patient bone, a surgeon can use an oscillating or rotary tool to resect patient bone in accordance with the cuts of the surgical plan to ensure precise alignment of the prosthetic implant.

Figure 31:
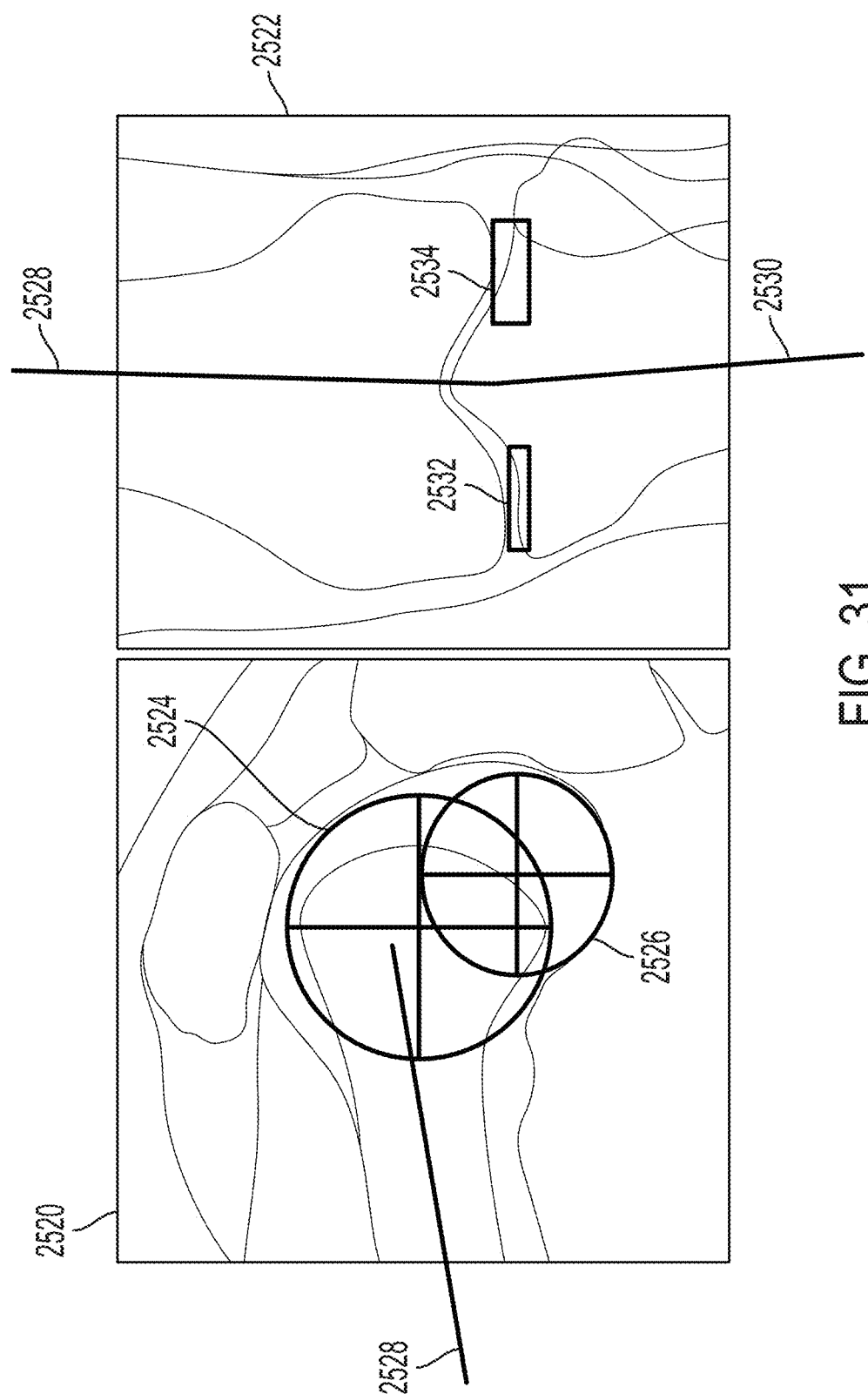
FIG. 31 is a pair of annotated x-ray images showing exemplary knee geometry that can be used in some embodiments.

TKA/PKA are especially well suited for custom cutting guides (or selection from a plurality of available cutting guides to find one that is best suited for a patient). FIG. 31 is an illustration of how relevant anatomical geometry can be extracted from images, such as x-rays, for a knee joint for creation or selection of the appropriate cutting guide. Medial-lateral image 2520 and posterior-anterior image 2522 show a patient knee in partial flexion. This process should be repeated for at least two or more knee poses (e.g., extension, 30-60-90 degrees flexion). From the lateral view, distal and posterior condyle radii can be determined from the x-ray image (2524 and 2526, respectively). These radii can be determined graphically, either automatically through image analysis and geometric fitting to the image via a basic searching algorithm to provide a best fit of radii, or manually by a surgeon using a graphical user interface, such as a touchscreen. This can be done manually or via any conventional image processing algorithm that fits circles to images. Here, circle 2524 is fit to the distal condyle radius and circle 2526 is fit to the posterior condyle radius. Once the circles are fit, pixel locations identify the center point and radius of each circle relative to an anatomical axis 2528 of the femur, which can be determined by bisecting the boundaries that define the anterior and posterior surfaces of the femur. The axis of the femur 2528 can be automatically added through similar image analysis or manually by a surgeon.

From the anterior-posterior image, medial and lateral condylar compartment gaps 2532 and 2534 can be determined by fitting rectangles (or parallel lines) to the boundaries of the femur and the tibia. These gaps are the space between the condyles and the bed of the tibia. For a balanced knee, these gaps should be matched and consistent through a range of motion. The distances of gaps 2532 and 2534 can be determined through any graphic processing algorithm that is suitable for measuring distances between features, or may be measured by manipulating points through user interface for a surgeon to identify the edges of the condyles and tibia for a distance measurements. An anatomical axis 2530 of the tibia can be determined by bisecting the medial lateral edges of the tibia (while anatomical axis 2528 can be similarly created). Comparing these axes reveals the degree of varus/valgus in the joint.

The process shown in FIG. 31 can be repeated for different angles of flexion and compared. Condylar center points and radii can be averaged from the different images, while the changes in the gaps can be plotted to better understand the degree of gap change and asymmetry in the joint. Medial-lateral force can also be applied to either determine an estimate of instability or to capture images showing how gaps are affected by the force to better understand the degree of ligament laxity.

Using Simulation to Improve Patella Performance

Traditionally, surgeons focus primary attention during a knee procedure on the tibiofemoral joint of the knee, ensuring that the condylar gaps are consistent throughout the range of motion and that ligament strain is below a threshold. The patellofemoral joint can then be adjusted once the tibiofemoral joint has been corrected. While this approach can create successful outcomes, the outcome is not necessarily optimized for a given patient. In some embodiments, simulation is used to simultaneously plan the tibiofemoral joint and the patellofemoral joint simultaneously to create a surgical plan that optimizes both joints in the knee.

The patellofemoral joint consists of a patella having a dome that rides in the patellar groove between the condyles of the femur. The patella is constrained by a patellar ligament, quadricep tendon, and laterally by the retinaculum. The angle at which the quadricep tendon sits relative to an axis of the knee is described as a quadricep angle or q-angle. When riding in the patellar groove, the dome of the patella experiences sheer stress, as it is being pulled relative to the groove (medially/laterally), creating shear.

During the arthroplasty, once the femoral and tibial prosthetic pieces have been implanted and secured to patient bone, the surgeon can adjust manually how the patella dome rides in the patellar groove between the femoral condyles. To do this, the surgeon will observe the laxity of the quadricep in the patient's passive knee and move/rotate the patella dome to add a desired amount of tension to the quadriceps while keeping the q-angle within a desired range. This process is typically referred to as packing the patella, and can be achieved by adjusting the tension of patellar ligaments and tendons to adjust how the dome of the patella travels in the groove, pushing the patella outward and increasing tension on the quadricep tendon. To move the patella into the desired geometry, a surgeon can perform tissue releases of any ligaments or tendons that are constraining the patella. Packing, by adjusting tissue/inserts between the patella and the condyles on either side of the trochlear groove, can reduce the amount of available strength or overly strain of the retinaculum if too much packing is done.

Because the amount of packing can reduce performance of the repaired knee, manual adjustment while all muscles are relaxed can arrive at a suitable geometry that may not have optimal performance for a repaired knee. Laxity is a very qualitative/subjective measure, especially in a passive muscle in surgery. Simulation can improve this. In comparison to a flexed knee in a passive state on the surgical table, simulation can add additional data to better understand the performance of the repaired knee. Simulation can add loads, such as body weight and quad strain, and a motion profile, such as gait where multiple muscle groups fire. Simulation can also consider deep knee bends, where the primary force is from extensor muscles.

Embodiments use simulation data to assist in the patellar packing step of surgery and in considering patellar performance to determine the target implantation pose of the tibial and femoral components. In existing surgical planning processes, it is common to optimize the femoral and tibial implantation poses without detailed consideration of the patella, relying on subsequent packing of the patella once the femoral and tibial poses are constrained. By utilizing simulation data, the preoperative plan and adjustments to the plan during surgery can consider simulated motions with real-world loads and muscle tensions and the expected patellar performance (and packing plan) before making recommendations for the implantation poses of tibial and femoral components (and the resections needed to achieve the target implantation poses).

Figure 32:
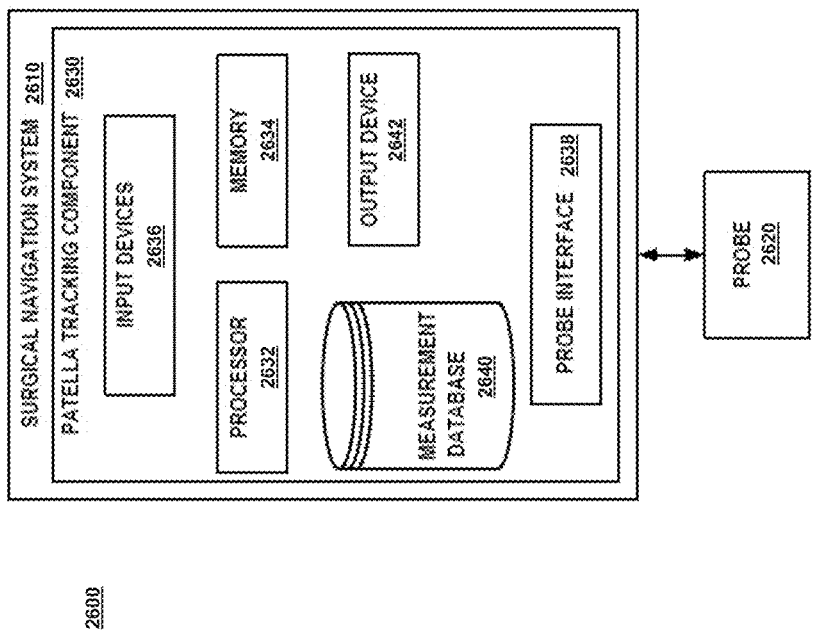
FIG. 32 is system diagram for an exemplary embodiment of a surgical system, for use with some embodiments.

FIGS. 32-33 illustrate an exemplary surgical system CASS 2600 that can include a supplemental system to aid in gathering additional information about patella tracking in a patient knee during a surgery. This additional information about the patella tracking in the pre-modified knee can be used to refine the anatomical model to provide a refined recommendation of implantation pose and patella packing strategy using the statistical model or transfer function on the fly during surgery. The exemplary surgical system 2600 can be configured to intraoperatively obtain positional data relating to a range of motion of a knee that will be subject to a surgical procedure. This positional data can correspond to discrete angles of flexion or extension of the operative knee. In certain embodiments, the system 2600 can include a surgical navigation system/CASS 2610 and a probe 2620, as described with respect to the CASS throughout. In operation, the knee of a patient is moved through a range of motion, so that the position of various anatomical components such as the femur, the tibia, and the patella can be tracked.

In some embodiments, the surgical navigation system 2610 can be configured to employ a patella tracking component 2630. The patella tracking component 2630 can be configured and implemented as an integral system or component within the surgical navigation system 2610 and may share hardware/software or implemented as a standalone component that connects to the surgical navigation system 2610. It should be appreciated that embodiments of the described subject matter can be implemented by various types of operating environments, computer networks, platforms, frameworks, computer architectures, and/or computing devices.

The surgical navigation system 2610 and/or the patella tracking component 2630 can include one or more processors and memory devices, as well as various input devices, output devices, communication interfaces, and/or other types of devices. The surgical navigation system 2610 and/or the patella tracking component 2630 can include a combination of hardware and software.

The surgical navigation system 2610 and/or the patella tracking component 2630 can implement and utilize one or more program modules. Generally, program modules include routines, programs, objects, components, data structures, and/or the like that perform particular tasks or implement particular abstract data types.

The surgical navigation system 2610 and/or the patella tracking component 2630 can be implemented by one or more computing devices configured to provide various types of services and/or data stores in accordance with aspects of the described subject matter. Exemplary computing devices can include, without limitation: personal computing devices, web servers, front end servers, application servers, database servers, domain controllers, domain name servers, directory servers, and/or other suitable computers. Components of the surgical navigation system 2610 and/or the patella tracking component 2630 can be implemented by software, hardware, firmware or a combination thereof.

The patella tracking component 2630 can include a processor 2632, memory 2634, input devices 2636, probe interface 2638, measurement database 2640, and output device 2642. The input devices 2636 can be configured and implemented to receive instructions from a surgeon before implementing a surgical plan.

The patella tracking component 2630 can be configured to characterize the anterior surface of the patella with the probe 2620 to relate the anterior geometry to the position of the posterior apex. The patella tracking component 2630 can implement the processor 2632 to communicate with the probe 2620 through the probe interface 2638 to obtain measurements of the position of the patella at discrete increments. The increments can represent discrete amounts of flexion and extension measured in degrees or other suitable units.

The processor 2632 can be configured to execute software instructions stored in memory 2634 to determine, for example, the posterior apex of the patella by using measurements from the probe 2620 before the patella tracking component 2630 evaluates patella movement. In some embodiments, the posterior apex of the patella can be determined with the probe 2620, so the relative position of the posterior apex to the anterior patella geometry can be recorded in the measurement database 2640.

The probe 2620 can be a handheld point probe, such as is shown in FIG. 25B. The probe 2620 is used to identify certain landmarks and to characterize surfaces. Alternatively, the probe 2620 can be a point probe that terminates in a curved tip to identify hard-to-reach landmarks that would otherwise be covered or blocked by, for example, soft tissue. The probe 2620 can be used to relate the position of the posterior apex to the anterior geometry.

In certain embodiments, the processor 2632 can approximate movement of the posterior apex during a full flexion and extension by locating specific anatomic features on the anterior patella or by probing the anterior patella surface at different increments. For example, the increments can include 30°, 60°, and 90° of flexion.

While some embodiments use a handheld probe to locate landmarks during the range of motion, some embodiments utilize fiducial marks that are temporarily affixed to the patella to automatically track the motion and pose of the patella relative to tibia and femur or place temporary visual marks on one or more location of the patella to index the location that should be contacted by the probe to expedite the patella tracking process.

Figure 34A:
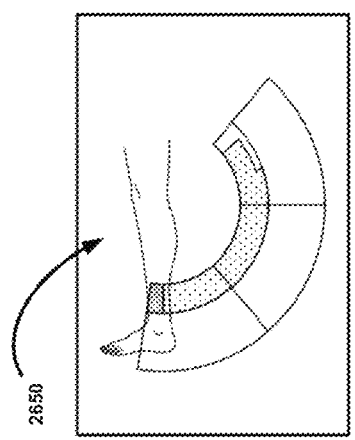
FIGS. 34A-B illustrates the process of measurement of a patient knee at various degrees of flexion.
Figure 34B:
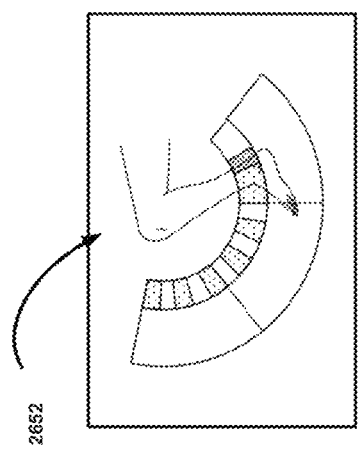

The output device 2642 can generate position measurements of the patella in various stages of extension and flexion. In certain embodiments, FIGS. 34A and 34B depict a display illustrating the collection of position data relating to the location and orientation of the patella through a range of motion from nearly full extension 2650 in FIG. 34A to nearly full flexion 2652 in FIG. 34B.

Co-owned Patent Application No. PCT/US2019/045536 ("Patella Tracking Method and System") describes various additional ways that a patella's physical characteristics and can be identified and its position/orientation determined during a surgery using a CASS, and is hereby incorporated by reference in its entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine-readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. No claim element herein is to be construed under the provisions of 35 U.S.C. 112(f) unless the element is expressly recited using the phrase "means for."

We claim:

1. A system for creating an activity-optimized cutting guide for a surgical procedure, the system comprising:
   one or more processors; and
   a non-transitory, computer-readable medium storing instructions that, when executed, cause the one or more processors to:
      determine, based on pre-operative image data, one or more patient-specific anatomical measurements associated with an anatomical joint of a patient,
      apply a statistical model of joint performance to the one or more patient-specific anatomical measurements, wherein the statistical model uses one or more transfer functions,
      identify one or more cut angles for performing a surgical procedure based on the applied statistical model,
      generate a model of a patient-specific cutting guide based on the one or more cut angles, and
      output the model to a computer-readable storage device.

2. The system of claim 1, wherein the one or more patient-specific anatomical measurements comprise a distal condyle radius and an anterior condyle radius.

3. The system of claim 1, wherein the instructions that cause the one or more processors to identify one or more cut angles comprise instructions that, when executed, cause the one or more processors to select a set of cut angles that substantially balance condylar gaps of the anatomical joint throughout a range of motion associated with one or more physical activities.

4. The system of claim 1, where the instructions that cause the one or more processors to determine one or more patient-specific anatomical measurements comprise instructions that, when executed, cause the one or more processors to:
   receive one or more pre-operative images depicting the anatomical joint;
   create a three-dimensional anatomical model of the anatomical joint based on the one or more pre-operative images; and
   determine the one or more patient-specific anatomical measurements based on the three-dimensional anatomical model.

5. The system of claim 1, wherein the instructions that cause the one or more processors to apply a statistical model of joint performance comprise instructions that, when executed, cause the one or more processors to apply a Monte Carlo method to iteratively evaluate a plurality of possible cut angles.

6. The system of claim 5, wherein each iteration of the Monte Carlo method comprises applying the one or more transfer functions with a distinct set of parameters.

7. The system of claim 1, wherein the statistical model of joint performance is a machine learning model.

8. The system of claim 1, wherein the instructions that cause the one or more processors to generate a model of a patient-specific cutting guide comprise instructions that, when executed, cause the one or more processors to modify a model of a cutting guide blank to include the one or more apertures based on the one or more cut angles.

9. The system of claim 1, wherein the computer-readable storage device is in operable communication with a manufacturing device configured to manufacture the patient-specific cutting guide.

10. A system for creating an activity-optimized cutting guide for a surgical procedure, the system comprising:
    one or more processors; and
    a non-transitory, computer-readable medium storing instructions that, when executed, cause the one or more processors to:
       determine, based on pre-operative image data, one or more patient-specific anatomical measurements associated with an anatomical joint of a patient,
       apply a statistical model of joint performance to the one or more patient-specific anatomical measurements, wherein the statistical model is based on simulation data for a plurality of joint geometries associated with a plurality of implants,
       identify one or more cut angles for performing a surgical procedure based on the applied statistical model,
       generate a model of a patient-specific cutting guide based on the one or more cut angles, and
       output the model to a computer-readable storage device.

11. The system of claim 10, wherein the one or more patient-specific anatomical measurements comprise a distal condyle radius and an anterior condyle radius.

12. The system of claim 10, wherein the instructions that cause the one or more processors to identify one or more cut angles comprise instructions that, when executed, cause the one or more processors to select a set of cut angles that substantially balance condylar gaps of the anatomical joint throughout a range of motion associated with one or more physical activities.

13. The system of claim 10, where the instructions that cause the one or more processors to determine one or more patient-specific anatomical measurements comprise instructions that, when executed, cause the one or more processors to:
    receive one or more pre-operative images depicting the anatomical joint;
    create a three-dimensional anatomical model of the anatomical joint based on the one or more pre-operative images; and
    determine the one or more patient-specific anatomical measurements based on the three-dimensional anatomical model.

14. The system of claim 10, wherein the instructions that cause the one or more processors to apply a statistical model of joint performance comprise instructions that, when executed, cause the one or more processors to apply a Monte Carlo method to iteratively evaluate a plurality of possible cut angles.

15. The system of claim 14, wherein each iteration of the Monte Carlo method comprises applying one or more transfer functions with a distinct set of parameters.

16. The system of claim 10, wherein the statistical model of joint performance is a machine learning model.

17. The system of claim 10, wherein the instructions that cause the one or more processors to generate a model of a patient-specific cutting guide comprise instructions that, when executed, cause the one or more processors to modify a model of a cutting guide blank to include the one or more apertures based on the one or more cut angles.

18. The system of claim 10, wherein the computer-readable storage device is in operable communication with a manufacturing device configured to manufacture the patient-specific cutting guide.

19. The system of claim 10, wherein each implant of the plurality of implants is defined by a distinct set of implantation features comprising one or more of an implant position, an implant orientation, and an implant type.

20. The system of claim 10, wherein the instructions, when executed, further cause the one or more processors to generate the statistical model by:
   selecting the plurality of implants;
   populating a database with the simulation data by simulating a motion of the plurality of joint geometries while performing one or more physical activities and an expected stress on the plurality of implants resulting from the motion; and
   generating the statistical model of joint performance based on the simulation data.

\* \* \* \* \*